US008183246B2

(12) United States Patent
Lampe et al.

(10) Patent No.: US 8,183,246 B2
(45) Date of Patent: May 22, 2012

(54) ACYCLICALLY SUBSTITUTED FUROPYRIMIDINE DERIVATIVES AND USE THEREOF

(75) Inventors: Thomas Lampe, Düsseldorf (DE); Eva-Maria Becker, Wuppertal (DE); Raimund Kast, Wuppertal (DE); Hartmut Beck, Köln (DE); Mario Jeske, Solingen (DE); Joachim Schuhmacher, Wuppertal (DE); Friederike Stoll, Düsseldorf (DE); Martina Klein, Düsseldorf (DE); Metin Akbaba, Ratingen (DE); Andreas Knorr, Erkrath (DE); Johannes-Peter Stasch, Solingen (DE); Lars Bärfacker, Oberhausen (DE); Alexander Hillisch, Solingen (AT); Gunter Karig, Hofheim am Taunus (DE); Mark Meininghaus, Wuppertal (DE); Karl-Heinz Schlemmer, Wuppertal (DE); Rudolf Schohe-Loop, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 841 days.

(21) Appl. No.: 12/086,783

(22) PCT Filed: Dec. 8, 2006

(86) PCT No.: PCT/EP2006/011826
§ 371 (c)(1),
(2), (4) Date: Dec. 1, 2008

(87) PCT Pub. No.: WO2007/079862
PCT Pub. Date: Jul. 19, 2007

(65) Prior Publication Data
US 2009/0318475 A1 Dec. 24, 2009

(30) Foreign Application Priority Data
Dec. 21, 2005 (DE) .......................... 10 2005 061 170

(51) Int. Cl.
*A01N 43/90* (2006.01)
*A61K 31/519* (2006.01)
*C07D 491/00* (2006.01)
*C07D 495/00* (2006.01)

(52) U.S. Cl. ..................... 514/260.1; 544/278

(58) Field of Classification Search ............... 514/260.1; 544/278
See application file for complete search history.

(56) References Cited

U.S. PATENT DOCUMENTS

| 3,577,420 | A | 5/1971 | Hess et al. |
| 7,312,224 | B2 | 12/2007 | Eggenweiler et al. |
| 2003/0225098 | A1 | 12/2003 | Hirst et al. |
| 2004/0259888 | A1 | 12/2004 | Bischoff et al. |

FOREIGN PATENT DOCUMENTS

| DE | 1817146 A1 | 11/1969 |
| DE | 10148883 | 4/2003 |
| EP | 1018514 A1 | 7/2000 |
| EP | 1132093 A1 | 9/2001 |
| WO | WO-00/75145 A1 | 12/2000 |
| WO | WO-02/092603 A1 | 11/2002 |
| WO | WO 03/018589 | 3/2003 |
| WO | WO-03/022852 A2 | 3/2003 |
| WO | WO-2005/092896 A1 | 10/2005 |
| WO | WO-2005/121149 A1 | 12/2005 |
| WO | WO 2006/004658 | 1/2006 |

OTHER PUBLICATIONS

Foloppe et. al. (J. Med. Chem. (2005) 48:4332-4345).*
Foloppe, N. et al., "Structure-Based Design of Novel Chk1 Inhibitors: Insights into Hydrogen Bonding and Protein-Ligand Affinity", Journal of Medicinal Chemistry 48(13), pp. 4332-4345.
G. J. Dusting et al.: "Prostacyclin and Vascular Function: Implications for Hypertension and Atherosclerosis," Pharmac. Ther., vol. 46, 1990, pp. 323-344.
J. Vane et al.: "Prostacyclin: a Vascular Mediator," Eur. J. Vasc. Endovasc. Surg., 26, 2003, pp. 571-578.
S. Narumiya et al.: "Prostanoid Receptors: Structures, Properties, and Functions," Physiological Review, vol. 79, No. 4, Oct. 1999, pp. 1183-1226.
K. Schrör et al.: "Roles of Vasodilatory Prostaglandins in Mitogenesis of Vascular Smooth Muscle Cells," Agents Action Supplement, vol. 48, 1997, pp. 63-91.
D. Kothapalli et al.: "Prostacyclin Receptor Activation Inhibits Proliferation of Aortic Smooth Muscle Cells by Regulating cAMP Response Element-Binding Protein- and Pocket Protein-Dependent Cyclin A Gene Expression," Molecular Pharmacology, vol. 64, No. 2, 2003, pp. 246-258.
P. Planchon et al.: "Evidence for Separate Mechanisms of Antiproliferative Action of Indomethacin and Prostaglandin on MCF-7 Breast Cancer Cells," Life Sciences, vol. 57, No. 12, 1995, pp. 1233-1240.
R. Daniel Rudic et al.: "COX-2-Derived Prostacyclin Modulates Vascular Remodeling," Circulation Research, vol. 96, 2005, pp. 1240-1247.
K. M. Egan et al.: "COX-2-Derived Prostacyclin Confers Atheroprotection on Female Mice," Science, vol. 306, Dec. 10, 2004, pp. 1954-1957.

(Continued)

*Primary Examiner* — Marcos Sznaidman
(74) *Attorney, Agent, or Firm* — Karen B. King

(57) ABSTRACT

The present application relates to novel, acyclically substituted furopyrimidine derivatives, methods for their production, their use for the treatment and/or prophylaxis of diseases and their use for the production of medicinal products for the treatment and/or prophylaxis of diseases, in particular for the treatment and/or prophylaxis of cardiovascular diseases.

9 Claims, No Drawings

OTHER PUBLICATIONS

M. R. Schneider et al.: "Prostacyclin and its Analogues: Antimetastatic Effects and Mechanisms of Action," Cancer and Metastasis Reviews, vol. 13, 1994, pp. 349-364.

H. Wise et al.: "Focus on Prostacyclin and its Novel Mimetics," TIPS, vol. 17, Jan. 1996, pp. 17-21.

D. B. Badesch et al.: "Prostanoid Therapy for Pulmonary Arterial Hypertension," Journal of the American College of Cardiology, vol. 43, No. 12, Supp. S, 2004, pp. 56-61.

S. C. Chattaraj: "Treprostinil Sodium Pharmacia," Current Opinion in Investigational Drugs, vol. 3, No. 4, 2002, pp. 582-586.

R. J. Barst et al.: "Beraprost Therapy for Pulmonary Arterial Hypertension," Journal of the American College of Cardiology, vol. 41, No. 12, 2003, pp. 2119-2125.

F. Johannsen et al.: "Phosphorus Pentoxide in Organic Synthesis," Chemica Scripta, vol. 26, 1986, pp. 337-342.

H. Saikachi et al.: "Synthesis of the Furan Derivatives. XLVIII. On the Synthesis of Difurylfuro[2,3-*d*]pyrimidines and Difurylfuro-[3,2-*d*]-s-triazolopyrimidines," Yakugaku Zasshi, vol. 10, 1969, pp. 1434-1439.

E. Hayashi et al.: "Anti-Tumor Activity of Eighty Four Synthesized N-Heteroaromatic Compounds," Yakugaku Zasshi, vol. 97, No. 9, 1977, pp. 1022-1033.

* cited by examiner

ACYCLICALLY SUBSTITUTED FUROPYRIMIDINE DERIVATIVES AND USE THEREOF

RELATED APPLICATIONS/PATENTS AND INCORPORATION BY REFERENCE

This application is a National Stage Application filed under. 35 U.S.C. §371 based on International Application No. PCT/EP2006/011826, filed Dec. 8, 2006, which claims priority to German Patent Application Number 102005061170.2, filed Dec. 21, 2005, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel, acyclically substituted furopyrimidine derivatives, methods of production thereof, and use thereof for the treatment and/or prophylaxis of diseases and use thereof for the production of medicinal products for the treatment and/or prophylaxis of diseases, in particular for the treatment and/or prophylaxis of cardiovascular diseases.

Prostacyclin ($PGI_2$) belongs to the class of bioactive prostaglandins, which are derivatives of arachidonic acid. $PGI_2$ is the main product of arachidonic acid metabolism in endothelial cells and is a potent vasodilator and inhibitor of platelet aggregation. $PGI_2$ is the physiological antagonist of thromboxane $A_2$ ($TxA_2$), a strong vasoconstrictor and stimulator of thrombocyte aggregation, and thus contributes to the maintenance of vascular homeostasis. A drop in $PGI_2$ levels is presumed to be partly responsible for the development of various cardiovascular diseases [Dusting, G. J. et al., *Pharmac. Ther.* 1990, 48: 323-344; Vane, J. et al., *Eur. J. Vasc. Endovasc. Surg.* 2003, 26: 571-578].

After release of arachidonic acid from phospholipids via phospholipases $A_2$, $PGI_2$ is synthesized by cyclooxygenases and then by $PGI_2$-synthase. $PGI_2$ is not stored, but is released immediately after synthesis, exerting its effects locally. $PGI_2$ is an unstable molecule, which is transformed rapidly (half-life approx. 3 minutes) and non-enzymatically, to an inactive metabolite, 6-keto-prostaglandin-F1alpha [Dusting, G. J. et al., *Pharmac. Ther.* 1990, 48: 323-344].

The biological effects of $PGI_2$ occur through binding to a membrane-bound receptor, called the prostacyclin receptor or IP receptor [Narumiya, S. et al., *Physiol. Rev.* 1999, 79: 1193-1226]. The IP receptor is one of the G-protein-coupled receptors, which are characterized by seven transmembrane domains. In addition to the human IP receptor, prostacyclin receptors have also been cloned from rat and mouse [Vane, J. et al., *Eur. J. Vasc. Endovasc. Surg.* 2003, 26: 571-578]. In smooth muscle cells, activation of the IP receptor leads to stimulation of adenylate cyclase, which catalyses the formation of cAMP from ATP. Increase in the intracellular cAMP concentration is responsible for prostacyclin-induced vasodilation and for inhibition of platelet aggregation. In addition to the vasoactive properties, anti-proliferative effects [Schroer, K. et al., *Agents Actions Suppl.* 1997, 48: 63-91; Kothapalli, D. et al., *Mol. Pharmacol.* 2003, 64: 249-258; Planchon, P. et al., *Life Sci.* 1995, 57: 1233-1240] and anti-arteriosclerotic effects [Rudic, R. D. et al., *Circ. Res.* 2005, 96: 1240-1247; Egan K. M. et al., *Science* 2004, 114: 784-794] have also been described for $PGI_2$. Furthermore, $PGI_2$ also inhibits the formation of metastases [Schneider, M. R. et al., *Cancer Metastasis Rev.* 1994, 13: 349-64]. It is unclear whether these effects are due to stimulation of cAMP formation or to IP receptor-mediated activation of other signal transduction pathways in the respective target cell [Wise, H. et al. *TIPS* 1996, 17: 17-21], such as the phosphoinositide cascade, and of potassium channels.

Although the effects of $PGI_2$ are on the whole of benefit therapeutically, clinical application of $PGI_2$ is severely restricted by its chemical and metabolic instability. $PGI_2$ analogues that are more stable, for example iloprost [Badesch, D. B. et al., *J. Am. Coll. Cardiol.* 2004, 43: 56S-61S] and treprostinil [Chattaraj, S. C., *Curr. Opion. Invest. Drugs* 2002, 3: 582-586] have been made available, but these compounds still have a very short time of action. Moreover, the substances can only be administered to the patient via complicated routes of administration, e.g. by continuous infusion, subcutaneously or via repeated inhalations. These routes of administration can also have additional side-effects, for example infections or pains at the site of injection. The use of beraprost, which to date is the only $PGI_2$ derivative available for oral administration to the patient [Barst, R. J. et al., *J. Am. Coll. Cardiol.* 2003, 41: 2119-2125], is once again limited by its short time of action.

The compounds described in the present application are, compared with $PGI_2$, chemically and metabolically stable, non-prostanoid activators of the IP receptor, which imitate the biological action of $PGI_2$ and thus can be used for the treatment of diseases, in particular of cardiovascular diseases.

DE 1 817 146, EP 1 018 514, EP 1 132 093, WO 02/092603, WO 03/022852, WO 2005/092896, WO 2005/121149 and WO 2006/004658 describe various 4-oxy-, 4-thio- and/or 4-aminofuro[2,3-d]pyrimidine derivatives and their use for the treatment of diseases. WO 03/018589 discloses 4-aminofuropyrimidines as adenosine kinase inhibitors for the treatment of cardiovascular diseases. The production of certain 4-aminofuropyrimidine derivatives was announced in *Chemica Scripta* 1986, 26 (2): 337-342, *Yakugaku Zasshi* 1969, 89 (10): 1434-1439 and *Yakugaku Zasshi* 1977, 97 (9): 1022-1033. Compounds with a bicyclic heteroaryl nuclear structure are claimed as inhibitors of cellular adhesion in WO 00/75145.

The compounds claimed within the framework of the present application are characterized, in contrast to the compounds from the state of the art, by a 5,6-diphenylfuro[2,3-d]pyrimidine nuclear structure, which is coupled via position 4, at a certain spatial distance, to a carboxylic acid or carboxylic acid-like functionality.

The present invention relates to compounds of general formula (I)

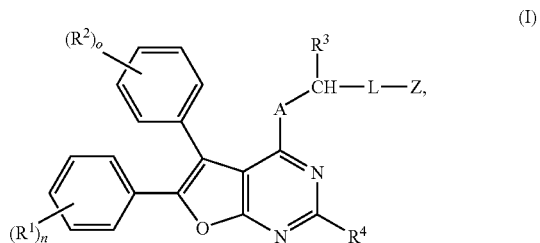

in which

A stands for O, S or N—$R^5$, where
$R^5$ denotes hydrogen, ($C_1$-$C_6$) alkyl, ($C_3$-$C_7$) cycloalkyl or ($C_4$-$C_7$) cycloalkenyl, L stands for $(C_1-C_7)$ alkanediyl or $(C_2-C_7)$ alkenediyl, which can be substituted singly or doubly with fluorine, or for a group of formula *-$L^1$-Q-$L^2$, where
* denotes the point of linkage with the $CHR^3$ group,
$L^1$ denotes $(C_1-C_5)$ alkanediyl, which can be substituted with $(C_1-C_4)$ alkyl or $(C_1-C_4)$ alkoxy,
$L^2$ denotes a bond or $(C_1-C_3)$ alkanediyl, which can be substituted singly or doubly with fluorine,
and
Q denotes O or N—$R^6$, where
$R^6$ represents hydrogen, $(C_1-C_6)$ alkyl or $(C_3-C_7)$ cycloalkyl,
Z stands for a group of formula

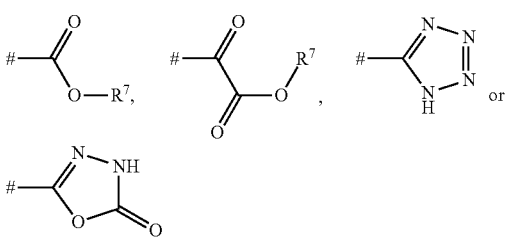

where
# denotes the point of linkage with group L
and
$R^7$ denotes hydrogen or $(C_1-C_4)$ alkyl,
$R^1$ and $R^2$, independently of one another, stand for a substituent selected from the group comprising halogen, cyano, nitro, $(C_1-C_6)$ alkyl, $(C_2-C_6)$ alkenyl, $(C_2-C_4)$ alkinyl, $(C_3-C_7)$ cycloalkyl, $(C_4-C_7)$ cycloalkenyl, $(C_1-C_6)$ alkoxy, trifluoromethyl, trifluoromethoxy, $(C_1-C_6)$ alkylthio, $(C_1-C_6)$ acyl, amino, mono-$(C_1-C_6)$ alkylamino, di-$(C_1-C_6)$ alkylamino and $(C_1-C_6)$ acylamino, and $(C_1-C_6)$ alkyl and $(C_1-C_6)$ alkoxy can in turn each be substituted with cyano, hydroxy, $(C_1-C_4)$ alkoxy, $(C_1-C_4)$ alkylthio, amino, mono- or di-$(C_1-C_4)$ alkylamino,
or
two residues $R^1$ and/or $R^2$ bound to adjacent carbon atoms of the respective phenyl ring, together form a group of formula —O—$CH_2$—O—, —O—CHF—O—, —O—$CF_2$—O—, —O—$CH_2$—$CH_2$—O— or —O—$CF_2$—$CF_2$—O—,
n and o, independently of one another, stand for the number 0, 1, 2 or 3,
and for the case when $R^1$ or $R^2$ occurs more than once, they can have the same or different meanings,
$R^3$ stands for hydrogen or $(C_1-C_4)$ alkyl, which can be substituted with hydroxy or amino,
and
$R^4$ stands for hydrogen, $(C_1-C_4)$ alkyl or cyclopropyl, and their salts, solvates and solvates of the salts.

Compounds according to the invention are the compounds of formula (I) and their salts, solvates and solvates of the salts, the compounds covered by formula (I) of the formulae stated below and their salts, solvates and solvates of the salts and the compounds covered by formula (I), stated below as examples of application, and their salts, solvates and solvates of the salts, provided the compounds covered by formula (I), stated below, are not already salts, solvates and solvates of the salts.

The compounds according to the invention can, depending on their structure, exist in stereoisomeric forms (enantiomers, diastereomers). The invention therefore comprises the enantiomers or diastereomers and their respective mixtures. The stereoisomerically uniform constituents can be isolated in a known manner from such mixtures of enantiomers and/or diastereomers.

If the compounds according to the invention can occur in tautomeric forms, the present invention comprises all tautomeric forms.

Physiologically acceptable salts of the compounds according to the invention are preferred as salts within the scope of the present invention. Salts which in themselves are not suitable for pharmaceutical applications, but can be used for example for the isolation or purification of the compounds according to the invention, are also included.

Physiologically acceptable salts of the compounds according to the invention comprise salts of acid addition of inorganic acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also comprise salts of the usual bases, for example and preferably salts of alkali metals (e.g. sodium and potassium salts), salts of alkaline earths (e.g. calcium and magnesium salts) and ammonium salts, derived from ammonia or organic amines with 1 to 16 carbon atoms, for example and preferably ethylamine, diethylamine, triethylamine, ethyldiisopropylamine, monoethanolamine, diethanolamine, trisethanolamine, dicyclohexylamine, dimethylaminoethanol, procaine, dibenzylamine, N-methylmorpholine, arginine, lysine, ethylendiamine and N-methylpiperidine.

Within the framework of the invention, such forms of the compounds according to the invention that form a complex in the solid or liquid state by coordination with solvent molecules are termed solvates. Hydrates are a special form of solvates, in which coordination is accomplished with water. Hydrates are preferred as solvates within the scope of the present invention.

In addition, the present invention also comprises prodrugs of the compounds according to the invention. The term "prodrugs" comprises compounds which in themselves may be biologically active or inactive, but are converted (e.g. metabolically or by hydrolysis) to compounds according to the invention while they are in the body.

In particular, for the compounds of formula (I) in which Z stands for a group of formula

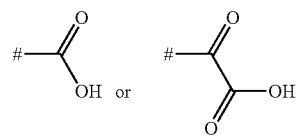

the present invention also comprises hydrolysable ester derivatives of these compounds. This comprises esters that can be hydrolysed to the free carboxylic acids, as the compounds that are mainly active biologically, in physiological media, in the conditions of the biological tests described later and in particular in vivo by enzymatic or chemical routes. $(C_1-C_4)$ alkyl esters, in which the alkyl group can be linear or branched, are preferred as such esters. Methyl or ethyl esters are especially preferred (see also the corresponding definitions of the residue $R^7$).

Within the scope of the present invention, unless specified otherwise, the substituents have the following meanings:

Within the scope of the invention, $(C_1-C_6)$ alkyl, $(C_1-C_5)$ alkyl, $(C_1-C_4)$ alkyl and $(C_1-C_3)$ alkyl stand for a linear or branched alkyl residue with 1 to 6, 1 to 5, 1 to 4 or 1 to 3 carbon atoms. A linear or branched alkyl residue with 1 to 4 carbon atoms is preferred, and one with 1 to 3 carbon atoms is especially preferred. The following may be mentioned as preferred examples: methyl, ethyl, n-propyl, isopropyl, n-butyl, iso-butyl, sec.-butyl, tert.-butyl, 1-ethylpropyl, n-pentyl and n-hexyl.

Within the scope of the invention, $(C_2-C_6)$ alkenyl and $(C_2-C_5)$ alkenyl stand for a linear or branched alkenyl residue with 2 to 6 or 2 to 5 carbon atoms and one or two double bonds. A linear or branched alkenyl residue with 2 to 5 carbon atoms and one double bond is preferred. The following may be mentioned as preferred examples: vinyl, allyl, isopropenyl and n-but-2-en-1-yl.

Within the scope of the invention, $(C_2-C_4)$ alkinyl stands for a linear or branched alkinyl residue with 2 to 4 carbon atoms and a triple bond. A linear alkinyl residue with 2 to 4 carbon atoms is preferred. The following may be mentioned as preferred examples: ethinyl, n-prop-1-in-1-yl, n-prop-2-in-1-yl, n-but-2-in-1-yl and n-but-3-in-1-yl.

Within the scope of the invention, $(C_1-C_7)$ alkanediyl, $(C_1-C_5)$ alkanediyl, $(C_1-C_3)$ alkanediyl and $(C_3-C_7)$ alkanediyl stand for a linear or branched divalent alkyl residue with 1 to 7, 1 to 5, 1 to 3 or 3 to 7 carbon atoms. A linear or branched alkanediyl residue with 1 to 5, 1 to 3 or 3 to 7 carbon atoms is preferred. The following may be mentioned as preferred examples: methylene, 1,2-ethylene, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl.

Within the scope of the invention, $(C_2-C_7)$ alkenediyl and $(C_3-C_7)$ alkenediyl stand for a linear or branched divalent alkenyl residue with 2 to 7 or 3 to 7 carbon atoms and up to 3 double bonds. A linear or branched alkenediyl residue with 3 to 7 carbon atoms and one double bond is preferred. The following may be mentioned as preferred examples: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

Within the scope of the invention, $(C_1-C_6)$ alkoxy and $(C_1-C_4)$ alkoxy stand for a linear or branched alkoxy residue with 1 to 6 or 1 to 4 carbon atoms. A linear or branched alkoxy residue with 1 to 4 carbon atoms is preferred. The following may be mentioned as preferred examples: methoxy, ethoxy, n-propoxy, isopropoxy, n-butoxy, tert.-butoxy, n-pentoxy and n-hexoxy.

Within the scope of the invention, $(C_1-C_6)$ alkylthio and $(C_1-C_4)$ alkylthio stand for a linear or branched alkylthio residue with 1 to 6 or 1 to 4 carbon atoms. A linear or branched alkylthio residue with 1 to 4 carbon atoms is preferred. The following may be mentioned as preferred examples: methylthio, ethylthio, n-propylthio, isopropylthio, n-butylthio, tert.-butylthio, n-pentylthio and n-hexylthio.

Within the scope of the invention, $(C_1-C_6)$ acyl $[(C_1-C_6)$ alkanoyl], $(C_1-C_5)$ acyl $[(C_1-C_5)$-alkanoyl] and $(C_1-C_4)$ acyl $[(C_1-C_4)$ alkanoyl] stand for a linear or branched alkyl residue with 1 to 6, 1 to 5 or 1 to 4 carbon atoms, which bears a double-bonded oxygen atom in position 1 and is linked via position 1. A linear or branched acyl residue with 1 to 4 carbon atoms is preferred. The following may be mentioned as preferred examples: formyl, acetyl, propionyl, n-butyryl, iso-butyryl and pivaloyl.

Within the scope of the invention, mono-$(C_1-C_6)$ alkylamino and mono-$(C_1-C_4)$ alkylamino stand for an amino group with a linear or branched alkyl substituent, which has 1 to 6 or 1 to 4 carbon atoms. A linear or branched monoalkylamino residue with 1 to 4 carbon atoms is preferred. The following may be mentioned as preferred examples: methylamino, ethylamino, n-propylamino, isopropylamino and tert.-butylamino.

Within the scope of the invention, di-$(C_1-C_6)$ alkylamino and di-$(C_1-C_4)$ alkylamino stand for an amino group with two identical or different linear or branched alkyl substituents, each having 1 to 6 or 1 to 4 carbon atoms. Linear or branched dialkylamino residues each with 1 to 4 carbon atoms are preferred. The following may be mentioned as preferred examples: N,N-dimethylamino, N,N-diethylamino, N-ethyl-N-methylamino, N-methyl-N-n-propylamino, N-isopropyl-N-n-propylamino, N-tert.-butyl-N-methylamino, N-ethyl-N-n-pentylamino and N-n-hexyl-N-methylamino.

Within the scope of the invention, $(C_1-C_6)$ acylamino and $(C_1-C_4)$ acylamino stand for an amino group with a linear or branched acyl substituent, which has 1 to 6 or 1 to 4 carbon atoms and is linked via the carbonyl group. An acylamino residue with 1 to 4 carbon atoms is preferred. The following may be mentioned as preferred examples: formamido, acetamido, propionamido, n-butyramido and pivaloylamido.

Within the scope of the invention, $(C_3-C_7)$ cycloalkyl and $(C_3-C_6)$ cycloalkyl stand for a mono-cyclic, saturated cycloalkyl group with 3 to 7 or 3 to 6 carbon atoms. A cycloalkyl residue with 3 to 6 carbon atoms is preferred. The following may be mentioned as preferred examples: cyclopropyl, cyclobutyl, cyclopentyl, cyclohexyl and cycloheptyl.

Within the scope of the invention, $(C_4-C_7)$ cycloalkenyl and $(C_4-C_6)$ cycloalkenyl stand for a mono-cyclic cycloalkyl group with 4 to 7 or 4 to 6 carbon atoms and a double bond. A cycloalkenyl residue with 4 to 6 carbon atoms is preferred. The following may be mentioned as preferred examples: cyclobutenyl, cyclopentenyl, cyclohexenyl and cycloheptenyl.

Within the scope of the invention, halogen includes fluorine, chlorine, bromine and iodine. Chlorine or fluorine is preferred.

If residues are substituted in the compounds according to the invention, unless otherwise specified the residues can be singly or multiply substituted. Within the scope of the present invention, for all residues occurring more than once, their meanings are independent of one another. Substitution with one, two or three identical or different substituents is preferred. Substitution with one substituent is quite especially preferred.

Within the scope of the present invention, compounds of formula (I) are preferred in which A stands for O, S or N—$R^5$, where
$R^5$ denotes hydrogen, $(C_1-C_6)$ alkyl, $(C_3-C_7)$ cycloalkyl or $(C_4-C_7)$ cycloalkenyl, L stands for $(C_1-C_7)$ alkanediyl or $(C_2-C_7)$ alkenediyl, which can be substituted singly or doubly with fluorine, or for a group of formula *-$L^1$-Q-$L^2$, where
* denotes the point of linkage with the $CHR^3$ group,
$L^1$ denotes $(C_1-C_5)$ alkanediyl,
$L^2$ denotes a bond or $(C_1-C_3)$ alkanediyl, which can be substituted singly or doubly with fluorine,
and
Q denotes O or N—$R^6$, where R⁶ represents hydrogen, (C₁-C₆) alkyl or (C₃-C₇) cycloalkyl, Z stands for a group of formula

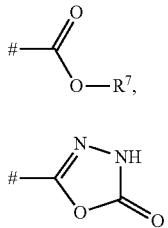

where

\# denotes the point of linkage with group L and

R⁷ denotes hydrogen or (C₁-C₄) alkyl,

R¹ and R², independently of one another, stand for a substituent selected from the group comprising halogen, cyano, nitro, (C₁-C₆) alkyl, (C₂-C₆) alkenyl, (C₂-C₄) alkinyl, (C₃-C₇) cycloalkyl, (C₄-C₇) cycloalkenyl, (C₁-C₆) alkoxy, trifluoromethyl, trifluoromethoxy, (C₁-C₆) alkylthio, (C₁-C₆) acyl, amino, mono-(C₁-C₆) alkylamino, di-(C₁-C₆) alkylamino and (C₁-C₆) acylamino, and (C₁-C₆) alkyl and (C₁-C₆) alkoxy can in turn each be substituted with hydroxy, (C₁-C₄) alkoxy, amino, mono- or di-(C₁-C₄) alkylamino, or two residues R¹ and/or R² bound to adjacent carbon atoms of the respective phenyl ring together form a group of formula —O—CH₂—O—, —O—CHF—O—, —O—CF₂—O—, —O—CH₂—CH₂—O— or —O—CF₂—CF₂—O—, n and o, independently of one another, stand for the number 0, 1, 2 or 3, and for the case when R¹ or R² occurs more than once, their meanings can each be identical or different, R³ stands for hydrogen or (C₁-C₄) alkyl, which can be substituted with hydroxy or amino, and R⁴ stands for hydrogen, (C₁-C₄) alkyl or cyclopropyl, and their salts, solvates and solvates of the salts.

Within the scope of the present invention, compounds of formula (I) are especially preferred in which A stands for O or N—R⁵, where R⁵ denotes hydrogen, (C₁-C₄) alkyl or (C₃-C₆) cycloalkyl, L stands for (C₃-C₇) alkanediyl or (C₃-C₇) alkenediyl, which can be substituted singly or doubly with fluorine, or for a group of formula *-L¹-Q-L², where

* denotes the point of linkage with the CHR³ group,

L¹ denotes (C₁-C₃) alkanediyl,

L² denotes (C₁-C₃) alkanediyl, which can be substituted singly or doubly with fluorine, and Q denotes O or N—R⁶, where R⁶ represents hydrogen, (C₁-C₃) alkyl or cyclopropyl, Z stands for a group of formula

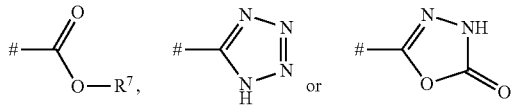

where

\# denotes the point of linkage with group L and

R⁷ denotes hydrogen, methyl or ethyl,

R¹ and R², independently of one another, stand for a substituent selected from the group comprising fluorine, chlorine, cyano, (C₁-C₅) alkyl, (C₂-C₅) alkenyl, (C₃-C₆) cycloalkyl, (C₄-C₆) cycloalkenyl, (C₁-C₄) alkoxy, trifluoromethyl, trifluoromethoxy, (C₁-C₄) alkylthio, (C₁-C₅) acyl, amino, mono-(C₁-C₄) alkylamino, di-(C₁-C₄) alkylamino and (C₁-C₄) acylamino or two residues R¹ and/or R² bound to adjacent carbon atoms of the respective phenyl ring, together form a group of formula —O—CH₂—O—, —O—CHF—O— or —O—CF₂—O—, n and o, independently of one another, stand for the number 0, 1, 2 or 3, and for the case when R¹ or R² occurs more than once, their meanings can in each case be identical or different, R³ stands for hydrogen or (C₁-C₃) alkyl, which can be substituted with hydroxy or amino, and R⁴ stands for hydrogen or (C₁-C₃) alkyl, and their salts, solvates and solvates of the salts.

Within the scope of the present invention, compounds of formula (I) are quite especially preferred in which A stands for O or NH, L stands for (C₃-C₇) alkanediyl, (C₃-C₇) alkenediyl or for a group of formula *-L¹-O-L², where

* denotes the point of linkage with the CHR³ group and

L¹ and L², independently of one another, denote (C₁-C₃) alkanediyl,

Z stands for a group of formula

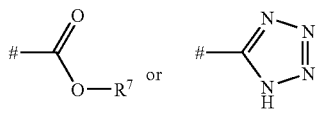

where

\# denotes the point of linkage with group L and

R⁷ denotes hydrogen, methyl or ethyl,

R¹ and R², independently of one another, stand for a substituent selected from the group comprising fluorine, chlorine, cyano, (C₁-C₅) alkyl, (C₂-C₅) alkenyl, (C₃-C₆) cycloalkyl, (C₄-C₆) cycloalkenyl, (C₁-C₄) alkoxy, trifluoromethyl, trifluoromethoxy, (C₁-C₄) alkylthio, (C₁-C₅) acyl, amino, mono-(C₁-C₄) alkylamino, di-(C₁-C₄) alkylamino and (C₁-C₄) acylamino or two residues R¹ and/or R², bound to adjacent carbon atoms of the respective phenyl ring, together form a group of formula —O—CH₂—O—, —O—CHF—O— or —O—CF₂—O—, n and o, independently of one another, stand for the number 0, 1 or 2,
and for the case when $R^1$ or $R^2$ occurs twice, their meanings can in each case be identical or different,
$R^3$ stands for hydrogen, methyl or ethyl
and
$R^4$ stands for hydrogen,
and their salts, solvates and solvates of the salts.

Within the scope of the present invention, compounds of formula (I) are also quite especially preferred in which
A stands for O or NH,
L stands for a group of formula *-$L^1$-N($CH_3$)-$L^2$, where
* denotes the point of linkage with the $CHR^3$ group
and
$L^1$ and $L^2$, independently of one another, denote ($C_1$-$C_3$) alkanediyl,
Z stands for a group of formula

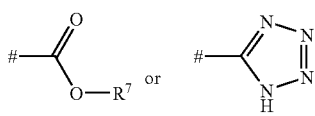

where
# denotes the point of linkage with group L
and
$R^7$ denotes hydrogen, methyl or ethyl,
$R^1$ and $R^2$, independently of one another, stand for a substituent selected from the group comprising fluorine, chlorine, cyano, ($C_1$-$C_5$) alkyl, ($C_2$-$C_5$) alkenyl, ($C_3$-$C_6$) cycloalkyl, ($C_4$-$C_6$) cycloalkenyl, ($C_1$-$C_4$) alkoxy, trifluoromethoxy, ($C_1$-$C_4$) alkylthio, ($C_1$-$C_5$) acyl, amino, mono-($C_1$-$C_4$) alkylamino, di-($C_1$-$C_4$) alkylamino and ($C_1$-$C_4$) acylamino
or
two residues $R^1$ and/or $R^2$, bound to adjacent carbon atoms of the respective phenyl ring, together form a group of formula —O—$CH_2$—O—, —O—CHF—O— or —O—$CF_2$—O—,
n and o, independently of one another, stand for the number 0, 1 or 2,
and for the case when $R^1$ or $R^2$ occurs twice, their meanings can in each case be identical or different,
$R^3$ stands for hydrogen, methyl or ethyl
and
$R^4$ stands for hydrogen,
and their salts, solvates and solvates of the salts.

Within the scope of the present invention, compounds of formula (I) are preferred above all in which
A stands for O or NH,
L stands for ($C_3$-$C_7$) alkanediyl, ($C_3$-$C_7$) alkenediyl or for a group of formula *-$L^1$-Q-$L^2$, where
* denotes the point of linkage with the $CHR^3$ group,
$L^1$ and $L^2$, independently of one another, denote ($C_1$-$C_3$) alkanediyl
and
Q denotes O or N($CH_3$), Z stands for a group of formula

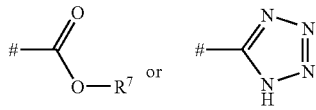

where
# denotes the point of linkage with group L
and
$R^7$ denotes hydrogen, methyl or ethyl,
$R^1$ stands for a substituent selected from the group comprising fluorine, chlorine, methyl, ethyl, vinyl, trifluoromethyl and methoxy,
$R^2$ stands for a substituent selected from the group comprising fluorine, chlorine, cyano, methyl, ethyl, n-propyl, vinyl, trifluoromethyl, methoxy, ethoxy, trifluoromethoxy, methylthio, ethylthio, amino, methylamino and ethylamino,
n and o, independently of one another, stand for the number 0, 1 or 2,
and for the case when $R^1$ or $R^2$ occurs twice, their meanings can in each case be identical or different,
$R^3$ stands for hydrogen, methyl or ethyl
and
$R^4$ stands for hydrogen,
and their salts, solvates and solvates of the salts.

Of particular importance, within the scope of the present invention, are compounds of formula (I) in which
A stands for O,
and their salts, solvates and solvates of the salts.

Also of particular importance, within the scope of the present invention, are compounds of formula (I) in which
L stands for a group of formula *-$L^1$-Q-$L^2$, where
* denotes the point of linkage with the $CHR^3$ group,
$L^1$ denotes ($C_1$-$C_5$) alkanediyl,
$L^2$ denotes a bond or ($C_1$-$C_3$) alkanediyl, which can be substituted singly or doubly with fluorine,
and
Q denotes O or N—$R^6$, where
$R^6$ represents hydrogen, ($C_1$-$C_6$) alkyl or ($C_3$-$C_7$) cycloalkyl,
and their salts, solvates and solvates of the salts.

The detailed definitions of residues given in the respective combinations and/or preferred combinations of residues are also replaced with any other definitions of residues of other combinations regardless of the respective combinations of residues stated.

Combinations of two or more of the aforementioned preferred ranges are quite especially preferred.

The invention further relates to a method of production of the compounds of formula (I) according to the invention, characterized in that either
[A] compounds of formula (II)

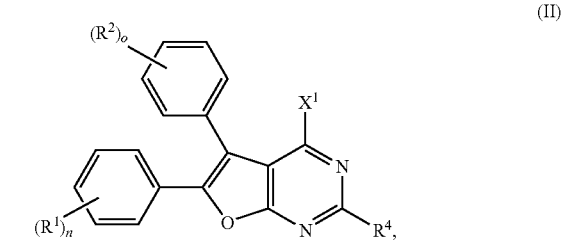

in which $R^1$, $R^2$, $R^4$, n and o have the respective meanings given above and $X^1$ stands for a leaving group, for example halogen, and especially chlorine, in the presence of a base and if necessary in an inert solvent with a compound of formula (III)

(III)

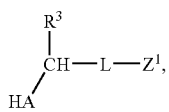

in which A, L and $R^3$ have the respective meanings given above and $Z^1$ stands for cyano or a group of formula $—[C(O)]_y COOR^{7A}$, where y denotes the number 0 or 1 and $R^{7A}$ denotes $(C_1\text{-}C_4)$ alkyl, are reacted to compounds of formula (IV)

(IV)

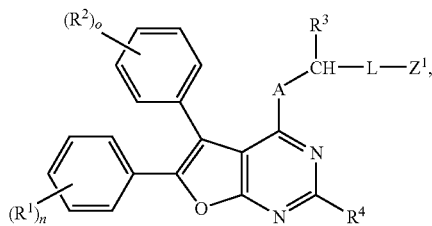

in which A, L, $Z^1$, $R^1$, $R^2$, $R^3$, $R^4$, n and o have the respective meanings given above, or

[B] compounds of formula (V-1)

(V-1)

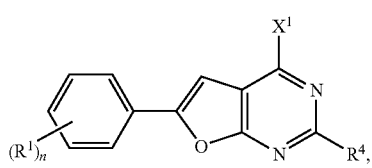

in which $R^1$, $R^4$, $X^1$ and n have the respective meanings given above, are reacted, in the presence of a base and if necessary in an inert solvent, with a compound of formula (III) to compounds of formula (VI-1)

(VI-1)

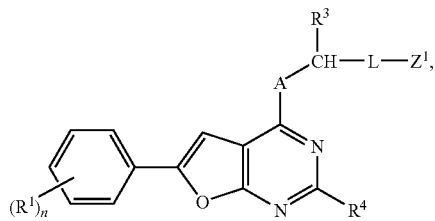

in which A, L, $Z^1$, $R^1$, $R^3$, $R^4$ and n have the respective meanings given above, and are then brominated, in an inert solvent, for example with N-bromosuccinimide to compounds of formula (VII-1)

(VII-1)

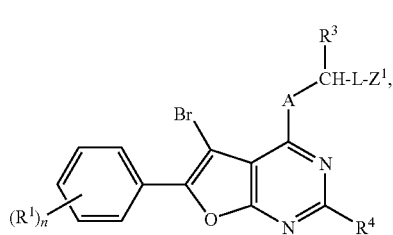

in which A, L, $Z^1$, $R^1$, $R^3$, $R^4$ and n have the respective meanings given above, and these are then coupled, in an inert solvent in the presence of a base and a suitable palladium catalyst, with a phenylboronic acid of formula (VIII-1)

(VIII-1)

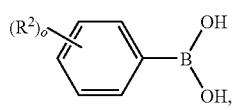

in which $R^2$ and o have the meanings given above, to compounds of formula (IV)

or

[C] compounds of formula (V-2)

(V-2)

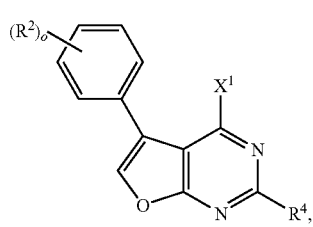

in which $R^2$, $R^4$, $X^1$ and o have the respective meanings given above, are reacted in the presence of a base and if necessary in an inert solvent, with a compound of formula (III) to compounds of formula (VI-2)

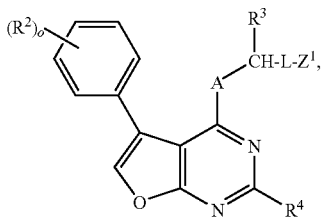

(VI-2)

in which A, L, $Z^1$, $R^2$, $R^3$, $R^4$ and o have the respective meanings given above, then brominated in an inert solvent for example with N-bromosuccinimide to compounds of formula (VII-2)

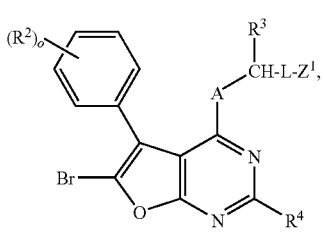

(VII-2)

in which A, L, $Z^1$, $R^2$, $R^3$, $R^4$ and o have the respective meanings given above, and these are then coupled, in an inert solvent in the presence of a base and a suitable palladium catalyst, with a phenylboronic acid of formula (VIII-2)

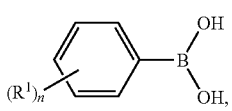

(VIII-2)

in which $R^1$ and n have the meanings given above,
to compounds of formula (IV),
and in each case the resultant compounds of formula (IV) are then transformed by hydrolysis of the ester- or cyano group $Z^1$ to the carboxylic acids of formula (I-A)

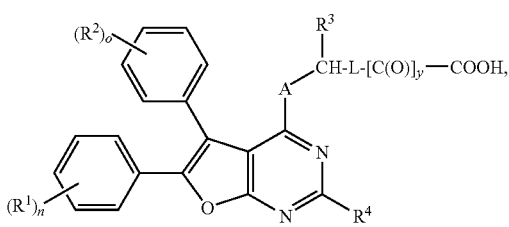

(I-A)

in which A, L, $R^1$, $R^2$, $R^3$, $R^4$, n, o and y have the respective meanings given above, and these are converted if necessary with the corresponding (i) solvents and/or (ii) bases or acids to their solvates, salts and/or solvates of the salts.

Inert solvents for steps (II)+(III)→(IV), (V-1)+(III)→(VI-1) and (V-2)+(III)→(VI-2) are for example ethers such as diethyl ether, methyl-tert.-butyl ether, dioxan, tetrahydrofuran, glycol dimethyl ether or diethyleneglycol dimethyl ether, hydrocarbons such as benzene, toluene, xylene, hexane, cyclohexane or petroleum fractions, halohydrocarbons such as dichloromethane, trichloromethane, tetrachloromethane, 1,2-dichlorethane, trichlorethane, tetrachlorethane, trichloroethylene, chlorobenzene or chlorotoluene, or other solvents such as dimethylformamide (DMF), dimethylsulphoxide (DMSO), N,N'-dimethylpropyleneurea (DMPU), N-methylpyrrolidone (NMP) or acetonitrile. It is also possible to use mixtures of the aforementioned solvents. Tetrahydrofuran, dimethylformamide, dimethylsulphoxide or mixtures thereof are preferably used.

However, steps (II)+(III)→(IV), (V-1)+(III)→(VI-1) and (V-2)+(III)→(VI-2) can if necessary also be carried out without solvents.

Usual inorganic or organic bases are suitable as bases for steps (II)+(III)→(IV), (V-1)+(III)→(VI-1) and (V-2)+(III)→(VI-2). Preferably these include alkali hydroxides, for example lithium, sodium or potassium hydroxide, alkali or alkaline-earth carbonates such as lithium, sodium, potassium, calcium or caesium carbonate, alkali-alcoholates such as sodium or potassium tert.-butylate, alkali hydrides such as sodium or potassium hydride, amides such as lithium or potassium bis(trimethylsilyl)amide or lithium diisopropylamide, organometallic compounds such as butyllithium or phenyllithium, or organic amines such as triethylamine, N-methylmorpholine, N-methylpiperidine, N,N-diisopropylethylamine or pyridine.

In the case of reaction with alcohol derivatives [A in (III)=O], phosphazene bases (so-called "Schwesinger bases"), for example P2-t-Bu or P4-t-Bu, are also suitable [cf. e.g. R. Schwesinger, H. Schlemper, *Angew. Chem. Int. Ed. Engl.* 26, 1167 (1987); T. Pietzonka, D. Seebach, *Chem. Ber.* 124, 1837 (1991)].

For reaction with amine derivatives [A in (III)=N], tertiary amines, such as in particular N,N-diisopropylethylamine, are preferably used as the base. If necessary, however, these reactions can also be carried out—using an excess of the amine component (III)—without addition of an auxiliary base. For reaction with alcohol derivatives [A in (III)=O], potassium or caesium carbonate or the phosphazene bases P2-t-Bu and P4-t-Bu are preferred.

Steps (II)+(III)→(IV), (V-1)+(III)→(VI-1) and (V-2)+(III)→(VI-2) can if necessary be carried out advantageously with addition of a crown ether.

In a variant of the process, reactions (II)+(III)→(IV), (V-1)+(III)→(VI-1) and (V-2)+(III)→(VI-2) can also be carried out in a two-phase mixture, comprising an aqueous alkali hydroxide solution as base and one of the aforementioned hydrocarbons or halohydrocarbons as additional solvent, using a phase-transfer catalyst such as tetrabutylammonium hydrogensulphate or tetrabutylammonium bromide.

Steps (II)+(III)→(IV), (V-1)+(III)→(VI-1) and (V-2)+(III)→(VI-2) are carried out, in the case of reaction with amine derivatives [A in (III)=N], generally in a temperature range from +50° C. to +150° C. For reaction with alcohol derivatives [A in (III)=O], the reactions are generally carried out in a temperature range from −20° C. to +120° C., and preferably at 0° C. to +60° C.

The bromination in steps (VI-1)→(VII-1) or (VI-2)→(VII-2) is preferably carried out in a halohydrocarbon as solvent, especially in tetrachloromethane, in a temperature range from +50° C. to +100° C. Suitable brominating agents are elemental bromine and especially N-bromosuccinimide (NBS), if necessary with addition of α,α'-azobis(isobutyronitrile) (AIBN) as initiator.

Inert solvents for steps (VII-1)+(VIII-1)→(IV) and (VII-2)+(VIII-2)→(IV) are for example alcohols such as methanol, ethanol, n-propanol, isopropanol, n-butanol or tert.-butanol, ethers such as diethyl ether, dioxan, tetrahydrofuran, glycol dimethyl ether or diethyleneglycol dimethyl ether, hydrocarbons such as benzene, xylene, toluene, hexane, cyclohexane or petroleum fractions, or other solvents such as dimethylformamide, dimethylsulphoxide, N,N'-dimethylpropyleneurea (DMPU), N-methylpyrrolidone (NMP), pyridine, acetonitrile or even water. It is also possible to use mixtures of the aforementioned solvents. A mixture of dimethylsulphoxide and water is preferred.

Usual inorganic bases are suitable as bases for steps (VII-1)+(VIII-1)→(IV) and (VII-2)+(VIII-2)→(IV). These include in particular alkali hydroxides such as lithium, sodium or potassium hydroxide, alkali hydrogencarbonates such as sodium or potassium hydrogencarbonate, alkali or alkaline-earth carbonates such as lithium, sodium, potassium, calcium or caesium carbonate, or alkali hydrogenphosphates such as disodium or dipotassium hydrogenphosphate. Sodium or potassium carbonate is preferably used.

Suitable palladium catalysts for steps (VII-1)+(VIII-1)→(IV) and (VII-2)+(VIII-2)→(IV) ["Suzuki coupling"] are for example palladium on activated charcoal, palladium(II) acetate, tetrakis-(triphenylphosphine)-palladium(0), bis-(triphenylphosphine)-palladium(II) chloride, bis-(acetonitrile)-palladium(II) chloride and [1,1'-bis(diphenylphosphino)ferrocene]dichloropalladium(II)-dichloromethane complex [cf. e.g. J. Hassan et al., Chem. Rev. 102, 1359-1469 (2002)].

Reactions (VII-1)+(VIII-1)→(IV) and (VII-2)+(VIII-2)→(IV) are generally carried out in a temperature range from +20° C. to +150° C., preferably at +50° C. to +100° C.

Hydrolysis of the ester or nitrile group $Z^1$ in step (IV)→(I-A) is carried out by usual methods, by treating the esters or nitrites in inert solvents with acids or bases, and in the latter case the salts that are formed initially are converted to the free carboxylic acids by treatment with acid. In the case of the tert.-butyl esters, ester cleavage is preferably carried out with acids.

Water or the usual organic solvents for ester cleavage are suitable as inert solvents for these reactions. These preferably include alcohols such as methanol, ethanol, n-propanol, isopropanol, n-butanol or tert.-butanol, or ethers such as diethyl ether, tetrahydrofuran, dioxan or glycoldimethyl ether, or other solvents such as acetone, dichloromethane, dimethylformamide or dimethylsulphoxide. It is also possible to use mixtures of the aforementioned solvents. In the case of basic ester hydrolysis, the use of mixtures of water with dioxan, tetrahydrofuran, methanol and/or ethanol is preferred, and for nitrile hydrolysis it is preferable to use water and/or n-propanol. The use of dichloromethane is preferred in the case of reaction with trifluoroacetic acid, and in the case of reaction with hydrogen chloride it is preferable to use tetrahydrofuran, diethyl ether, dioxan or water.

The usual inorganic bases are suitable as bases. These preferably include alkali or alkaline-earth hydroxides such as sodium, lithium, potassium or barium hydroxide, or alkali or alkaline-earth carbonates such as sodium, potassium or calcium carbonate. Sodium or lithium hydroxide is especially preferred.

Sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid or mixtures thereof are generally suitable as acids for ester cleavage, if necessary with addition of water. Hydrogen chloride or trifluoroacetic acid is preferred in the case of the tert.-butyl esters and hydrochloric acid in the case of the methyl esters.

Ester cleavage is generally carried out in a temperature range from 0° C. to +100° C., preferably at +0° C. to +50° C. Nitrile hydrolysis is generally carried out in a temperature range from +50° C. to +150° C., preferably at +80° C. to +120° C.

The aforementioned reactions can be carried out at normal, at increased or at reduced pressure (e.g. from 0.5 to 5 bar). Normal pressure is generally used in each case.

The compounds according to the invention of formula (I), in which Z stands for a group of formula

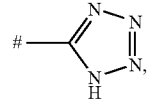

can be produced by reacting compounds of formula (IV), in which $Z^1$ stands for cyano, in an inert solvent with an alkali azide in the presence of ammonium chloride or with trimethylsilylazide if necessary in the presence of a catalyst.

Inert solvents for this reaction are for example ethers such as diethyl ether, dioxan, tetra-hydrofuran, glycol dimethyl ether or diethyleneglycol dimethyl ether, hydrocarbons such as benzene, toluene, xylene, hexane, cyclohexane or petroleum fractions, or other solvents such as dimethylsulphoxide, dimethylformamide, N,N'-dimethylpropyleneurea (DMPU) or N-methylpyrrolidone (NMP). It is also possible to use mixtures of the aforementioned solvents. Use of toluene is preferred.

In particular sodium azide is suitable as azide reagent, in the presence of ammonium chloride or trimethylsilylazide. The latter reaction can be carried out more advantageously in the presence of a catalyst. Compounds such as di-n-butyltin oxide, trimethylaluminium or zinc bromide are especially suitable for this. It is preferable to use trimethylsilylazide in combination with di-n-butyltin oxide.

The reaction is generally carried out in a temperature range from +50° C. to +150° C., preferably at +60° C. to +110° C. The reaction can be carried out at normal, increased or reduced pressure (e.g. from 0.5 to 5 bar). It is generally carried out at normal pressure.

The compounds according to the invention of formula (I), in which Z stands for a group of formula

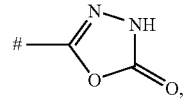

can be produced by converting compounds of formula (IV), in which $Z^1$ stands for methoxy- or ethoxycarbonyl, first in an inert solvent with hydrazine to compounds of formula (IX)

(IX)

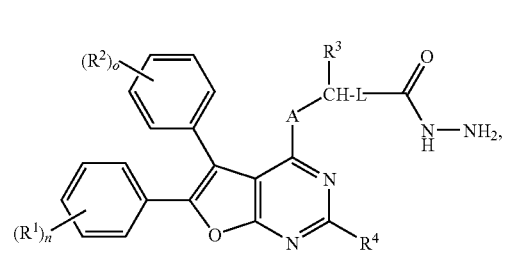

in which A, L, $R^1$, $R^2$, $R^3$, $R^4$, n and o have the respective meanings given above, and then reacting them in an inert solvent with phosgene or a phosgene equivalent, such as N,N'-carbonyl diimidazole.

Suitable inert solvents for the first step of this reaction sequence are in particular alcohols such as methanol, ethanol, n-propanol, isopropanol, n-butanol or tert.-butanol, or ethers such as diethyl ether, dioxan, tetrahydrofuran, glycol dimethyl ether or diethyleneglycol dimethyl ether. It is also possible to use mixtures of these solvents. A mixture of methanol and tetrahydrofuran is preferably used. The second reaction step is preferably carried out in an ether, in particular in tetrahydrofuran. The reactions are generally carried out in a temperature range from 0° C. to +70° C. at normal pressure.

The compounds according to the invention of formula (I), in which L stands for a group of formula *-$L^1$-Q-$L^2$, where $L^1$, $L^2$ and Q have the meanings given above, can alternatively also be produced by converting compounds of formula (X)

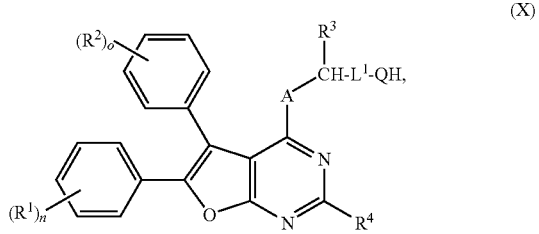
(X)

in which A, $L^1$, Q, $R^1$, $R^2$, $R^3$, $R^4$, n and o have the respective meanings given above,
in the presence of a base and if necessary in an inert solvent with a compound of formula (XI)

$X^2$-$L^2$-$Z^1$ (XI), in which $L^2$ and $Z^1$ have the meanings given above
and
$X^2$ stands for a leaving group, such as halogen, mesylate or tosylate,
or in the case when $L^2$ stands for —$CH_2CH_2$—, with a compound of formula (XII)

(XII)

in which $Z^1$ has the meaning given above,
to compounds of formula (IV-A)

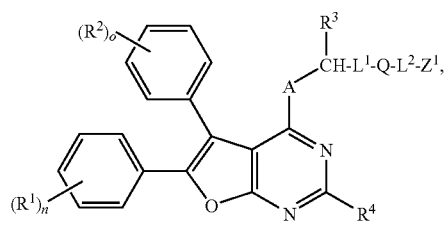
(IV-A)

in which A, $L^1$, $L^2$, Q, $Z^1$, $R^1$, $R^2$, $R^3$, $R^4$, n and o have the respective meanings given above,
and these are then processed further in accordance with the method described previously.

The compounds of formula (X) can be obtained starting from a compound of formula (II), (V-1) or (V-2) by base-catalysed reaction with a compound of formula (XIII)

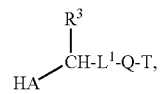
(XIII)

in which A, $L^1$, Q and $R^3$ have the respective meanings given above
and
T stands for hydrogen or a temporary O- or N-protecting group,
and correspondingly by further reaction similar to the process variants [B] or [C] described previously, and in the case of the reaction sequence (V-1) or (V-2)→(IV-A), the order of the individual process steps can also be varied if that is desirable (cf. the reaction schemes 2-8 given below).

For steps (X)+(XI) or (XII)→(IV-A) and (II)+(XIII)→(X), the reaction parameters such as solvents, bases and reaction temperatures described for reactions (II)+(III)→(IV), (V-1)+(III)→(VI-1) or (V-2)+(III)→(VI-2) are used similarly.

The compounds of formulae (II), (III), (V-1), (VIII-1), (V-2), (VIII-2), (XI), (XII) and (XIII) are commercially available, known from the literature or can be produced by analogy with methods known in the literature (cf. e.g. WO 03/018589; see also Reaction Scheme 1).

Production of the compounds according to the invention can be illustrated by the following synthesis schemes:

Scheme 1

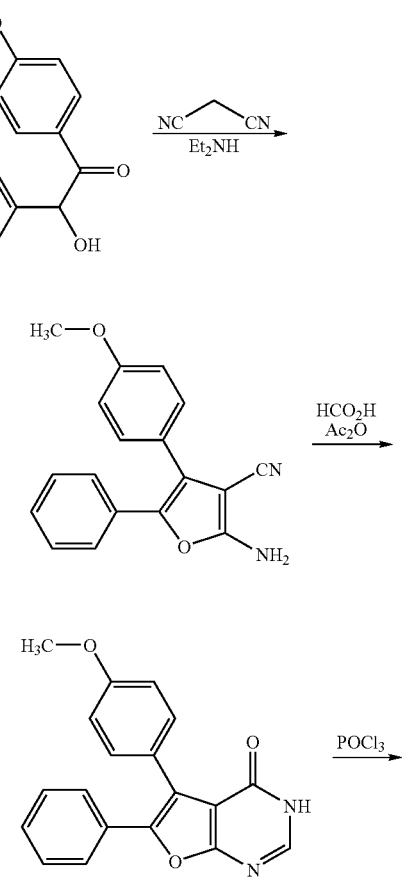

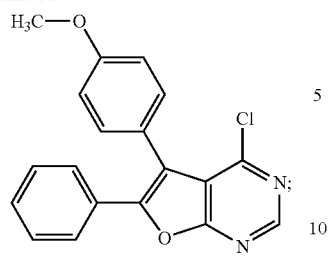
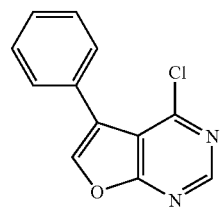
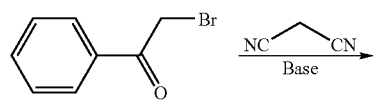
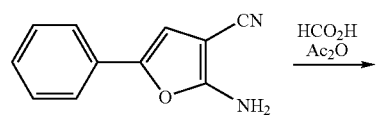
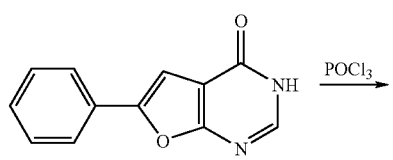
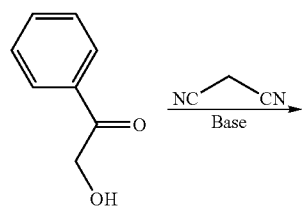
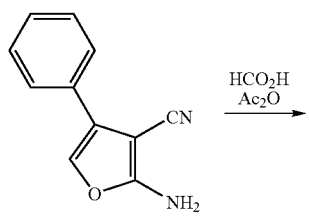
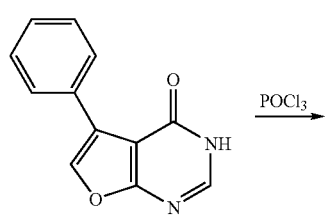
Scheme 2
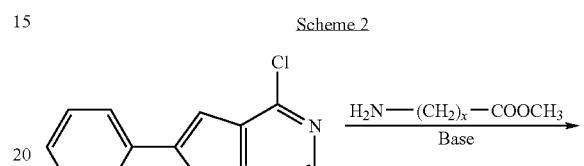
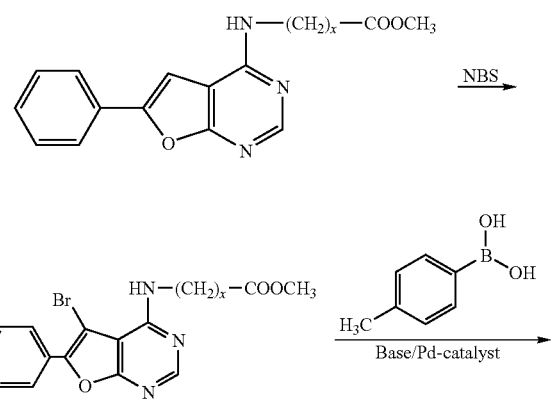
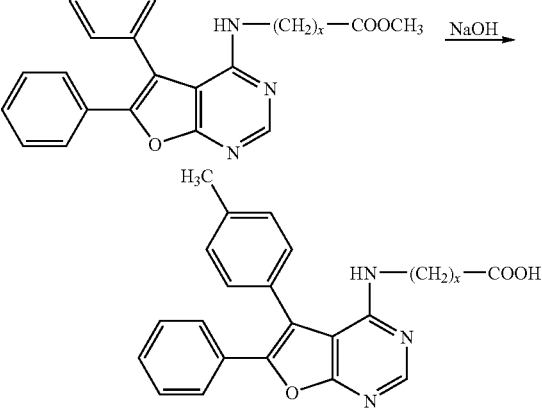
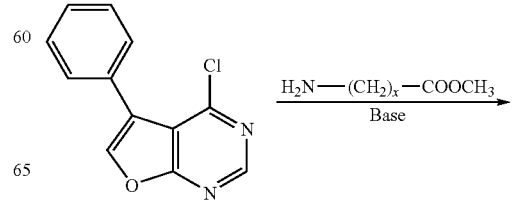

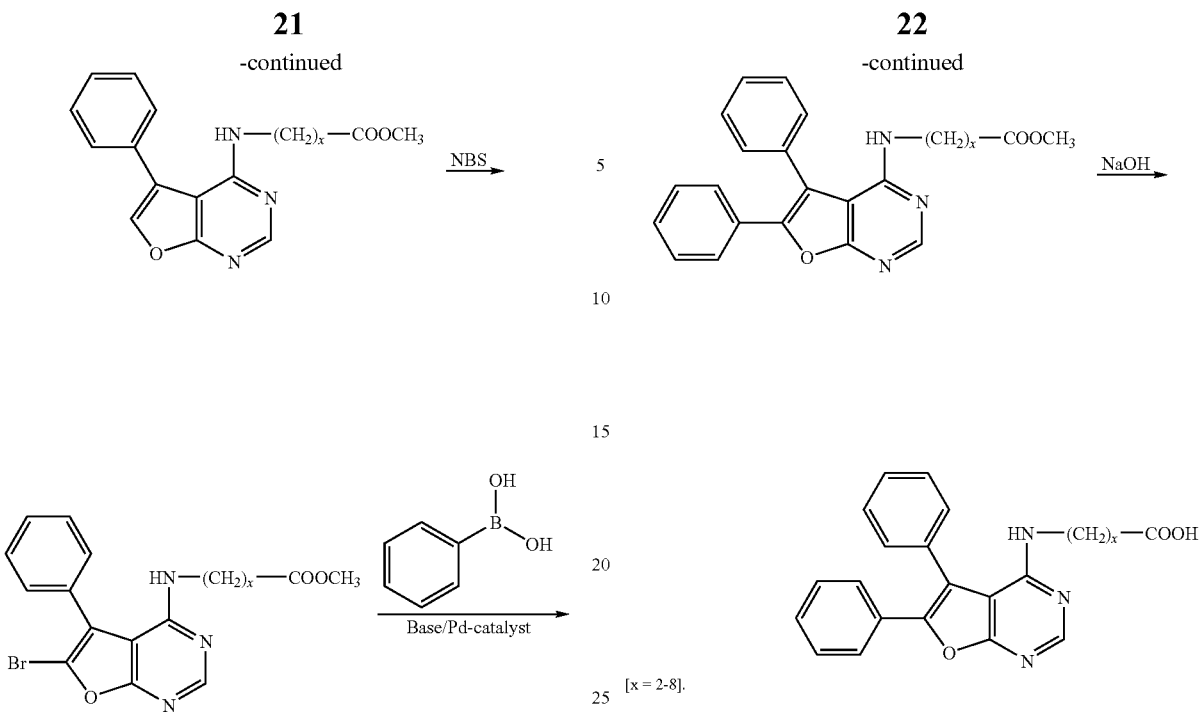
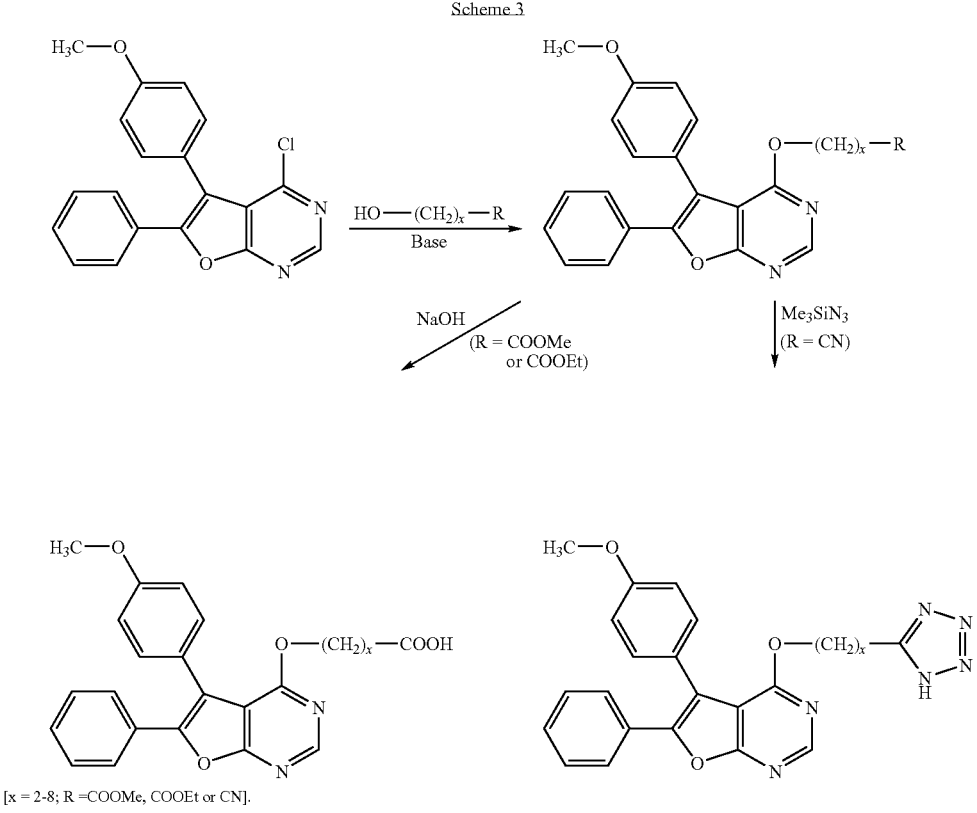
Scheme 3
[x = 2-8; R =COOMe, COOEt or CN].

Scheme 4
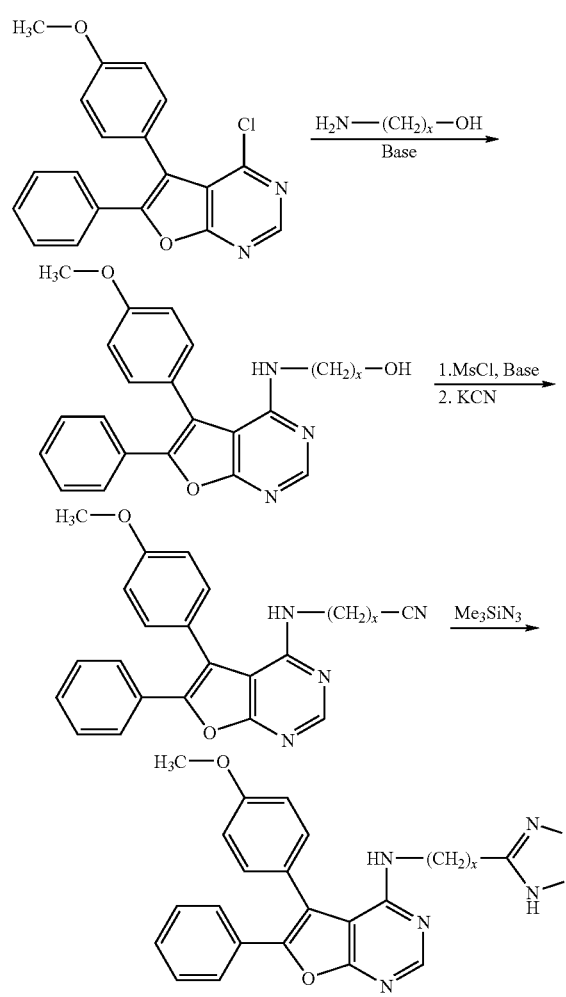
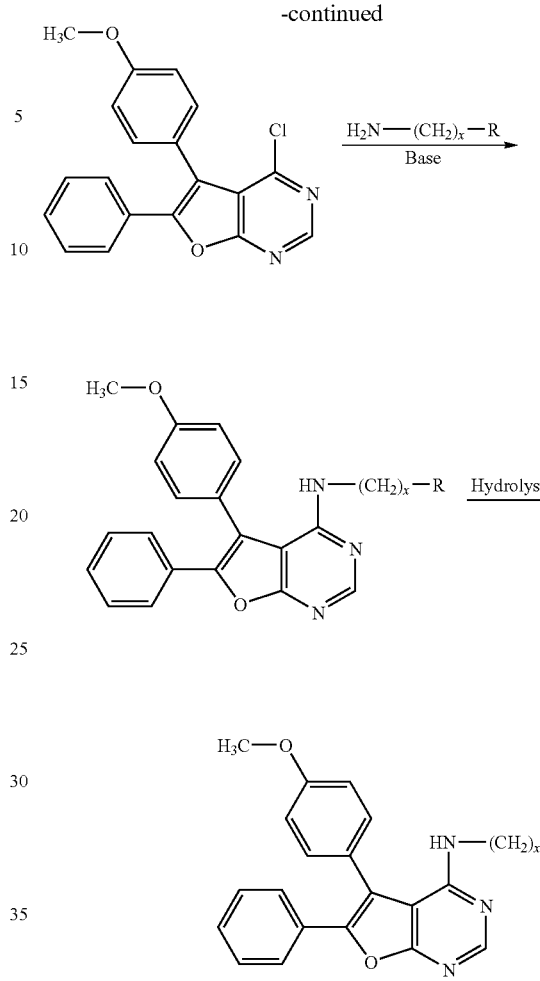
[x = 2-8; R = COOMe, COOEt or CN].
Scheme 5
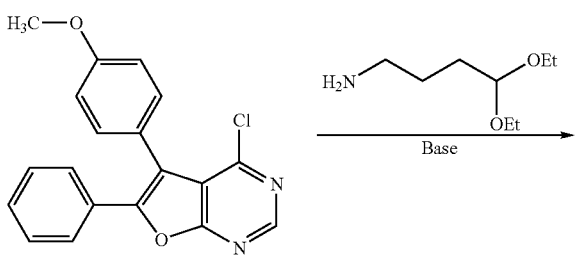
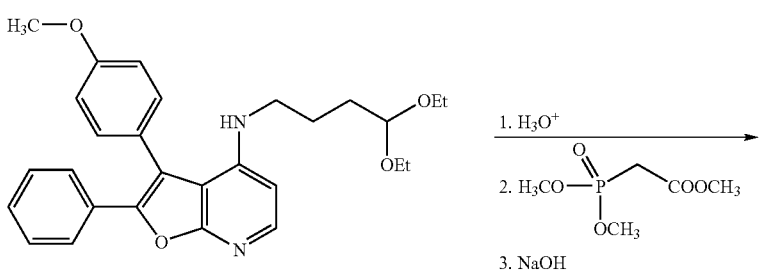

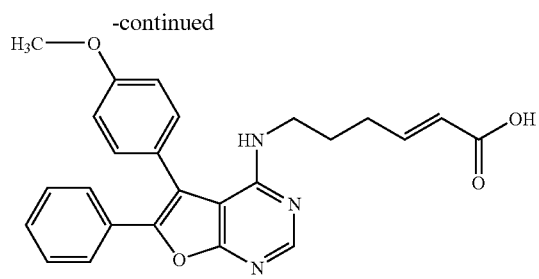
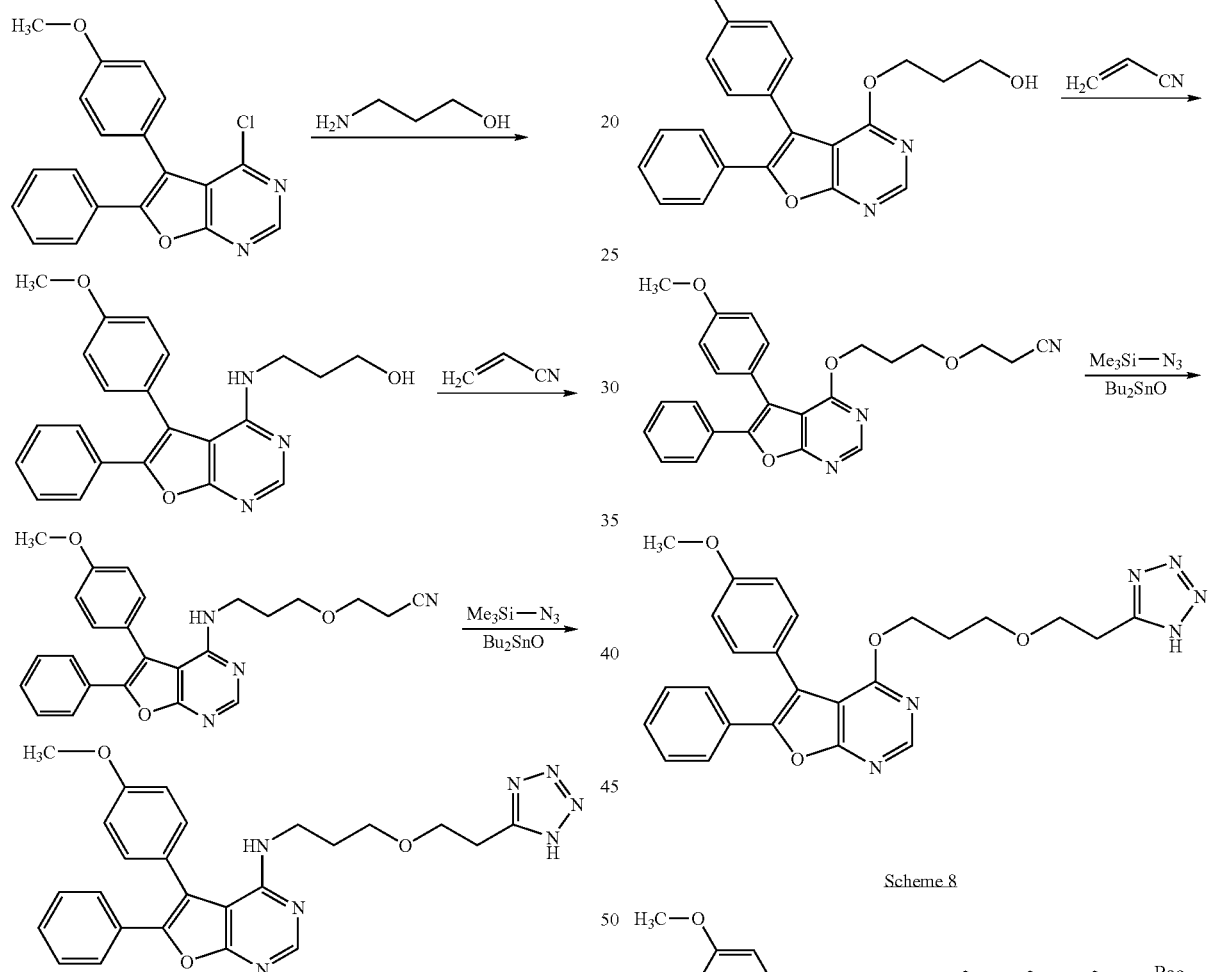
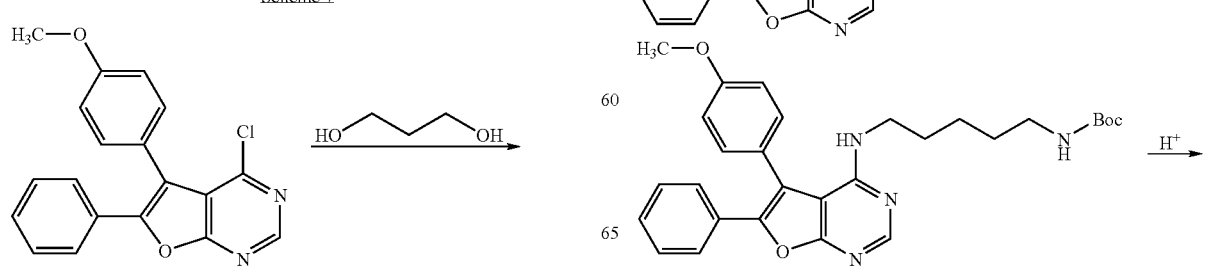

-continued

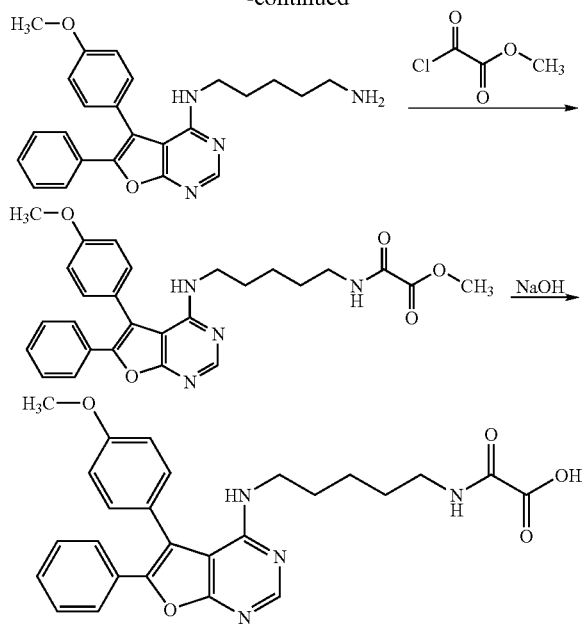

The compounds according to the invention possess valuable pharmacological properties and can be used for the prevention and treatment of diseases in humans and animals.

They are suitable in particular for the prophylaxis and/or treatment of cardiovascular diseases such as stable and unstable angina pectoris, of peripheral and cardiac vascular diseases, of hypertension and heart failure, pulmonary hypertension, peripheral circulatory disturbances, for the prophylaxis and/or treatment of thromboembolic diseases and ischaemias such as myocardial infarction, stroke, transient and ischaemic attacks and subarachnoid haemorrhage, and for the prevention of restenosis such as after thrombolytic treatments, percutaneous transluminal angioplasty (PTA), coronary angioplasty (PTCA) and bypass surgery.

Furthermore, the compounds according to the invention can be used for the treatment of arterio-sclerosis, hepatitis, asthmatic diseases, chronic obstructive pulmonary diseases (COPD), fibrosing lung diseases such as idiopathic pulmonary fibrosis (IPF) and ARDS, inflammatory vascular diseases such as scleroderma and lupus erythematosus, renal failure, arthritis and osteoporosis.

In addition, the compounds according to the invention can be used for the prophylaxis and/or treatment of cancers, especially of metastasizing tumours.

Moreover, the compounds according to the invention can also be used as an addition to the preserving medium of an organ transplant, e.g. kidneys, lungs, heart or islet cells.

The present invention further relates to the use of the compounds according to the invention for the treatment and/or prevention of diseases, and especially of the aforementioned diseases.

The present invention further relates to the use of the compounds according to the invention for the production of a medicinal product for the treatment and/or prevention of diseases, and especially of the aforementioned diseases.

The present invention further relates to a method for the treatment and/or prevention of diseases, especially of the aforementioned diseases, using an effective amount of at least one of the compounds according to the invention.

The compounds according to the invention can be used alone or if necessary in combination with other active substances. The present invention further relates to medicinal products containing at least one of the compounds according to the invention and one or more additional active substances, in particular for the treatment and/or prevention of the aforementioned diseases. The following may be mentioned as preferred examples of suitable combination active substances:

organic nitrates and NO-donors, such as sodium nitroprusside, nitroglycerin, isosorbide mononitrate, isosorbide dinitrate, molsidomine or SIN-1, and inhalational NO;

compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil;

NO-independent, but haem-dependent stimulators of guanylate cyclase, such as in particular the compounds described in WO 00/06568, WO 00/06569, WO 02/42301 and WO 03/095451;

NO- and haem-independent activators of guanylate cyclase, such as in particular the compounds described in WO 01/19355, WO 01/19776, WO 01/19778, WO 01/19780, WO 02/070462 and WO 02/070510;

compounds which inhibit human neutrophilic elastase, such as sivelestat or DX-890 (Reltran);

compounds inhibiting the signal transduction cascade, such as tyrosine kinase and/or serine/threonine kinase inhibitors, in particular imatinib, gefitinib, erlotinib, sorafenib and sunitinib;

compounds influencing the energy metabolism of the heart, for example and preferably etomoxir, dichloroacetate, ranolazine or trimetazidine;

antithrombotic agents, for example and preferably from the group comprising platelet aggregation inhibitors, anticoagulants or profibrinolytic substances;

active substances for lowering blood pressure, for example and preferably from the group comprising calcium antagonists, angiotensin AII antagonists, ACE inhibitors, endothelin antagonists, renin inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

"Agents with antithrombotic action" preferably means compounds from the group comprising inhibitors of platelet aggregation, anticoagulants or profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, melagatran, bivalirudin or Clexane.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably BAY 59-7939, DU-176b, Fidexaban, Razaxaban, Fondaparinux, Idraparinux, PMD-3112, YMi-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, for example and preferably coumarin.

"Agents for lowering blood pressure" are preferably understood to be compounds from the group comprising calcium antagonists, angiotensin AII antagonists, ACE inhibitors, endothelin antagonists, renin inhibitors, alpha receptor blockers, beta receptor blockers, mineralocorticoid receptor antagonists, Rho-kinase inhibitors and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1 receptor blocker, for example and preferably prazosin.

In a preferred embodiment of the invention, the compounds according to the invention are administered in combination with a beta receptor blocker, for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, for example and preferably losartan, candesartan, valsartan, telmisartan or embusartan.

In a preferred embodiment of the invention, the compounds according to the invention are administered in combination with an ACE inhibitor, for example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist, for example and preferably bosentan, darusentan, ambrisentan or sitaxsentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably spironolactone or eplerenone.

In a preferred embodiment of the invention, the compounds according to the invention are administered in combination with a Rho-kinase inhibitor, for example and preferably fasudil, Y-27632, SLx-2119, BF-66851, BF-66852, BF-66853, KI-23095 or BA-1049.

In a preferred embodiment of the invention, the compounds according to the invention are administered in combination with a diuretic, for example and preferably furosemide.

"Agents modifying lipid metabolism" are preferably understood to be compounds from the group comprising CETP inhibitors, thyroid receptor agonists, inhibitors of cholesterol synthesis such as HMG-CoA-reductase or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds according to the invention are administered in combination with a CETP inhibitor, for example and preferably torcetrapib (CP-529 414), JJT-705 or CETP-vaccine (Avant).

In a preferred embodiment of the invention, the compounds according to the invention are administered in combination with a thyroid receptor agonist, for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA-reductase inhibitor from the class of the statins, for example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, for example and preferably BMS-188494 or TAK475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, BMS-201038, R-103757 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyramine, colestipol, Colesolvam, CholestaGel or Colestimid.

In a preferred embodiment of the invention, the compounds according to the invention are administered in combination with a bile acid reabsorption inhibitor, for example and preferably ASBT (=IBAT) inhibitors such as AZD-7806, S-8921, AK-105, BARI-1741, SC435 or SC-635.

In a preferred embodiment of the invention, the compounds according to the invention are administered in combination with a lipoprotein(a) antagonist, for example and preferably Gemcabene calcium (CI-1027) or nicotinic acid.

The present invention further relates to medicinal products that contain at least one compound according to the invention, usually together with one or more inert, nontoxic, pharmaceutically acceptable excipients, and use thereof for the purposes mentioned previously.

The compounds according to the invention can have systemic and/or local action. For this purpose they can be applied by a suitable route, e.g. oral, parenteral, pulmonary, nasal, sublingual, lingual, buccal, rectal, dermal, transdermal, conjunctival, otic or as implant or stent.

For these routes of administration, the compounds according to the invention can be administered in suitable dosage forms.

Dosage forms suitable for oral administration are those that function according to the state of the art, which provide rapid and/or modified release of the compounds according to the invention, and which contain the compounds according to the invention in crystalline and/or amorphized and/or dissolved form, for example tablets (uncoated or coated tablets, e.g. with enteric coatings or with insoluble coatings or coatings with delayed dissolution, which control the release of the compound according to the invention), tablets that disintegrate rapidly in the oral cavity or films/wafers, films/lyophilizates, capsules (e.g. hard-gelatin or soft-gelating capsules), sugar-coated tablets, granules, pellets, powders, emulsions, suspensions, aerosols or solutions.

Parenteral administration can take place with avoidance of an absorption step (e.g. intravenous, intra-arterial, intracardial, intraspinal or intralumbal) or with inclusion of absorption (e.g. intramuscular, subcutaneous, intracutaneous, percutaneous or intraperitoneal). Suitable dosage forms for parenteral administration include injection and infusion preparations in the form of solutions, suspensions, emulsions, lyophilizates or sterile powders.

The following are examples of forms that are suitable for other routes of administration: pharmaceutical forms for inhalation (including powder inhalers, nebulizers), nasal drops, solutions or sprays, tablets for lingual, sublingual or buccal application, films/wafers or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Oral or parenteral application, and especially oral application, are preferred.

The compounds according to the invention can be converted to the aforementioned dosage forms. This can be done in a known manner by mixing with inert, nontoxic, pharmaceutically acceptable excipients. These excipients include, among others: vehicles (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinyl pyrrolidone), synthetic and natural polymers (for example albumin), stabilizers (e.g. antioxidants such as ascorbic acid), colorants (e.g. inorganic pigments such as iron oxides) and agents for correcting taste and/or odour.

Generally it has proved advantageous, in the case of parenteral application, to administer amounts from about 0.001 to 1 mg/kg, preferably about 0.01 to 0.5 mg/kg body weight, for achieving effective results. For oral application the dosage is about 0.01 to 100 mg/kg, preferably about 0.01 to 20 mg/kg and quite especially preferred, 0.1 to 10 mg/kg of body weight.

In certain circumstances it may, however, be necessary to deviate from the stated amounts, depending on body weight, route of administration, individual response to the active substance, type of preparation and point of time or time interval for administration. Thus, in some cases a smaller amount than the minimum amount stated above may prove sufficient, whereas in other cases the stated upper limit must be exceeded. If larger amounts are administered, it may be advisable to distribute these in several divided doses over the day.

The following examples of application explain the invention. The invention is not limited to the examples.

Unless stated otherwise, the percentages in the following tests and examples are percentages by weight; parts are parts by weight. Proportions of solvents, dilution ratios and concentration data for liquid/liquid solutions always relate to the volume.

A. EXAMPLES

Abbreviations

| | |
|---|---|
| abs. | absolute |
| Ac | acetyl |
| $Ac_2O$ | acetic anhydride |
| Boc | tert.-butoxycarbonyl |
| Bu | butyl |
| c | concentration |
| TLC | thin-layer chromatography |
| DCI | direct chemical ionization (in MS) |
| DIBAH | diisobutylaluminium hydride |
| DIEA | diisopropylethylamine ("Hünig base") |
| DMAP | 4-N,N-dimethylaminopyridine |
| DME | 1,2-dimethoxyethane |
| DMF | N,N-dimethylformamide |
| DMSO | dimethylsulphoxide |
| of theor. | of theoretical (for Percentage Yield) |
| ee | enantiomeric excess |
| EI | electron impact ionization (in MS) |
| ESI | electrospray ionization (in MS) |
| Et | ethyl |
| m.p. | melting point |
| GC | gas chromatography |
| satd. | saturated |
| h | hour(s) |
| HPLC | high-performance liquid chromatography |
| conc. | concentrated |
| LC-MS | liquid chromatography-coupled mass spectrometry |
| Me | methyl |
| min | minute(s) |
| Ms | methanesulphonyl (mesyl) |
| MS | mass spectrometry |
| NBS | N-bromosuccinimide |
| NMR | nuclear magnetic resonance spectrometry |
| Pd/C | palladium on activated charcoal |
| rac. | racemic |
| RP | reverse phase (in HPLC) |
| RT | room temperature |
| $R_t$ | retention time (in HPLC) |
| TFA | trifluoroacetic acid |
| THF | tetrahydrofuran |

LC-MS, HPLC and GC Methods:
Method 1 (HPLC):
Instrument: HP 1100 with DAD detection; column: Kromasil 100 RP-18, 60 mm×2.1 mm, 3.5 µm; eluent A: 5 ml $HClO_4$ (70%)/litre water, eluent B: acetonitrile; gradient: 0 min 2% B→0.5 min 2% B→4.5 min 90% B→6.5 min 90% B→6.7 min 2% B→7.5 min 2% B; flow: 0.75 ml/min; column temperature: 30° C.; UV detection: 210 nm.
Method 2 (LC-MS):
Equipment type MS: Micromass ZQ; equipment type HPLC: Waters Alliance 2795; column: Phenomenex Synergi 2µ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 3 (LC-MS):

Instrument: Micromass Platform LCZ with HPLC Agilent Series 1100; column: Thermo Hypersil GOLD 3μ 20 mm×4 mm; eluent A: 1 l water+0.5 ml 50% formic acid, eluent B: 1 l acetonitrile+0.5 ml 50% formic acid; gradient: 0.0 min 100% A→0.2 min 100% A→2.9 min 30% A→3.1 min 10% A→5.5 min 10% A; furnace: 50° C.; flow: 0.8 ml/min; UV detection: 210 nm.

Method 4 (LC-MS):

Equipment type MS: Micromass ZQ; equipment type HPLC: HP 1100 Series; UV DAD; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 5 (LC-MS):

Instrument: Micromass Quattro LCZ with HPLC Agilent Series 1100; column: Phenomenex Synergi 2μ Hydro-RP Mercury 20 mm×4 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 208-400 nm.

Method 6 (HPLC):

Instrument: HP 1100 with DAD detection; column: Kromasil 100 RP-18, 60 mm×2.1 mm, 3.5 μm; eluent A: 5 ml HClO$_4$ (70%)/litre water, eluent B: acetonitrile; gradient: 0 min 2% B→0.5 min 2% B→4.5 min 90% B→9 min 90% B→9.2 min 2% B→10 min 2% B; flow: 0.75 ml/min; column temperature: 30° C.; UV detection: 210 nm.

Method 7 (LC-MS):

Instrument: Micromass Quattro LCZ with HPLC Agilent Series 1100; column: Phenomenex Onyx Monolithic C18, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow: 2 ml/min; furnace: 40° C.; UV detection: 208-400 nm.

Method 8 (LC-MS):

Equipment type MS: Micromass ZQ; equipment type HPLC: HP 1100 series; UV DAD; column: Phenomenex Gemini 3μ 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 210 nm.

Method 9 (LC-MS):

Equipment type MS: Waters ZQ; equipment type HPLC: Waters Alliance 2795; column: Merck Chromolith RP18e, 100 mm×3 mm; eluent A: 1 l water+0.5 ml 50% formic acid, eluent B: 1 l acetonitrile+0.5 ml 50% formic acid; gradient: 0.0 min 90% A→2 min 65% A→4.5 min 5% A→6 min 5% A; flow: 2 ml/min; furnace: 40° C.; UV detection: 210 nm.

Method 10 (LC-MS):

Instrument: Micromass Quattro LCZ with HPLC Agilent Series 1100; column: Phenomenex Gemini 3μ, 30 mm×3.00 mm; eluent A: 1 l water+0.5 ml 50% formic acid, eluent B: 1 l acetonitrile+0.5 ml 50% formic acid; gradient: 0.0 min 90% A→2.5 min 30% A→3.0 min 5% A→4.5 min 5% A; flow: 0.0 min 1 ml/min→2.5 min/3.0 min/4.5 min 2 ml/min; furnace: 50° C.; UV detection: 208-400 nm.

Method 11 (LC-MS):

Equipment type MS: Micromass ZQ; equipment type HPLC: Waters Alliance 2795; column: Merck Chromolith SpeedROD RP-18e 100 mm×4.6 mm; eluent A: water+500 μl 50% formic acid/l, eluent B: acetonitrile+500 μl 50% formic acid/l; gradient: 0.0 min 10% B→7.0 min 95% B→9.0 min 95% B; flow: 0.0 min 1.0 ml/min→7.0 min 2.0 ml/min→9.0 min 2.0 ml/min; furnace: 35° C.; UV detection: 210 nm.

Method 12 (GC):

Instrument: Micromass GCT, GC 6890; column: Restek RTX-35, 15 m×200 μm×0.33 μm; constant flow with helium: 0.88 ml/min; furnace: 70° C.; inlet: 250° C.; gradient: 70° C., 30° C./min→310° C. (hold 3 min).

Starting Compounds and Intermediates:

Example 1A (4-Methoxyphenyl)[(trimethylsilyl)oxy]acetonitrile

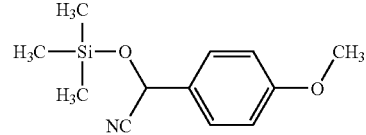

As in the published procedure [*J. Chem. Soc. Perkin Trans. I*, 1992, 2409-2417], add a solution of 221.88 g (2236 mmol) trimethylsilyl cyanide in 25 litre benzene to a mixture of 290.0 g (2130 mmol) 4-methoxybenzaldehyde and 1.156 g (3.622 mmol) zinc iodide in 37.5 litre benzene at RT with cooling in the space of approx. 5 min. Stir the mixture for 90 min at RT and then concentrate by vacuum evaporation. Purify the residue by column filtration on silica gel (solvent: cyclohexane/ethyl acetate 4:1). 442.4 g (88.3% of theor.) of the target compound is obtained.

HPLC (Method 1): R$_t$=3.76 min

MS (DCI): m/z=253 (M+NH$_4$)$^+$ $^1$H-NMR (400 MHz, CDCl$_3$): δ=7.49 (d, 2H), 6.92 (d, 2H), 5.42 (s, 1H), 3.81 (s, 3H).

Example 2A

2-Hydroxy-1-(4-methoxyphenyl)-2-phenylethanone

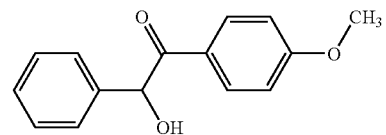

According to the procedure in the literature [*J. Chem. Soc. Perkin Trans. I*, 1992, 2409-2417], dissolve 292 ml (2.08 mol) diisopropylamine in 3.6 litre 1,2-dimethoxyethane and cool to −78° C. Add 826 ml n-butyllithium solution (2.5 M in n-hexane, 2.066 mol) at a temperature below −60° C. Stir the mixture for a further 15 min at <−60° C. and then add a solution of 442 g (1.877 mol) (4-methoxyphenyl)[(trimethylsilyl)oxy]acetonitrile in 1.41 litre 1,2-dimethoxyethane dropwise at <−60° C. After further stirring for 30 min at −60° C., add a solution of 199.3 g (1.878 mol) benzaldehyde in 1.4 litre 1,2-dimethoxyethane in the space of 20 min at −60° C. Next, heat the reaction mixture slowly to RT in 4 h. Add 7 litre saturated ammonium chloride solution and extract with ethyl acetate. Wash the organic phase with saturated ammonium chloride solution, dry, and concentrate under vacuum. Take up the residue in 7 litre dioxan and 5 litre methanol, and add 6 litre 1 N hydrochloric acid. Stir the mixture for 3 h at RT, then add 3 litre saturated sodium chloride solution and extract the mixture with 6.5 litre ethyl acetate. Wash the organic phase with 1.0 litre 1 N sodium hydroxide solution and with saturated sodium chloride solution, dry, and concentrate under vacuum. Take up the residue in 2 litre diisopropyl ether, decant from the insoluble matter and seed with crystals. Stir the resultant suspension for 2 h at RT and then filter off the crystals with suction. Wash with 300 ml diisopropyl ether and petroleum ether and dry under vacuum. 236.8 g (47.8% of theor.) of the target compound is obtained.

HPLC (Method 1): $R_t$=4.23 min

MS (DCI): m/z=260 (M+NH$_4$)$^+$, 243 (M+H)$^+$ $^1$H-NMR (400 MHz, CDCl$_3$): δ=7.92 (d, 2H), 7.38-7.28 (m, 5H), 6.88 (d, 2H), 5.90 (d, 1H), 4.64 (d, 1H), 3.82 (s, 3H).

Example 3A

2-Amino-4-(4-methoxyphenyl)-5-phenyl-3-furonitrile

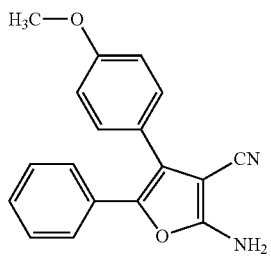

Dissolve 236 g (974 mmol) 2-hydroxy-1-(4-methoxyphenyl)-2-phenylethanone and 83.66 g (1266 mmol) malononitrile in 470 ml DMF and, with cooling on an ice bath, add 86.6 ml (836.7 mmol) diethylamine. After 1 h, heat the mixture to RT and continue stirring for 4 h at RT, before adding 2.5 litre water and a few seed crystals. After 30 min, decant the supernatant water and replace with 1.25 litre of fresh water. Stir the suspension thoroughly and again decant the supernatant water. Take up the sticky crystalline residue in ethyl acetate and then concentrate under vacuum almost completely. Stir the residue with 730 ml diisopropyl ether and leave the suspension to stand overnight at RT. Then filter off the solid matter with suction and dry under vacuum. 211.5 g (57.6% of theor.) of the title compound is obtained.

HPLC (Method 1): $R_t$=4.60 min

MS (DCI): m/z=308 (M+NH$_4$)$^+$, 291 (M+H)$^+$ $^1$H-NMR (400 MHz, CDCl$_3$): δ=7.39-7.33 (m, 5H), 7.28-7.18 (m, 3H), 6.93 (d, 2H), 5.02 (s, 2H), 3.85 (s, 3H).

Example 4A 5-(4-Methoxyphenyl)-6-phenylfuro[2,3-d]pyrimidin-4(3H)-one

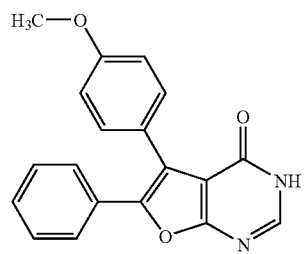

Add 800 ml (21.21 mol) formic acid dropwise to 1600 ml (16.96 mol) acetic anhydride at 0° C. Stir the mixture for 30 min at 0° C. and then add 211 g (727 mmol) 2-amino-4-(4-methoxyphenyl)-5-phenyl-3-furonitrile. Remove the cooling and heat the mixture; evolution of gas begins at approx. 80° C., and ceases after approx. 3 h. Stir for a total of 24 h under reflux (bath temperature approx. 130° C.). After cooling to RT, stir for 2 h at 10° C. and filter off the solid matter that forms. Wash the residue with diethyl ether and dry at high vacuum. 135.6 g (58.6% of theor.) of the title compound is obtained.

HPLC (Method 1): $R_t$=4.38 min

MS (DCI): m/z=336 (M+NH$_4$)$^+$, 319 (M+H)$^+$ $^1$H-NMR (400 MHz, CDCl$_3$): δ=10.3 (br. s, 1H), 7.95 (s, 1H), 7.58-7.53 (m, 2H), 7.47 (d, 2H), 7.33-7.27 (m, 3H), 6.95 (d, 2H), 3.86 (s, 3H).

Example 5A

4-Chloro-5-(4-methoxyphenyl)-6-phenylfuro[2,3-d]pyrimidine

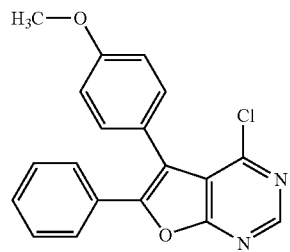

Suspend 135 g (424 mmol) 5-(4-methoxyphenyl)-6-phenylfuro[2,3-d]pyrimidin-4(3H)-one at RT in 675 ml (7241 mmol) phosphoryl chloride and heat the mixture to boiling (evolution of HCl). After 1 h, cool the dark solution to RT and add dropwise to a vigorously stirred mixture of 2.25 litre water and 4.05 litre conc. ammonia solution (25 wt. %) (heating to 55-75° C., pH>9). At the end of addition, cool to RT and extract the mixture three times with 1.0 litre dichloromethane each time. Combine the organic phases, dry, and concentrate by vacuum evaporation. Stir the residue with diethyl ether, filter with suction and dry at high vacuum. 134.4 g (94.1% of theor.) of the title compound is obtained.

HPLC (Method 1): $R_t$=4.96 min

MS (DCI): m/z=354 (M+NH$_4$)$^+$, 337 (M+H)$^+$ $^1$H-NMR (400 MHz, CDCl$_3$): δ=8.76 (s, 1H), 7.62 (d, 2H), 7.40-7.30 (m, 5H), 7.03 (d, 2H), 3.90 (s, 3H).

Example 6A

2-Amino-5-phenyl-3-furonitrile

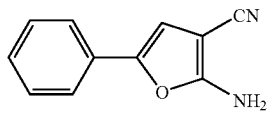

Add 68.6 ml (663 mmol) diethylamine dropwise to a mixture of 60.0 g (301 mmol) bromoacetophenone and 25.89 g (391.86 mmol) malononitrile in 130 ml DMF at RT (cooling is required to maintain the temperature). Towards the end of addition, remove the cooling, stir the mixture for 1 h at RT and then add water to 385 ml. Dilute with a further 125 ml water and stir for 20 min at RT. Filter off the precipitated solids with suction, wash twice with 125 ml water each time, dry under suction and wash with petroleum ether. Dry the residue at high vacuum. 33.3 g (50.1% of theor.) of the target compound is obtained as yellowish-brown crystals.

HPLC (Method 1): $R_t$=4.27 min

MS (DCI): m/z=202 (M+NH$_4$)$^+$, 185 (M+H)$^+$ $^1$H-NMR (400 MHz, CDCl$_3$): δ=7.51-7.45 (m, 2H), 7.39-7.32 (m, 3H), 6.54 (s, 1H), 4.89 (br. s, 1H).

Example 7A

6-Phenylfuro[2,3-d]pyrimidin-4(3H)-one

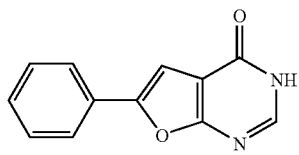

Add 424.5 ml (11.25 mol) formic acid dropwise to 884.9 ml (9.378 mol) acetic anhydride at 0° C. Stir the mixture for 30 min at 0° C. and then add 69.1 g (0.375 mol) 2-amino-5-phenyl-3-furonitrile. Remove the cooling and heat the mixture; evolution of gas begins at approx. 80° C., and stops after approx. 3 h. Stir for a total of 24 h under reflux (bath temperature approx. 130° C.). After cooling the suspension to RT, add 750 ml diisopropyl ether, cool to 0° C. and filter. Wash the residue with diisopropyl ether and dry at high vacuum. 50.83 g (58.7% of theor.) of the target compound is obtained as a brown solid.

HPLC (Method 1): $R_t$=3.92 min

MS: m/z=213 (M+H)$^+$ $^1$H-NMR (400 MHz, DMSO-d$_6$): δ=12.68 (br. s, 1H), 8.17 (s, 1H), 7.88 (d, 2H), 7.52-7.48 (m, 3H), 7.42-7.38 (m, 1H).

Example 8A

4-Chloro-6-phenylfuro[2,3-d]pyrimidine

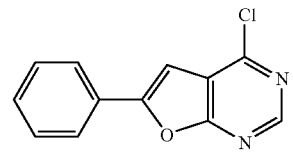

Suspend 50 g (235.6 mmol) 6-phenylfuro[2,3-d]pyrimidin-4(3H)-one at RT in 375 ml (4023 mmol) phosphoryl chloride and heat the mixture to boiling (evolution of HCl). After 1 h, cool the dark solution to RT and add dropwise to a vigorously stirred mixture of 1.25 litre water and 2.25 litre conc. ammonia solution (25 wt. %) (heating to 55-75° C., pH>9). At the end of addition, cool to RT and extract the mixture three times with 1.6 litre dichloromethane each time. Combine the organic phases, dry, and concentrate by vacuum evaporation. Stir the residue with diethyl ether, filter with suction, and dry at high vacuum. 47.3 g (87% of theor.) of the target compound is obtained.

HPLC (Method 1): $R_t$=4.67 min

MS: m/z=231 (M+H)$^+$ $^1$H-NMR (300 MHz, DMSO-d$_6$): δ=8.84 (s, 1H), 8.05 (m, 2H), 7.77 (s, 1H), 7.61-7.50 (m, 3H).

Example 9A

2-Amino-4-phenyl-3-furonitrile

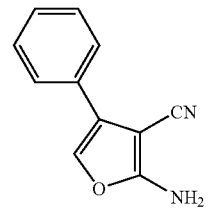

Add 3.78 ml (36.7 mmol) diethylamine dropwise to a mixture of 10 g (73.4 mmol) hydroxyacetophenone and 4.852 g (73.4 mmol) malononitrile in 24 ml DMF with cooling at RT. Stir the dark mixture for 2 h at RT and then add slowly to water (200 ml), with stirring and cooling. Continue stirring the precipitate for 30 min at approx. 10° C., filter with suction, suspend in water twice more, and filter with suction again. Dry the residue at high vacuum to constant weight. 10.99 g (81.2% of theor.) of the target compound is obtained as a yellowish-brown solid.

LC-MS (Method 2): $R_t$=1.81 min; m/z=185 (M+H)$^+$ $^1$H-NMR (400 MHz, DMSO-d$_6$): δ=7.54 (d, 2H), 7.50 (s, 2H), 7.45-7.32 (m, 4H).

Example 10A

5-Phenylfuro[2,3-d]pyrimidin-4(3H)-one

Cool 108.5 ml (1154 mmol) acetic anhydride to 0° C. and, under argon, add 52.2 ml (1384 mmol) formic acid. Stir the mixture for approx. 45 min at 0° C. and then add 8.5 g (46.2 mmol) 2-amino-4-phenyl-3-furonitrile in portions. A dark mixture is formed, and it turns violet after 15 min at 0° C. Remove the cooling and heat the suspension, which is now blue, to RT. After 15 min, heat the mixture to reflux (bath temperature 125-130° C.), whereupon gas begins to be evolved. Stir the mixture overnight under reflux. After cooling, concentrate the mixture under vacuum and dry the residue at high vacuum. Approx. 3 g of a deep dark red to black solid is obtained from the raw product by column filtration on silica gel (solvent gradient: dichloromethane→dichloromethane/methanol 50:1). Dissolve this in approx. 8 ml dichloromethane, precipitate with diisopropyl ether, filter with suction, and dry at high vacuum. 1.81 g (purity approx. 84%, yield approx. 15% of theor.) of the target compound is obtained as a dark red solid.

LC-MS (Method 3): R$_t$=3.2 min; m/z=211 (M−H)$^+$ $^1$H-NMR (400 MHz, DMSO-d$_6$): δ=12.7 (s, 1H), 8.26 (s, 1H), 8.19 (s, 1H), 7.98 (d, 2H), 7.50-7.30 (m, 3H).

Example 11A

4-Chloro-5-phenylfuro[2,3-d]pyrimidine

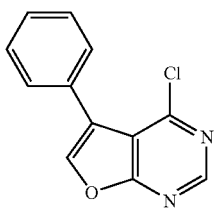

Add 9.5 ml (101.8 mmol) phosphoryl chloride to 1.8 g (approx. 6.8 mmol) 5-phenylfuro[2,3-d]pyrimidin-4(3H)-one at RT and heat the mixture for 1 h under reflux. Cool the resultant black mixture to RT and carefully add dropwise at <10° C. to a well-stirred solution of 70 ml conc. ammonia solution and 50 ml water cooled to 0° C. (pH>9). At the end of addition, heat the black suspension to RT and stir for a further 15 min. Filter off the black solid with suction, resuspend with water three times, filter with suction again, and dry at high vacuum. Dissolve the solid in dichloromethane and column-filter on silica gel (solvent: dichloromethane). 1371 mg (80.6% of theor.) of the target compound is obtained as a yellow solid.

LC-MS (Method 4): R$_t$=2.47 min; m/z=231 (M+H)$^+$ $^1$H-NMR (400 MHz, DMSO-d$_6$): δ=8.90 (s, 1H), 8.49 (s, 1H), 7.64-7.58 (m, 2H), 7.52-7.45 (m, 3H).

Example 12A

N-(4,4-Diethoxybutyl)-5-(4-methoxyphenyl)-6-phenylfuro[2,3-d]pyrimidine-4-amine

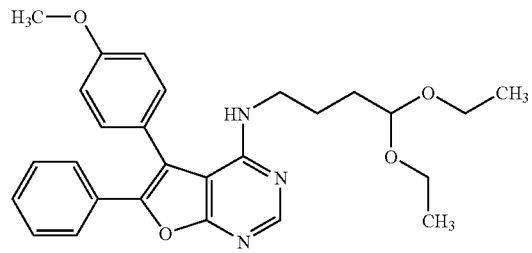

Stir 600 mg (1.78 mmol) 4-chloro-5-(4-methoxyphenyl)-6-phenylfuro[2,3-d]pyrimidine, 344.7 mg (2.14 mmol) 4-aminobutyraldehyde-diethylacetal and 0.465 ml (2.67 mmol) DIEA in 5 ml DMF overnight at 80° C. After cooling, purify the mixture directly by preparative RP-HPLC (gradient acetonitrile/water). 746 mg (90.7% of theor.) of the target compound is obtained.

LC-MS (Method 2): R$_t$=2.87 min; m/z=462 (M+H)$^+$ $^1$H-NMR (400 MHz, DMSO-d$_6$): δ=8.34 (s, 1H), 7.48-7.41 (m, 4H), 7.38-7.30 (m, 3H), 7.13 (d, 2H), 5.12 (t, 1H), 4.40 (t, 1H), 3.35 (s, 3H), 3.55-3.47 (m, 2H), 3.42-3.35 (m, 4H), 1.49-1.38 (m, 4H), 1.09 (t, 6H).

Example 13A

4-{[5-(4-Methoxyphenyl)-6-phenylfuro[2,3-d]pyrimidin-4-yl]amino}butanal

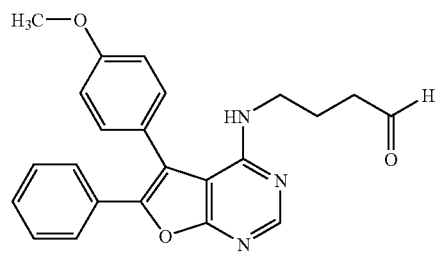

Dissolve 640 mg (1.39 mmol) N-(4,4-diethoxybutyl)-5-(4-methoxyphenyl)-6-phenylfuro[2,3-d]pyrimidine-4-amine in 5 ml acetone and, at RT, add 1 ml 1 N hydrochloric acid. After 1 h, add the reaction mixture to water and extract three times with dichloromethane. Combine the organic phases and wash with buffer solution (pH 7) and saturated sodium chloride solution, dry over magnesium sulphate and concentrate under vacuum. Purify the raw product by chromatography on silica gel (solvent: dichloromethane/ethyl acetate 2:1). 191 mg (35.6% of theor.) of the target compound is obtained.

LC-MS (Method 5): R$_t$=2.57 min; m/z=388 (M+H)$^+$.

Example 14A

6-[(6-Phenylfuro[2,3-d]pyrimidin-4-yl)amino]hexanoic acid methyl ester

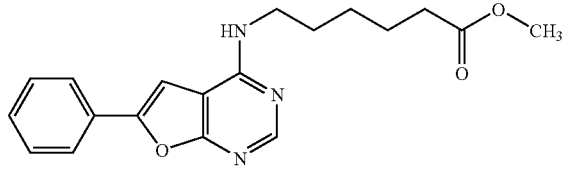

Heat 2.0 g (8.67 mmol) 4-chloro-6-phenylfuro[2,3-d]pyrimidine and 6.04 ml (34.7 mmol) DIEA in 5 ml DMF to 160° C. Add 3.15 g (17.34 mmol) 6-aminohexanoic acid methyl ester hydrochloride and stir for 4 h at 160° C. After cooling, add the mixture to ice water and extract three times with ethyl acetate. Combine the organic phases and wash with saturated ammonium chloride solution, dry over magnesium sulphate and concentrate under vacuum. Add methanol to the oil residue. Filter off the precipitated solid with suction, wash with methanol again and dry the solid at high vacuum. 1.85 g (57.2% of theor.) of the target compound is obtained.

LC-MS (Method 5): $R_t$=2.38 min; m/z=340 (M+H)$^+$ $^1$H-NMR (400 MHz, DMSO-d$_6$): δ=8.24 (s, 1H), 7.98 (br. s, 1H), 7.79 (d, 2H), 7.51 (t, 2H), 7.43-7.37 (m, 2H), 3.59 (s, 3H), 3.49 (q, 2H), 2.32 (t, 2H), 1.65-1.56 (m, 4H), 1.41-1.35 (m, 2H).

Example 15A

6-[(5-Bromo-6-phenylfuro[2,3-d]pyrimidin-4-yl)amino]hexanoic acid methyl ester

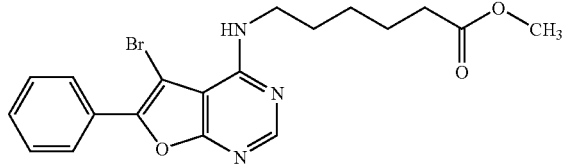

Put 1.75 g (5.15 mmol) 6-[(6-phenylfuro[2,3-d]pyrimidin-4-yl)amino]hexanoic acid methyl ester in 5.2 ml tetrachloromethane. At RT, add 1.054 g (5.92 mmol) N-bromosuccinimide and then heat the mixture under reflux for approx. 1 h. After cooling, concentrate by vacuum evaporation and chromatograph the residue on silica gel (solvent: cyclohexane/ethyl acetate 4:1). 0.89 g (41.2% of theor.) of the target compound is obtained.

LC-MS (Method 2): $R_t$=2.64 min; m/z=420 (M+H)$^+$ $^1$H-NMR (400 MHz, DMSO-d$_6$): δ=8.33 (s, 1H), 8.02 (d, 2H), 7.61-7.49 (m, 3H), 7.04 (t, 1H), 3.59 (s, 3H), 3.59-3.52 (m, 2H), 2.31 (t, 2H), 1.68-1.54 (m, 4H), 1.40-1.31 (m, 2H).

Example 16A

6-[(5-Phenylfuro[2,3-d]pyrimidin-4-yl)amino]hexanoic acid methyl ester

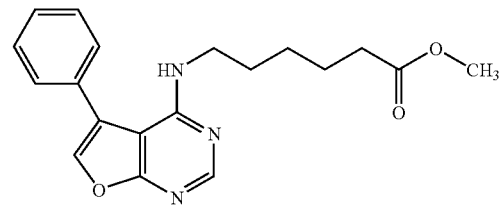

Heat 500 mg (2.19 mmol) 4-chloro-5-phenylfuro[2,3-d]pyrimidine, 1.51 ml (8.67 mmol) DIEA and 1 ml DMF to 160° C. and add 787.6 mg (4.34 mmol) 6-aminohexanoic acid methyl ester hydrochloride. After 4 h at 160° C., cool the reaction mixture, add to ice water and extract three times with ethyl acetate. Combine the organic phases and wash with saturated ammonium chloride solution, dry over magnesium sulphate and concentrate under vacuum. Purify the residue by chromatography on silica gel (solvent: cyclohexane/ethyl acetate 10:1→3:1). 470 mg (63.9% of theor.) of the target compound is obtained.

LC-MS (Method 5): $R_t$=2.43 min; m/z=340 (M+H)$^+$ $^1$H-NMR (400 MHz, DMSO-d$_6$): δ=8.35 (s, 1H), 7.48 (s, 1H), 7.55-7.45 (m, 5H), 5.82 (t, 1H), 3.49 (s, 3H), 3.44 (q, 2H), 2.31 (t, 2H), 1.60-1.50 (m, 4H), 1.33-1.25 (m, 2H).

Example 17A

6-[(6-Bromo-5-phenylfuro[2,3-d]pyrimidin-4-yl)amino]hexanoic acid methyl ester

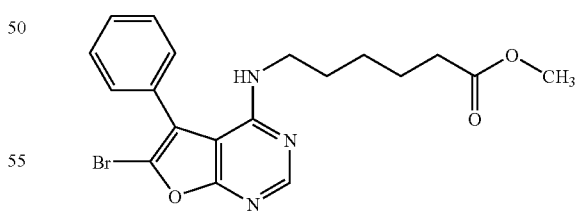

Add 57.7 mg (0.324 mmol) N-bromosuccinimide to a mixture of 100 mg (0.295 mmol) 4-chloro-5-phenylfuro[2,3-d]pyrimidine and 0.3 ml tetrachloromethane at RT. After 1 h at RT, concentrate the reaction mixture by vacuum evaporation and purify the residue by preparative RP-HPLC (gradient acetonitrile/water). 72 mg (58.4% of theor.) of the target compound is obtained.

LC-MS (Method 2): $R_t$=2.52 min; m/z=418/420 (M+H)$^+$ $^1$H-NMR (400 MHz, DMSO-d$_6$): δ=8.32 (s, 1H), 7.61-7.50 (m, 5H), 5.07 (t, 1H), 3.57 (s, 3H), 3.49 (q, 2H), 2.29 (t, 2H), 1.52-1.42 (m, 4H), 1.28-1.20 (m, 2H).

Example 18A

6-{[5-(4-Methoxyphenyl)-6-phenylfuro[2,3-d]pyrimidin-4-yl]amino}hexanenitrile

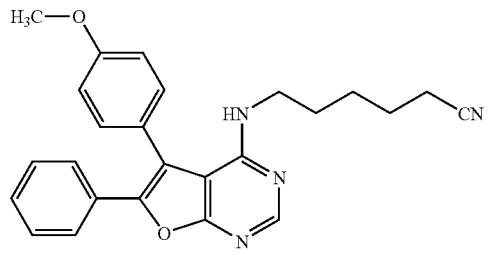

Add 1.15 g (8.9 mmol) DIEA and 0.67 g (5.9 mmol) 6-aminocapronitrile to 1.0 g (3.0 mmol) 4-chloro-5-(4-methoxyphenyl)-6-phenylfuro[2,3-d]pyrimidine in 10 ml DMF and heat for 2 h to 120° C. After cooling, add water to the mixture and extract three times with ethyl acetate. Wash the organic phase with water, with dilute hydrochloric acid and with saturated sodium chloride solution, dry, and concentrate by evaporation. 1.2 g (98% of theor.) of a yellow oil is obtained, and is used as the raw product in further reactions.

LC-MS (Method 5): R$_t$=2.87 min; m/z=412 (M+H)$^+$ $^1$H-NMR (400 MHz, DMSO-d$_6$): δ=8.4 (s, 1H), 7.55 (m, 2H), 7.4 (m, 2H), 7.25 (m, 3H), 7.15 (m, 2H), 4.4 (br. s, 1H), 3.9 (s, 3H), 3.5 (m, 2H), 2.35 (t, 2H), 1.65 (m, 2H), 1.5 (m, 2H), 1.4 (m, 2H).

Example 19A

7-{[5-(4-Methoxyphenyl)-6-phenylfuro[2,3-d]pyrimidin-4-yl]amino}heptanenitrile

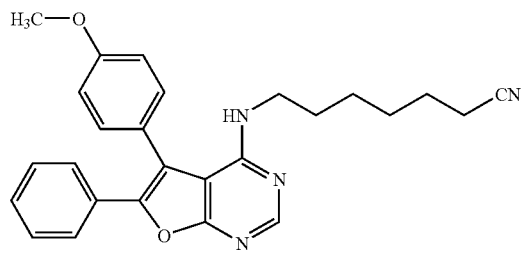

The title compound can be obtained from 4-chloro-5-(4-methoxyphenyl)-6-phenylfuro[2,3-d]-pyrimidine in three stages:

Stage 1:

Add 1.15 g (8.9 mmol) DIEA to 1.0 g (3.0 mmol) 4-chloro-5-(4-methoxyphenyl)-6-phenylfuro[2,3-d]pyrimidine and 0.70 g (5.9 mmol) 6-aminohexanol in 10 ml DMF and heat for 4 h to 120° C. Then dilute the mixture with ethyl acetate, wash with water and dilute hydrochloric acid, dry, and concentrate by evaporation. Purify the residue by RP-HPLC (column: Gromsil 250 mm×40 mm, 10 µm; acetonitrile/water gradient: 0-3 min 5% acetonitrile, 3-34 min 5%→98% acetonitrile, 34-38 min 98% acetonitrile). 364 mg (29% of theor.) 6-{[5-(4-methoxyphenyl)-6-phenylfuro[2,3-d]pyrimidin-4-yl]amino}hexan-1-ol is obtained as a yellow oil, which solidifies after standing for 2 days.

Stage 2:

Dissolve 333 mg (0.80 mmol) 6-{[5-(4-methoxyphenyl)-6-phenylfuro[2,3-d]pyrimidin-4-yl]amino}hexan-1-ol and 122 µl (0.88 mmol) triethylamine in dichloromethane and, at 0° C., add 62 µl (0.80 mmol) methanesulphonyl chloride, dissolved in dichloromethane (the total amount of dichloromethane is 20 ml). After stirring overnight at RT, wash the mixture with water and with saturated sodium chloride solution and dry over magnesium sulphate. Concentrating by evaporation gives 400 mg (quant.) of 6-{[5-(4-methoxyphenyl)-6-phenylfuro[2,3-d]pyrimidin-4-yl]amino}hexyl-methanesulphonate, which is used as raw product in further reactions.

Stage 3:

Stir a mixture of 400 mg (approx. 0.80 mmol) 6-{[5-(4-methoxyphenyl)-6-phenylfuro[2,3-d]-pyrimidin-4-yl]amino}hexyl-methanesulphonate and 526 mg (8.1 mmol) potassium cyanide in 20 ml DMF overnight at 80° C. After cooling, dilute with ethyl acetate and wash with water and saturated sodium chloride solution. Dry the organic phase over magnesium sulphate and concentrate by evaporation. Purify the raw product by RP-HPLC (column: Gromsil 250 mm×40 mm, 10 µm; acetonitrile/water gradient: 0-3 min 5% acetonitrile, 3-50 min 5%→98% acetonitrile, 50-55 min 98% acetonitrile). 249 mg (72% of theor.) of the title compound is obtained as a yellowish oil.

LC-MS (Method 4): R$_t$=2.90 min; m/z=426 (M+H)$^+$ $^1$H-NMR (400 MHz, DMSO-d$_6$): δ=8.35 (s, 1H), 7.55 (m, 4H), 7.35 (m, 3H), 7.15 (m, 2H), 5.0 (t, 1H), 3.85 (s, 3H), 3.45 (m, 2H), 2.45 (t, 2H), 1.55 (m, 2H), 1.4 (m, 2H), 1.3 (m, 2H), 1.15 (m, 2H).

Example 20A

6-{[5-(4-Methoxyphenyl)-6-phenylfuro[2,3-d]pyrimidin-4-yl]oxy}hexanenitrile

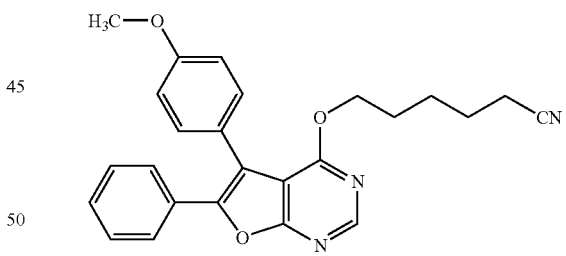

Dissolve 850 mg (3.8 mmol) 6-hydroxyhexanenitrile [obtained according to *Eur. J. Med. Chem.* 36 (4), 303-311 (2001)] in 15 ml DMF, add, at 0° C., 180 mg 60% sodium hydride (dispersion in mineral oil; approx. 4.5 mmol) and stir the mixture for 1 h at room temperature. Next, add 1.26 g (3.8 mmol) 4-chloro-5-(4-methoxyphenyl)-6-phenylfuro[2,3-d] pyrimidine and stir the mixture overnight at 120° C. After cooling, add water to the mixture and extract with ethyl acetate. Dry the organic phase, and concentrate by evaporation. Purify the residue by flash chromatography on silica gel (solvent: cyclohexane/ethyl acetate 2:1→cyclohexane/ethyl acetate 1:2). 1.05 g (68% of theor.) of an orange-coloured oil is obtained, which is used as raw product in further reactions.

LC-MS (Method 5): R$_t$=2.97 min; m/z=413 (M+H)$^+$ $^1$H-NMR (400 MHz, DMSO-$d_6$): δ=8.60 (s, 1H), 7.55 (m, 2H), 7.25-7.45 (m, 5H), 7.0-7.1 (m, 2H), 4.4 (t, 2H), 3.85 (s, 3H), 2.4 (t, 2H), 1.6 (m, 2H), 1.5 (m, 2H), 1.25 (m, 2H).

Example 21A 5-(4-Methoxyphenyl)-6-phenyl-N-{3-[2-cyanoethoxy]propyl}furo[2,3-d]pyrimidine-4-amine

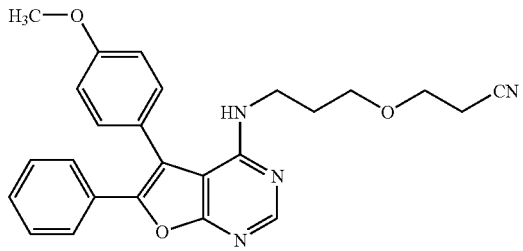

Stage 1:

Dissolve 1.00 g (3.0 mmol) 4-chloro-5-(4-methoxyphenyl)-6-phenylfuro[2,3-d]pyrimidine in 10 ml DMF and add 1.15 g (8.9 mmol) DIEA. Add 0.45 g (5.9 mmol) 3-aminopropanol and then heat the mixture over a period of 2 h to 120° C. After cooling, dilute the mixture with ethyl acetate and wash successively with dilute hydrochloric acid and saturated sodium chloride solution. Dry the organic phase over magnesium sulphate and concentrate by evaporation. Purify the residue by RP-HPLC (column: Gromsil 250 mm×30 mm, 10 μm; acetonitrile/water gradient: 0-3 min 5% acetonitrile, 3-50 min 5%→98% acetonitrile, 50-55 min 98% acetonitrile). 671 mg (60% of theor.) 3-{[5-(4-methoxyphenyl)-6-phenylfuro[2,3-d]pyrimidin-4-yl]amino}propan-1-ol is obtained in the form of beige crystals.

LC-MS (Method 2): $R_t$=2.13 min; m/z=376 (M+H)$^+$

Stage 2:

Add 47 mg (0.89 mmol) acrylonitrile and 57 mg (0.83 mmol) sodium ethylate to 300 mg (0.80 mmol) of the compound from Stage 1. Stir the mixture overnight at 80° C. After cooling, take up the mixture in DMSO and purify directly by RP-HPLC (column: Gromsil 250 mm×30 mm, 10 μm; acetonitrile/water gradient: 0-3 min 5% acetonitrile, 3-50 min 5%→98% acetonitrile, 50-55 min 98% acetonitrile). 160 mg (47% of theor.) of the title compound is obtained as a yellow oil.

LC-MS (Method 2): $R_t$=2.43 min; m/z=429 (M+H)$^+$ $^1$H-NMR (400 MHz, DMSO-$d_6$): δ=8.3 (s, 1H), 7.1-7.45 (m, 9H), 5.2 (m, 1H), 3.85 (s, 3H), 3.5 (m, 4H), approx. 3.3 (m, 2H, partially masked by H$_2$O), 2.7 (t, 2H), 1.7 (quin, 2H).

Example 22A 5-(4-Methoxyphenyl)-6-phenyl-N-(5-aminopentyl)-furo[2,3-d]pyrimidine-4-amine

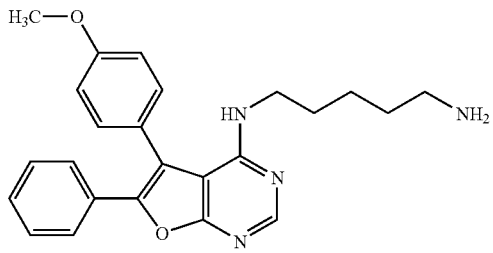

Stage 1:

Dissolve 1.00 g (3.0 mmol) 4-chloro-5-(4-methoxyphenyl)-6-phenylfuro[2,3-d]pyrimidine in 5 ml DMF and add 1.15 g (8.9 mmol) DIEA. Add 1.20 g (5.9 mmol) 5-[(tert.-butyloxycarbonyl)amino]-1-pentylamine [obtainable from 1,5-diaminopentane according to J. Med. Chem. 47 (20), 4933-4940 (2004)] and then heat the mixture to 80° C. for 3 h. After cooling, dilute the mixture with dichloromethane and wash successively with water and saturated sodium chloride solution. Dry the organic phase over magnesium sulphate and concentrate by evaporation. Purify the residue by RP-HPLC (column: Gromsil 250 mm×30 mm, 10 μm; acetonitrile/water gradient: 0-3 min 5% acetonitrile, 3-50 min 5%→98% acetonitrile, 50-55 min 98% acetonitrile). A total of 1.07 g (67% of theor.) of tert.-butyl-(5-{[5-(4-methoxyphenyl)-6-phenyl-furo[2,3-d]pyrimidin-4-yl]amino}pentyl)carbamate is obtained in two fractions, in the form of beige crystals.

LC-MS (Method 2): $R_t$=2.85 min; m/z=503 (M+H)$^+$

Stage 2:

Dissolve 380 mg (0.76 mmol) of the compound from Stage 1 in 5 ml methylene chloride and add 0.4 ml anisole and then 5.5 ml trifluoroacetic acid. Stir for 2 h at room temperature. Dilute the mixture with dichloromethane and wash with sodium hydrogencarbonate solution until reaction is neutral. After washing the organic phase with saturated sodium chloride solution, dry over magnesium sulphate. The residue left after concentration by evaporation is dissolved in ethanol and concentrated by evaporation; this operation is repeated three times. 349 mg (82% of theor.) of the title compound is obtained as a yellowish foam.

LC-MS (Method 2): $R_t$=2.43 min; m/z=429 (M+H)$^+$ $^1$H-NMR (400 MHz, DMSO-$d_6$): δ=8.3 (s, 1H), 7.1-7.45 (m, 9H), 5.4 (br. M, 1H), 5.1 (m, 1H), 3.85 (s, 3H), approx. 3.3 (m, 2H, partially masked by H$_2$O), 2.6 (t, 2H), 1.1-1.57 (m, 6H).

Example 23A

4-[3-(2-Cyanoethoxy)ethoxy]-5-(4-methoxyphenyl)-6-phenylfuro[2,3-d]pyrimidine

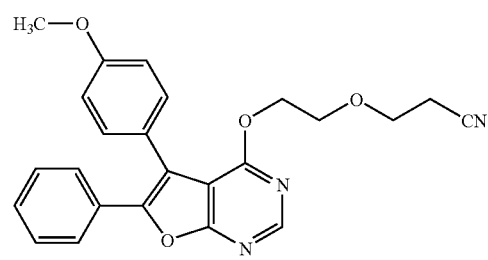

Stage 1:

Add, at 0° C., 59 mg (1.5 mmol) of 60% sodium hydride to a solution of 461 mg (7.4 mmol) ethylene glycol in 10 ml DMF. After warming to room temperature, continue stirring for 1 h. Then add 0.50 g (1.5 mmol) 4-chloro-5-(4-methoxyphenyl)-6-phenylfuro[2,3-d]pyrimidine and stir the mixture for 3 h at room temperature. Next, dilute with water and extract with ethyl acetate. Wash the organic phase with saturated sodium chloride solution, dry over magnesium sulphate and concentrate by evaporation. The raw product thus obtained is purified by RP-HPLC (column: Gromsil 250 mm×30 mm, 10 μm; acetonitrile/water gradient: 0-3 min 5% acetonitrile, 3-50 min 5%→98% acetonitrile, 50-55 min 98% acetonitrile). In this way, 412 mg (77% of theor.) 2-{[5-(4-methoxyphenyl)-6-phenylfuro[2,3-d]pyrimidin-4-yl]oxy}ethanol is obtained.

Stage 2:

As in Example 21A, Stage 2, 245 mg (61% of theor.) of the title compound is obtained in the form of yellow crystals from 350 mg (0.97 mmol) of the compound from Stage 1.

m.p.: 103-104° C.

LC-MS (Method 2): $R_t$=2.84 min; m/z=416 (M+H)$^+$ $^1$H-NMR (400 MHz, DMSO-d$_6$): δ=8.6 (s, 1H), 7.35-7.55 (m, 7H), 7.05 (m, 2H), 4.55 (m, 2H), 3.85 (s, 3H), 3.7 (m, 2H), 3.45 (t, 2H), 2.7 (t, 2H).

Example 24A

4-[3-(2-Cyanoethoxy)propoxy]-5-(4-methoxyphenyl)-6-phenylfuro[2,3-d]pyrimidine

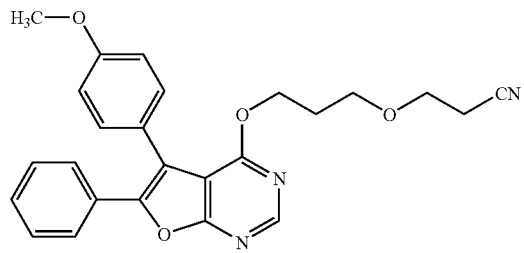

The title compound is obtained as in Example 23A in two stages from 1,3-propanediol and 4-chloro-5-(4-methoxyphenyl)-6-phenylfuro[2,3-d]pyrimidine.

Yield: 304 mg (89% of theor.)

m.p.: 88-89° C.

LC-MS (Method 4): $R_t$=2.94 min; m/z=430 (M+H)$^+$ $^1$H-NMR (400 MHz, DMSO-d$_6$): δ=8.6 (s, 1H), 7.35-7.55 (m, 7H), 7.05 (m, 2H), 4.45 (m, 2H), 3.85 (s, 3H), 3.7 (m, 2H), 3.5 (t, 2H), 2.7 (t, 2H), 1.7 (quin, 2H).

Example 25A (4-Ethylphenyl)[(trimethylsilyl)oxy]acetonitrile

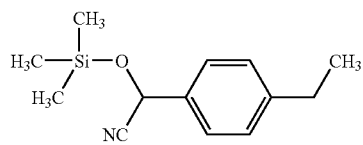

Mix 600 g (4.47 mol) 4-ethylbenzaldehyde in 5.3 litres toluene with 2.4 g (7.5 mmol) zinc iodide. At RT, with gentle cooling, add 587.4 ml (4.7 mol) trimethylsilyl cyanide, dissolved in 3.6 litres toluene, over a period of approx. 5 min. Stir the mixture for 90 min at RT, before removal of volatile components under vacuum and quick chromatography of the residue on silica gel (eluent: petroleum ether/ethyl acetate 9:1). 990 g (94.9% of theor.) of the title compound is obtained as a colourless oil.

$^1$H-NMR (400 MHz, CDCl$_3$): δ=7.38 (d, 2H), 7.23 (d, 2H), 4.97 (s, 1H), 2.68 (q, 2H), 1.25 (t, 3H), 0.23 (s, 9H).

Example 26A 1-(4-Ethylphenyl)-2-hydroxy-2-phenylethanone

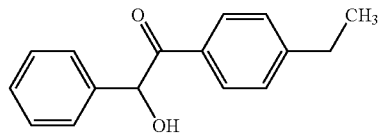

Dissolve 290 ml (2.069 mol) diisopropylamine in 3.6 litres DME and precool to −78° C. Add 820 ml (2.05 mol) n-butyllithium (2.5 M solution in hexane) dropwise in the space of approx. 20 min (temperature<−60° C.). After 15 min at −60° C., add a solution of 435 g (1.864 mol) (4-ethylphenyl)[(trimethylsilyl)oxy]acetonitrile in 1.4 litres DME dropwise (temperature<−60° C.). Stir the mixture for a further 30 min at −60° C., before adding a solution of 189.5 ml (1.864 mol) benzaldehyde in 1.4 litres DME (time approx. 20 min, temperature −60° C.). Heat the mixture over a period of 4 h to RT, before adding 7 litre satd. ammonium chloride solution. Extract the reaction mixture with ethyl acetate. After phase separation, wash the organic phase with satd. ammonium chloride solution, dry, and concentrate by vacuum evaporation. Dissolve the residue in 7 litres dioxan and 5 litres methanol, and add 6 litres 1 N hydrochloric acid. Stir the mixture overnight at RT, then, after adding 11 litres satd. sodium chloride solution, extract with 6.5 litres ethyl acetate. Wash the organic phase with water and with satd. sodium chloride solution, dry, and concentrate by vacuum evaporation. Dissolve the residue in 2 litres diisopropyl ether, add seed crystals and stir for 2 h. The precipitated solid is filtered with suction, washed with 300 ml diisopropyl ether and petroleum ether and dried under vacuum. Concentrate the mother liquor, and after storing for 2 days at 4° C., again filter off the precipitated solid with suction, wash with approx. 100 ml diisopropyl ether and petroleum ether and dry under vacuum. On combining the two solids, 154.9 g (34% of theor.) of the target product is obtained.

HPLC (Method 1): $R_t$=4.55 min

MS (DCI): m/z=258 (M+NH$_4$)$^+$ $^1$H-NMR (400 MHz, CDCl$_3$): δ=7.85 (d, 2H), 7.48-7.35 (m, 5H), 7.21 (d, 2H), 5.92 (d, 1H), 4.59 (d, 1H), 2.65 (q, 2H), 1.20 (t, 3H).

Example 27A

2-Amino-4-(4-ethylphenyl)-5-phenyl-3-furonitrile

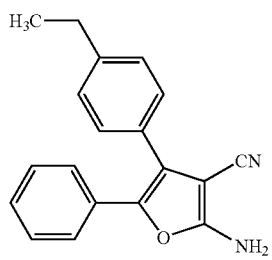

Cool a mixture of 145 g (603 mmol) 1-(4-ethylphenyl)-2-hydroxy-2-phenylethanone and 51.8 g (784.4 mmol) malononitrile in 2.23 litres DMF to 0° C. and add 53.7 ml (518 mmol)

diethylamine, with cooling. After 1 h, heat the reaction mixture to RT and stir for a further 4 h, before adding 1.5 litre water. After 30 min, pour off a large proportion of the water and replace with 750 ml of fresh water. Stir the mixture vigorously, before decanting from the sticky organic residue. Dissolve the residue in ethyl acetate, dry, and concentrate under vacuum, until the product begins to crystallize. Add 450 ml diisopropyl ether, stir and then leave to stand overnight. Filter off the crystalline precipitate with suction, wash twice with 50 ml diisopropyl ether and dry under vacuum. 98.5 g (56.6% of theor.) of the target product is obtained.

HPLC (Method 1): $R_t$=5.10 min

MS (DCI): m/z=306 $(M+NH_4)^+$ $^1$H-NMR (400 MHz, CDCl$_3$): δ=7.90-7.82 (m, 4H), 7.28-7.18 (m, 5H), 4.98 (s, 2H), 2.69 (q, 2H), 1.28 (t, 3H).

Example 28A 5-(4-Ethylphenyl)-6-phenylfuro[2,3-d]pyrimidin-4(3H)-one

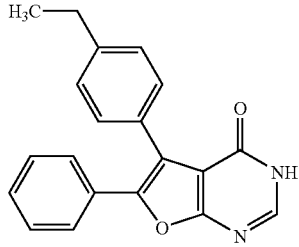

Cool 770 ml (8.16 mol) acetic anhydride to 0° C. and, with cooling, add 372 ml (10.4 mol) formic acid. Stir the mixture for 30 min at 0° C., before adding 98 g (340 mmol) 2-amino-4-(4-ethylphenyl)-5-phenyl-3-furonitrile. Heat the mixture to reflux (with increasing intensity of evolution of gas) and stir for 24 h under reflux. After cooling, stir for about 2 h at 10° C. and then suction-filter the precipitated solid, wash with diisopropyl ether and dry at high vacuum. 69.3 g (64.5% of theor.) of the target product is obtained.

HPLC (Method 1): $R_t$=4.77 min

MS (DCI): m/z=334 $(M+NH_4)^+$, 317 $(M+H)^+$ $^1$H-NMR (400 MHz, DMSO-d$_6$): δ=12.63 (br. s, 1H), 8.19 (s, 1H), 7.43 (d, 2H), 7.40-7.30 (m, 5H), 7.25 (m, 2H), 3.35 (s, 2H), 2.68 (d, 2H), 1.25 (t, 3H).

Example 29A

4-Chloro-5-(4-ethylphenyl)-6-phenylfuro[2,3-d]pyrimidine

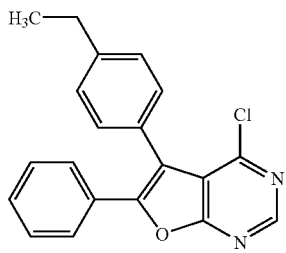

Put 72 g (227.6 mmol) 5-(4-ethylphenyl)-6-phenylfuro[2,3-d]pyrimidin-4(3H)-one in 360 ml (4.6 mol) phosphoryl chloride and heat to reflux. Stir the mixture for approx. 1 h at 120° C., before adding the reaction mixture dropwise, after cooling to RT, at controlled dose and with vigorous stirring, to a mixture of 2.2 litres of 25% ammonia solution and 1.2 litres water (pH>9, temperature 55-75° C.). Extract the aqueous mixture three times with dichloromethane, combine the organic phases, dry over sodium sulphate and concentrate by vacuum evaporation. Wash the residue with a little diisopropyl ether, and after filtration and drying at high vacuum, 66.1 g (85.2% of theor.) of the target product is obtained.

HPLC (Method 6): $R_t$=5.68 min

MS (DCI): m/z=335 $(M+H)^+$ $^1$H-NMR (400 MHz, CDCl$_3$): δ=8.76 (s, 1H), 7.61 (d, 2H), 7.48-7.30 (m, 7H), 2.78 (q, 2H), 1.36 (t, 3H).

Example 30A

6-Phenylfuro[2,3-d]pyrimidine-4-amine

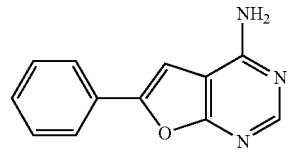

Suspend 110 g (597 mmol) 2-amino-5-phenyl-3-furonitrile in 355 ml (9 mol) formamide and heat for 1.5 h (bath temperature approx. 210° C.). Then cool the mixture to RT and stir into water. Filter off the precipitated solid with suction, and wash with water. Stir the still moist product in dichloromethane, filter with suction again and dry under vacuum. 106 g (80% of theor.) of the target compound is obtained.

LC-MS (Method 3): $R_t$=3.1 min; m/z=212 $(M+H)^+$

HPLC (Method 1): $R_t$=3.63 min $^1$H-NMR (400 MHz, DMSO-d$_6$): δ=8.20 (s, 1H), 7.8 (d, 2H), 7.55-7.32 (m, 6H).

Example 31A

5-Bromo-6-phenylfuro[2,3-d]pyrimidine-4-amine

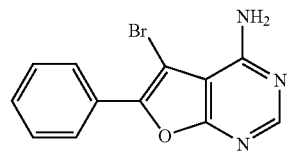

Heat 80 g (378.7 mmol) 6-phenylfuro[2,3-d]pyrimidine-4-amine in 770 ml carbon tetrachloride to 60° C. Add 84.3 g (473.4 mmol) N-bromosuccinimide, and stir the mixture overnight under reflux. After cooling, filter, mix the filter cake successively with dichloromethane and acetonitrile, and filter again. Then dry the filter cake under vacuum. 86 g of the target product (78.2% of theor.) is obtained.

MS (DCI): m/z=290/292 $(M+H)^+$

¹H-NMR (400 MHz, DMSO-d₆): δ=8.28 (s, 1H), 8.03 (d, 2H), 7.60-7.50 (m, 5H).

Example 32A

5-Bromo-4-chloro-6-phenylfuro[2,3-d]pyrimidine

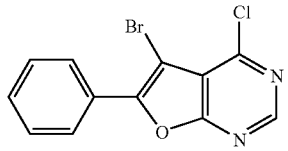

Put 54 g (186 mmol) 5-bromo-6-phenylfuro[2,3-d]pyrimidine-4-amine in 135 ml chloroform, add 70 ml 4 N hydrogen chloride in dioxan (280 mmol) and heat to reflux. Add 50 ml (372 mmol) isoamyl nitrite dropwise (evolution of gas). At the end of addition, stir for 3 h under reflux, before adding the cooled reaction mixture to water and extracting it with dichloromethane. Wash the organic phase with satd. sodium hydrogencarbonate solution, dry over sodium sulphate and concentrate by vacuum evaporation. Purify the raw product by chromatography on silica gel (eluent: dichloromethane). For further purification, mix the product in methanol, filter with suction, and dry at high vacuum. 32 g of the target product (55.5% of theor.) is obtained.

LC-MS (Method 2): $R_t$=2.54 min; m/z=309/310 (M+H)⁺

HPLC (Method 1): $R_t$=5.08 min

¹H-NMR (400 MHz, CDCl₃): δ=8.79 (s, 1H), 8.23-8.20 (m, 2H), 7.58-7.51 (m, 3H).

Example 33A

[(5-Bromo-6-phenylfuro[2,3-d]pyrimidin-4-yl)(methyl)amino]hexanoic acid methyl ester

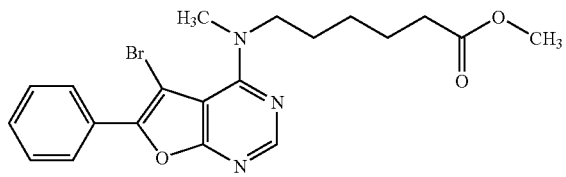

Add 52.5 mg (1.32 mmol) of 60% sodium hydride in portions at 0° C. to a mixture of 500 mg (1.2 mmol) 6-[(5-bromo-6-phenylfuro[2,3-d]pyrimidin-4-yl)amino]hexanoic acid methyl ester and 112 μl (1.79 mmol) methyl iodide in 1 ml DMF. Remove the ice cooling and heat the mixture to RT. After 1 h, dilute with water and dichloromethane and extract the separated aqueous phase with dichloromethane. Combine the organic phases and wash with satd. sodium chloride solution, dry over sodium sulphate and concentrate by vacuum evaporation. 472.6 mg (91.2% of theor.) of an oil is obtained.

LC-MS (Method 7): $R_t$=4.24 min; m/z=432/434 (M+H)⁺

¹H-NMR (400 MHz, DMSO-d₆): δ=8.38 (s, 1H), 8.0 (d, 2H), 7.60-7.50 (m, 3H), 3.70 (t, 2H), 3.29 (s, 3H), 2.29 (t, 2H), 1.72-1.65 (m, 2H), 1.60-1.52 (m, 2H), 1.31-1.26 (m, 2H).

Example 34A (−)-(2R)-2-Methyl-3-(trityloxy)propionic acid methyl ester

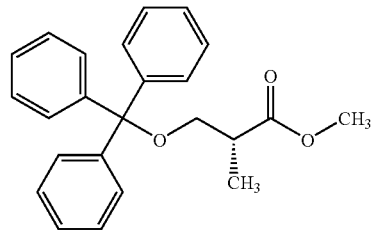

Put 1.5 g (12.7 mmol) (−)-methyl-D-β-hydroxyisobutyrate in 13 ml dichloromethane and 2.5 ml (17.8 mmol) triethylamine, cool to 0° C. and add 4.43 g (15.9 mmol) triphenylmethyl chloride, dissolved in dichloromethane. Remove the cooling and stir the mixture for 2 h, then after diluting with dichloromethane, wash several times with water and with satd. sodium chloride solution. Dry the organic phase over magnesium sulphate and concentrate by vacuum evaporation. Purify the product by chromatography on silica gel (eluent: cyclohexane/ethyl acetate 20:1). 2.81 g of the target product (61.4% of theor.) is obtained.

LC-MS (Method 2): $R_t$=2.98 min; m/z=243

¹H-NMR (400 MHz, DMSO-d₆): δ=7.38-7.20 (m, approx. 15H), 3.63 (s, 3H), 3.17-3.09 (m, 2H), 2.72 (q, 1H), 1.05 (d, 3H).

$[\alpha]_D^{20}$=−15.5°, c=0.545, chloroform.

Example 35A (−)-(2S)-2-Methyl-3-(trityloxy)propan-1-ol

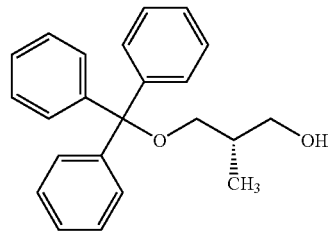

Dissolve 1.4 g (3.88 mmol) (−)-(2R)-2-methyl-3-(trityloxy)propionic acid methyl ester in 5 ml abs. THF, cool to −20° C. and add dropwise 1.94 ml (1.94 mmol) of a 1 M solution of lithium-aluminum hydride in THF. Stir the mixture for 1 h at −10° C., then dilute with a mixture of acetone and dichloromethane and add water. Extract the aqueous phase twice with dichloromethane. Combine the organic phases, wash with satd. sodium chloride solution, dry over magnesium sulphate and concentrate under vacuum. After chromatography on silica gel (eluent: cyclohexane/ethyl acetate 8:1→4:1), 0.98 g (75.5% of theor.) of the target product is obtained.

LC-MS (Method 8): $R_t$=2.85 min; m/z=243, 355 (M+Na)⁺

MS (DCI): m/z=243, 350 (M+NH₄)⁺

¹H-NMR (400 MHz, DMSO-d₆): δ=7.40-7.24 (m, approx. 15H), 4.38 (t, 1H), 3.43-3.37 (m, 1H), 3.32-3.28 (m, 1H), 3.01 (dd, 1H), 2.83 (dd, 1H), 1.84 (m, 1H), 0.88 (d, 3H)

$[\alpha]_D^{20}$=−30°, c=0.49, chloroform.

Example 36A (−)-{[(2S)-2-Methyl-3-(trityloxy)propyl]oxy}acetic acid tert.-butyl ester

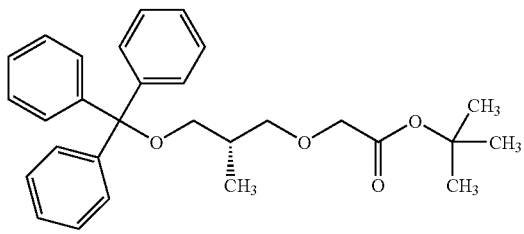

Add 53.2 mg (0.12 mmol) rhodium diacetate [as dimer Rh$_2$(OAc)$_4$] to a solution of 800 mg (2.41 mmol) (−)-(2S)-2-methyl-3-(trityloxy)propan-1-ol in 2 ml dichloromethane. Slowly add an excess of tert.-butyl diazoacetate (approx. 2 equivalents) dropwise to the vigorously stirred suspension, with evolution of N$_2$ (time approx. 1 h). Then dilute the reaction mixture with dichloromethane, wash three times with water and once with satd. sodium chloride solution, dry over magnesium sulphate and concentrate by vacuum evaporation. Purify the product by chromatography on silica gel (eluent: cyclohexane/ethyl acetate 10:1). Approx. 1000 mg of slightly contaminated target product is obtained.

MS (DCI): m/z=464 (M+NH$_4$)$^+$ $^1$H-NMR (400 MHz, DMSO-d$_6$): δ=7.40-7.25 (m, 15H), 3.91 (s, 2H), 3.48 (dd, 1H), 3.35 (dd, 1H), 2.98 (dd, 1H), 2.88 (dd, 1H), 1.98 (m, 1H), 1.41 (s, 9H), 0.89 (d, 3H).

$[α]_D^{20}$=−6.6°, c=0.505, chloroform.

Example 37A (+)-{[(2R)-3-Hydroxy-2-methylpropyl]oxy}tert.-butyl acetate

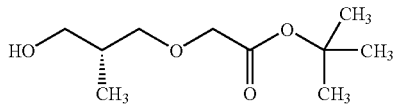

Dissolve 900 mg (approx. 2.02 mmol) (−)-{[(2S)-2-methyl-3-(trityloxy)propyl]oxy}tert.-butyl acetate in 2 ml dichloromethane and 0.5 ml methanol and then add an excess (approx. 3 equivalents) of anhydrous zinc bromide in portions, firstly at 0° C., then at RT. Stir the mixture for 2-3 h at RT, then after diluting with dichloromethane, wash twice with water and with satd. sodium chloride solution. Dry over magnesium sulphate and concentrate by vacuum evaporation. 257 mg of the target product (approx. 62% of theor.) is isolated by chromatography on silica gel (eluent: cyclohexane/ethyl acetate 10:1→2:1).

MS (DCI): m/z=222 (M+NH$_4$)$^+$ $^1$H-NMR (400 MHz, DMSO-d$_6$): δ=4.40 (t, 1H), 3.95 (s, 2H), 3.42-3.36 (m, 2H), 3.28-3.22 (m, 2H), 1.77 (m, 1H), 1.44 (s, 9H), 0.85 (d, 3H).

$[α]_D^{20}$=+10.5°, c=0.525, chloroform.

Example 38A (+)-(2S)-2-Methyl-3-(trityloxy)propionic acid methyl ester

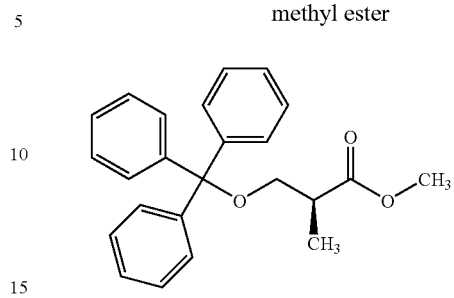

Put 10.33 g (87.5 mmol) (+)-methyl-L-β-hydroxyisobutyrate in 10 ml dichloromethane and 14.2 ml (174.9 mmol) pyridine, cool to 0° C. and add 1.07 g (8.7 mmol) DMAP and then, with ice cooling, 30.5 g (109 mmol) triphenylmethyl chloride, dissolved in dichloromethane. Remove the cooling and stir the mixture for 5 h, then after diluting with ample dichloromethane, wash successively with water, 1 N hydrochloric acid, satd. sodium hydrogencarbonate solution and satd. sodium chloride solution. Dry the organic phase over sodium sulphate and concentrate by vacuum evaporation. Mix the precipitated crystals with methanol, filter, and dry under vacuum. 25.36 g of the target product (41.4% of theor.) is obtained.

MS (DCI): m/z=378 (M+NH$_4$)$^+$ $[α]_D^{20}$=+6.4°, c=0.555, chloroform.

Example 39A (+)-(2R)-2-Methyl-3-(trityloxy)propan-1-ol

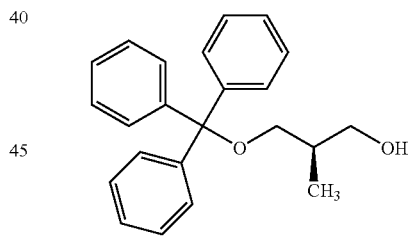

Dissolve 23 g (63.8 mmol) (+)-(2S)-2-methyl-3-(trityloxy) propionic acid methyl ester in 100 ml abs. THF, cool to −20° C. and add, dropwise, 31.9 ml (31.9 mmol) of a 1 M solution of lithium-aluminum hydride in THF. At the end of addition, stir for a further 10 min at −10° C., then dilute with dichloromethane and, at approx. 0° C., carefully add satd. ammonium chloride solution. Wash the organic phase with satd. sodium chloride solution, dry over sodium sulphate and concentrate by vacuum evaporation. Purify the product by chromatography on silica gel (eluent: cyclohexane/ethyl acetate 5:1). 11.16 g of the target compound (52.6% of theor.) is obtained.

$^1$H-NMR (400 MHz, DMSO-d$_6$): δ=7.40-7.25 (m, approx. 15H), 4.39 (t, 1H), 3.43-3.38 (m, 1H), 3.32-3.28 (m, 1H), 3.02 (dd, 1H), 2.82 (dd, 1H), 1.84 (m, 1H), 0.88 (d, 3H).

$[α]_D^{20}$=+25.1°, c=0.575, chloroform.

Example 40A (−)-{[(2R)-2-Methyl-3-(trityloxy)propyl]oxy}acetic acid ethyl ester

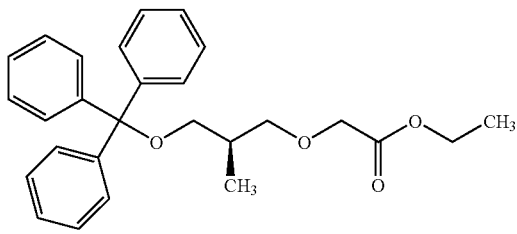

Add 3.4 ml (33.1 mmol) diazoethyl acetate to a suspension of 5.0 g (15.0 mmol) (+)-(2R)-2-methyl-3-(trityloxy)propan-1-ol and 0.332 g (0.75 mmol) rhodium(II) acetate dimer in 25 ml dry dichloromethane, stirring vigorously, at 0° C. At the end of addition, stir for a further 5 min at 0° C., then heat to RT and continue stirring for 2.5 h at RT. After diluting with dichloromethane, wash with water and satd. sodium chloride solution, dry over sodium sulphate and concentrate by vacuum evaporation. Purify the raw product by chromatography on silica gel (eluent: cyclohexane/ethyl acetate 20:1). 5.18 g of the target compound (79.7% of theor.) is obtained.

MS (DCI): m/z=436 (M+NH$_4$)$^+$ $^1$H-NMR (400 MHz, DMSO-d$_6$): δ=7.40-7.25 (m, 15H), 4.10 (q, 2H), 4.03 (s, 2H), 3.48 (dd, 1H), 3.38 (dd, 1H), 2.98 (dd, 1H), 2.40 (dd, 1H), 1.98 (m, 1H), 1.18 (t, 3H), 0.90 (d, 3H).

[α]$_D^{20}$=−0.9°, c=0.47, chloroform.

Example 41A (−)-{[(2S)-3-Hydroxy-2-methylpropyl]oxy}acetic acid ethyl ester

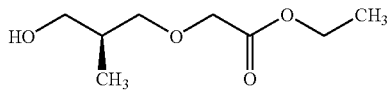

Dissolve 2.75 g (6.58 mmol) (−)-{[(2R)-2-methyl-3-(trityloxy)propyl]oxy}acetic acid ethyl ester in 25 ml ethanol, add 300 mg of 10% Pd/C and stir at RT for 3 h under a hydrogen atmosphere (normal pressure). Filter on Celite and concentrate the filtrate under vacuum. Purify the raw product by filtration on silica gel (eluent: ethyl/ethyl acetate 7:1→4:1). 1.05 g of the target compound (90.6% of theor.) is obtained.

$^1$H-NMR (400 MHz, DMSO-d$_6$): δ=4.40 (t, 1H), 4.12 (q, 2H), 4.05 (s, 2H), 3.41 (dd, 1H), 3.38-3.32 (m, 1H), 3.30-3.23 (m, 2H), 1.78 (m, 1H), 1.20 (t, 3H), 0.85 (d, 3H).

[α]$_D^{20}$=−12.4°, c=0.50, chloroform.

Example 42A

3-[(1S)-2-Benzyloxy-1-methylethoxy]propionic acid tert.-butyl ester

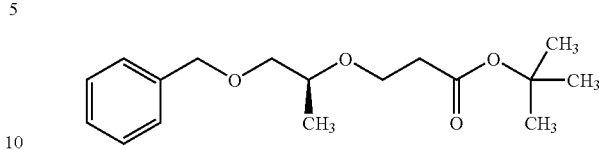

Cool a mixture of 20 g (120.3 mmol) (+)-(S)-1-benzyloxy-2-propanol and 123 g (962 mmol) tert.-butyl acrylate to 0° C. and add 962 mg (24 mmol, 60%) sodium hydride in several portions. Stir the mixture for 10 min at 0° C., then carefully add satd. ammonium chloride solution. After phase separation, extract the aqueous phase twice with dichloromethane. Combine the organic phases, dry over magnesium sulphate and concentrate under vacuum, then at high vacuum. Purify the raw product by chromatography on silica gel (eluent: cyclohexane/ethyl acetate 30:1). 18.4 g of the target compound (51.9% of theor.) is obtained.

$^1$H-NMR (400 MHz, DMSO-d$_6$): δ=7.38-7.25 (m, 5H), 4.49 (s, 2H), 3.64 (t, 2H), 3.61-3.58 (m, 1H), 3.40 (dd, 1H), 3.32 (dd, 1H), 2.39 (t, 2H), 1.39 (s, 9H), 1.05 (d, 3H).

Example 43A (+)-3-[(1S)-2-Hydroxy-1-methylethoxy]propionic acid tert.-butyl ester

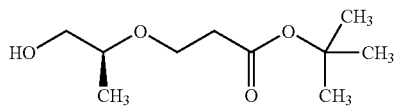

Dissolve 18.1 g (61.5 mmol) 3-[(1S)-2-benzyloxy-1-methylethoxy]propionic acid tert.-butyl ester in 100 ml ethanol, add 1.96 g of 10% Pd/C and stir at RT for 2 h under a hydrogen atmosphere (normal pressure). Filter on Celite and concentrate the filtrate under vacuum. 13.8 g of the target compound is obtained as raw product, which is not purified further (approx. 92% of theor.).

MS (DCI): m/z=222 (M+NH$_4$)$^+$ $^1$H-NMR (400 MHz, DMSO-d$_6$): δ=4.50 (t, 1H), 3.67-3.60 (m, 2H), 3.40-3.34 (m, approx. 2H), 3.27-3.21 (m, 1H), 2.39 (t, 2H), 1.39 (s, 9H), 1.02 (d, 3H).

[α]$_D^{20}$=+15.0°, c=0.49, chloroform.

Example 44A

Methyl 6-oxo-heptanoate

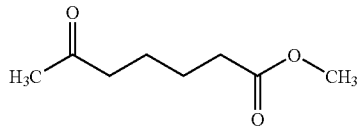

Dissolve 10 g 6-oxoheptanoic acid (69.4 mmol) in 100 ml methanol. Add a few drops of concentrated sulphuric acid and stir for 1.5 h under reflux. Then concentrate by evaporation. Take up in dichloromethane and wash once with satd. sodium hydrogencarbonate solution. Separate the phases, dry the organic phase and concentrate by evaporation. 10.1 g (91.1% of theor.) of the target compound is obtained.

¹H-NMR (400 MHz, CDCl₃): δ=3.67 (s, 3H), 2.44 (t, 2H), 2.32 (t, 2H), 2.13 (s, 3H), 1.67-1.55 (m, 4H).

Example 45A (+/−)-6-Hydroxy-heptanoic acid methyl ester

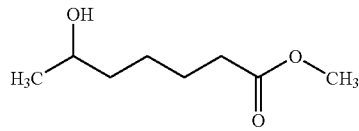

Put 10 g (63.2 mmol) 6-oxo-heptanoic acid methyl ester in 50 ml methanol. Add, in portions, 1.196 g (31.6 mmol) sodium borohydride. After the exothermic reaction has subsided, stir for a further 30 min under reflux. Then concentrate by evaporation. Take up the residue in water, acidify with 1 M hydrochloric acid and extract twice with dichloromethane. Dry the organic phases and concentrate by evaporation. 7.9 g (78.0% of theor.) of the target compound is obtained.

¹H-NMR (400 MHz, CDCl₃): δ=3.83-3.75 (m, 1H), 3.67 (s, 3H), 2.32 (t, 2H), 1.69-1.58 (m, 2H), 1.53-1.30 (m, 4H), 1.19 (d, 3H).

Example 46A

[(3R)-3-Hydroxybutyl]oxy-acetic acid tert.-butyl ester

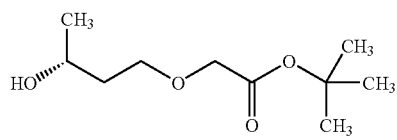

Put 1.0 g (11.1 mmol) (3R)-butane-1,3-diol in 20 ml THF at 0° C. Add dropwise 5.55 ml (11.1 mmol) of a 2 M solution of the phosphazene base P2-tert.-butyl in THF and stir for 30 min at 0° C. Then add 2.27 g (11.65 mmol) tert.-butyl bromoacetate. Stir for 30 min at 0° C., then leave to return to RT and stir for a further 1 h. Then dilute with ethyl acetate, add water and acidify with 10% citric acid solution. Extract once more with ethyl acetate, combine the organic phases, wash once with satd. sodium chloride solution, dry over magnesium sulphate and concentrate by evaporation. Purify by chromatography on silica gel (solvent: cyclohexane/ethyl acetate 8:2). 730 mg (32.2% of theor.) of the target compound is obtained, which according to ¹H-NMR (doublet at 1.18 ppm) contains approx. 10% of the regioisomer [(1R)-3-hydroxy-1-methylpropyl]oxy}acetic acid tert.-butyl ester.

¹H-NMR (400 MHz, CDCl₃): δ=4.11-4.02 (m, 1H), 3.96 (d, 2H), 3.76-3.62 (m, 2H), 1.79-1.62 (m, 2H), 1.48 (s, 9H), 1.21 (d, 3H).

Example 47A (2R)-1-{[5-(4-Methoxyphenyl)-6-phenylfuro[2,3-d]pyrimidin-4-yl]oxy}propan-2-ol

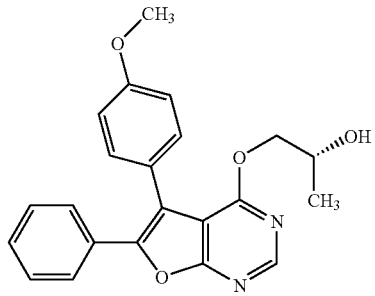

and (2R)-2-{[5-(4-methoxyphenyl)-6-phenylfuro[2,3-d]pyrimidin-4-yl]oxy}propan-1-ol

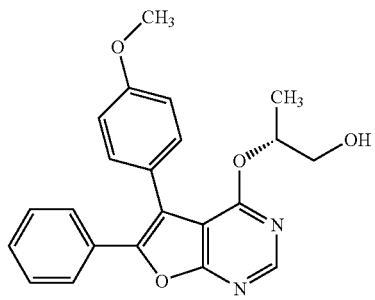

Put 5.648 g (74.23 mmol) (2R)-propane-1,2-diol in 30 ml THF. Add 4.165 g (37.11 mmol) potassium tert.-butylate and stir for a further 15 min at RT. Then cool to 0° C. and add a solution of 5.00 g (14.85 mmol) 4-chloro-5-(4-methoxyphenyl)-6-phenylfuro[2,3-d]pyrimidine in 15 ml THF dropwise over a time of 30 min. Then leave to return to RT and stir for a further 3 h. Then dilute with dichloromethane, add water and acidify with 10% citric acid solution. Separate the phases, extract the aqueous phase once with dichloromethane, combine the organic phases, wash once with satd. sodium chloride solution, dry over magnesium sulphate and concentrate by evaporation. Purify by chromatography on silica gel (solvent: cyclohexane/ethyl acetate 7:3). According to ¹H-NMR, the isolate is a mixture of the two title compounds. A total of 3.56 g (63.7% of theor.) is obtained.

LC-MS (Method 8): $R_t$=2.71 min (single peak); m/z=377 (M+H)⁺

¹H-NMR (400 MHz, CDCl₃): δ=8.50 (2×s, 2×1H), 7.62 (m, 2×2H), 7.42 (m, 2×2H), 7.31 (m, 2×3H), 6.97 (m, 2×2H), 5.31 (m, 1×1H), 4.48 (dd, 1×1H), 4.14 (dd, 1×1H), 4.01 (m, 1×1H), 3.39 (2×s, 2×3H), 3.72 (m, 1×1H), 3.55 (m, 1×1H), 1.31 (d, 1×3H), 1.15 (d, 1×3H).

Production of the compounds listed in the following table is analogous to the synthesis described above. It starts correspondingly from 4-chloro-5-(4-methoxyphenyl)-6-phenylfuro[2,3-d]-pyrimidine or from 4-chloro-5-(4-ethylphenyl)-6-phenylfuro[2,3-d]pyrimidine and uses (2S)-propane-1,2-diol or (2R)-propane-1,2-diol respectively:

| Example | Structure | Analytical data |
|---|---|---|
| 48A | 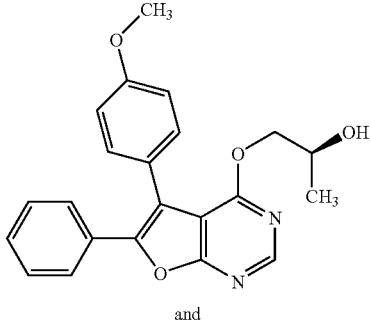 and 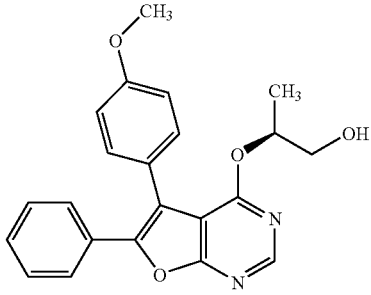 | LC-MS (Method 7): $R_t$ = 3.76 min (single peak); m/z = 377 (M + H)$^+$<br>$^1$H-NMR (400 MHz, DMSO-$d_6$):<br>δ = 8.58 (2x s, 2x 1 H), 7.52 (m, 2x 2 H), 7.40 (m, 2x 5 H), 7.00 (m, 2x 2 H), 5.36 (m, 1x 1 H), 4.80-4.70 (m, 1x 1 H), 4.37 (dd, 1x 1 H), 4.14 (dd, 1x 1 H), 3.81 (2x s, 2x 3 H), 3.46 (m, 1x 2 H), 1.20 (d, 1x 3 H). |
| 49A | 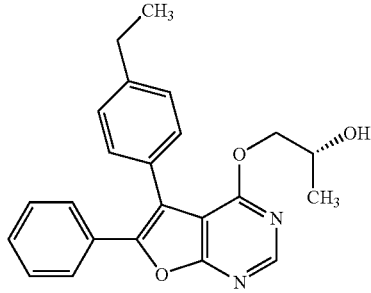 and 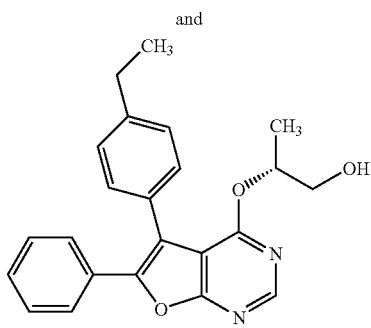 | LC-MS (Method 8): $R_t$ = 3.06 min (single peak); m/z = 375 (M + H)$^+$<br>$^1$H-NMR (400 MHz, DMSO-$d_6$):<br>δ = 8.57 (2x s, 2x, 1 H), 7.55 (m, 2x 2 H), 7.41 (m, 2x 5 H), 7.29 (m, 2x 2 H), 5.33 (m, 1x 1 H), 4.78 (t, 1x 1 H), 4.72 (d, 1x 1 H), 4.35 (dd, 1x 1 H), 4.11 (dd, 1x 1 H), 3.79 (m, 1x 1 H), 3.42 (m, 1x 2 H), 2.69 (2x q, 2x 2 H), 1.22 (2x t, 2x 3 H), 1.18 (d, 1x 3 H), 0.90 (d, 1x 3 H). |
| 50A | 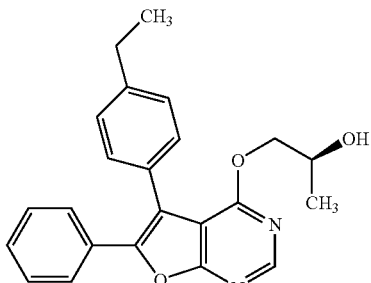 and 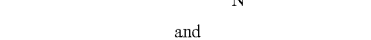 | LC-MS (Method 2): $R_t$ = 2.75 min (single peak); m/z = 375 (M + H)$^+$<br>$^1$H-NMR (400 MHz, DMSO-$d_6$):<br>δ 8.57 (2x s, 2x 1 H), 7.53 (m, 2x 2 H), 7.41 (m, 2x 5 H), 7.28 (m, 2x 2 H), 5.32 (m, 1x 1 H), 4.78 (t, 1x 1 H), 4.72 (d, 1x 1 H), 4.35 (dd, 1x 1 H), 4.11 (dd, 1x 1 H), 3.79 (m, 1x 1 H), 3.43 (m, 1x 2 H), 2.69 (2x q, 2x 2 H), 1.22 (2x t, 2x 3 H), 1.18 (d, 1x 3 H), 0.90 (d, 1x 3 H). |

Example 51A

1-[Benzyl(methyl)amino]acetone

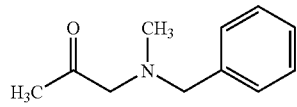

Put 12.118 g (100 mmol) N-methylbenzylamine with 16.584 g (120 mmol) potassium carbonate in 100 ml toluene. Add dropwise 11.103 g (120 mmol) chloroacetone and stir overnight under reflux. Then cool to RT, filter to remove the salt and concentrate by evaporation. Purify the residue by chromatography on silica gel (solvent: cyclohexane/ethyl acetate 8:2), obtaining 9.0 g (50.8% of theor.) of the target compound.

$^1$H-NMR (400 MHz, CDCl$_3$): δ=7.36-7.22 (m, 5H), 3.57 (s, 2H), 3.13 (s, 2H), 2.29 (s, 3H), 2.13 (s, 3H).

Example 52A (+/−)-1-[Benzyl(methyl)amino]propan-2-ol

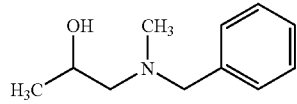

Put 8.00 g (45.13 mmol) 1-[benzyl(methyl)amino]acetone in 40 ml methanol. Add, at RT in portions with stirring, 854 mg (22.57 mmol) sodium borohydride. Stir for 30 min at RT and then for a further 30 min under reflux. Concentrate by evaporation and take up the residue in water. Extract twice with ethyl acetate, wash the combined organic phases once with satd. sodium hydrogencarbonate solution, dry over magnesium sulphate and concentrate by evaporation. 7.80 g (81.9% of theor.) of the target compound is obtained without further purification.

$^1$H-NMR (400 MHz, CDCl$_3$): δ=7.36-7.22 (m, 5H), 3.90-3.80 (m, 1H), 3.66 (d, 1H), 3.43 (d, 1H), 2.33 (dd, 1H), 2.31 (dd, 1H), 2.21 (s, 3H), 1.11 (d, 3H).

Example 53A (+/−)-N-Benzyl-2-{[5-(4-methoxyphenyl)-6-phenyl-furo[2,3-d]pyrimidin-4-yl]oxy}-N-propane-1-amine

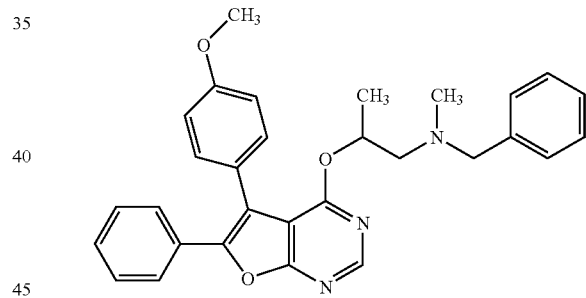

Put 1.878 g (8.91 mmol) (+/−)-1-[benzyl(methyl)amino] propan-2-ol under argon in 20 ml THF and cool to 0° C. Add 4.5 ml (8.91 mmol) of a 2 M solution of the phosphazene base P2-tert.-butyl in THF and stir for a further 10 min at RT. Then cool to 0° C. again. Add 2.00 g (5.94 mmol) 4-chloro-5-(4-methoxyphenyl)-6-phenylfuro[2,3-d]pyrimidine and stir for 1 h at RT. Then dilute with ethyl acetate and wash with water. Extract the aqueous phase once more with ethyl acetate. Combine the organic phases and wash with satd. sodium chloride solution, dry over magnesium sulphate and concentrate by evaporation. Purify by chromatography on silica gel (solvent: cyclohexane/ethyl acetate 85:15), obtaining 1.71 g (60.0% of theor.) of the target compound.

LC-MS (Method 8): R$_t$=1.88 min; m/z=480 (M+H)$^+$ $^1$H-NMR (400 MHz, DMSO-d$_6$): δ=8.50. (s, 1H), 7.62 (m, 2H), 7.36 (d, 2H), 7.32-7.15 (m, 8H), 6.86 (d, 2H), 5.65-5.57

(m, 1H), 3.81 (s, 3H), 3.41 (dd, 2H), 2.62 (dd, 1H), 2.43 (dd, 1H), 2.10 (s, 3H), 1.29 (d, 3H).

Example 54A (+/−)-2-{[5-(4-Methoxyphenyl)-6-phenylfuro[2,3-d]pyrimidin-4-yl]oxy}-N-methylpropane-1-amine

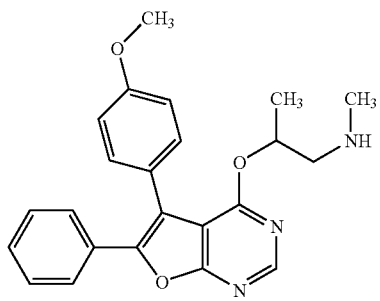

Put 500 mg palladium on charcoal (10%) under argon in 100 ml methanol. Add 1.7 g (3.55 mmol) (+/−)-N-Benzyl-2-{[5-(4-methoxyphenyl)-6-phenylfuro[2,3-d]pyrimidin-4-yl]oxy}-N-methylpropane-1-amine and 2.5 ml acetic acid, and hydrogenate at RT and normal pressure. After 2 h filter with a diatomite filter and concentrate by evaporation. Dissolve the residue in water and wash twice with ethyl acetate. Discard the ethyl acetate phases. Make the aqueous phase basic with solid sodium hydrogencarbonate and extract twice with ethyl acetate. Wash the combined ethyl acetate phases once with satd. sodium chloride solution, dry over magnesium sulphate and concentrate by evaporation. 900 mg (65.2% of theor.) of the target compound is obtained.

LC-MS (Method 2): $R_t$=1.57 min; n/z 390 (M+H)$^+$ $^1$H-NMR (400 MHz, CDCl$_3$): δ=8.50 (s, 1H), 7.63 (m, 2H), 7.38 (d, 2H), 7.34-7.25 (m, 3H), 6.96 (d, 2H), 5.45-5.35 (m, 1H), 3.88 (s, 3H), 2.64 (m, 2H), 2.30 (s, 3H), 1.35 (d, 3H).

Example 55A (+)-tert.-Butyl{[1,5-dimethylhex-4-en-1-yl]oxy}diphenylsilane

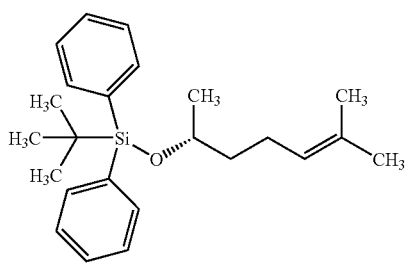

Put 50 g (390.0 mmol) (6R)-6-methyl-5-hepten-2-ol in 500 ml dichloromethane. Add 53.10 g (779.9 mmol) imidazole and 2.382 g (19.50 mmol) 4-dimethylaminopyridine. Cool to 0° C. and add dropwise 117.91 g (429.0 mmol) tert.-butyldiphenylchlorosilane. Remove the cooling, leave to return to RT and stir for a further 1 h at RT. Add 250 ml dichloromethane and wash twice with 500 ml water each time. Dry the organic phase over magnesium sulphate and concentrate by evaporation. Purify the residue by chromatography on silica gel (solvent: petroleum ether/ethyl acetate 95:5). 135.0 g (94.4% of theor.) of the target compound is obtained.

$^1$H-NMR (400 MHz, CDCl$_3$): δ=7.69 (m, 4H), 7.42-7.32 (m, 6H), 5.00-4.95 (t, 1H), 3.88-3.80 (m, 1H), 2.02-1.88 (m, 2H), 1.62 (s, 3H), 1.52 (s, 3H), 1.52-1.48 (m, 2H), 1.06 (s, 3H), 1.05 (s, 9H).

$[α]_D^{20}$=+20.2°, c=0.689, methanol.

Example 56A (+)-(2E)-6-{[tert.-Butyl(diphenyl)silyl]oxy}hept-2-enoic acid tert.-butyl ester

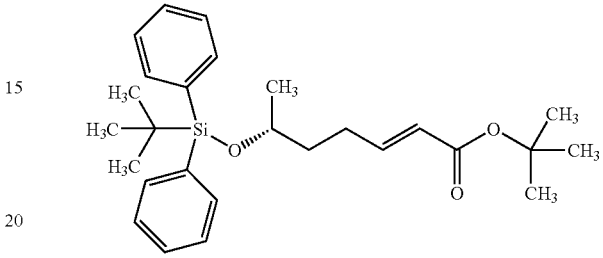

Put 22.20 g (60.55 mmol) (+)-tert.-butyl{[1,5-dimethylhex-4-en-1-yl]oxy}diphenylsilane with 165 mg (1.96 mmol) sodium hydrogencarbonate in 240 ml dichloromethane and cool to −78° C. Feed in ozone gas at −78° C., until there is a light bluish coloration of the solution. Then add 47.376 g (762 mmol) dimethylsulphide, leave to return to RT and stir for a further 1 h at RT. Then add 27.352 g (72.66 mmol) triphenylphosphoranylidene-tert.-butyl acetate and stir the mixture overnight at RT. Then concentrate the mixture by evaporation. Purify the residue by chromatography on silica gel (solvent: cyclohexane/ethyl acetate 95:5), obtaining 25.1 g (95.4% of theor.) of the target compound. According to $^1$H-NMR, the E/Z ratio is >10:1.

MS (DCI): m/z=456 (M+NH$_4$)$^+$ $^1$H-NMR (400 MHz, CDCl$_3$): δ=7.67 (d, 4H), 7.43-7.33 (m, 6H), 6.82-6.73 (dt, 1H), 5.65 (d, 1H), 3.91-3.82 (m, 1H), 2.28-2.10 (m, 2H), 1.65-1.42 (m, 2H), 1.48 (s, 9H), 1.06 (d, 3H), 1.05 (s, 9H).

$[α]_D^{20}$=+22.5°, c=0.520, methanol.

Example 57A (2E,6R)-6-Hydroxyhept-2-enoic acid tert.-butyl ester

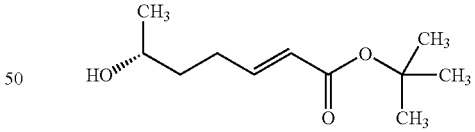

Solution A: suspend 10.71 g (267.7 mmol) of 60% sodium hydride in 150 ml abs. THF and add dropwise, with cooling, 43.3 ml (276.7 mmol) P,P-dimethylphosphonoacetic acid tert.-butyl ester. Stir the mixture at RT, obtaining a solution after approx. 30 min.

Add 187.4 ml (187.4 mmol) of a 1 M solution of DIBAH in THF dropwise to a solution of 17.87 g (178.5 mmol) (R)-γ-valerolactone [(5R)-5-methyldihydrofuran-2(3H)-one] in 200 ml abs. THF cooled to −78° C. Stir the solution for a further 1 h at −78° C. and then add solution A prepared above. At the end of addition, slowly heat the mixture to RT and stir overnight at RT. Add the reaction mixture to 300 ml ethyl acetate and precipitate with 50 ml concentrated potassium sodium tartrate solution. After phase separation, extract the aqueous phase again with ethyl acetate. Combine the organic phases, wash with satd. sodium chloride solution, dry over magnesium sulphate and concentrate under vacuum. Purify the residue by chromatography on silica gel (eluent: cyclohexane/ethyl acetate 5:1). 32.2 g (90.1% of theor.) of the target product, containing small amounts of the cis-isomer, is obtained.

MS (DCI): m/z=218 (M+NH$_4$)$^+$ $^1$H-NMR (400 MHz, DMSO-d$_6$): δ=6.70 (dt, 1H), 5.73 (d, 1H), 4.44 (d, 1H), 3.58 (m, 1H), 2.28-2.13 (m, 2H), 1.47-1.40 (m, 2H), 1.45 (s, 9H), 1.04 (d, 3H).

Example 58A (+)-6-{[tert.-Butyl(diphenyl)silyl]oxy}heptanoic acid tert.-butyl ester

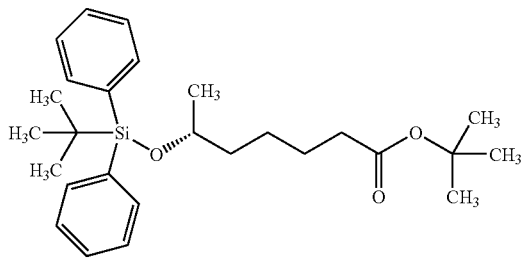

Put 149.0 g (339.64 mmol) (+)-(2E)-6-{[tert.-butyl(diphenyl)silyl]oxy}hept-2-enoic acid tert.-butyl ester in 1000 ml ethanol at RT under argon. Add 15.0 g palladium/charcoal (20%, moist with water) and hydrogenate at normal pressure at RT. At the end of hydrogen uptake, filter the mixture on diatomite and concentrate by evaporation. 142.0 g (95.0% of theor.) of the target compound is obtained.

MS (DCI): m/z=458 (M+NH$_4$)$^+$ $^1$H-NMR (400 MHz, CDCl$_3$): δ=7.68 (d, 4H), 7.43-7.33 (m, 6H), 3.87-3.80 (m, 1H), 2.12 (t, 2H), 1.53-1.20 (m, 6H), 1.45 (s, 9H), 1.05 (d, 3H), 1.05 (s, 9H).

[α]$_D^{20}$=+14.7°, c=0.7925, methanol.

Example 59A (−)-6-Hydroxyheptanoic acid tert.-butyl ester

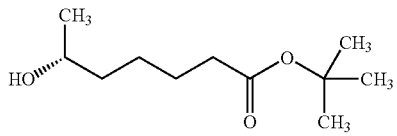

Method 1:

Put 141.0 g (319.94 mmol) (+)-6-{[tert.-butyl(diphenyl)silyl]oxy}heptanoic acid tert.-butyl ester in 280 ml THF. Add dropwise 479.90 ml (479.90 mmol) of a 1 M solution of tetrabutylammonium fluoride in THF and stir overnight at RT. Then add 4000 ml of a 10% aqueous sodium chloride solution and adjust to a pH value of about 3-4 with citric acid. Extract twice with 2000 ml ethyl acetate each time, and wash the combined ethyl acetate phases once with 2000 ml satd. sodium chloride solution. Dry over magnesium sulphate, concentrate by evaporation and purify by chromatography on silica gel (solvent: cyclohexane/ethyl acetate 7:3). 50.2 g (77.5% of theor.) of the target product is obtained.

MS (DCI): m/z=220 (M+NH$_4$)$^+$ $^1$H-NMR (400 MHz, CDCl$_3$): δ=3.85-3.75 (m, 1H), 2.22 (t, 2H), 1.68-1.54 (m, 2H), 1.53-1.30 (m, 4H), 1.45 (s, 9H), 1.18 (d, 3H).

[α]$_D^{20}$=−6.8°, c=1.073, methanol.

Method 2:

Dissolve 32.2 g (160.8 mmol) (2E,6R)-6-hydroxyhept-2-enoic acid tert.-butyl ester in 200 ml ethanol and add 1.7 g 10% palladium on charcoal. Stir the mixture for 2 h at RT under a hydrogen atmosphere (normal pressure) and then filter on Celite. Concentrate the filtrate by vacuum evaporation. After chromatography on silica gel (eluent: cyclohexane/ethyl acetate 10:1→6:1), 15.66 g of the target product (48.1% of theor.) is obtained from the residue.

[α]$_D^{20}$=−21°, c=0.118, chloroform.

Example 60A (+)-{[5-(4-Methoxyphenyl)-6-phenylfuro[2,3-d]pyrimidin-4-yl]amino}propan-2-ol

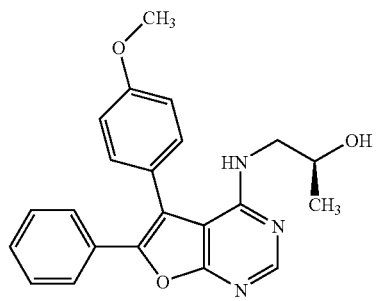

Add 2 ml DMF, 223 mg (2.97 mmol) (S)-(+)-1-amino-2-propanol and 768 mg (5.94 mmol) N,N-diisopropylethylamine to 500 mg (1.49 mmol) 4-chloro-5-(4-methoxyphenyl)-6-phenylfuro[2,3-d]pyrimidine. Heat to 100° C. for 2 h and then leave to cool to RT. Separate the mixture without further processing, directly by preparative RP-HPLC (solvent: acetonitrile/water gradient). 230 mg (41.3% of theor.) of the target compound is obtained.

LC-MS (Method 2): R$_t$=2.25 min; m/z=376 (M+H)$^+$ $^1$H-NMR (400 MHz, CDCl$_3$): δ=8.36 (s, 1H), 7.53 (m, 2H), 7.40 (d, 2H), 7.27 (m, 3H), 7.07 (d, 2H), 5.13 (m, 1H), 3.92 (m, 4H), 3.56 (m, 1H), 3.32 (m, 1H), 1.15 (d, 2H).

[α]$_D^{20}$=+3.0°, c=0.298, methanol.

Example 61A (−)-1-{[5-(4-Methoxyphenyl)-6-phenylfuro[2,3-d]pyrimidin-4-yl]amino}propan-2-ol

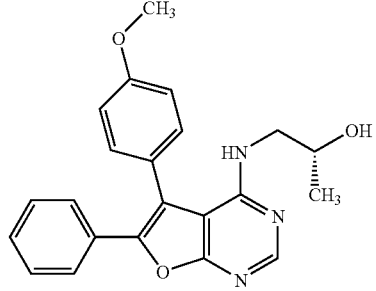

Add 5 ml DMSO, 446 mg (5.94 mmol) (R)-(−)-1-amino-2-propanol and 2.07 ml (11.88 mmol) N,N-diisopropylethylamine to 1.00 g (2.97 mmol) 4-chloro-5-(4-methoxyphenyl)-

6-phenylfuro[2,3-d]pyrimidine. Heat to 100° C. for 2 h and then leave to cool to RT. Then pour onto an ice-water mixture and wait for the ice to melt. Decant the aqueous phase, dilute the organic phase with dichloromethane and wash once with water. Re-extract the aqueous phase once with dichloromethane. Combine the organic phases and wash once with satd. sodium chloride solution, dry over magnesium sulphate and concentrate by evaporation. 1.10 g (98.7% of theor.) of the target compound is obtained.

LC-MS (Method 2): $R_t$=2.25 min; m/z=376 (M+H)$^+$
$^1$H-NMR (400 MHz, CDCl$_3$): δ=8.36 (s, 1H), 7.53 (m, 2H), 7.40 (d, 2H), 7.27 (m, 3H), 7.07 (d, 2H), 5.13 (t, 1H), 3.92 (m, 4H), 3.56 (m, 1H), 3.32 (m, 1H), 1.15 (d, 2H).
$[α]_D^{20}$=3.1°, c=0.455, methanol.

Example 62A

3-{[5-(4-Methoxyphenyl)-6-phenylfuro[2,3-d]pyrimidin-4-yl]oxy}-2,2-dimethylpropan-1-ol

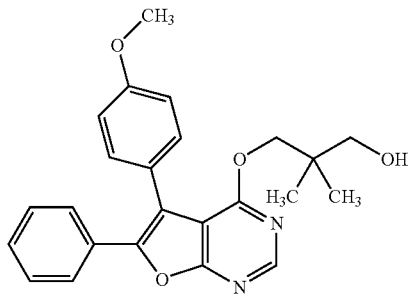

Put 1.546 g (14.85 mmol) 2,2-dimethylpropane-1,3-diol in 30 ml THF. Add 833 mg (7.42 mmol) potassium tert.-butylate and stir for a further 15 min at RT. Then cool to 0° C. and add a solution of 1.00 g (2.97 mmol) 4-chloro-5-(4-methoxyphenyl)-6-phenylfuro[2,3-d]pyrimidine in 15 ml THF dropwise over a time of 30 min. Leave to return to RT and stir for a further 30 min at RT. Then add dichloromethane and water, acidify with 10% citric acid solution and separate the phases. Extract the aqueous phase once with dichloromethane. Combine the organic phases and wash once with satd. sodium chloride solution, dry over magnesium sulphate and concentrate by evaporation. 1.20 g (99.9% of theor.) of the target compound is obtained.

LC-MS (Method 7): $R_t$=3.99 min; m/z=405 (M+H)$^+$
$^1$H-NMR (400 MHz, DMSO-d$_6$): δ=8.57 (s, 1H), 7.53 (d, 2H), 7.42-7.33 (m, 5H), 7.02 (d, 2H), 4.52 (t, 1H), 4.11 (s, 2H), 3.81 (s, 3H), 3.01 (d, 2H), 0.69 (s, 6H).

Example 63A (+)-4-(Trityloxy)butan-2-ol

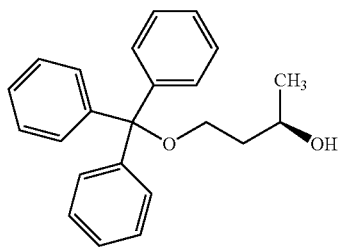

Put 18.560 g (205.94 mmol) (R)-(−)-1,3-butanediol in 260 ml dichloromethane and add 27.092 g (267.72 mmol) triethylamine. Cool to 0° C. and slowly add 57.987 g (208.00 mmol) chlorotriphenylmethane. Leave to return to RT and stir overnight at RT. Then add 12.9 ml methanol and stir for 30 min. Wash twice with water, twice with satd. ammonium chloride solution and once with satd. sodium chloride solution, dry over magnesium sulphate and concentrate by evaporation. Purify the residue by chromatography on silica gel (solvent: cyclohexane/ethyl acetate 10:1→2:1). 60.990 g (89.1% of theor.) of the target compound is obtained.

MS (DCI): m/z=350 (M+NH$_4$)$^+$
$^1$H-NMR (400 MHz, DMSO-d$_6$): δ=7.40-7.30 (m, 12H), 7.38-7.23 (m, 3H), 4.32 (d, 1H), 3.80-3.70 (m, 1H), 3.10-2.97 (m, 2H), 1.70-1.55 (m, 2H), 1.00 (d, 3H).
$[α]_D^{20}$=+24.20°, c=0.520, chloroform.

Example 64A (−)-[{[3-(Benzyloxy)butyl]oxy}(diphenyl)methyl]benzene

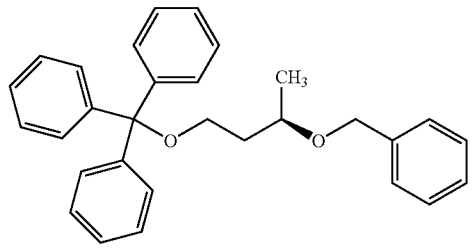

Put 10.997 g (274.95 mmol) sodium hydride in 150 ml DMF at RT. Add 60.937 g (183.29 mmol) (+)-4-(trityloxy)butan-2-ol and stir for a further 15 min at RT. Cool to 0° C. and add 62.704 g (366.59 mmol) benzyl bromide. Then add a further 50 ml DMF, leave to return to RT and stir overnight. Carefully add water and extract twice with ethyl acetate. Combine the organic phases and wash twice with satd. sodium chloride solution, dry over magnesium sulphate and concentrate by evaporation. Purify the residue by chromatography on silica gel (solvent: cyclohexane/dichloromethane 5:1→1:1). 71.750 g (92.6% of theor.) of the target compound is obtained.

MS (DCI): m/z=440 (M+NH$_4$)$^+$
$^1$H-NMR (400 MHz, DMSO-d$_6$): δ=7.40-7.23 (m, 18H), 7.16 (d, 2H), 4.48 (d, 1H), 4.31 (d, 1H), 3.73-3.66 (m, 1H), 3.13-3.02 (m, 2H), 1.81-1.68 (m, 2H), 1.10 (d, 3H).
$[α]_D^{20}$=−10.8°, c=0.500, chloroform.

Example 65A (−)-3-(Benzyloxy)butan-1-ol

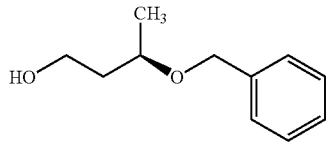

Add a mixture of water/acetic acid/methanol (3:4:3) to 71.750 g (169.79 mmol) (−)-[{[3-(benzyloxy)butyl]oxy}(diphenyl)methyl]benzene and stir overnight at 50° C. Then add water and extract with dichloromethane. Dry the organic phase over magnesium sulphate and concentrate by evaporation. Mix the residue with cyclohexane. Filter off the solid on a frit, wash three times with cyclohexane, discard the solid and concentrate the filtrate by evaporation. Purify the residue by chromatography on silica gel (solvent: cyclohexane/ethyl acetate 10:1→4:1). 21.97 g (71.8% of theor.) of the target compound is obtained.

MS (DCI): m/z=190 (M+NH$_4$)$^+$ $^1$H-NMR (400 MHz, DMSO-d$_6$): δ=7.35-7.24 (m, 5H), 4.52 (d, 1H), 4.39 (d, 1H), 4.33 (t, 1H); 3.65-3.58 (m, 1H), 3.52-3.45 (m, 2H), 1.74-1.65 (m, 1H), 1.57-1.48 (m, 1H), 1.13 (d, 3H).

[α]$_D^{20}$=−65.7°, c=0.530, chloroform.

Example 66A (−)-4-{[3-(Benzyloxy)butyl]oxy}-5-(4-methoxyphenyl)-6-phenylfuro[2,3-d]pyrimidine

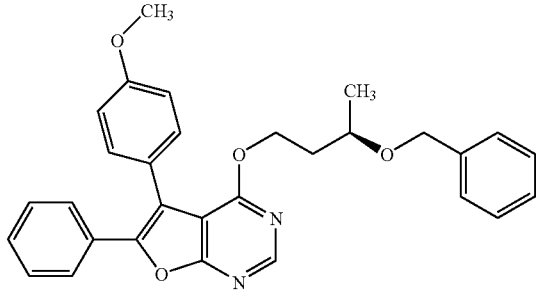

Put 802 mg (4.45 mmol) (3R)-3-benzyloxy)butan-1-ol under argon in 10 ml THF and cool to 0° C. Add 2.30 ml (4.45 mmol) of a 2 M solution of the phosphazene base P2-tert.-butyl in THF and stir for 10 min at RT. Then cool again to 0° C. Add 1.0 g (2.97 mmol) 4-chloro-5-4-methoxyphenyl)-6-phenylfuro[2,3-d]pyrimidine and stir overnight at RT. Then dilute with ethyl acetate, add water and acidify with 10% citric acid solution. Extract the aqueous phase once with ethyl acetate. Wash the combined ethyl acetate phases once with satd. sodium chloride solution, dry over magnesium sulphate and concentrate by evaporation. Purify by chromatography on silica gel (solvent: cyclohexane/ethyl acetate 9:1), obtaining 1.16 g (81.3% of theor.) of the target compound.

LC-MS (Method 7): R$_t$=4.70 min; m/z=481 (M+H)$^+$ $^1$H-NMR (400 MHz, DMSO-d$_6$): δ=8.52 (s, 1H), 7.62 (m, 2H), 7.31 (m, 5H), 7.25-7.12 (m, 5H), 6.91 (d, 2H), 4.55-4.44 (m, 3H), 4.22 (d, 1H), 3.82 (s, 3H), 3.40-3.31 (m, 1H), 1.88-1.82 (m, 1H), 1.79-1.71 (m, 1H), 1.12 (d, 3H).

[α]$_D^{20}$=−79.0°, c=0.455, methanol.

Example 67A (−)-4-{[5-(4-Methoxyphenyl)-6-phenylfuro[2,3-d]pyrimidin-4-yl]oxy}butan-2-ol

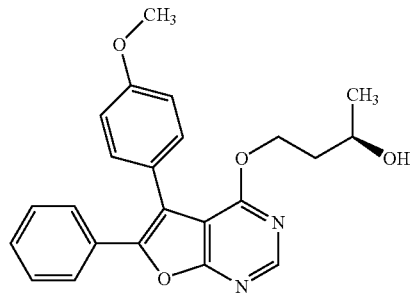

Dissolve 1.0 g (2.08 mmol) (−)-4-{[3-(benzyloxy)butyl]oxy}-5-(4-methoxyphenyl)-6-phenylfuro[2,3-d]pyrimidine in 20 ml dioxan and add 100 mg palladium/charcoal (10%). Hydrogenate at normal pressure and RT for approx. 5 h until hydrogen uptake ceases. Then filter the catalyst on Celite and concentrate the filtrate by evaporation. Purify the residue by chromatography on silica gel (solvent: cyclohexane/ethyl acetate 7:3→1:1). 675 mg (83.1% of theor.) of the target compound is obtained.

LC-MS (Method 7): R$_t$=3.78 min; m/z=391 (M+H)$^+$ $^1$H-NMR (400 MHz, CDCl$_3$): δ=8.51 (s, 1H), 7.62 (m, 2H), 7.38 (d, 2H), 7.31 (m, 3H), 6.95 (d, 2H), 4.73-4.67 (m, 1H), 4.46-4.40 (m, 1H), 3.88 (s, 3H), 3.75-3.65 (m, 1H), 2.20 (br. s, 1H), 1.83-1.76 (m, 1H), 1.75-1.68 (m, 1H), 1.16 (d, 3H).

[α]$_D^{20}$=−60.0°, c=0.5305, methanol.

Example 68A

3-{[5-(4-Methoxyphenyl)-6-phenylfuro[2,3-d]pyrimidin-4-yl]oxy}propan-1-ol

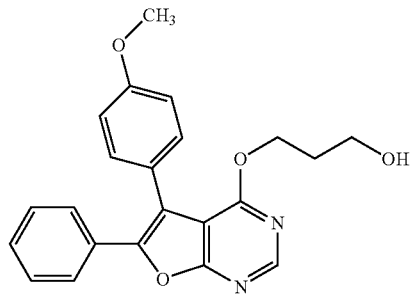

Put 1.13 g (14.85 mmol) 1,3-propanediol in 30 ml THF. Add 833 mg (7.42 mmol) potassium tert.-butylate and stir for 15 min at RT. Then cool to 0° C. and add a solution of 1.0 g (2.97 mmol) 4-chloro-5-(4-methoxyphenyl)-6-phenylfuro[2,3-d]pyrimidine in 15 ml THF dropwise over a time of 30 min. Then leave to return to RT and stir for a further 2 h. Dilute with dichloromethane and water, acidify with 10% citric acid solution and separate the phases. Extract the aqueous phase once with dichloromethane. Combine the organic phases and wash once with satd. sodium chloride solution. Dry over magnesium sulphate, concentrate by evaporation and purify the residue by chromatography on silica gel (solvent: cyclohexane/ethyl acetate 7:3→1:1). 772 mg (69.0% of theor.) of the target compound is obtained.

LC-MS (Method 9): R$_t$=3.47 min; m/z=377 (M+H)$^+$ $^1$H-NMR (400 MHz, CDCl$_3$): δ=8.52 (s, 1H), 7.62 (m, 2H), 7.39 (d, 2H), 7.31 (m, 3H), 6.96 (d, 2H), 4.58 (t, 2H), 3.89 (s, 3H), 3.58 (t, 2H), 1.90 (quin, 2H).

Example 69A

1-[(Z)-2-Chloro-2-nitrovinyl]-4-methoxybenzene

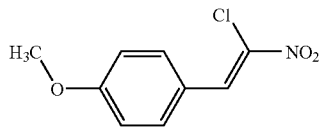

As in a procedure described in the literature [D. Dauzonne, *Synthesis*, 1990, 66-70], stir a mixture of 10.0 g (73.5 mmol) 4-methoxybenzaldehyde, 9.0 ml (13.5 g, 96.2 mmol) bromonitromethane, 53.9 g (661.0 mmol) dimethylammonium chloride and 0.6 g (1.0 mmol) potassium fluoride in 150 ml xylene on a water separator at 160° C. for 15 hours. After adding 25 ml water and 100 ml dichloromethane, separate the organic phase and extract the aqueous phase three times with 100 ml dichloromethane each time. Dry the combined organic extracts over sodium sulphate, filter and concentrate by vacuum evaporation. Chromatograph the residue on silica gel (solvent: cyclohexane/dichloromethane 1:1). 9.6 g (59% of theor.) of the target compound is obtained.

LC-MS (Method 8): $R_t$=2.52 min $^1$H-NMR (400 MHz, CDCl$_3$): δ=8.60 (s, 1H), 8.03 (d, 2H), 7.15 (d, 2H), 3.86 (s, 3H).

Example 70A 5-(4-Methoxyphenyl)furo[2,3-d]pyrimidin-4(3H)-one

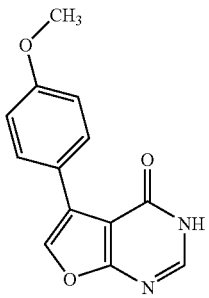

As in the procedure described in the literature [D. Dauzonne, *Tetrahedron*, 1992, 3069-3080], stir a suspension of 10.1 g (47.4 mmol) 1-[(Z)-2-chloro-2-nitrovinyl]-4-methoxybenzene and 5.8 g (52.2 mmol) 4,6-dihydroxypyrimidine in 200 ml ethanol for ten minutes at 85° C. Next, slowly add 15.6 ml (15.9 g, 104.3 mmol) 1,8-diazabicyclo[5.4.0]undec-7-ene. Stir for 15 h at this temperature and then concentrate by vacuum evaporation. Take up the residue in dichloromethane and chromatograph on silica gel (solvent: dichloromethane/methanol 95:5). Mix the solid obtained with acetonitrile and then filter. 2.3 g (20% of theor.) of the target product is obtained.

LC-MS (Method 2): $R_t$=1.57 min; m/z=290 (M+H)$^+$ $^1$H-NMR (400 MHz, CDCl$_3$): δ=12.66 (s, 1H), 8.15 (s, 1H), 8.14 (s, 1H), 7.92 (d, 2H), 6.98 (d, 2H), 3.79 (s, 3H).

Example 71A

4-Chloro-5-(4-methoxyphenyl)furo[2,3-d]pyrimidine

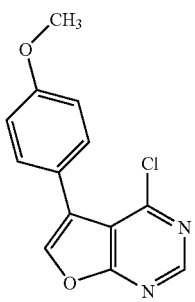

Add 14.5 ml (13.6 g, 90.8 mmol) N,N-diethylaniline to a suspension of 10.0 g (41.3 mmol) 5-(4-methoxyphenyl)furo[2,3-d]pyrimidin-4(3H)-one in 250 ml toluene and heat to 100° C. At this temperature, add 4.2 ml (7.0 g, 45.4 mmol) phosphoryl chloride dropwise, and stir the reaction mixture for 15 h at 100° C. Then add a further 1.2 ml (2.0 g, 13 mmol) phosphoryl chloride and stir the reaction mixture again for 22 h at 100° C. After cooling to room temperature, quickly wash the reaction solution with, successively, 250 ml ice water, twice with 250 ml cold 20% sodium hydroxide solution each time, again with 250 ml ice water, 250 ml satd. sodium chloride solution, 1 N hydrochloric acid and 250 ml ice water. Dry the organic phase over sodium sulphate, filter and concentrate by vacuum evaporation. 6.3 g (59% of theor.) of the title compound is obtained.

LC-MS (Method 10): $R_t$=2.28 min; m/z=261 (M+H)$^+$ $^1$H-NMR (400 MHz, CDCl$_3$): δ=8.86 (s, 1H), 8.40 (s, 1H), 7.52 (d, 2H), 7.08 (d, 2H), 3.82 (s, 3H).

Example 72A

6-{[5-(4-Methoxyphenyl)furo[2,3-d]pyrimidin-4-yl]amino}hexanoic acid methyl ester

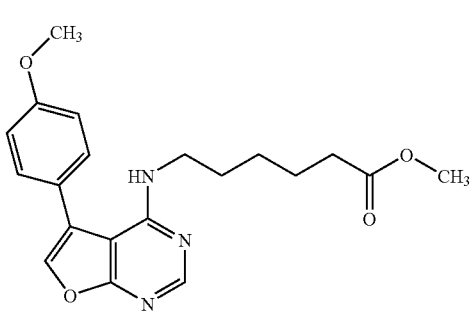

Dissolve 7.1 g (27.2 mol) 4-chloro-5-(4-methoxyphenyl)furo[2,3-d]pyrimidine in 250 ml acetonitrile and add 5.9 g (32.7 mmol) 6-aminohexanoic acid methyl ester hydrochloride and 9.4 g (68.1 mmol) potassium carbonate. Heat the mixture under reflux for 18 hours and then filter after cooling to room temperature. Mix the residue three times in 50 ml water each time, filter and dry under vacuum. 4.1 g (41% of theor.) of the title compound is obtained.

LC-MS (Method 8): $R_t$=2.47 min; m/z=370 (M+H)$^+$ $^1$H-NMR (400 MHz, CDCl$_3$): δ=8.31 (s, 1H), 7.88 (s, 1H), 7.42 (d, 2H), 7.10 (d, 2H), 5.79 (t, NH), 3.82 (s, 3H), 3.57 (s, 3H), 3.43 (q, 2), 2.30 (t, 2H), 1.57-1.48 (m, 4H), 1.31-1.24 (m, 2H).

Example 73A

6-{[6-Bromo-5-(4-methoxyphenyl)furo[2,3-d]pyrimidin-4-yl]amino}hexanoic acid methyl ester

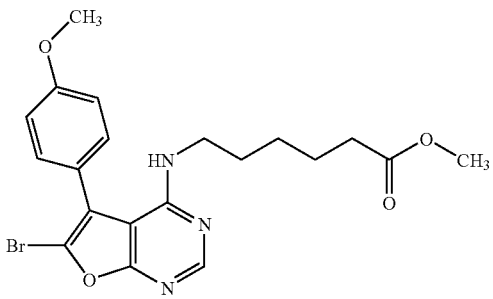

Dissolve 4.1 g (11.1 mmol) 6-{[5-(4-methoxyphenyl)furo[2,3-d]pyrimidin-4-yl]amino}hexanoic acid methyl ester at room temperature in 150 ml carbon tetrachloride and add 2.2 g (12.2 mmol) N-bromosuccinimide. Stir the mixture under reflux for three hours, then filter after cooling to room temperature and concentrate the filtrate by vacuum evaporation. 4.8 g (96% of theor.) of the title compound is obtained.

LC-MS (Method 10): $R_t$=2.65 min; m/z=448 (M+H)$^+$

¹H-NMR (400 MHz, CDCl₃): δ=8.29 (s, 1H), 7.41 (d, 2H), 7.12 (d, 2H), 5.61 (t, NH), 3.82 (s, 3H), 3.57 (s, 3H), 3.38 (q, 2H), 2.28 (t, 2H), 1.54-1.42 (m, 4H), 1.26-1.18 (m, 2H).

Example 74A 2-(2-Fluorophenyl)-2-hydroxy-1-(4-methoxyphenyl)ethanone

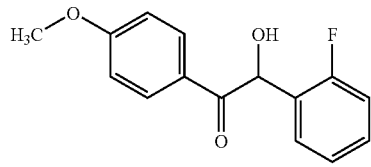

Add 441 ml (1.10 mol) of a 2.5 M n-butyllithium solution in n-hexane dropwise at −78° C. to a solution of 156 ml (1.11 mol) N,N-diisopropylamine in 1937 ml 1,2-dimethoxyethane in such a way that a temperature of −60° C. is not exceeded. After stirring for 15 min at this temperature, add a solution of 236 g (1.00 mol) (4-methoxyphenyl)[(trimethylsilyl)oxy]acetonitrile [N. Kurono, *J. Org. Chem.* 2005, 16, 6530-6532] in 753 ml 1,2-dimethoxyethane dropwise in the space of 30 min. Next, after stirring for 30 min at this temperature, add a solution of 128 g (1.00 mol) 2-fluorobenzaldehyde in 753 ml 1,2-dimethoxyethane dropwise in the space of 20 min. Leave the reaction mixture to warm to room temperature in 4 h. After adding 3800 ml satd. aqueous ammonium chloride solution, extract with ethyl acetate. Wash the organic phase with satd. ammonium chloride solution, dry over sodium sulphate, filter, and concentrate the filtrate by vacuum evaporation. Add 3800 ml dioxan, 2700 ml methanol and 3120 ml 1 M hydrochloric acid to the residue and stir for 16 h at room temperature. After adding 8000 ml satd. aqueous sodium chloride solution, extract with 4000 ml ethyl acetate. Re-extract the aqueous phase with 2000 ml ethyl acetate. Combine the organic phases and wash with 2000 ml water and 2000 ml satd. sodium chloride solution, dry over sodium sulphate, filter, and concentrate the filtrate by vacuum evaporation. Mix the residue with 600 ml diisopropyl ether and filter. Concentrate the mother liquor by vacuum evaporation. Take up the residue in dichloromethane and purify by flash chromatography on silica gel (solvent: cyclohexane/ethyl acetate 4:1). Mix the product fraction thus obtained with diisopropyl ether/petroleum ether (1:1), filter, and dry under vacuum. 94 g (80% purity, 29% of theor.) of the title compound is obtained.

LC-MS (Method 11): R_t=4.59 min; m/z=261 (M+H)⁺

¹H-NMR (400 MHz, CDCl₃): δ=7.93-7.91 (m, 2H), 7.28-7.18 (m, 2H), 7.10-7.04 (m, 2H), 6.89-6.86 (m, 2H), 6.19 (d, 1H), 4.69 (s, 1H), 3.82 (s, 3H).

Example 75A

2-Amino-5-2-fluorophenyl)-4-(4-methoxyphenyl)-3-furonitrile

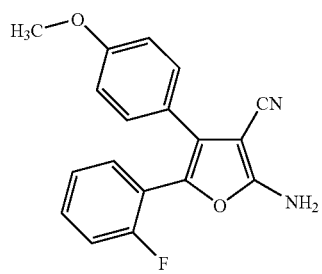

Put 84 g (0.32 mol) 2-(2-fluorophenyl)-2-hydroxy-1-(4-methoxyphenyl)ethanone and 32 g (0.48 mol) malononitrile in 153 ml THF. After stirring for five minutes, add 49 ml (36 g, 0.36 mol) triethylamine, with ice cooling. Stir the reaction mixture for 1 h with ice cooling. Then leave the reaction mixture to warm to room temperature and stir for 4 h at this temperature. After adding 1000 ml ethyl acetate, wash the organic phase five times with 300 ml water, dry over sodium sulphate and filter. Concentrate the filtrate by vacuum evaporation. Take up the residue in dichloromethane and purify by flash chromatography on silica gel (solvent: dichloromethane/methanol 70:1, then cyclohexane/ethyl acetate 2:1). 37 g (0.11 mol) of 2-(2-fluorophenyl)-2-hydroxy-1-(4-methoxyphenyl)ethanone thus recovered is again reacted with 14 g (0.03 mol) malononitrile and 21 ml (15 g, 0.15 mol) triethylamine in 67 ml THF in accordance with the above procedure. A total of 70 g (52% purity, 36% of theor.) of the target compound is obtained.

¹H-NMR (400 MHz, CDCl₃): δ=7.23-7.11 (m, 4H), 7.03-6.95 (m, 2H), 6.82-6.79 (m, 2H), 4.86 (s, NH₂), 3.74 (s, 3H).

Example 76A 6-(2-Fluorophenyl)-5-(4-methoxyphenyl)furo[2,3-d]pyrimidin-4(3H)-one

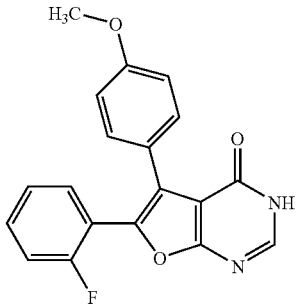

Add 268 ml formic acid dropwise to 436 ml acetic anhydride at 0° C. and stir for 30 min at this temperature. Then add a solution of 70 g (0.12 mol) 2-amino-5-(2-fluorophenyl)-4-(4-methoxyphenyl)-3-furonitrile in 100 ml acetic anhydride and stir the mixture for 24 h at 130° C. After cooling to room temperature, concentrate the mixture by evaporation in an oil-pump vacuum at 50° C. Mix the residue with 250 ml diisopropyl ether for 30 min with ice cooling, filter, wash with 70 ml diisopropyl ether and dry under vacuum. 23.7 g (60% of theor.) of the title compound is obtained.

HPLC (Method 1): R_t=4.27 min

MS (DCI): m/z=354 (M+NH₄)⁺

¹H-NMR (400 MHz, CDCl₃): δ=12.68 (br. s, NH), 8.19 (d, 1H), 7.53-7.45 (m, 2H), 7.34-7.25 (m, 4H), 6.91-6.88 (m, 2H), 3.76 (s, 3H).

Example 77A

4-Chloro-6-(2-fluorophenyl)-5-(4-methoxyphenyl) furo[2,3-d]pyrimidine

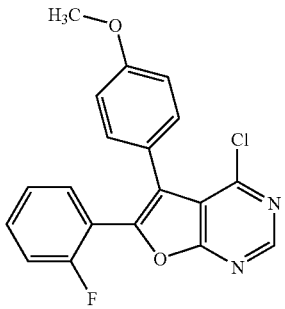

Stir a mixture of 20 g (0.06 mol) 6-(2-fluorophenyl)-5-4-(methoxyphenyl)furo[2,3-d]pyrimidin-4(3H)-one in 78 ml sulpholane and 11 ml (18 g, 0.12 mol) phosphoryl chloride for 1 h at 120° C. After cooling to room temperature, add the reaction solution dropwise to a mixture of 1000 ml water and 100 ml 25% aqueous ammonia solution, stirring vigorously and cooling with ice. Filter off the solid that is precipitated at 10° C. and wash several times with water. Dissolve the solid in 700 ml ethyl acetate again and wash the solution twice with 500 ml water each time. Dry the organic phase over sodium sulphate, filter, and concentrate the filtrate by vacuum evaporation. Mix the residue with 60 ml diisopropyl ether, filter, and dry under vacuum. 18 g (81% of theor.) of the title compound is obtained.

HPLC (Method 1): $R_t$=5.03 min $^1$H-NMR (400 MHz, DMSO-$d_6$): δ=8.90 (s, 1H), 7.58-7.50 (m, 2H), 7.36-7.27 (m, 4), 7.01-6.97 (m, 2H), 3.79 (s, 3H).

Example 78A 1-(4-Ethylphenyl)-2-(2-fluorophenyl)-2-hydroxyethanone

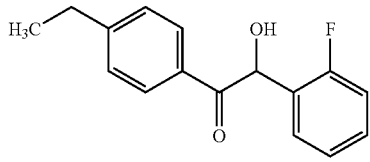

Add 217 ml (0.54 mol) of a 2.5 M n-butyllithium solution in hexane dropwise at −78° C. to a solution of 77 ml (56 g, 0.55 mol) N,N-diisopropylamine in 960 ml 1,2-dimethoxyethane in such a way that the temperature does not exceed −60° C. After stirring for 15 min at this temperature, add a solution of 116 g (0.50 mol) (4-ethylphenyl)[(trimethylsilyl)oxy]acetonitrile [D. S. Dhanoa, *J. Med. Chem.* 1993, 36 (23), 3738-3742] in 373 ml 1,2-dimethoxyethane dropwise in the space of 30 min. Next, after stirring for 30 min at this temperature, add a solution of 64 g (0.50 mol) 2-fluorobenzaldehyde in 373 ml 1,2-dimethoxyethane dropwise in the space of 20 min. Leave the reaction mixture to warm to room temperature in 4 h. After adding 1900 ml satd. aqueous ammonium chloride solution, extract with ethyl acetate. Wash the organic phase with satd. ammonium chloride solution, dry over sodium sulphate and filter. Concentrate the filtrate by vacuum evaporation. Add 1900 ml dioxan, 1350 ml methanol and 1560 ml 1 M hydrochloric acid to the residue and stir for 16 h at room temperature. After adding 4000 ml satd. aqueous sodium chloride solution, extract with 2000 ml ethyl acetate. Wash the organic phase with 1000 ml water and 1000 ml satd. sodium chloride solution, dry over sodium sulphate and filter. Concentrate the filtrate by vacuum evaporation. Purify the residue by flash chromatography on silica gel (solvent: cyclohexane/ethyl acetate 5:1). Mix the product fraction thus obtained in 80 ml diisopropyl ether and 240 ml petroleum ether, filter, wash with petroleum ether and dry under vacuum. 50 g (85% purity, 33% of theor.) of the title compound is obtained.

HPLC (Method 1): $R_t$=4.50 min

MS (DCI): m/z=276 (M+NH$_4$)$^+$ $^1$H-NMR (400 MHz, CDCl$_3$): δ=7.87-7.85 (m, 2H), 7.28-7.19 (m, 4H), 7.11-7.04 (m, 2H), 6.22 (d, 1H), 4.64 (d, 1H), 2.65 (q, 2H), 1.21 (t, 3H).

Example 79A

2-Amino-4-(4-ethylphenyl)-5-(2-fluorophenyl)-3-furonitrile

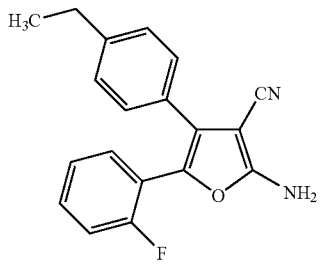

Put 50 g (0.19 mol) 1-(4-ethylphenyl)-2-(2-fluorophenyl)-2-hydroxyethanone and 17 g (0.25 mol) malononitrile in 93 ml DMF. After stirring for five minutes, add 17 ml (12 g, 0.12 mol) diethylamine, cooling with ice. Stir the reaction mixture for 1 h with ice cooling. Then leave to warm to room temperature and stir for 4 h at this temperature. After adding 500 ml water and stirring for 30 min, decant the aqueous phase. Add 500 ml water again and decant again, obtaining an oily residue, which is dissolved in ethyl acetate, dried over sodium sulphate and filtered. Concentrate the filtrate by vacuum evaporation. According to DC analysis (solvent: cyclohexane/ethyl acetate 4:1), the residue still contains 1-(4-ethylphenyl)-2-(2-fluorophenyl)-2-hydroxyethanone. Therefore, the residue is again reacted in 90 ml DMF with 5.5 g (0.08 mol) malononitrile and 10 ml (7 g, 0.10 mol) diethylamine in accordance with the above procedure. Add the reaction mixture to 500 ml ethyl acetate and wash three times with 300 ml water each time and once with 300 ml satd. sodium chloride solution. Dry the organic phase over sodium sulphate, and filter. Concentrate the filtrate by vacuum evaporation. Purify the residue by flash chromatography on silica gel (solvent: cyclohexane/ethyl acetate 3:1). 36 g (61% of theor.) of the title compound is obtained, and is reacted without further characterization.

Example 80A 5-(4-Ethylphenyl)-6-(2-fluorophenyl)furo[2,3-d]pyrimidin-4(3H)-one

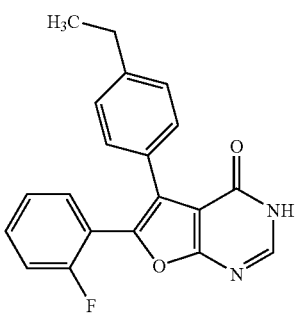

Add 140 ml (3.71 mol) formic acid dropwise to 280 ml (2.97 mol) acetic anhydride at 0° C. and stir for 30 min at this temperature. Then add 36.0 g (0.12 mol) 2-amino-4-(4-ethylphenyl)-5-(2-fluorophenyl)-3-furonitrile and stir the mixture for 24 h at 130° C. After cooling to room temperature, concentrate the mixture by evaporation under oil-pump vacuum at 50° C. Mix the residue in 150 ml diisopropyl ether at −10° C. for 30 min, filter, wash with 50 ml ice-cooled diisopropyl ether and dry under vacuum. 20.6 g (86% purity, 45% of theor.) of the title compound is obtained.

HPLC (Method 1): $R_t$=4.65 min
MS (ESIpos): m/z=335 (M+H)$^+$
$^1$H-NMR (400 MHz, DMSO-$d_6$): δ=12.68 (br. s, NH), 8.20 (s, 1H), 7.53-7.45 (m, 2H), 7.36-7.25 (m, 4H), 7.21-7.16 (m, 2H), 2.61 (q, 2H), 1.19 (t, 3H).

Example 81A

4-Chloro-5-(4-ethylphenyl)-6-(2-fluorophenyl)furo[2,3-d]pyrimidine

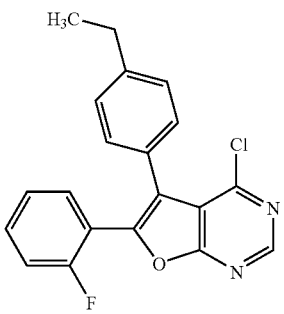

Stir a suspension of 20.0 g (0.06 mol) 5-(4-ethylphenyl)-6-(2-fluorophenyl)furo[2,3d]pyrimidin-4(3H)-one in 100 ml (165 g, 1.07 mol) phosphoryl chloride for 1 h at 120° C. After cooling to r temperature, add the reaction solution dropwise to a mixture of 330 ml water and 610 ml 25% aqueous ammonia solution, stirring vigorously; a temperature rise to 55-65° C. is observed. Leave the reaction mixture to cool to room temperature. After extracting twice with 500 ml dichloromethane each time, wash the organic phase with satd. aqueous sodium chloride solution, dry over sodium sulphate and filter. Concentrate the filtrate by vacuum evaporation. Mix the residue with 150 ml petroleum ether, filter, wash with ice-cooled petroleum ether and dry under vacuum. 18.7 g (90% purity, 80% of theor.) of the title compound is obtained.

LC-MS (Method 5): $R_t$=3.14 min; m/z=353 (M+H)$^+$ $^1$H-NMR (400 MHz, DMSO-$d_6$): δ=8.91 (s, 1H), 7.58-7.49 (m, 2H), 7.36-7.24 (m, 6H), 2.66 (q, 2H), 1.21 (t, 3H).

Example 82A

3-{[5-(4-Methoxyphenyl)-6-phenylfuro[2,3-d]pyrimidin-4-yl]oxy}-2-methylpropan-1-ol

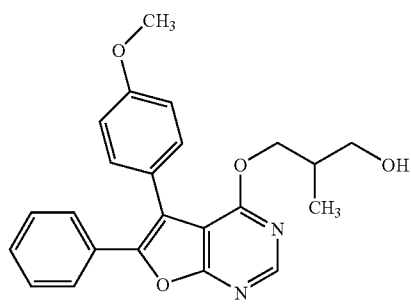

Add 4.8 ml of 12.5 N sodium hydroxide solution to a solution of 2.68 g (29.7 mmol) 2-methylpropane-1,3-diol in 45 ml toluene, 15 ml 1,2-dimethoxyethane and 15 ml water at 70° C. After adding 202 mg (0.59 mmol) tetra-n-butylammonium hydrogensulphate and 2.0 g (5.94 mmol) 4-chloro-5-(4-methoxyphenyl)-6-phenylfuro[2,3-d]pyrimidine, stir the reaction mixture for 17 h at 70° C. After cooling to room temperature, adjust to pH 7 with concentrated hydrochloric acid. Extract three times with 50 ml dichloromethane each time. Wash the combined organic extracts with satd. sodium chloride solution, dry over sodium sulphate, filter and concentrate by vacuum evaporation. Mix the raw product with methanol, filter, and purify the filtrate by preparative RP-HPLC (gradient: water/acetonitrile). 1.26 g (54% of theor.) of the desired product (racemate) is obtained.

LC-MS (Method 8): $R_t$=2.73 min; m/z=391 (M+H)$^+$
$^1$H-NMR (400 MHz, CDCl$_3$): δ=8.58 (s, 1H), 7.55 (d, 2H), 7.48-7.35 (m, 5H), 7.00 (d, 2H), 4.48 (t, OH), 4.34 (dd, 1H), 4.24 (dd, 1H), 3.81 (s, 3H), 3.23-3.14 (m, 2H), 1.86-1.78 (m, 1H), 0.72 (d, 3H).

Example 83A (2R,3R)-3-{[5-(4-Methoxyphenyl)-6-phenylfuro[2,3-d]pyrimidin-4-yl]oxy}butan-2-ol

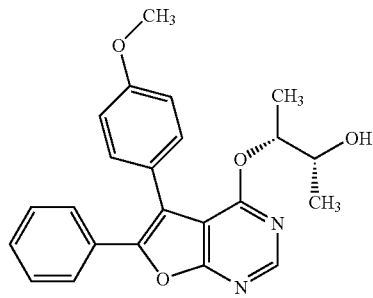

Add 2.4 ml of a 12.5 N sodium hydroxide solution to a solution of 1.34 g (14.8 mmol) (2R,3R)-butane-2,3-diol in 20 ml toluene, 7 ml 1,2-dimethoxyethane and 7 ml water at 70° C. After adding 101 mg (0.30 mmol) tetra-n-butylammonium hydrogensulphate and 1.00 g (2.97 mmol) 4-chloro-5-(4-methoxyphenyl)-6-phenylfuro[2,3-d]pyrimidine, stir the reaction mixture for 17 h at 70° C. After cooling to room temperature, adjust to pH 7 with concentrated hydrochloric acid. Extract three times with 50 ml dichloromethane each time. Wash the combined organic extracts with satd. sodium chloride solution, dry over sodium sulphate, filter and concentrate by vacuum evaporation. Mix the raw product with methanol, filter, and purify the filtrate by preparative RP-HPLC (gradient: water/acetonitrile). 0.60 g (50% of theor.) of the desired product is obtained.

LC-MS (Method 7): $R_t$=3.95 min; m/z=391 (M+H)$^+$
$^1$H-NMR (400 MHz, CDCl$_3$): δ=8.56 (s, 1H), 7.55 (d, 2H), 7.48-7.35 (m, 5H), 7.00 (d, 2H), 5.29 (dt, 1H), 4.71 (d, OH), 3.81 (s, 3H), 3.73-3.62 (m, 1H), 1.13 (d, 3H), 0.85 (d, 3H).

Example 84A (2R)-1-[Benzyl(methyl)amino]propan-2-ol

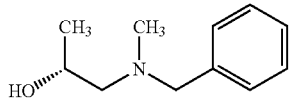

Stir a mixture of 3.5 g (21.2 mmol) (2R)-1-(benzylamino)propan-2-ol [F. L. Delft, *Synthesis* 1997, 4, 450-454], 1.85 ml (2.0 g, 23.3 mmol) of a 35% aqueous formaldehyde solution and 3.6 ml (4.4 g, 95.3 mmol) formic acid for 16 h under reflux. After cooling to room temperature, first neutralize with 45% sodium hydroxide solution and then adjust to a pH value of 9. Extract with ethyl acetate. Wash the organic phase three times with 10 ml water each time, dry over sodium sulphate and filter. Concentrate the filtrate by vacuum evaporation, and dry. 3.08 g (78% of theor.) of the desired product is obtained.

LC-MS (Method 3): $R_t$=1.85 min; m/z=180 (M+H)$^+$
$^1$H-NMR (400 MHz, DMSO-d$_6$): δ=7.31-7.21 (m, 5H), 4.28 (d, 1H), 3.81-3.72 (m, 1H), 3.48 (q, 2H), 2.24 (dq, 2H), 2.13 (s, 3H), 1.04 (d, 3H).

Example 85A (2R)-N-Benzyl-2-{[5-(4-ethylphenyl)-6-phenylfuro[2,3-d]pyrimidin-4-yl]oxy}-N-methylpropane-1-amine

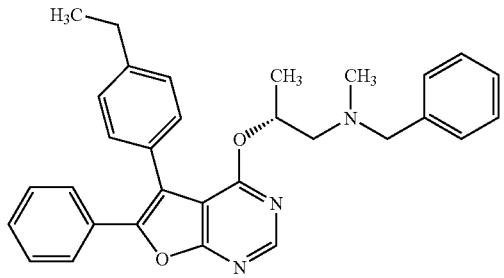

Add 167 mg (4.18 mmol) sodium hydride (as 60% dispersion in mineral oil) to a solution of 600 mg (3.35 mmol) (2R)-1-[benzyl(methyl)amino]propan-2-ol in 7 ml THF at room temperature. After stirring for ten minutes, add a solution of 1177 mg (3.51 mmol) 4-chloro-5-(4-ethylphenyl)-6-phenylfuro[2,3-d]pyrimidine in 8 ml THF and 62 mg (0.17 mmol) tetra-n-butylammonium iodide. Stir the reaction mixture for 16 h under reflux. After adding water and ethyl acetate, wash the separated organic phase with 1 N hydrochloric acid and satd. sodium chloride solution. Re-extract the aqueous phase with ethyl acetate. Combine the organic phases and dry over sodium sulphate, and filter. Concentrate the filtrate by vacuum evaporation. Take up the residue in cyclohexane/ethyl acetate/dichloromethane and chromatograph on silica gel (solvent: cyclohexane/ethyl acetate 5:1, 2:1, 1:1, then ethyl acetate). 1366 mg (83% of theor.) of the desired product is obtained.

LC-MS (Method 8): $R_t$=2.08 min; m/z=478 (M+H)$^+$
$^1$H-NMR (400 MHz, DMSO-d$_6$): δ=8.57 (s, 1H), 7.55-7.53 (m, 2H), 7.42-7.34 (m, 5H), 7.26-7.17 (m, 5H), 7.13-7.11 (m, 2H), 5.57-5.49 (m, 1H), 3.36 (d, 2H), 2.63 (q, 2H), 2.48-2.39 (m, 2H), 1.98 (s, 3H), 1.23-1.17 (m, 6H).

Example 86A (2R)-2-{[5-(4-Ethylphenyl)-6-phenylfuro[2,3-d]pyrimidin-4-yl]oxy}-N-methylpropane-1-ammonium formate

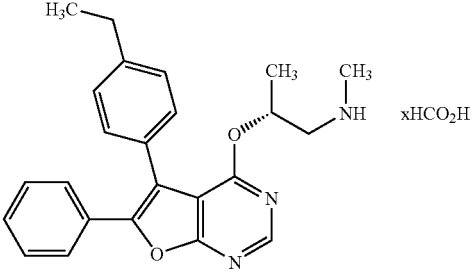

Add 0.50 g (4.70 mmol) palladium black to a solution of 1.45 g (3.04 mmol) (2R)-N-benzyl-2-{[5-(4-ethylphenyl)-6-phenylfuro[2,3-d]pyrimidin-4-yl]oxy}-N-methylpropane-1-amine in 20 ml of 4.4% methanolic formic acid under argon, and stir for 14 h at room temperature. After filtration with a Millipore filter and washing several times with methanol/water, concentrate the filtrate by vacuum evaporation. Take up the residue in acetonitrile/methanol and purify by preparative RIP-HPLC (gradient: water/acetonitrile). 1.03 g (77% of theor.) of the desired product is obtained.

LC-MS (Method 8): $R_t$=1.79 min; m/z=388 (M—HCO$_2$H+H)$^+$
$^1$H-NMR (400 MHz, DMSO-d$_6$): δ=8.60 (s, 1H), 8.18 (s, HCOO$^-$), 7.56-7.52 (m, 2H), 7.46-7.35 (m, 5H), 7.34-7.28 (m, 2H), 5.48-5.40 (m, 1H), 4.22-2.93 (br. s, H$_2$N$^+$), 2.86-2.82 (m, 1H), 2.72-2.62 (m, 3H), 2.24 (s, 3H), 1.27-1.23 (m, 6H).

Example 87A

4-{[(2S)-2-Hydroxypropyl]amino}butyric acid tert.-butyl ester

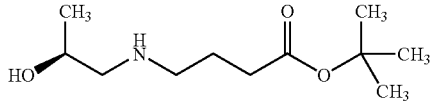

Add 2583 mg (18.69 mmol) potassium carbonate, 2780 mg (12.46 mmol) 4-bromobutyric acid tert.-butyl ester and 184 mg (0.50 mmol) tetra-n-butylammonium iodide to a solution of 936 mg (12.46 mmol) (2S)-1-aminopropan-2-ol in 10 ml THF. Stir the reaction mixture for 48 h at room temperature. After filtering-off the inorganic salts, concentrate the filtrate by vacuum evaporation. Take up the residue in dichloromethane and chromatograph on silica gel (solvent: dichloromethane/methanol/35% aqueous ammonia solution 9:1:0.1). 810 mg (30% of theor.) of the desired product is obtained.

GC-MS (Method 12): $R_t$=4.73 min; m/z=172 (M—CH$_3$CHOH)$^+$ $^1$H-NMR (400 MHz, DMSO-d$_6$): δ=4.39 (br. s, OH), 3.67-3.59 (m, 1H), 3.38-3.20 (br. s, NH), 2.51-2.47 (m, 2H), 2.39-2.37 (m, 2H), 2.21 (t, 2H), 1.60 (quin, 2H), 1.39 (s, 9H), 1.02 (d, 3H).

Example 88A

4-{[(2S)-2-Hydroxypropyl](methyl)amino}butyric acid tert.-butyl ester

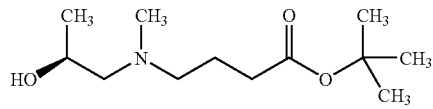

Add 0.62 ml (670 mg, 7.81 mmol) of 35% aqueous formaldehyde solution and 101 mg (1.61 mmol) sodium cyanoborohydride to a solution of 350 mg (1.61 mmol) 4-{[(2S)-2-hydroxypropyl]amino}butyric acid tert.-butyl ester in 10 ml methanol. Stir the reaction mixture for 16 h at room temperature. After adding 30 ml water and 40 ml dichloromethane, dry the organic phase over sodium sulphate, and filter. Concentrate the filtrate by vacuum evaporation, and dry. 323 mg (81% of theor.) of the desired product is obtained.

GC-MS (Method 12): $R_t$=4.57 min; m/z=186 (M—CH$_3$CHOH)$^+$ $^1$H-NMR (400 MHz, DMSO-d$_6$): δ=4.16 (d, 1H), 3.71-3.62 (m, 1H), 2.29 (t, 2H), 2.23-2.18 (m, 3H), 2.16-2.10 (m, 4H), 1.63-1.55 (m, 2H), 1.39 (s, 9H), 1.02 (d, 3H).

Example 89A

4-{[5-(4-Methoxyphenyl)-6-phenylfuro[2,3-d]pyrimidin-4-yl]oxy}pentan-2-ol

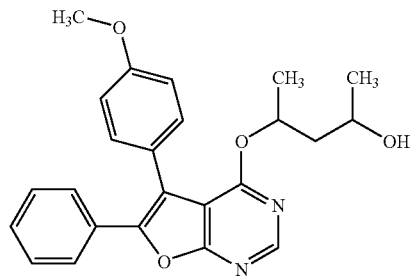

Add 7.9 ml of 11.25 N sodium hydroxide solution to a solution of 4.64 g (44.54 mmol) pentane-2,4-diol in 75 ml toluene, 27 ml 1,2-dimethoxyethane and 25 ml water at 70° C. After adding 302 mg (0.89 mmol) tetra-n-butylammonium hydrogensulphate and 3.00 g (8.91 mmol) 4-chloro-5-(4-methoxyphenyl)-6-phenylfuro[2,3-d]pyrimidine, stir the reaction mixture for 17 h at 70° C. After cooling to room temperature, adjust to pH 7 with concentrated hydrochloric acid. Extract three times with 150 ml dichloromethane each time. Wash the combined organic extracts with satd. sodium chloride solution, dry over sodium sulphate, and filter. Concentrate the filtrate by vacuum evaporation. Mix the residue with acetonitrile, filter, and chromatograph the filtrate on silica gel (solvent: dichloromethane/methanol). 2.37 g (65% of theor.) of the desired product is obtained as a racemic diastereomeric mixture.

LC-MS (Method 8): $R_t$=2.81 min; m/z=405 (M+H)$^+$ $^1$H-NMR (400 MHz, DMSO-d$_6$): [lesser stereoisomer in square brackets] δ=[8.57, s, 1H], 8.56 (s, 1H), 7.56-7.52 (m, 2H), 7.42-7.37 (m, 5H), 7.02-6.99 (m, 2H), 5.54-5.46 (m, 1H), [5.38-5.30, m, 1H], 4.46 (d, OH), [4.39, d, OH], 3.82 (s, 3H), [3.81, s, 3H], 3.69-3.60 (m, 1H), [3.46-3.37, m, 1H], 1.77-1.70 (m, 1H), 1.47-1.41 (m, 1H), [1.28, d, 3H], 1.26 (d, 3H), 1.00 (d, 3H), [0.93, d, 3H].

Example 90A 2-({[5-(4-Ethylphenyl)-6-phenylfuro[2,3-d]pyrimidin-4-yl]oxy}methyl)-3,3-dimethylbutan-1-ol

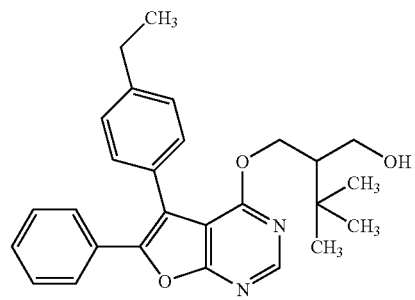

Add 2.7 ml of 11.25 N sodium hydroxide solution to a solution of 1974 mg (14.93 mmol) 2-tert.-butylpropane-1,3-diol in 25 ml toluene, 8 ml 1,2-dimethoxyethane and 8 ml water at 70° C. After adding 101 mg (0.30 mmol) tetra-n-butylammonium hydrogensulphate and 1000 mg (2.99 mmol) 4-chloro-5-(4-ethylphenyl)-6-phenylfuro[2,3-d]pyrimidine, stir the reaction mixture for 17 h at 70° C. After cooling to room temperature, adjust to pH 7 with concentrated hydrochloric acid. Extract with dichloromethane. Wash the organic phase with satd. sodium chloride solution, dry over sodium sulphate, and filter. Concentrate the filtrate by vacuum evaporation. Mix the residue with methanol, filter, and wash with diethyl ether. Purify the filtrate by preparative RP-HPLC (gradient: water/acetonitrile). 275 mg (21% of theor.) of the desired product (racemate) is obtained.

LC-MS (Method 9): $R_t$=4.55 min; m/z=431 (M+H)$^+$ $^1$H-NMR (400 MHz, DMSO-d$_6$): δ=8.60 (s, 1H), 7.53-7.51 (m, 2H), 7.39-7.36 (m, 5H), 7.30-7.28 (m, 2H), 4.53 (dd, 1H), 4.45 (dd, 1H), 4.40 (t, 1H), 3.45-3.41 (m, 1H), 3.30-3.25 (m, 1H), 2.68 (q, 2H), 1.39-1.34 (m, 1H), 1.29 (t, 3H), 0.67 (s, 9H).

Example 91A

3-{[5-(4-Methoxyphenyl)-6-phenylfuro[2,3-d]pyrimidin-4-yl]oxy}butan-2-ol

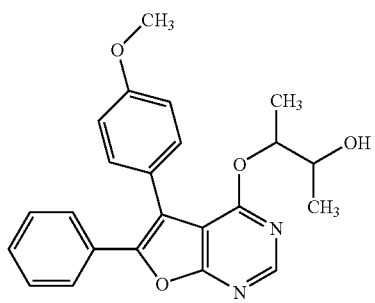

Add 4.8 ml of 12.5 N sodium hydroxide solution to a mixture of 2.68 g (29.70 mmol) (2R,3S)-butane-2,3-diol in 45 ml toluene, 15 ml 1,2-dimethoxyethane and 15 ml water at 70° C. After adding 0.20 g (0.60 mmol) tetra-n-butylammonium hydrogensulphate and 2.00 g (5.94 mmol) 4-chloro-5-(4-methoxyphenyl)-6-phenylfuro[2,3-d]pyrimidine, stir the reaction mixture for 17 h at 70° C. After cooling to room temperature, adjust to pH 7 with concentrated hydrochloric acid. Extract three times with 100 ml dichloromethane each time. Wash the combined organic extracts with satd. sodium chloride solution, dry over sodium sulphate, filter, and concentrate by vacuum evaporation. Purify the raw product by preparative RP-HPLC (gradient: water/acetonitrile). 1.26 g (54% of theor.) of the desired product is obtained as (R,S/S,R) racemate.

LC-MS (Method 8): $R_t$=2.81 min; m/z=391 (M+H)$^+$ $^1$H-NMR (400 MHz, DMSO-d$_6$): δ=8.57 (s, 1H), 7.55-7.53 (m, 2H), 7.43-7.36 (m, 5H), 7.01-7.00 (m, 2H), 5.21-5.16 (m, 1H), 4.68 (d, OH), 3.81 (s, 3H), 3.61-3.55 (m, 1H), 1.19 (d, 3H), 0.86 (d, 3H).

Example 92A (+/−)-2-Methoxy-3-{[5-(4-methoxyphenyl)-6-phenylfuro[2,3-d]pyrimidin-4-yl]oxy}propan-1-ol

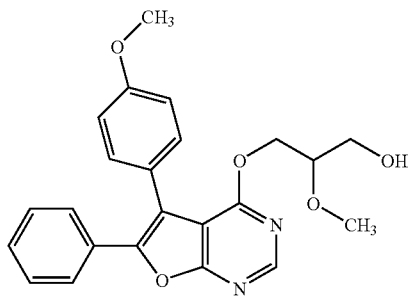

Put 1.014 g (9.65 mmol) 2-methoxypropane-1,3-diol in 20 ml THF. Add 542 mg (4.825 mmol) potassium tert.-butylate and stir for 15 min at RT. Then cool to 0° C. and add a solution of 650 mg (1.93 mmol) 4-chloro-5-(4-methoxyphenyl)-6-phenylfuro[2,3-d]pyrimidine in 10 ml THF dropwise in the space of 30 min. Then leave to return to RT and stir overnight at RT. Next, dilute with tert.-butylmethyl ether and water. Acidify with 10% citric acid solution and separate the phases. Re-extract the aqueous phase once with tert.-butylmethyl ether. Combine the organic phases and wash once with satd. sodium chloride solution. Then dry over magnesium sulphate and concentrate by evaporation. Purify the residue by chromatography on silica gel (solvent: cyclohexane/ethyl acetate 7:3); 587 mg (74.8% of theor.) of the target compound is obtained.

LC-MS (Method 8): $R_t$=2.53 min; m/z=407 (M+H)$^+$ $^1$H-NMR (400 MHz, CDCl$_3$): δ=8.53 (s, 1H), 7.62 (m, 2H), 7.39 (m, 2H), 7.32 (m, 3H), 6.97 (d, 2H), 4.53 (d, 2H), 3.88 (s, 3H), 3.62-3.52 (m, 1H), 3.52-3.43 (m, 2H), 3.32 (s, 3H).

Example 93A

6-{[(1R)-1-Phenylethyl]amino}heptanoic acid methyl ester

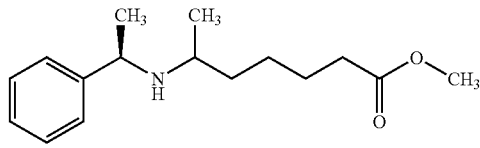

Put 8.80 g (55.63 mmol) 6-oxoheptanoic acid and 6.741 g (55.63 mmol) (R)-(+)-1-phenylethylamine together in 100 ml toluene at RT. Add a catalytic amount (approx. 50 mg) of p-toluenesulphonic acid and heat overnight with stirring on a water separator. Then partially concentrate by evaporation, filter off any solids using a paper filter, and fully concentrate the filtrate by evaporation. Dissolve the residue in 170 ml methanol. Add approx. 1.7 g Raney Nickel (moist with water) and hydrogenate for 48 h at 4 bar. Next, filter on diatomite and concentrate the filtrate by evaporation. Purify the residue by column chromatography on silica gel (solvent: dichloromethane/methanol 95:5), obtaining 4.15 g (48.5% of theor.) of the target compound, which is reacted without further characterization.

Examples of Application

Example 1

6-{[5-(4-Methoxyphenyl)-6-phenylfuro[2,3-d]pyrimidin-4-yl]amino}hexanoic acid

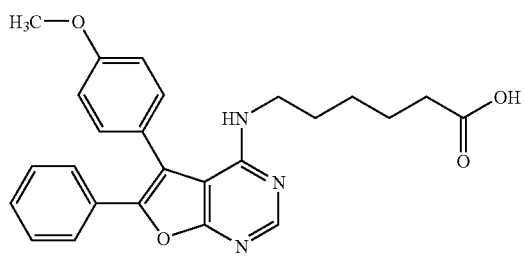

Stir 1.0 g (3.0 mmol) 4-chloro-5-(4-methoxyphenyl)-6-phenylfuro[2,3-d]pyrimidine, 0.78 g (5.94 mmol) 6-aminohexanoic acid and 1.5 ml DIEA in 10 ml DMF overnight at 120° C. Add the reaction mixture to water and extract three times with ethyl acetate. Combine the organic phases and wash with saturated sodium chloride solution, dry over magnesium sulphate and concentrate by vacuum evaporation. Chromatograph the residue on silica gel (solvent: cyclohexane/ethyl acetate 2:1→1:2). 560 mg (43.7% of theor.) of the target compound is obtained.

LC-MS (Method 4): $R_t$=2.62 min; m/z=432 (M+H)$^+$

¹H-NMR (400 MHz, DMSO d₆): δ=12.0 (br. s, 1H), 8.31 (s, 1H), 7.47-7.42 (m, 4H), 7.40-7.30 (m, 3H), 7.15 (d, 2H), 5.08 (t, 1H), 3.87 (s, 3H), 2.08 (t, 2H), 1.50-1.35 (m, 4H), 1.25-1.10 (m, 4H).

Example 2

7-{[5-(4-Methoxyphenyl)-6-phenylfuro[2,3-d]pyrimidin-4-yl]amino}heptanoic acid

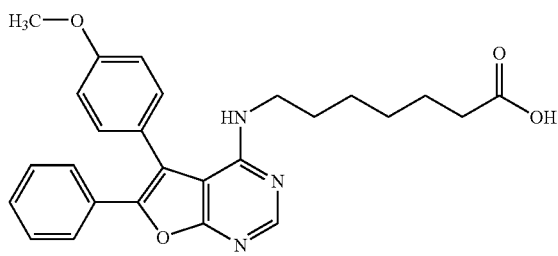

The title compound is obtained similarly to Example 1 at a yield of 55.1% of theor.

LC-MS (Method 4): $R_t$=2.72 min; m/z=446 (M+H)⁺

¹H-NMR (400 MHz, DMSO-d₆): δ=8.33 (s, 1H), 7.48-7.43 (m, 4H), 7.40-7.30 (m, 3H), 7.15 (d, 2H), 5.04 (t, 1H), 3.85 (s, 3H), 2.08 (t, 2H), 1.50-1.38 (m, 4H), 1.20-1.11 (m, 2H).

Example 3

6-{[5-(4-Methoxyphenyl)-6-phenylfuro[2,3-d]pyrimidin-4-yl]amino}hexanoic acid sodium salt

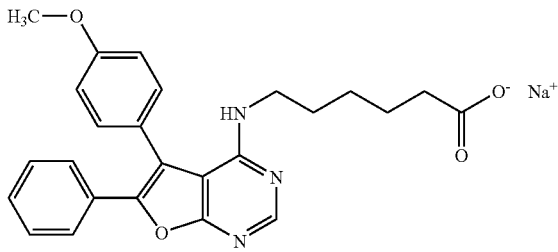

Dissolve 200 mg (0.464 mmol) 6-{[5-(4-methoxyphenyl)-6-phenylfuro[2,3-d]pyrimidin-4-yl]amino}hexanoic acid at RT in 0.75 ml methanol, 0.5 ml THF and a few drops of water, and add 0.464 ml 1 N sodium hydroxide solution. Stir the mixture for 5 min, then concentrate by vacuum evaporation and dry the residue at high vacuum. 221 mg of the target compound is obtained.

LC-MS (Method 2): $R_t$=2.34 min; m/z=432 (M—Na+2H)⁺

¹H-NMR (300 MHz, DMSO-d₆): δ=8.32 (s, 1H), 7.48-7.43 (m, 4H), 7.39-7.30 (m, 3H), 7.17 (d, 2H), 5.04 (t, 1H), 3.88 (s, 3H), 1.72 (t, 2H), 1.40-1.32 (m, 4H), 1.15-1.08 (m, 2H).

Example 4

5-(4-Methoxyphenyl)-6-phenyl-N-[5-(1H-tetrazol-5-yl)pentyl]furo[2,3-d]pyrimidine-4-amine

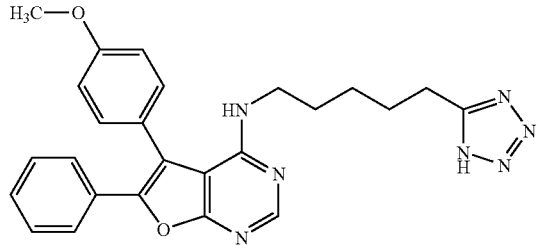

Stir 1.00 g (2.4 mmol) 6-{[5-(4-methoxyphenyl)-6-phenylfuro[2,3-d]pyrimidin-4-yl]amino}hexanenitrile, 4.19 g (26.3 mmol) trimethylsilylazide and 0.91 g (3.6 mmol) di-n-butyltin oxide in 50 ml toluene overnight at 80° C. After concentrating by evaporation, take up the residue in water, acidify with dilute hydrochloric acid and extract with methylene chloride. Wash the organic phase with sodium chloride solution, dry over magnesium sulphate and concentrate by evaporation. Purify the raw product by RP-HPLC (column: Gromsil 250 mm×40 mm, 10 µm; acetonitrile/water gradient: 0-3 min 10% acetonitrile, 3-50 min 10%→98% acetonitrile, 50-55 min 98% acetonitrile). Crystallize the combined product fractions from diethyl ether and dry overnight at 50° C. in a vacuum drying cabinet. 598 mg (54% of theor.) of the title compound is obtained as almost white crystals.

LC-MS (Method 2): $R_t$=2.22 min; m/z=455 (M+H)⁺

¹H-NMR (400 MHz, DMSO-d₆): δ=16 (br. s, 1H), 8.3 (s, 1H), 7.5-7.25 (m, 7H), 7.1 (m, 2H), 5.1 (m, 1H), 3.85 (s, 3H), approx. 3.5 (m, masked by DMSO signal), 2.75 (t, 2H), 1.65 (m, 2H), 1.45 (m, 2H), 1.2 (m, 2H).

Example 5

(2E)-6-{[5-(4-Methoxyphenyl)-6-phenylfuro[2,3-d]pyrimidin-4-yl]amino}-hex-2-enoic acid methyl ester

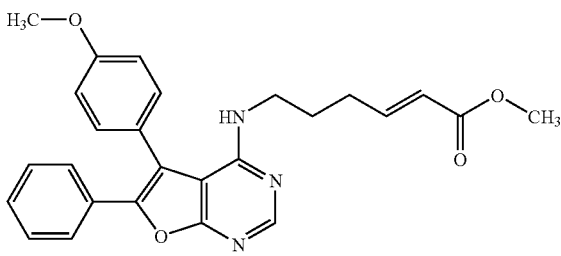

Add 0.095 ml (0.588 mmol) trimethyl phosphonoacetate dropwise at RT to a suspension of 21.6 mg sodium hydride (60% dispersion in oil, approx. 0.539 mmol) in 2 ml THF. Stir the mixture for a further 1 h and then add 190 mg (0.49 mmol) 4-{[5-(4-methoxyphenyl)-6-phenylfuro-[2,3-d]pyrimidin-4-yl]amino}butanal. Stir overnight at RT and then dilute the mixture with dichloromethane and water. Wash the organic phase with saturated sodium chloride solution, dry, and concentrate under vacuum. The target compound is isolated from the raw product by preparative RP-HPLC (twice) (gradient: water/acetonitrile). 23.4 mg (10.8% of theor.) of the desired product is obtained.

LC-MS (Method 2): $R_t$=2.65 min; m/z=444 (M+H)$^+$ $^1$H-NMR (400 MHz, DMSO-d$_6$): δ=8.33 (s, 1H), 7.47-7.43 (m, 4H), 7.40-7.31 (m, 3H), 7.14 (d, 2H), 6.85 (dd, 1H), 5.84-5.78 (m, 1H), 5.68 (t, 1H), 3.85 (s, 3H), 3.63 (s, 3H), 3.49 (q, 2H), 2.17-2.10 (m, 2H), 1.63-1.57 (m, 2H).

Example 6

(2E)-6-{[5-(4-Methoxyphenyl)-6-phenylfuro[2,3-d]pyrimidin-4-yl]amino}-hex-2-enoic sodium salt

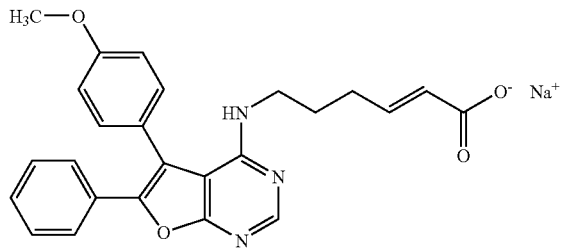

Put 19 mg (0.043 mmol) (2E)-6-{[5-(4-methoxyphenyl)-6-phenylfuro[2,3-d]pyrimidin-4-yl]amino}-hex-2-enoic acid methyl ester in 0.5 ml THF and, at RT, add 0.43 ml 1 N sodium hydroxide solution. Stir the mixture for 24 h at RT, then neutralize with 1 N hydrochloric acid and concentrate by vacuum evaporation. Add a little 1 N sodium hydroxide solution to the residue and purify directly by preparative RP-HPLC (gradient: water/acetonitrile). 9 mg (46.5% of theor.) of the target compound is isolated.

LC-MS (Method 5): $R_t$=2.51 min; m/z=429 (M—Na+2H)$^+$ $^1$H-NMR (400 MHz, DMSO-d$_6$): δ=8.3 (s, 1H), 7.48-7.3 (m, 7H), 7.12 (d, 2H), 6.20 (dd, 1H), 5.58 (d, 2H), 5.60 (t, 1H), 3.85 (s, 3H), 1.95 (q, 2H), 1.52 (m, 2H).

Example 7

5-(4-Methoxyphenyl)-6-phenyl-N-[6-(1H-tetrazol-5-yl)hexyl]furo[2,3-d]pyrimidine-4-amine

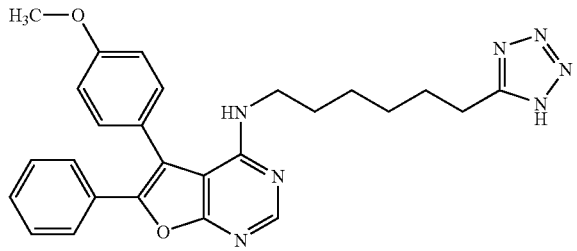

Stir 0.098 g (0.23 mmol) 7-{[5-(4-methoxyphenyl)-6-phenylfuro[2,3-d]pyrimidin-4-yl]amino}-heptanenitrile, 0.41 g (3.5 mmol) trimethylsilylazide and 86 mg (0.25 mmol) di-n-butyltin oxide in 5 ml toluene overnight at 80° C. After concentrating by evaporation, take up the residue in water, acidify with dilute hydrochloric acid and extract with methylene chloride. Wash the organic phase with sodium chloride solution, dry over magnesium sulphate and concentrate by evaporation. Purify the raw product by RP-HPLC (column: Gromsil 250 mm×30 mm, 10 μm; acetonitrile/water gradient: 0-3 min 5% acetonitrile, 3-34 min 5%→98% acetonitrile, 34-38 min 98% acetonitrile). 61 mg (55% of theor.) of the title compound is obtained as white crystals.

LC-MS (Method 2): $R_t$=2.30 min; m/z=469 (M+H)$^+$ $^1$H-NMR (400 MHz, DMSO-d$_6$): δ=16 (br. s, 1H), 8.3 (s, 1H), 7.5-7.25 (m, 7H), 7.15 (m, 2H), 5.1 (m, 1H), 3.85 (s, 3H), approx. 3.5 (m, masked by DMSO signal), 2.85 (t, 2H), 1.65 (m, 2H), 1.35 (m, 2H), 1.1-1.3 (m, 4H).

Example 8

6-[(5,6-Diphenylfuro[2,3-d]pyrimidin-4-yl)amino]hexanoic acid methyl ester

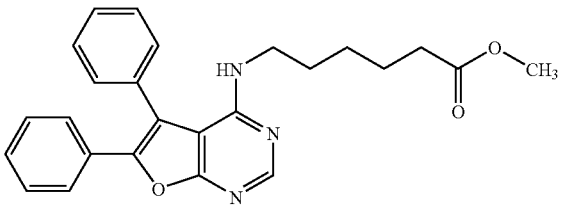

Stir 55 mg (0.131 mmol) 6-[(6-bromo-5-phenylfuro[2,3-d]pyrimidin-4-yl)amino]hexanoic acid methyl ester, 0.131 ml of 2 M aqueous sodium carbonate solution (0.26 mmol), 4.6 mg (0.006 mmol) bis(triphenylphosphine)palladium(II) chloride and 20 mg (0.164 mmol) phenylboronic acid under argon in 0.4 ml DMSO for 1 h at 80° C. After cooling, purify the mixture directly by preparative RP-HPLC (gradient: water/acetonitrile). 35 mg (64.1% of theor.) of the target compound is obtained.

LC-MS (Method 4): $R_t$=3.01 min; m/z=416 (M+H)$^+$ $^1$H-NMR (400 MHz, DMSO-d$_6$): δ=8.34 (s, 1H), 7.62-7.53 (m, 5H), 7.47-7.42 (m, 2H), 7.39-7.30 (m, 3H), 4.97 (t, 1H), 3.60 (s, 3H), 3.35 (q, 2H), 2.17 (t, 2H), 1.50-1.35 (m, 4H), 1.18-1.10 (m, 2H).

Example 9

6-{[5-(4-Methylphenyl)-6-phenylfuro[2,3-d]pyrimidin-4-yl]amino}hexanoic acid methyl

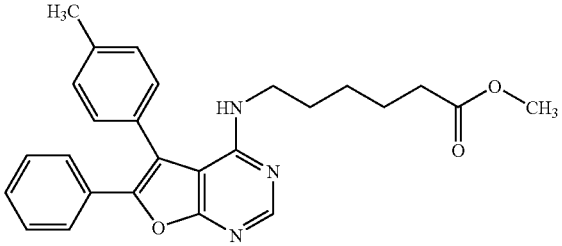

Stir 50 mg (0.12 mmol) 6-[(5-bromo-6-phenylfuro[2,3-d]pyrimidin-4-yl)amino]hexanoic acid methyl ester, 0.12 ml of 2 M aqueous sodium carbonate solution (0.24 mmol), 4.2 mg (0.006 mmol) bis(triphenylphosphine)palladium(II) chloride and 20.3 mg (0.149 mmol) p-tolueneboronic acid under argon in 0.4 ml DMSO for 1 h at 80° C. After cooling, purify the mixture directly by preparative RP-HPLC (gradient: water/acetonitrile) followed by chromatography on silica gel (solvent: cyclohexane/ethyl acetate). 38.1 mg (74.2% of theor.) of the target compound is obtained.

LC-MS (Method 4): $R_t$=3.15 min; m/z=430 (M+H)$^+$

¹H-NMR (400 MHz, DMSO-d₆): δ=8.32 (s, 1H), 7.48-7.30 (m, 10H), 5.01 (t, 1H), 3.58 (s, 3H), 3.38 (q, 2H), 2.43 (s, 3H), 2.27 (t, 2H), 1.50-1.35 (m, 4H), 1.17-1.10 (m, 2H).

Example 10

6-[(5,6-Diphenylfuro[2,3-d]pyrimidin-4-yl)amino]hexanoic acid

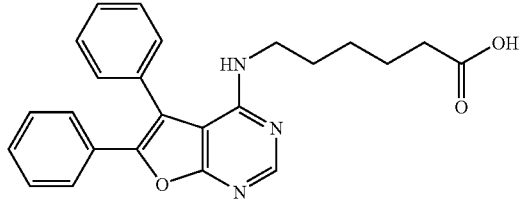

Dissolve 27.5 mg (0.066 mmol) 6-[(5,6-diphenylfuro[2,3-d]pyrimidin-4-yl)amino]hexanoic acid methyl ester in 0.1 ml methanol, 0.05 ml THF and one drop of water and add 0.09 ml 2.5 M sodium hydroxide solution. Stir the mixture for 1 h at RT and then lightly acidify with 1 N hydrochloric acid. Extract the aqueous phase three times with dichloromethane. Combine the organic phases and dry over magnesium sulphate, concentrate by vacuum evaporation and dry the residue at high vacuum. 25 mg (96.1% of theor.) of the target compound is obtained.

LC-MS (Method 5): $R_t$=2.51 min; m/z=402 (M+H)⁺

¹H-NMR (300 MHz, DMSO-d₆): δ=12.0 (br. s, 1H), 8.35 (s, 1H), 7.62-7.51 (m, 5H), 7.46-7.41 (m, 2H), 7.39-7.30 (m, 3H), 4.97 (t, 1H), 3.39 (q, 2H), 2.18 (t, 2H), 1.45-1.35 (m, 4H), 1.18-1.10 (m, 2H).

Example 11

6-{[5-(4-Methylphenyl)-6-phenylfuro[2,3-d]pyrimidin-4-yl]amino}hexanoic acid

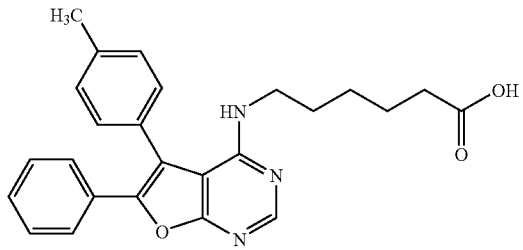

Dissolve 30 mg (0.07 mmol) 6-{[5-(4-methylphenyl)-6-phenylfuro[2,3-d]pyrimidin-4-yl]amino}-hexanoic acid methyl ester in 0.1 ml methanol, 0.05 ml THF and one drop of water, and add 0.1 ml of 2.5 M sodium hydroxide solution. Stir the mixture for 1 h at RT and then lightly acidify with 1 N hydrochloric acid. Filter off the precipitate with suction, wash several times with water, and dry at high vacuum. 28 mg (96.5% of theor.) of the target compound is obtained.

LC-MS (Method 4): $R_t$=2.70 min; m/z=416 (M+H)⁺

¹H-NMR (400 MHz, DMSO-d₆): δ=12.0 (br. s, 1H), 8.33 (s, 1H), 7.48-7.30 (m, 10H), 4.99 (t, 1H), 3.38 (q, 2H), 2.45 (s, 3H), 2.18 (t, 2H), 1.46-1.37 (m, 4H), 1.18-1.10 (m, 2H).

Example 12

6-{[5-(4-Methoxyphenyl)-6-phenylfuro[2,3-d]pyrimidin-4-yl]oxy}hexanoic acid ethyl ester

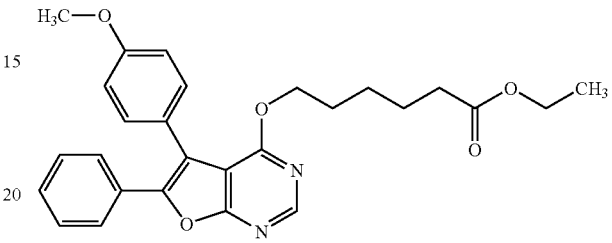

Add 42.8 mg sodium hydride (60% dispersion in oil, approx. 1.07 mmol) in portions, at RT, to a mixture of 300 mg (0.89 mmol) 4-chloro-5-(4-methoxyphenyl)-6-phenylfuro[2,3-d]pyrimidine and 214 mg (1.34 mmol) 6-hydroxyhexanoic acid ethyl ester in 1.0 ml THF and 0.7 ml DMF. Stir the mixture for 1 h at RT, and then add dichloromethane and water. Wash the organic phase with saturated sodium chloride solution, dry over sodium sulphate and concentrate by vacuum evaporation. After preparative RP-HPLC, 120.9 mg (29.5% of theor.) of the target compound is isolated from the residue.

LC-MS (Method 5): $R_t$=3.25 min; m/z=461 (M+H)⁺

¹H-NMR (400 MHz, DMSO-d₆): δ=8.57 (s, 1H), 7.56 (m, 2H), 7.44-7.39 (m, 5H), 7.03 (d, 2H), 4.37 (t, 2H), 4.04 (q, 2H), 3.81 (s, 3H), 2.21 (t, 2H), 1.61-1.55 (m, 2H), 1.50-1.42 (m, 2H), 1.18 (m, 5H).

Example 13

6-{[5-(4-Methoxyphenyl)-6-phenylfuro[2,3-d]pyrimidin-4-yl]oxy}hexanoic acid

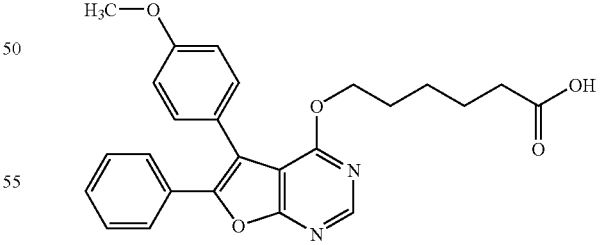

Dissolve 103 mg (0.224 mmol) 6-{[5-(4-methoxyphenyl)-6-phenylfuro[2,3-d]pyrimidin-4-yl]oxy}-hexanoic acid ethyl ester in 2 ml THF and, at RT, add 2.2 ml of 1 N sodium hydroxide solution. Stir the mixture overnight, then neutralize with 1 N hydrochloric acid and concentrate by vacuum evaporation. Purify the residue by preparative RP-HPLC. 23.2 mg (24% of theor.) of the target compound is obtained LC-MS (Method 5): $R_t$=2.73 min; m/z=433 (M+H)⁺. .

Example 14

5-(4-Methoxyphenyl)-6-phenyl-4-{[5-(1H-tetrazol-5-yl)pentyl]oxy}-furo[2,3-d]pyrimidine

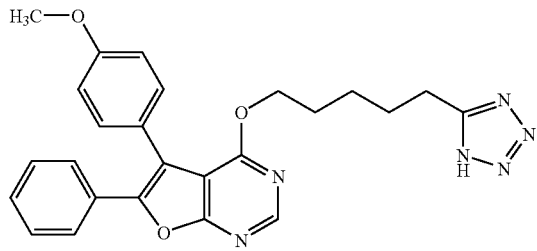

Stir 1.00 g (2.1 mmol) 6-{[5-(4-methoxyphenyl)-6-phenylfuro[2,3-d]pyrimidin-4-yl]oxy}hexanenitrile, 0.79 g (3.2 mmol) di-n-butyltin oxide and 3.68 g (32 mmol) trimethylsilylazide in 44 ml toluene overnight at 80° C. Then add 1 ml ethylene glycol, stir for 1 h under reflux and then concentrate by evaporation. Take up the residue in ethyl acetate, wash with dilute hydrochloric acid and with sodium chloride solution, dry, and concentrate by evaporation. Purify the raw product by RP-HPLC (column: Gromsil 250 mm×40 mm, 10 μm; acetonitrile/water gradient: 0-3 min 5% acetonitrile, 3-50 min 5%→98% acetonitrile, 50-55 min 98% acetonitrile). Crystallize the combined product fractions from diethyl ether. 372 mg (38% of theor.) of the title compound is obtained as beige crystals.

LC-MS (Method 5): $R_t$=2.39 min; m/z=456 (M+H)$^+$ $^1$H-NMR (400 MHz, DMSO-d$_6$): δ=approx. 16-14 (broad, 1H), 8.6 (s, 1H), 7.55 (m, 2H), 7.4 (m, 5H), 7.0 (m, 2H), 4.35 (t, 2H), 3.8 (s, 3H), 2.3 (t, 2H), 1.6 (m, 4H), 1.2 (m, 2H).

Example 15

5-(4-Methoxyphenyl)-6-phenyl-N-{3-[2-(1H-tetrazol-5-yl)ethoxy]propyl}furo[2,3-d]pyrimidine-4-amine

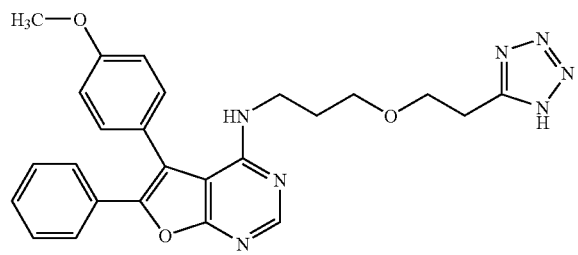

Stir 137 mg (0.32 mmol) 5-(4-methoxyphenyl)-6-phenyl-N-{3-[2-cyanoethoxy]propyl}furo[2,3-d]-pyrimidine-4-amine, 552 mg (4.8 mmol) trimethylsilylazide and 119 mg (0.48 mmol) di-n-butyltin oxide in 10 ml toluene overnight at 80° C. Then cool the mixture and concentrate by evaporation. Dissolve the residue that remains in methylene chloride and wash with water and sodium chloride solution. Dry the organic phase over magnesium sulphate and concentrate in the rotary evaporator at reduced pressure. Purify the residue by RP-HPLC (column: Gromsil 250 mm×30 mm, 10 μm; acetonitrile/water gradient: 0-3 min 5% acetonitrile, 3-34 min 5%→98% acetonitrile, 34-38 min 98% acetonitrile). 48.6 mg (32% of theor.) of the title compound is obtained as a colourless solid.

LC-MS (Method 4): $R_t$=2.44 min; m/z=472 (M+H)$^+$ $^1$H-NMR (400 MHz, DMSO-d$_6$): δ=16.0 (br. s, 1H), 8.35 (s, 1H), 7.1-7.45 (m, 9H), 5.2 (m, 1H), 3.85 (s, 3H), 3.65 (t, 2H), approx. 3.3 (m, 2H, partially masked by H$_2$O), 3.05 (t, 2H), 1.65 (quin, 2H).

Example 16

3-(3-{[5-(4-Methoxyphenyl)-6-phenylfuro[2,3-d]pyrimidin-4-yl]amino}propoxy)propionic acid

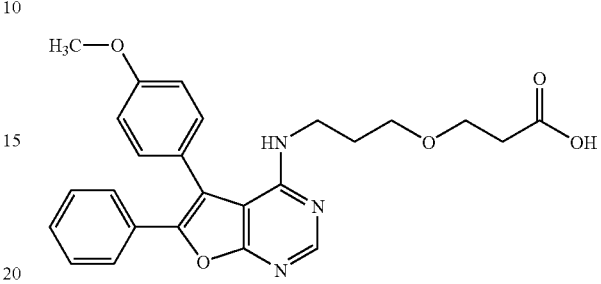

Heat 160 mg (0.37 mmol) 5-(4-methoxyphenyl)-6-phenyl-N-{3-[2-cyanoethoxy]propyl}furo[2,3-d]pyrimidine-4-amine in 6 ml conc. hydrochloric acid to boiling, and stir for 7 h. After cooling to room temperature, dilute with water and extract with ethyl acetate. Dry the organic phases over magnesium sulphate and concentrate by evaporation. Repeated purification of the residue by RP-HPLC (column: Gromsil 250 mm×30 mm, 10 μm; acetonitrile/water gradient: 0-3 min 5% acetonitrile, 3-34 min 5%→98% acetonitrile, 34-38 min 98% acetonitrile) and flash chromatography on silica gel (solvent gradient: ethyl acetate→ethyl acetate/methanol 5:1) yields an oil, which is then dissolved in ethyl acetate. While hot, add diisopropyl ether until clouding occurs. After standing overnight in the refrigerator, a yellowish solid is obtained, which is taken up in dichloromethane. After concentrating by evaporation once again, mix the residue with diethyl ether. In this way, 7.1 mg (4.3% of theor.) of the title compound is obtained as a grey powder, which becomes oily again after some time.

LC-MS (Method 4): $R_t$=2.42 min; m/z=448 (M+H)$^+$ $^1$H-NMR (400 MHz, DMSO-d$_6$): δ=8.35 (s, 1H), 7.1-7.45 (m, 9H), 5.2 (m, 1H), 3.85 (s, 3H), 3.65 (t, 2H), approx. 3.3 (m, 4H, partially masked by H$_2$O), 2.1 (t, 2H), 1.6 (m, 2H).

Example 17

(5-{[5-(4-Methoxyphenyl)-6-phenylfuro[2,3-d]pyrimidin-4-yl]amino}pentyl)amino(oxo)methyl acetate

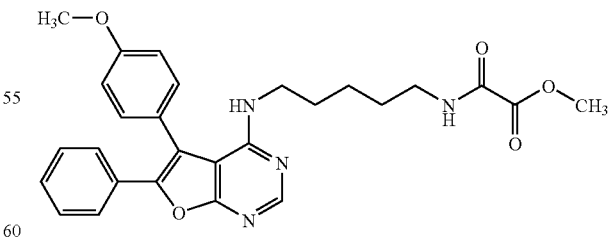

Dissolve 150 mg (0.37 mmol) 5-(4-methoxyphenyl)-6-phenyl-N-(5-aminopentyl)furo[2,3-d]pyrimidine-4-amine in 10 ml methylene chloride. At 0° C., slowly add, dropwise, 50 mg (0.41 mmol) methyl oxalate chloride and 72 mg (0.56 mmol) DIEA simultaneously. Stir for a further 1 h at room temperature. Dilute the mixture with methylene chloride and wash with water and sodium chloride solution. Combine the organic phases and dry over magnesium sulphate and concentrate in the rotary evaporator. Purify the residue by RP-HPLC (column: Gromsil 250 mm×30 nm, 10 μm; acetonitrile/water gradient: 0-3 min 5% acetonitrile, 3-34 min 5%→98% acetonitrile, 34-38 min 98% acetonitrile). After concentrating the product fractions by evaporation, chromatograph the residue on silica gel (Analogix cartridge F12M, eluent: cyclohexane/ethyl acetate 1:1). 47.8 mg (26% of theor.) of the title compound is obtained as a colourless foam.

LC-MS (Method 4): $R_t$=2.60 min; m/z=489 (M+H)$^+$ $^1$H-NMR (400 MHz, DMSO-d$_6$): δ=8.9 (m, 1H), 8.30 (s, 1H), 7.1-7.45 (m, 9H), 5.1 (m, 3H), 3.75 (s, 3H), approx. 3.4 (m, 2H, partially masked by H$_2$O), 3.1 (q, 2H), 1.6-1.1 (m, 6H).

Example 18

(5-{[5-(4-Methoxyphenyl)-6-phenylfuro[2,3-d]pyrimidin-4-yl]amino}pentyl)amino(oxo)acetic acid

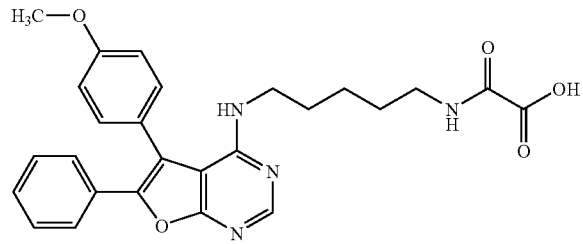

Dissolve 30 mg (0.06 mmol) (5-{[5-(4-methoxyphenyl)-6-phenylfuro[2,3-d]pyrimidin-4-yl]amino}pentyl)amino (oxo)methyl acetate in 3 ml dioxan and add 0.12 ml 1 N sodium hydroxide solution. Next, stir for 1 h at 50° C. Concentrate the mixture by evaporation, take up the residue in water and wash with methylene chloride. Acidify the aqueous phase with 1 N hydrochloric acid and extract with ethyl acetate. Separate the organic phase, dry over magnesium sulphate and concentrate by evaporation. 26.5 mg (91% of theor.) of the title compound is obtained as a white foam.

LC-MS (Method 4): $R_t$=2.10 min; m/z=475 (M+H)$^+$ $^1$H-NMR (400 MHz, DMSO-d$_6$): δ=8.75 (m, 1H), 8.30 (s, 1H), 7.1-7.45 (m, 9H), 5.05 (m, 1H), 3.85 (s, 3H), approx. 3.4 (m, 2H, partially masked by H$_2$O), 3.05 (q, 2H), 1.6-1.1 (m, 6H).

Example 19

5-(4-Methoxyphenyl)-6-phenyl-4-{2-[2-(1H-tetrazol-5-yl)ethoxy]ethoxy}furo[2,3-d]pyrimidine

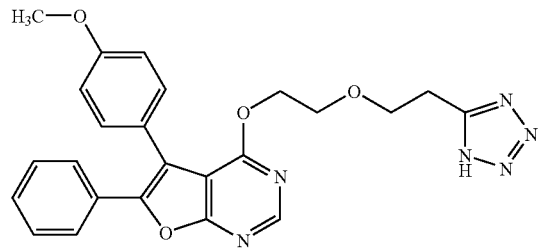

Stir 180 mg (0.43 mmol) 4-[3-(2-cyanoethoxy)ethoxy]-5-(4-methoxyphenyl)-6-phenylfuro[2,3-d]-pyrimidine, 749 mg (6.5 mmol) trimethylsilylazide and 161 mg (0.65 mmol) di-n-butyltin oxide in 10 ml toluene overnight at 80° C. Concentrate the mixture by evaporation, take up the residue in water and acidify with dilute hydrochloric acid. Next, extract with methylene chloride. Wash the organic extracts with sodium chloride solution, dry over magnesium sulphate and concentrate by evaporation. Purify the residue that remains by RP-HPLC (column: Gromsil 250 mm×30 mm, 10 μm; acetonitrile/water gradient: 0-3 min 5% acetonitrile, 3-50 min 5%→98% acetonitrile 55 min 98% acetonitrile). To remove organotin compounds, dissolve the beige foam obtained in 10 ml toluene and add 1 ml ethylene glycol. After heating for 1 h under reflux, remove the solvent under vacuum. Dissolve the residue in methylene chloride, wash with dilute hydrochloric acid and with sodium chloride solution, dry, and concentrate by evaporation. Purification of the residue by RP-HPLC (column: Gromsil 250 mm×30 mm, 10 μm; acetonitrile/water gradient: 0-3 min 5% acetonitrile, 3-34 min 5%→98% acetonitrile, 34-38 min 98% acetonitrile) gives 82.6 mg (42% of theor.) of the title compound as a beige foam.

LC-MS (Method 5): $R_t$=2.38 min; m/z=459 (M+H)$^+$ $^1$H-NMR (400 MHz, DMSO-d$_6$): δ=8.55 (s, 1H), 7.3-7.55 (m, 7H), 6.9 (m, 2H), 4.5 (m, 2H), 3.8 (s, 3), 3.6 (m, 4H), 3.0 (t, 2H).

Example 20

5-(4-Methoxyphenyl)-6-phenyl-4-{3-[2-(1H-tetrazol-5-yl)ethoxy]propoxy}furo[2,3-d]pyrimidine

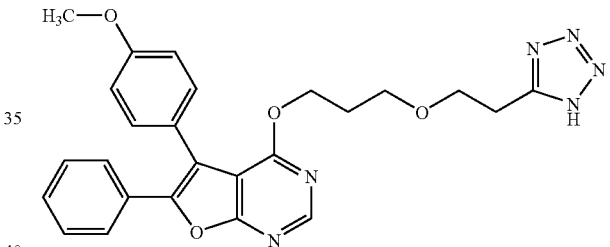

Stir 200 mg (0.47 mmol) 4-[3-(2-cyanoethoxy)propoxy]-5-(4-methoxyphenyl)-6-phenylfuro[2,3-d]-pyrimidine, 804 mg (7.0 mmol) trimethylsilylazide and 174 mg (0.70 mmol) di-n-butyltin oxide in 10 ml toluene overnight at 80° C. Concentrate the mixture by evaporation, take up the residue in water and acidify with dilute hydrochloric acid. Next, extract with methylene chloride. Wash the organic extracts with sodium chloride solution, dry over magnesium sulphate and concentrate by evaporation. Purify the residue that remains by RP-HPLC (column: Gromsil 250 mm×30 mm, 10 μm; acetonitrile/water gradient: 0-3 min 5% acetonitrile, 3-50 min 5%→98% acetonitrile, 50-55 min 98% acetonitrile). To remove organotin compounds, dissolve the beige foam obtained in 10 ml toluene and add 1 ml ethylene glycol. After heating for 1 h under reflux, remove the solvent under vacuum. Dissolve the residue in methylene chloride, wash with dilute hydrochloric acid and with sodium chloride solution, dry, and concentrate by evaporation. Purification of the residue by RP-HPLC (column: Gromsil 250 mm×30 mm, 10 μm; acetonitrile/water gradient: 0-3 min 5% acetonitrile, 3-34 min 5%→98% acetonitrile, 34-38 min 98% acetonitrile) gives 46 mg (21% of theor.) of the title compound as a beige foam.

LC-MS (Method 4): $R_t$=2.62 min; m/z=473 (M+H)$^+$ $^1$H-NMR (400 MHz, DMSO-d$_6$): δ=16.0 (br. s, 1H), 8.55 (s, 1H), 7.3-7.55 (m, 7H), 6.9 (m, 2H), 4.35 (m, 2H), 3.8 (s, 3H), 3.65 (t, 2H), approx. 3.4 (m, 2H, partially masked by H$_2$O), 3.05 (t, 2H), 1.65 (quin, 2H).

General Procedure A: Palladium-Catalysed Arylation of 5-bromo-6-phenylfuro[2,3-d]pyrimidine Derivatives Add successively, at RT, 1.2 to 1.5 eq. of the corresponding arylboronic acid, approx. 2.0 eq. sodium carbonate (as 2 M aqueous solution) and approx. 5 mol-% bis(triphenyl-phosphine)palladium(II) chloride to a solution of 1.0 eq. 6-[(5-bromo-6-phenylfuro[2,3-d]pyrimidin-4-yl)amino]-hexanoic acid methyl ester in DMSO (approx. 3 mol/l). Stir the mixture for a period of 3-18 h at temperatures of 70-90° C. After cooling, isolate the target product directly from the reaction solution by RP-HPLC (eluent: acetonitrile/water gradient). If necessary, it can be further purified by chromatography on silica gel (solvent: dichloromethane/methanol or cyclohexane/ethyl acetate mixtures).

The following examples are prepared according to General Procedure A:

| Example | Structure | Analytical data |
|---|---|---|
| 21 | 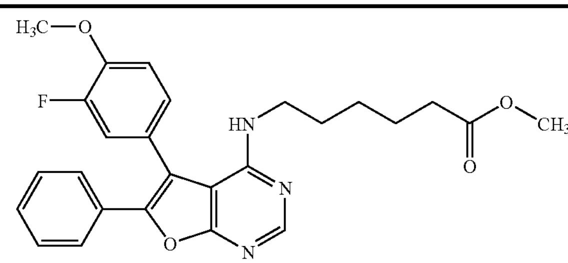 | LC-MS (Method 5): R$_t$ = 2.95 min; m/z = 464 (M + H)$^+$ $^1$H-NMR (400 MHz, DMSO-d$_6$): δ = 8.33 (s, 1 H), 7.45-7.25 (m, 8 H), 5.35 (t, 1 H), 3.94 (s, 3 H), 3.59 (s, 3 H), 3.39 (q, 2 H), 2.29 (t, 2 H), 1.54-1.40 (m, 4 H), 1.26-1.17 (m, 2 H). |
| 22 | 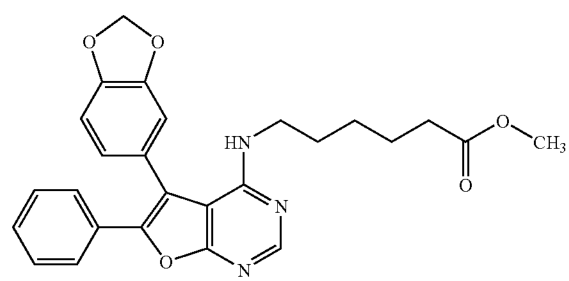 | LC-MS (Method 5): R$_t$ = 2.89 min; m/z = 460 (M + H)$^+$ $^1$H-NMR (400 MHz, DMSO-d$_6$): δ = 8.32 (s, 1 H), 7.46 (d, 2 H), 7.41-7.32 (m, 3 H), 7.13-7.08 (m, 2 H), 6.97 (d, 1 H), 5.30 (t, 1 H), 3.59 (s, 3 H), 3.42-3.35 (m, 2 H), 2.29 (t, 2 H), 1.54-1.40 (m, 4 H), 1.24-1.15 (m, 2 H). |
| 23 | 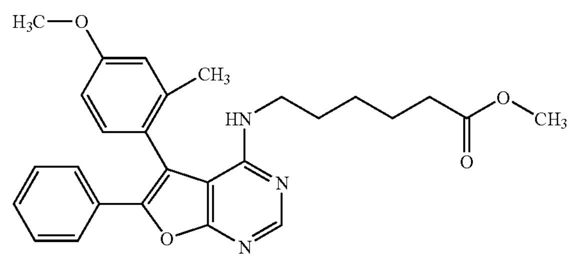 | LC-MS (Method 5): R$_t$ = 2.79 min; m/z = 460 (M + H)$^+$ $^1$H-NMR (400 MHz, DMSO-d$_6$): δ = 8.32 (s, 1 H), 7.42-7.30 (m, 6 H), 7.09 (d, 1 H), 6.98 (d, 1 H), 4.88 (t, 1 H), 3.84 (s, 3 H), 3.59 (s, 3 H), 3.39-3.30 (m, 2 H), 2.26 (t, 2 H), 2.06 (s, 3 H), 1.49-1.33 (m, 4 H), 1.14-1.07 (m, 2 H). |
| 24 | 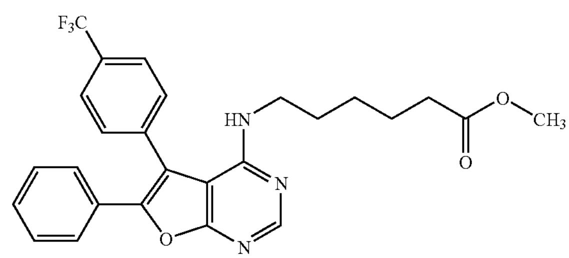 | LC-MS (Method 2): R$_t$ = 2.90 min; m/z = 484 (M + H)$^+$ $^1$H-NMR (400 MHz, DMSO-d$_6$): δ = 8.36 (s, 1 H), 7.91 (d, 2 H), 7.72 (d, 2 H), 7.38 (s, 5 H), 5.37 (t, 1 H), 3.59 (s, 3 H), 3.37 (q, 2 H), 2.29 (t, 2 H), 1.51-1.40 (m, 4 H), 1.23-1.14 (m, 2 H). |
| 25 | 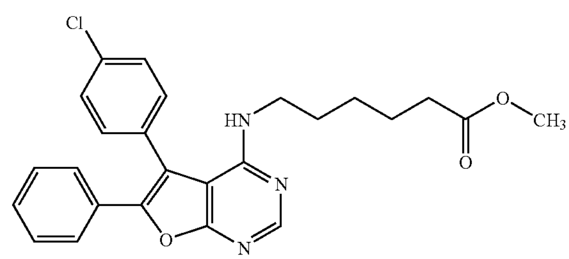 | LC-MS (Method 5): R$_t$ = 3.06 min; m/z = 450 (M + H)$^+$ $^1$H-NMR (400 MHz, DMSO-d$_6$): δ = 8.35 (s, 1 H), 7.62 (d, 2 H), 7.52 (d, 2 H), 7.41-7.31 (m, 5 H), 3.60 (s, 3 H), 3.39 (q, 2 H), 2.30 (t, 2 H), 1.55-1.41 (m, 4 H), 1.24-1.15 (m, 2 H). |

| Example | Structure | Analytical data |
|---|---|---|
| 26 | [structure: 5-(4-vinylphenyl)-6-phenylfuro[2,3-d]pyrimidin-4-yl amino hexanoic acid methyl ester] | LC-MS (Method 2): $R_t$ = 2.93 min; m/z = 442 (M + H)$^+$<br>$^1$H-NMR (400 MHz, DMSO-d$_6$):<br>δ = 8.35 (s, 1 H), 7.19 (d, 2 H), 7.50 (d, 2 H), 7.45-7.31 (m, 5 H), 6.84 (dd, 1 H), 5.99 (d, 1 H), 5.39 (d, 1 H), 5.15 (d, 1 H), 3.58 (s, 3 H), 3.37 (q, 2 H), 2.25 (t, 2 H), 1.49-1.39 (m, 4 H), 1.19-1.10 (m, 2 H). |
| 27 | [structure: 5-(4-trifluoromethoxyphenyl)-6-phenylfuro[2,3-d]pyrimidin-4-yl amino hexanoic acid methyl ester] | LC-MS (Method 2): $R_t$ = 2.99 min; m/z = 500 (M + H)$^+$<br>$^1$H-NMR (400 MHz, DMSO-d$_6$):<br>δ = 8.36 (s, 1 H), 7.66 (d, 2 H), 7.56 (m, 2 H), 7.40-7.31 (m, 5 H), 5.21 (t, 1 H), 3.59 (s, 3 H), 3.38 (q, 2 H), 2.28 (t, 2 H), 1.51-1.39 (m, 4 H), 1.22-1.13 (m, 2 H). |

General Procedure B: Hydrolysis of Methyl Esters to Corresponding Carboxylic Acid Derivatives Add, at RT, 1.5 to 10 eq. sodium hydroxide as 1 N aqueous solution to a solution of the methyl ester in THF or THF/methanol (1:1) (concentration approx. 0.05 to 0.5 mol/l). Stir the mixture for a period of 0.5-18 h at RT and then neutralize or lightly acidify with 1 N hydrochloric acid. If precipitation of a solid occurs, the product can be isolated by filtration, washing with water and drying at high vacuum. Alternatively, the target compound is isolated directly from the raw product, if necessary after extraction with dichloromethane, by preparative RP-HPLC (eluent: water/acetonitrile gradient).

The following examples are prepared according to General Procedure B:

| Example | Structure | Analytical data |
|---|---|---|
| 28 | [structure: 5-(3-fluoro-4-methoxyphenyl)-6-phenylfuro[2,3-d]pyrimidin-4-yl amino hexanoic acid] | LC-MS (Method 4): $R_t$ = 2.63 min; m/z = 450 (M + H)$^+$<br>$^1$H-NMR (400 MHz, DMSO-d$_6$):<br>δ = 12.01 (br. s, 1 H), 7.47-7.25 (m, 9 H), 5.35 (br. s, 1 H), 3.96 (s, 3 H), 3.42-3.30 (m, 2 H), 2.19 (t, 2 H), 1.52-1.40 (m, 4 H), 1.28-1.16 (m, 2 H). |
| 29 | [structure: 5-(benzo[1,3]dioxol-5-yl)-6-phenylfuro[2,3-d]pyrimidin-4-yl amino hexanoic acid] | LC-MS (Method 5): $R_t$ = 2.43 min; m/z = 446 (M + H)$^+$<br>$^1$H-NMR (400 MHz, DMSO-d$_6$):<br>δ = 8.32 (s, 1 H), 7.49 (d, 2 H), 7.41-7.32 (m, 3 H), 7.12 (d, 1 H), 7.07 (s, 1 H), 6.99 (d, 1 H), 6.19 (s, 2 H), 5.21 (t, 1 H), 3.45-3.25 (m, 2 H), 1.82 (t, 2 H), 1.45-1.35 (m, 4 H), 1.18-1.10 (m, 2 H). |

| Example | Structure | Analytical data |
| --- | --- | --- |
| 30 | [Structure: 5-(4-methoxy-2-methylphenyl)-6-phenylfuro[2,3-d]pyrimidine with 4-NH-(CH2)5-COOH] | LC-MS (Method 4): $R_t$ = 2.69 min; m/z = 446 (M + H)$^+$<br>$^1$H-NMR (400 MHz, DMSO-d$_6$):<br>δ = 8.33 (s, 1 H), 7.42-7.30 (m, 7 H), 7.09 (d, 1 H), 6.99 (dd, 1 H), 4.82 (t, 1 H), 3.86 (s, 3 H), 3.40-3.38 (m, 2 H), 2.08 (s, 3 H), 1.76 (t, 2 H), 1.38-1.26 (m, 4 H), 1.10-1.01 (m, 2 H). |
| 31 | [Structure: 5-(4-trifluoromethylphenyl)-6-phenylfuro[2,3-d]pyrimidine with 4-NH-(CH2)5-COOH] | LC-MS (Method 5): $R_t$ = 2.98 min; m/z = 470 (M + H)$^+$<br>$^1$H-NMR (400 MHz, DMSO-d$_6$):<br>δ = 11.99 (s, 1 H), 8.37 (s, 1 H), 7.92 (d, 2 H), 7.74 (d, 2 H), 7.40-7.34 (m, 5 H), 5.38 (t, 1 H), 3.38 (q, 2 H), 2.19 (t, 2 H), 1.50-1.40 (m, 4 H), 1.21-1.13 (m, 2 H). |
| 32 | [Structure: 5-(4-chlorophenyl)-6-phenylfuro[2,3-d]pyrimidine with 4-NH-(CH2)5-COOH] | LC-MS (Method 4): $R_t$ = 2.79 min; m/z = 436 (M + H)$^+$<br>$^1$H-NMR (400 MHz, DMSO-d$_6$):<br>δ = 11.99 (s, 1 H), 8.33 (s, 1 H), 7.64 (d, 2 H), 7.52 (d, 2 H), 7.43-7.31 (m, 5 H), 6.35 (t, 1 H), 3.39 (q, 2 H), 2.19 (m, 2 H), 1.50-1.40 (m, 4 H), 1.24-1.15 (m, 2 H). |
| 33 | [Structure: 5-(4-vinylphenyl)-6-phenylfuro[2,3-d]pyrimidine with 4-NH-(CH2)5-COOH] | LC-MS (Method 4): $R_t$ = 2.82 min; m/z = 428 (M + H)$^+$<br>$^1$H-NMR (400 MHz, DMSO-d$_6$):<br>δ = 11.99 (s, 1 H), 8.35 (s, 1 H), 7.68 (d, 2 H), 7.50 (d, 2 H), 7.45 (d, 2 H), 7.40-7.30 (m, 5 H), 6.87 (dd, 1 H), 5.99 (d, 1 H), 5.39 (d, 1 H), 5.15 (t, 1 H), 3.42-3.30 (m, 2 H), 2.16 (t, 2 H), 1.48-1.12 (m, 6 H). |
| 34 | [Structure: 5-(4-trifluoromethoxyphenyl)-6-phenylfuro[2,3-d]pyrimidine with 4-NH-(CH2)5-COOH] | LC-MS (Method 5): $R_t$ = 2.80 min; m/z = 486 (M + H)$^+$<br>$^1$H-NMR (400 MHz, DMSO-d$_6$):<br>δ = 12.01 (br. s, 1 H), 8.35 (s, 1 H), 7.67 (br. s, 2 H), 7.58 (br. s, 2 H), 7.45-7.30 (m, 5 H), 5.19 (br. s, 1 H), 2.20 (br. s, 2 H), 1.51-1.35 (m, 4 H), 1.25-1.12 (m, 2 H). |

The following examples are prepared according to General Procedure A (for description see above) from the corresponding 5-bromo-6-phenylfuro[2,3-d]pyrimidine and phenylboronic acid derivatives:

| Example | Structure | Analytical data |
|---|---|---|
| 35 | 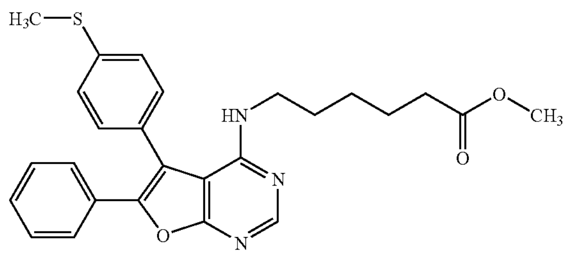 | LC-MS (Method 5): $R_t$ = 3.06 min; m/z = 462 (M + H)$^+$<br>$^1$H-NMR (400 MHz, DMSO-d$_6$): δ = 8.34 (s, 1 H), 7.48-7.33 (m, 9 H), 5.18 (t, 1 H), 3.58 (s, 3 H), 3.38 (q, 2 H), 2.55 (s, approx. 3 H), 2.29 (t, 2 H), 1.50-1.40 (m, 4 H), 1.20-1.12 (m, 2 H). |
| 36 | 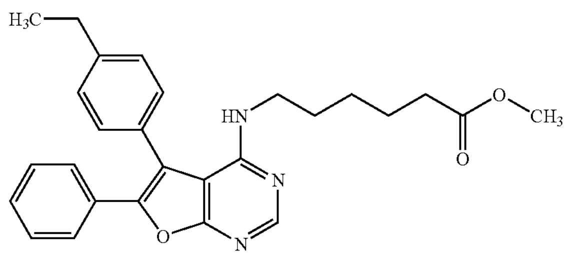 | LC-MS (Method 8): $R_t$ = 3.19 min; m/z = 444 (M + H)$^+$<br>$^1$H-NMR (400 MHz, DMSO-d$_6$): δ = 8.34 (s, 1 H), 7.49-7.42 (m, 5 H), 7.39-7.28 (m, 4 H), 4.93 (t, 1 H), 3.35 (m, 2 H), 2.75 (q, 2 H), 2.28 (t, 2 H), 1.49-1.35 (m, 4 H), 1.28 (t, 3 H), 1.16-1.10 (m, 2 H). |
| 37 | 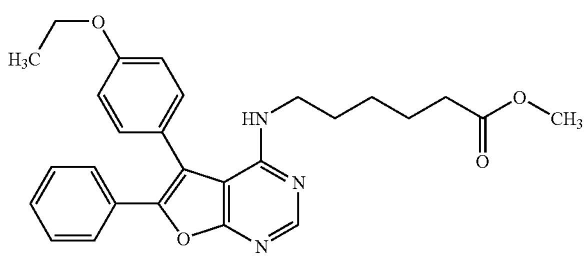 | LC-MS (Method 8): $R_t$ = 3.08 min; m/z = 460 (M + H)$^+$<br>$^1$H-NMR (400 MHz, DMSO-d$_6$): δ = 8.32 (s, 1 H), 7.48-7.30 (m, 7 H), 7.12 (d, 2 H), 5.07 (t, 1 H), 4.11 (q, 2 H), 3.60 (s, 3 H), 3.36 (q, 2 H), 2.27 (t, 2 H), 1.50-1.38 (m, 4 H), 1.40 (t, 3 H), 1.18-1.11 (m, 2 H). |
| 38 | 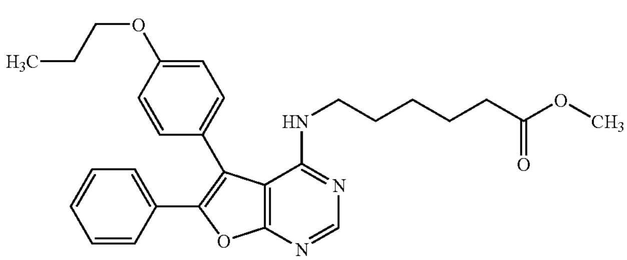 | LC-MS (Method 8): $R_t$ = 3.22 min; m/z = 474 (M + H)$^+$<br>$^1$H-NMR (400 MHz, DMSO-d$_6$): δ = 8.32 (s, 1 H), 7.48-7.30 (m, 7 H), 7.12 (d, 2 H), 5.08 (t, 1 H), 4.03 (t, 3 H), 3.60 (s, 3 H), 3.37 (q, 2 H), 2.28 (t, 2 H), 1.82-1.77 (m, 2 H), 1.50-1.60 (m, 4 H), 1.18-1.10 (m, 2 H), 1.02 (t, 3 H). |
| 39 | 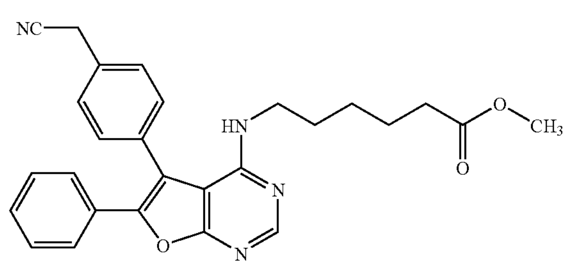 | LC-MS (Method 8): $R_t$ = 2.73 min; m/z = 455 (M + H)$^+$<br>$^1$H-NMR (400 MHz, CDCl$_3$): δ = 8.43 (s, 1 H), 7.58-7.48 (m, 6 H), 7.30-7.24 (m, approx. 3 H), 4.55 (t, 1 H), 3.91 (s, 2 H), 3.68 (s, 3 H), 3.45 (q, 2 H), 2.30 (t, 2 H), 1.65-1.45 (m, approx. 4 H), 1.30-1.22 (m, 2 H). |
| 40 | 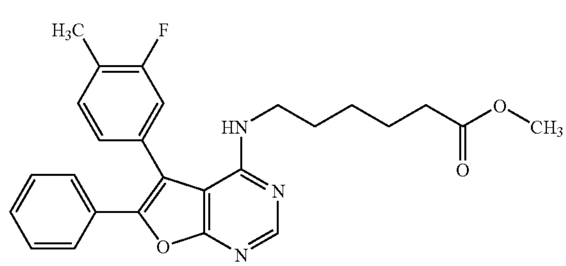 | LC-MS (Method 2): $R_t$ = 2.92 min; m/z = 448 (M + H)$^+$<br>$^1$H-NMR (400 MHz, CDCl$_3$): δ = 8.41 (s, 1 H), 7.55-7.50 (m, 2 H), 7.38 (t, 1 H), 7.32-7.25 (m, approx. 3 H), 7.16 (dd, 2 H), 4.66 (t, 1 H), 3.68 (s, 3 H), 3.44 (q, 2 H), 2.41 (s, 3 H), 2.29 (t, 2 H), 1.65-1.45 (m, 4 H), 1.30-1.22 (m, 2 H). |

| Example | Structure | Analytical data |
|---|---|---|
| 41 | 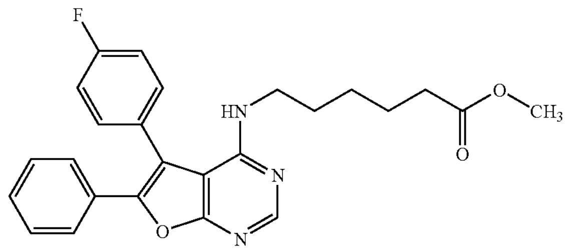 | LC-MS (Method 2): R$_t$ = 2.77 min; m/z = 434 (M + H)$^+$<br>$^1$H-NMR (400 MHz, CDCl$_3$): δ = 8.41 (s, 1 H), 7.53-7.47 (m, 4 H), 7.31-7.22 (m, approx. 5 H), 4.54 (br. s, 1 H), 3.69 (s, 3 H), 3.45 (q, 2 H), 2.29 (t, 2 H), 1.67-1.55 (m, approx. 2 H), 1.50-1.42 (m, 2 H), 1.30-1.22 (m, 2 H). |
| 42 | 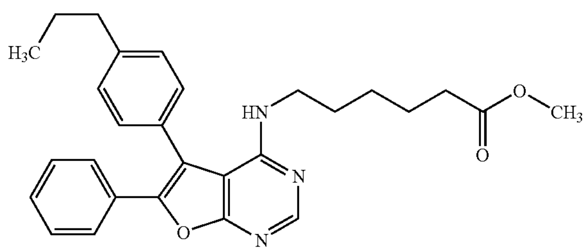 | LC-MS (Method 8): R$_t$ = 3.31 min; m/z = 458 (M + H)$^+$<br>$^1$H-NMR (400 MHz, DMSO-d$_6$): δ = 8.35 (s, 1 H), 7.48-7.40 (m, 5 H), 7.38-7.30 (m, 4 H), 4.89 (t, 1 H), 3.59 (s, 3 H), 3.35 (q, 2 H), 2.69 (t, 2 H), 2.25 (t, 2 H), 1.69 (q, 2 H), 1.50-1.42 (m, 2 H), 1.40-1.35 (m, 2 H), 1.17-1.11 (m, 2 H), 0.95 (t, 3 H). |
| 43 | 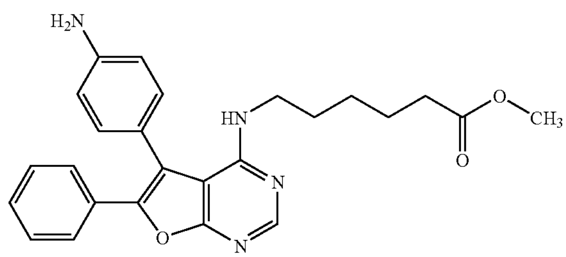 | LC-MS (Method 5): R$_t$ = 2.52 min; m/z = 431 (M + H)$^+$<br>$^1$H-NMR (400 MHz, DMSO-d$_6$): δ = 8.31 (s, 1 H), 7.51 (d, 2 H), 7.40-7.30 (m, 3 H), 7.15 (d, 2 H), 6.72 (d, 2 H), 5.49 (s, 2 H), 5.14 (t, 1 H), 3.60 (s, 3 H), 3.38 (q, 2 H), 2.29 (t, 2 H), 1.52-1.38 (m, 4 H), 1.22-1.17 (m, 2 H). |
| 44 | 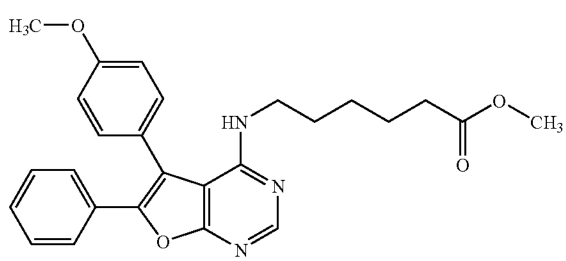 | LC-MS (Method 5): R$_t$ = 2.93 min; m/z = 446 (M + H)$^+$<br>$^1$H-NMR (500 MHz, CDCl$_3$): δ = 8.40 (s, 1 H), 7.55 (d, 2 H), 7.40 (d, 2 H), 7.30-7.23 (m, approx. 3 H), 7.07 (d, 2 H), 4.68 (br. s, 1 H), 3.93 (s, 3 H), 3.69 (s, 3 H), 3.43 (q, 2 H), 2.29 (t, 2 H), 1.62-1.55 (m, 2 H), 1.50-1.42 (m, 2 H), 1.27-1.21 (m, 2 H). |

Example 45

6-{[5-(4-Methoxyphenyl)-6-phenylfuro[2,3-d]pyrimidin-4-yl](methyl)amino}hexanoic acid methyl ester

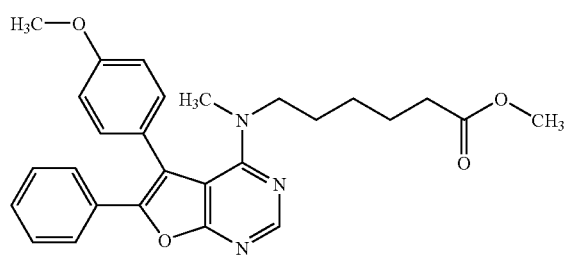

Dissolve 200 mg (0.463 mmol) [(5-bromo-6-phenylfuro[2,3-d]pyrimidin-4-yl)(methyl)amino]hexanoic acid methyl ester in 1.25 ml DMSO and 0.125 ml methanol. Add successively, under argon at RT, 16.2 mg (0.023 mmol) bis(triphenylphosphine)palladium(II) chloride, 127 mg (0.925 mmol) potassium carbonate and 105.4 mg (0.694 mmol) 4-methoxyphenylboronic acid. Heat the mixture to 80° C. for approx. 3 h, stirring vigorously. After cooling, purify the reaction mixture directly by preparative RP-HPLC (gradient: acetonitrile/water). 133.9 mg (63% of theor.) of the target product is obtained.

LC-MS (Method 2): R$_t$=2.85 min; m/z=460 (M+H)$^+$ $^1$H-NMR (400 MHz, DMSO-d$_6$): δ=8.33 (s, 1H), 7.40-7.30 (m, 7H), 7.07 (d, 2H), 3.83 (s, 3H), 3.58 (s, 3H), 3.30 (m, approx. 2H), 2.58 (s, 3H), 2.25 (t, 2H), 1.50-1.33 (m, 4H), 1.12-1.03 (m, 2H).

Example 46

6-({5-[4-(Ethylamino)phenyl]-6-phenylfuro[2,3-d]pyrimidin-4-yl}amino)hexanoic acid methyl ester

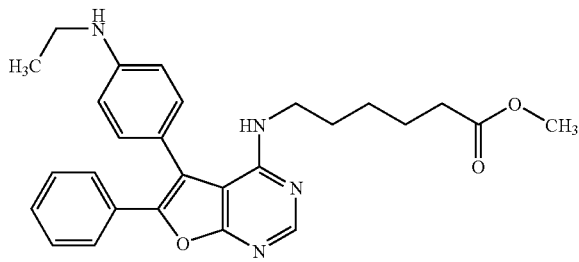

Put 29.2 mg (0.068 mmol) 6-({5-[4-aminophenyl]-6-phenylfuro[2,3-d]pyrimidin-4-yl}amino)-hexanoic acid methyl ester in 0.5 ml acetonitrile with 14 µl (0.102 mmol) triethylamine and add an excess of ethyl iodide in portions at 45° C. in closed apparatus over a period of 12 h. After cooling, dilute the reaction mixture with dichloromethane, wash successively with satd. sodium hydrogencarbonate solution and satd. sodium chloride solution, dry over sodium sulphate and concentrate by vacuum evaporation. After preparative RP-HPLC (gradient: acetonitrile/water), 6.2 mg of the target compound (19.9% of theor.) is isolated from the raw product mixture.

LC-MS (Method 5): $R_t$=2.96 min; m/z=459 (M+H)$^+$ $^1$H-NMR (400 MHz, CDCl$_3$): δ=8.39 (s, 1H), 7.61 (d, 2H), 7.30-7.21 (m, approx. 5H), 6.73 (d, 2H), 4.83 (t, 1H), 3.88 (br. s, 1H) 3.68 (s, 3H), 3.43 (q, 2H), 3.25 (q, 2H), 2.29 (t, 2H), 1.66-1.60 (m, 2H), 1.52-1.45 (m, 2H), 1.35 (t, 3H), 1.29-1.21 (m, 2H).

Example 47

(+)-{[(2S)-3-{[5-(4-Ethylphenyl)-6-phenylfuro[2,3-d]pyrimidin-4-yl]oxy}-2-methylpropyl]oxy}-acetic acid tert.-butyl ester

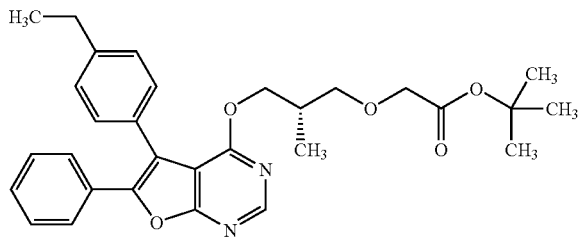

Dissolve 85 mg (0.416 mmol) (+)-{[(2R)-3-hydroxy-2-methylpropyl]oxy}acetic acid tert.-butyl ester in 2 ml abs. THF, cool to 0° C. and add 0.21 ml (0.416 mmol) phosphazene base P2-t-Bu (2 M solution in THF). After 10 min at 0° C., add 126.7 mg (0.378 mmol) 4-chloro-5-4-ethylphenyl)-6-phenylfuro[2,3-d]pyrimidine, and stir the mixture for 10 min at 0° C. and for a further 2 h at RT. Then add water, adjust to approx. pH 7 with 1 N hydrochloric acid and extract with dichloromethane. Wash the organic phase with satd. sodium chloride solution, dry over sodium sulphate and concentrate by vacuum evaporation. 125.1 mg of the target product (65.8% of theor.) is isolated from the raw product by chromatography on silica gel (eluent: cyclohexane/ethyl acetate 1:1).

LC-MS (Method 9): $R_t$=4.88 min; m/z=503 (M+H)$^+$ $^1$H-NMR (400 MHz, DMSO-d$_6$): δ=8.59 (s, 1H), 7.54 (d, 2H), 7.43-7.38 (m, 5H), 7.32 (d, 2H), 4.30 (m, 2H), 3.84 (s, 2H), 3.13 (d, 2H), 2.69 (q, 2H), 1.98 (m, 1H), 1.40 (s, 9H), 1.24 (t, 3H), 0.72 (d, 3H).

$[α]_D^{20}$=+11°, c=0.255, chloroform.

Example 48

(−)-{[(2R)-3-{[5-(4-Ethylphenyl)-6-phenylfuro[2,3-d]pyrimidin-4-yl]oxy}-2-methylpropyl]oxy}acetic acid ethyl ester

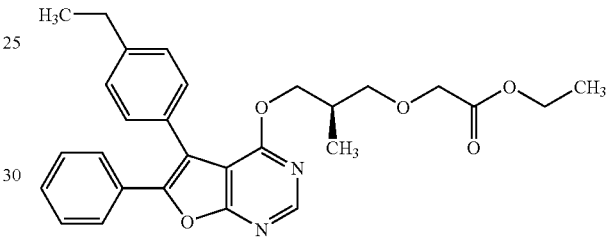

Cool a solution of 670.3 mg (2.0 mmol) 4-chloro-5-(4-ethylphenyl)-6-phenylfuro[2,3-d]pyrimidine and 441 mg (2.5 mmol) (−)-{[(2S)-3-hydroxy-2-methylpropyl]oxy}acetic acid ethyl ester in 5.5 ml abs. THF to 0° C. and add 2.4 ml (2.4 mmol) phosphazene base P4-t-Bu (1 M solution in hexane). At the end of addition, heat to RT and stir for 2 h at RT, then add water to the reaction mixture and neutralize with 1 N hydrochloric acid. Extract with dichloromethane, dry the organic phase over sodium sulphate and concentrate under vacuum. After preparative RP-HPLC (gradient: water/acetonitrile), 107.6 mg of the target product (65.8% of theor.) is obtained from the raw product.

LC-MS (Method 8): $R_t$=3.36 min; m/z=475 (M+H)$^+$ $^1$H-NMR (400 MHz, DMSO-d$_6$): δ=8.59 (s, 1H), 7.54 (d, 2H), 7.43-7.37 (m, 5H), 7.31 (d, 2H), 4.35-4.27 (m, 2H), 4.09 (q, 2H), 3.97 (s, 2H), 3.19-3.11 (m, 2H), 2.68 (q, 2H), 1.98 (m, 1H), 1.22 (t, 3H), 1.17 (t, 3H), 0.71 (d, 3H).

$[α]_D^{20}$=−17.1°, c=0.52, chloroform.

The following examples are prepared according to General Procedure B (hydrolysis of methyl or similarly ethyl esters) from the corresponding carboxylic acid esters:

| Example | Structure | Analytical data |
|---|---|---|
| 49 | 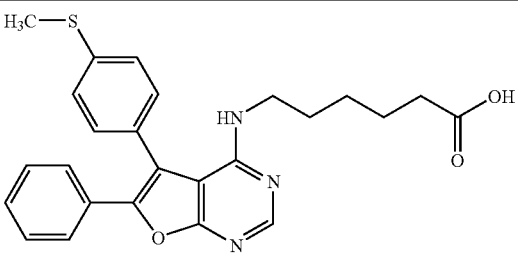 | LC-MS (Method 8): $R_t$ = 2.70 min; m/z = 338 (M + H)$^+$ |

-continued

| Example | Structure | Analytical data |
|---|---|---|
| 50 | 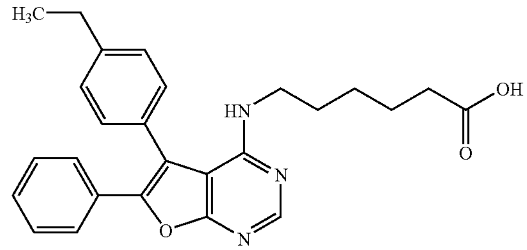 | LC-MS (Method 2): $R_t$ = 2.61 min; m/z = 430 (M + H)$^+$ $^1$H-NMR (400 MHz, DMSO-d$_6$): δ = 8.33 (s, 1 H), 7.49-7.42 (m, 6 H), 7.40-7.30 (m, 3 H), 4.89 (br. t, 1 H), 3.35 (q, approx. 2 H), 2.75 (q, 2 H), 1.84 (t, 2 H), 1.39-1.30 (m, 4 H), 1.28 (t, 3 H), 1.11-1.05 (m, 2 H). |
| 51 | 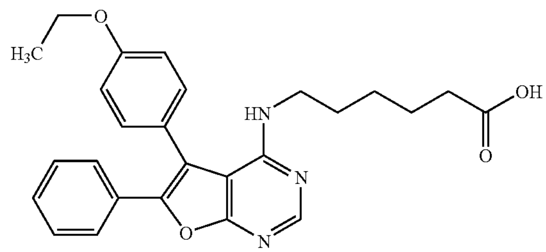 | LC-MS (Method 5): $R_t$ = 2.66 min; m/z = 466 (M + H)$^+$ $^1$H-NMR (400 MHz, CDCl$_3$): δ = 8.30 (s, 1 H), 7.46-7.41 (m, 2 H), 7.29 (d, 2 H), 7.20-7.15 (m, 2 H), 6.98 (d, 2 H), 4.71 (br. t, 1 H), 4.04 (q, 2 H), 3.35-3.25 (m, 2 H), 2.14-2.07 (m, 2 H), 1.52-1.43 (m, 2 H), 1.40 (t, 3 H), 1.40-1.32 (m, 2 H), 1.20-1.10 (m, 2 H). |
| 52 | 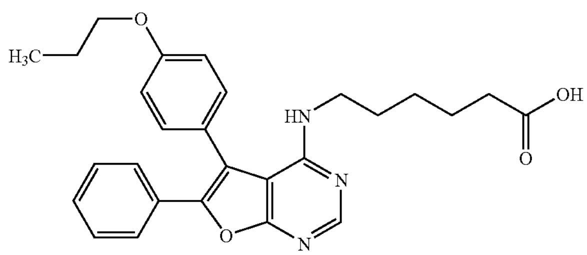 | LC-MS (Method 8): $R_t$ = 2.86 min; m/z = 460 (M + H)$^+$ $^1$H-NMR (400 MHz, CDCl$_3$): δ = 8.38 (s, 1 H), 7.55 (d, 2 H), 7.38 (d, 2 H), 7.30-7.23 (m, approx. 3 H), 7.08 (d, 2 H), 4.74 (t, 1 H), 4.03 (t, 2 H), 3.40 (q, 2 H), 2.30-2.23 (m, 2 H), 1.87 (q, 2 H), 1.65-1.57 (m, 2 H), 1.48-1.41 (m, 2 H), 1.30-1.22 (m, approx. 2 H), 1.10 (t, 3 H). |
| 53 | 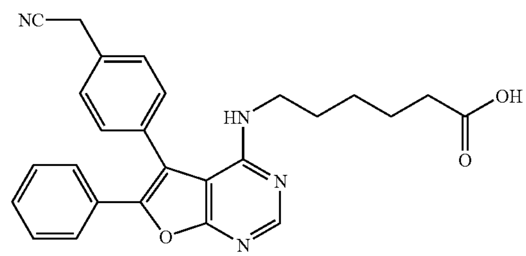 | LC-MS (Method 8): $R_t$ = 2.42 min; m/z = 441 (M + H)$^+$ $^1$H-NMR (400 MHz, CDCl$_3$): δ = 8.30 (s, 1 H), 7.55-7.40 (m, 7 H), 7.27-7.19 (m, 3 H), 4.55 (br. t, 1 H), 3.98 (s, approx. 2 H), 3.37-3.29 (m, 2 H), 2.15-2.09 (m, 2 H), 1.52-1.42 (m, 2 H), 1.40-1.30 (m, 2 H), 1.18-1.09 (m, 2 H). |
| 54 | 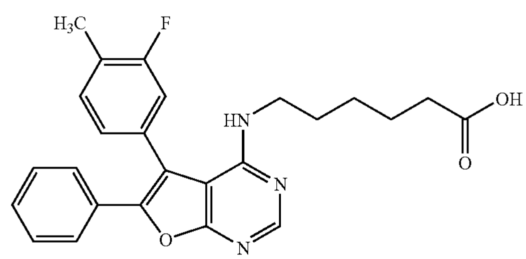 | LC-MS (Method 2): $R_t$ = 2.50 min; m/z = 434 (M + H)$^+$ $^1$H-NMR (400 MHz, CDCl$_3$): δ = 8.33 (s, 1 H), 7.53-7.22 (m, approx. 6 H), 7.15-7.05 (m, 2 H), 4.66 (t, 1 H), 3.41-3.35 (m, 2 H), 2.37 (s, 3 H), 2.25-2.15 (m, 2 H), 1.58-1.49 (m, 2 H), 1.47-1.38 (m, 2 H), 1.27-1.18 (m, 2 H). |
| 55 | 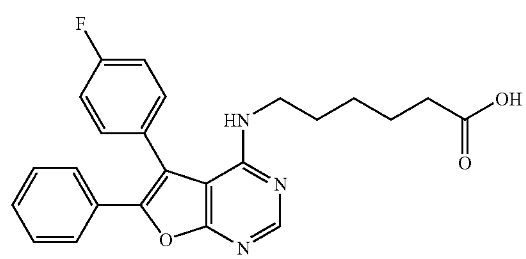 | LC-MS (Method 5): $R_t$ = 2.55 min; m/z = 420 (M + H)$^+$ |

| Example | Structure | Analytical data |
|---|---|---|
| 56 | 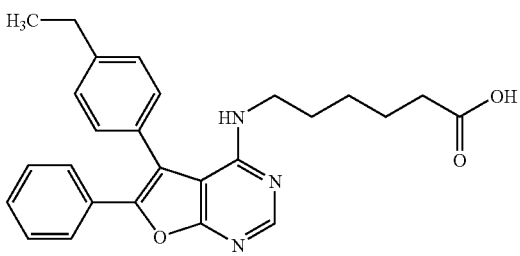 | LC-MS (Method 2): $R_t$ = 2.61 min; m/z = 430 (M + H)$^+$<br>$^1$H-NMR (400 MHz, DMSO-d$_6$):<br>δ = 8.34 (s, 1 H), 7.49-7.42 (m, 6 H), 7.39-7.30 (m, 3 H), 4.39 (t, 1 H), 3.33 (q, 2 H), 2.73 (q, 2 H), 1.82 (t, 2 H), 1.39-1.30 (m, 4 H), 1.28 (t, 3 H), 1.10-1.03 (m, 2 H). |
| 57 | 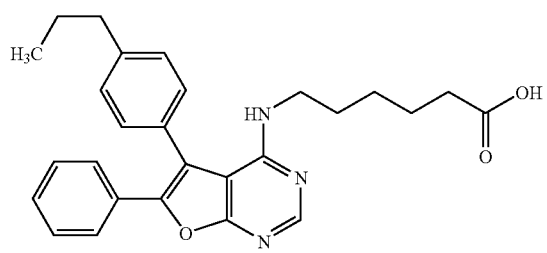 | LC-MS (Method 8): $R_t$ = 3.07 min; m/z = 444 (M + H)$^+$<br>$^1$H-NMR (400 MHz, DMSO-d$_6$):<br>δ = 8.33 (s, 1 H), 7.50-7.40 (m, 6 H), 7.38-7.30 (m, 3 H), 4.85 (t, 1 H), 3.35 (q, 2 H), 2.70 (t, 2 H), 1.82 (t, 2 H), 1.72-1.65 (m, 2 H), 1.40-1.30 (m, 4 H), 1.13-1.04 (m, 2 H), 0.93 (t, 3 H). |
| 58 | 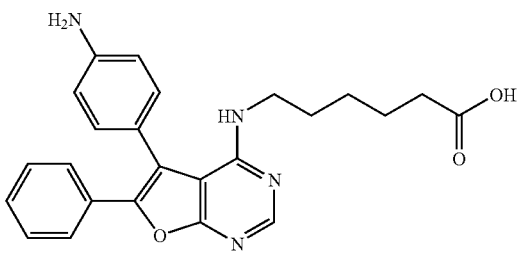 | LC-MS (Method 2): $R_t$ = 2.03 min; m/z = 416 (M + H)$^+$<br>$^1$H-NMR (400 MHz, DMSO-d$_6$):<br>δ = 8.30 (s, 1 H), 7.56 (d, 2 H), 7.40-7.28 (m, 3 H), 7.14 (d, 2 H), 6.78 (d, 2 H), 5.60 (br. s, 2 H), 5.07 (t, 1 H), 3.34 (q, approx. 2 H), 1.81 (t, 2 H), 1.41-1.32 (m, 4 H), 1.16-1.10 (m, 2 H). |
| 59 | 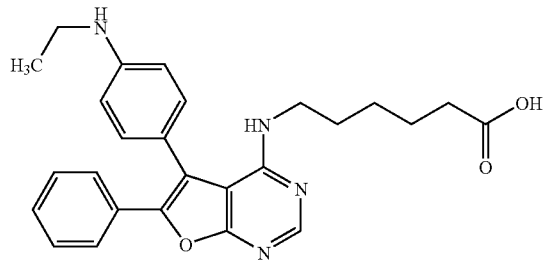 | LC-MS (Method 5): $R_t$ = 2.55 min; m/z = 455 (M + H)$^+$ |
| 60 | 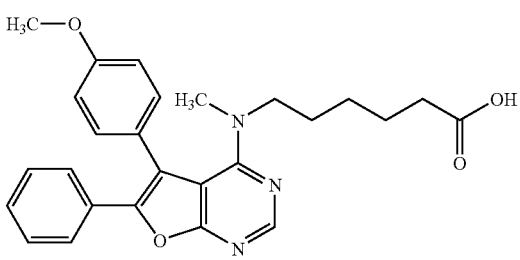 | LC-MS (Method 2): $R_t$ = 2.45 min; m/z = 446 (M + H)$^+$<br>$^1$H-NMR (400 MHz, DMSO-d$_6$):<br>δ = 8.34 (s, 1 H), 7.40-7.28 (m, approx. 7 H), 7.11-7.06 (m, 2 H), 3.83 (s, 3 H), 3.27 (m, approx. 2 H), 2.58 (s, approx. 3 H), 1.89-1.80 (m, 2 H), 1.40-1.30 (m, 4 H), 1.08-0.98 (m, 2 H). |

Example 61

(+)-{[(2S)-3-{[5-(4-Ethylphenyl)-6-phenylfuro[2,3-d]pyrimidin-4-yl]oxy}-2-methylpropyl]oxy}-acetic acid

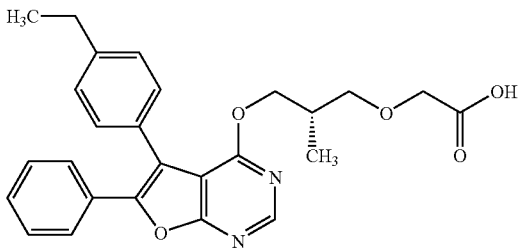

First treat 120 mg (0.239 mmol) {[(2S)-3-{[5-(4-ethylphenyl)-6-phenylfuro[2,3-d]pyrimidin-4-yl]oxy}-2-methylpropyl]oxy}acetic acid tert.-butyl ester with 0.46 ml TFA in 2.0 ml dichloromethane at RT. Stir the mixture at RT for approx. 4 h, adding more TFA in portions. Then concentrate the reaction mixture by vacuum evaporation, isolating the target product after preparative RP-HPLC (gradient: acetonitrile/water). 106.8 mg (96.1% of theor.) is obtained.

LC-MS (Method 8): $R_t$=2.98 min; m/z=447 (M+H)$^+$ $^1$H-NMR (400 MHz, DMSO-$d_6$): δ=8.58 (s, 1H), 7.55 (d, 2H), 7.42-7.37 (m, 5H), 7.30 (d, 2H), 4.30 (m, approx. 2H), 3.89 (s, 2H), 3.20-3.10 (m, 2H), 2.69 (q, 2H), 1.95 (m, 1H), 1.24 (t, 3H), 0.71 (d, 3H).

$[α]_D^{20}$=+12.8°, c=0.41, chloroform.

Example 62

(−)-{[(2R)-3-{[5-(4-Ethylphenyl)-6-phenylfuro[2,3-d]pyrimidin-4-yl]oxy}-2-methylpropyl]oxy}-acetic acid

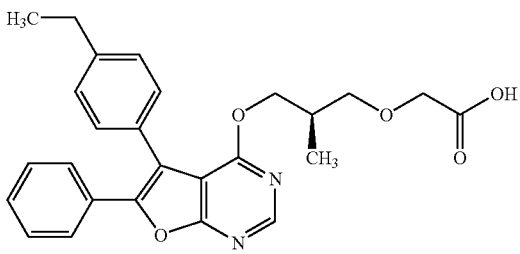

Dissolve 85.3 Mg (0.18 mmol) (−)-{[(2R)-3-{[5-(4-ethylphenyl)-6-phenylfuro[2,3-d]pyrimidin-4-yl]oxy}-2-methylpropyl]oxy}acetic acid ethyl ester in 1 ml THF and add 0.9 ml 1 N sodium hydroxide solution. Stir the mixture for 3.5 h at RT, then neutralize with 1 N hydrochloric acid and extract with dichloromethane. Concentrate the organic phase by vacuum evaporation. 18.3 mg of the target product (22.8% of theor.) is isolated from the residue after preparative RP-HPLC (gradient: acetonitrile/water).

LC-MS (Method 9): $R_t$=4.02 min; m/z=447 (M+H)$^+$ $^1$H-NMR (400 MHz, DMSO-$d_6$): δ=8.59 (s, 1H), 7.54 (d, 2H), 7.42-7.36 (m, 5H), 7.32 (d, 2H), 4.30 (m, 2H), 3.85 (s, 2H), 3.20-3.10 (m, 2H), 2.69 (q, 2H), 1.98 (m, 1H), 1.21 (t, 3H), 0.70 (d, 3H).

$[α]_D^{20}$=−18.5°, c=0.585, chloroform.

Example 63

(+/−)-6-{[5-(4-Methoxyphenyl)-6-phenylfuro[2,3-d]pyrimidin-4-yl]oxy}heptanoic acid methyl ester

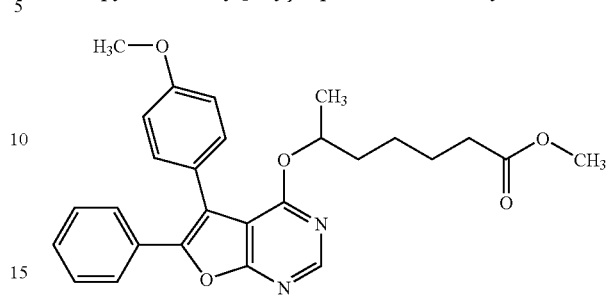

Put 1.902 g (11.9 mmol) (+/−)-6-hydroxyheptanoic acid methyl ester under argon in 20 ml THF and cool to 0° C. Add 6 ml (11.9 mmol) of a 2 M solution of the phosphazene base P2-tert.-butyl in THF and stir for a further 10 min at RT. Then cool to 0° C. again. Add 2.00 g (5.94 mmol) 4-chloro-5-(4-methoxyphenyl)-6-phenylfuro[2,3-d]pyrimidine and then stir for a further 1 h at RT. Dilute with water, acidify with 10% aqueous citric acid solution and extract twice with ethyl acetate. Combine the ethyl acetate phases and wash once with satd. sodium chloride solution. Dry over magnesium sulphate, concentrate by evaporation and purify the residue by column chromatography on silica gel (solvent: cyclohexane/ethyl acetate 9:1). 1.38 g (78.0% of theor.) of the target compound is obtained.

LC-MS (Method 2): $R_t$=3.12 min; m/z=461 (M+H)$^+$ $^1$H-NMR (400 MHz, DMSO-$d_6$): δ=8.50 (s, 1H), 7.62 (m, 2H), 7.36 (d, 2H), 7.30 (m, 3H), 6.94 (d, 2H), 5.35-5.26 (m, 1H), 3.88 (s, 3H), 3.64 (s, 3H), 2.22 (m, 2H), 1.61-1.47 (m, 4H), 1.28 (d, 3H), 1.28-1.15 (m, 2H).

Example 64

(+/−)-6-{[5-(4-Methoxyphenyl)-6-phenylfuro[2,3-d]pyrimidin-4-yl]oxy}heptanoic acid tert.-butyl ester

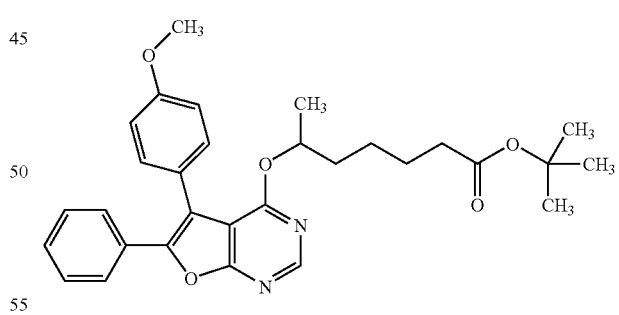

Put 9.010 g (44.54 mmol) (+/−)-6-hydroxyheptanoic acid tert.-butyl ester under argon in 100 ml THF and cool to 0° C. Add 15.117 g (44.54 mmol) phosphazene base P2-ethyl and stir for a further 10 min at RT. Then cool to 0° C. again. Add 10.00 g (29.69 mmol) 4-chloro-5-(4-methoxyphenyl)-6-phenylfuro[2,3-d]pyrimidine and then stir overnight at RT. Then dilute with water, acidify with 10% citric acid solution and extract twice with ethyl acetate. Combine the ethyl acetate phases and wash once with satd. sodium chloride solution. Dry over magnesium sulphate, concentrate by evaporation and purify the residue by chromatography on silica gel (solvent: cyclohexane/ethyl acetate 9:1). 11.4 g (76.4% of theor.) of the target compound is obtained.

LC-MS (Method 8): $R_t$=3.53 min; m/z=503 (M+H)$^+$ $^1$H-NMR (400 MHz, DMSO-$d_6$): δ=8.49 (s, 1H), 7.62 (m, 2H), 7.36 (d, 2H), 7.30 (m, 3H), 6.94 (d, 2H), 5.36-5.27 (m, 1H), 3.89 (s, 3H), 2.12 (t, 2H), 1.64-1.45 (m, 4H), 1.42 (s, 9H), 1.28 (d, 3H), 1.28-1.12 (m, 2H).

Separation of the Enantiomers:

Separate the racemate obtained above by preparative chiral-phase HPLC into the enantiomers [column: Daicel Chiralpak AD-H, 250 mm×20 mm; flow: 25 ml/min; detection: 260 nm; injection volume: 1500 µl; temperature: 24° C.; eluent: 98% iso-hexane/2% 2-propanol]. 3.9 g (7.76 mmol) (+)-6-{[5-(4-methoxyphenyl)-6-phenylfuro[2,3-d]pyrimidin-4-yl]oxy}heptanoic acid tert.-butyl ester (Example 65) and 4.8 g (9.45 mmol) (−)-6-{[5-(4-methoxyphenyl)-6-phenylfuro[2,3-d]pyrimidin-4-yl]oxy}heptanoic acid tert.-butyl ester (Example 66) are obtained from 11.4 g of the racemate in this way.

Example 65

(+)-6-{[5-(4-Methoxyphenyl)-6-phenylfuro[2,3-d]pyrimidin-4-yl]oxy}heptanoic acid tert.-butyl ester (Enantiomer 1)

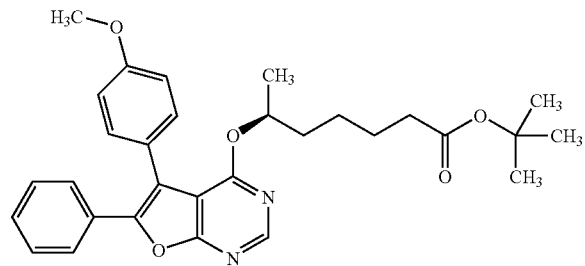

HPLC: $R_t$=11.76 min; ee>99.5% [column: Daicel AD-H, 250 mm×4 mm; eluent: isopropanol/isohexane 3:97; flow: 1 ml/min; UV detection: 250 nm].

Example 66

(−)-6-{[5-(4-Methoxyphenyl)-6-phenylfuro[2,3-d]pyrimidin-4-yl]oxy}heptanoic acid tert.-butyl ester (Enantiomer 2)

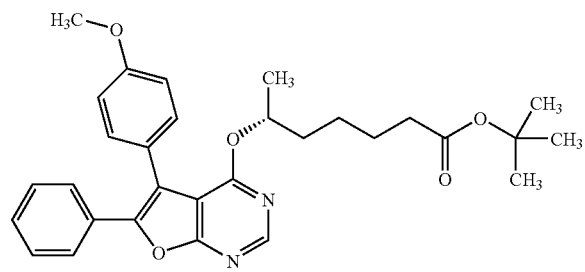

HPLC: $R_t$=14.00 min; ee>98.9% [column: Daicel AD-H, 250 mm×4 mm; eluent: isopropanol/isohexane 3:97; flow: 1 ml/min; UV detection: 250 nm].

Alternatively, (−)-6-{[5-(4-methoxyphenyl)-6-phenylfuro[2,3-d]pyrimidin-4-yl]oxy}heptanoic acid tert.-butyl ester can be produced by reaction of 4-chloro-5-(4-methoxyphenyl)-6-phenylfuro[2,3-d]pyrimidine with (−)-6-hydroxyheptanoic acid tert.-butyl ester:

Cool a solution of 5.50 g (27.19 mmol) (−)-6-hydroxyheptanoic acid tert.-butyl ester in 10 ml DMF under argon to 0° C. and, with ice cooling, add 1.054 g (26.36 mmol, 60%) sodium hydride. Stir the mixture for approx. 20 min between 0° C. and RT. Then, after cooling to 0° C. again, add 5.549 g (16.47 mmol) 4-chloro-5-(4-methoxyphenyl)-6-phenylfuro[2,3-d]pyrimidine. At the end of addition, heat the mixture slowly to RT and stir overnight at RT, then add water and neutralize with 1 N hydrochloric acid. Extract the mixture with dichloromethane. Wash the organic phase with satd. sodium chloride solution, dry over sodium sulphate and concentrate by vacuum evaporation. Purify the residue by chromatography on silica gel (solvent: cyclohexane/ethyl acetate 10:1). 4.68 g of the target compound (56.5% of theor.) is obtained.

LC-MS (Method 2): $R_t$=3.33 min; m/z=503 (M+H)$^+$ $^1$H-NMR (400 MHz, DMSO-$d_6$): δ=8.56 (s, 1H), 7.53 (d, 2H), 7.43-7.35 (m, 5H), 7.02 (d, 2H), 5.29 (m, 1H), 3.83 (s, 3H), 2.10 (t, 2H), 1.54-1.36 (m, 4H), 1.36 (s, 9H), 1.22 (d, 3H), 1.21-1.09 (m, 2H).

$[α]_D^{20}$=−61.4°, c=0.55, chloroform.

Example 67

(+/−)-6-{[5-(4-Methoxyphenyl)-6-phenylfuro[2,3-d]pyrimidin-4-yl]oxy}heptanoic acid

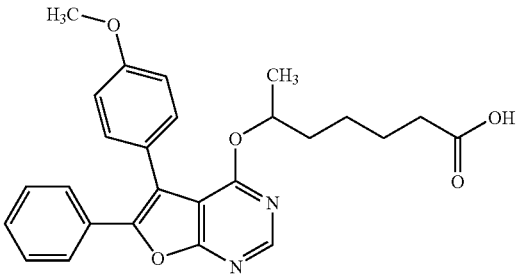

Method 1:

Preparation starting from (+/−)-6-{[5-(4-methoxyphenyl)-6-phenylfuro[2,3-d]pyrimidin-4-yl]oxy}-heptanoic acid methyl ester:

Put 1.38 g (3.0 mmol) (+/−)-6-{[5-(4-methoxyphenyl)-6-phenylfuro[2,3-d]pyrimidin-4-yl]oxy}-heptanoic acid methyl ester in 40 ml THF. Add 30 ml 1 N sodium hydroxide solution and stir overnight at RT. Then add approx. 40 ml 1 M hydrochloric acid up to a pH of approx. 2, dilute with a little water and extract twice with ethyl acetate. Combine the ethyl acetate phases and wash once with satd. sodium chloride solution. Dry over magnesium sulphate and concentrate by evaporation. 1.34 g (78.0% of theor.) of the target compound is obtained.

Method 2:

Preparation starting from (+/−)-6-{[5-(4-methoxyphenyl)-6-phenylfuro[2,3-d]pyrimidin-4-yl]-oxy}heptanoic acid tert.-butyl ester:

Dissolve 800 mg (1.59 mmol) (+/−)-6-{[5-(4-methoxyphenyl)-6-phenylfuro[2,3-d]pyrimidin-4-yl]oxy}heptanoic acid tert.-butyl ester in 10 ml dichloromethane. Add 2.5 ml trifluoroacetic acid and stir for 2 h at RT. Then concentrate by evaporation, add petroleum ether to the residue and leave the product to crystallize. Then add a little more tert.-butylmethyl ether, stir for several minutes and then filter on a frit with suction. 640 mg (89.9% of theor.) of the target compound is obtained.

LC-MS (Method 2): $R_t$=2.71 min; m/z=447 (M+H)$^+$ $^1$H-NMR (400 MHz, DMSO-d$_6$): δ=8.55 (s, 1H), 7.55 (d, 2H), 7.45-7.35 (m, 5H), 7.02 (d, 2H), 5.31-5.25 (m, 1H), 3.81 (s, 3H), 2.21 (m, 2H), 1.55-1.35 (m, 4H), 1.22 (d, 3H), 1.22-1.05 (m, 2H).

Separation of the Enantiomers:

Dissolve 1.330 g (+/−)-6-{[5-(4-methoxyphenyl)-6-phenylfuro[2,3-d]pyrimidin-4-yl]oxy}heptanoic acid in 240 ml of warm ethanol. Separate the racemate by preparative chiral-phase HPLC into the enantiomers [column: Daicel Chiralpak AS-H, 5 μm, 250 mm×20 mm; flow: 15 ml/min; detection: 220 nm; injection volume: 1000 μl; temperature: 30° C.; eluent: 50% iso-hexane/50% ethanol+0.2% glacial acetic acid+1% water] (see Examples 68 and 69).

Example 68

(+)-6-{[5-(4-Methoxyphenyl)-6-phenylfuro[2,3-d]pyrimidin-4-yl]oxy}heptanoic acid (Enantiomer 1)

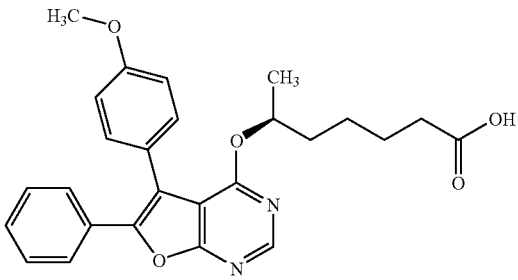

$[α]_D^{20}$=+86.2°, c=0.630, methanol.
LC-MS (Method 2): R$_t$=2.68 min; m/z=447 (M+H)$^+$.

Example 69

(−)-6-{[5-(4-Methoxyphenyl)-6-phenylfuro[2,3-d]pyrimidin-4-yl]oxy}heptanoic acid (Enantiomer 2)

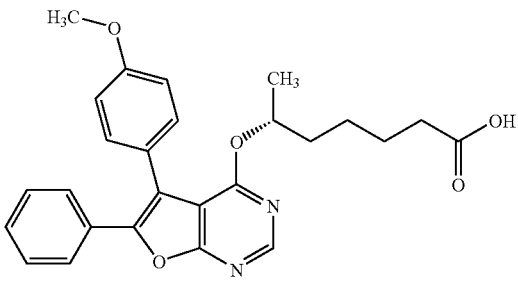

$[α]_D^{20}$=−79.5°, c=0.520, methanol.
LC-MS (Method 8): R$_t$=2.93 min; m/z=447 (M+H)$^+$.

Alternatively, (−)-6-{[5-(4-methoxyphenyl)-6-phenylfuro[2,3-d]pyrimidin-4-yl]oxy}heptanoic acid can be prepared by ester cleavage of (−)-6-{[5-(4-methoxyphenyl)-6-phenylfuro[2,3-d]pyrimidin-4-yl]oxy}heptanoic acid tert.-butyl ester:

Dissolve 9.24 g (18.38 mmol) (−)-6-{[5-(4-methoxyphenyl)-6-phenylfuro[2,3-d]pyrimidin-4-yl]oxy}heptanoic acid tert.-butyl ester at RT in 100 ml dichloromethane and add 25 ml TFA. After 2 h at RT, dilute the mixture with dichloromethane, wash several times with water and once with satd. sodium chloride solution, dry over sodium sulphate and concentrate by vacuum evaporation. Purify the residue by chromatography on silica gel (solvent: cyclohexane/ethyl acetate 5:1→2:1, then cyclohexane/ethyl acetate 2:1+0.5% acetic acid). Concentrate fractions containing the product by vacuum evaporation, take up the residue in dichloromethane again and wash several times with water and satd. sodium chloride solution. Dry the organic phase over sodium sulphate, concentrate by evaporation and dry at high vacuum. 6.89 g of the target compound (83.9% of theor.) is obtained.

LC-MS (Method 7): R$_t$=4.10 min; m/z=447 (M+H)$^+$
$^1$H-NMR (400 MHz, DMSO-d$_6$): δ=11.98 (br. s, 1H), 8.57 (s, 1H), 7.55 (d, 2H), 7.45-7.36 (m, 5H), 7.02 (d, 2H), 5.29 (m, 1H), 3.72 (s, 3H), 2.12 (t, 2H), 1.54-1.37 (m, 4H), 1.22 (d, 3H), 1.21-1.08 (m, 2H).
$[α]_D^{20}$=−70.8°, c=0.685, chloroform.

Example 70

(−)-6-{[5-(4-Methoxyphenyl)-6-phenylfuro[2,3-d]pyrimidin-4-yl]oxy}heptanoic acid sodium salt

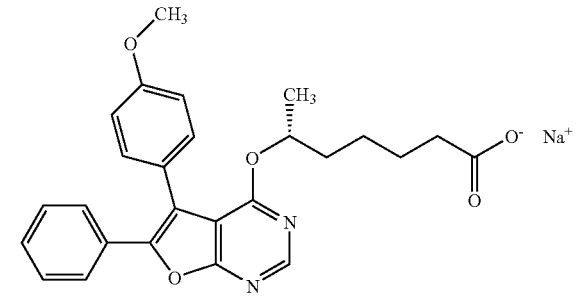

Add 5.0 ml demineralized water (Millipore ion exchanger) to 893 mg (2.0 mmol) (−)-6-{[5-(4-methoxyphenyl)-6-phenylfuro[2,3-d]pyrimidin-4-yl]oxy}heptanoic acid. Add 2.0 ml (2.0 mmol) of 1 N sodium hydroxide solution and stir for 30 min at RT. Next, treat for a few minutes in an ultrasonic bath. Add 50 ml of demineralized water, filter once through a paper filter and wash the filter again with 10 ml demineralized water. Add a further 200 ml demineralized water to the filtrate and lyophilize overnight. 935 mg (99.7% of theor.) of the target compound is obtained.

LC-MS (Method 8): R$_t$=2.93 min; m/z=447 (M+H)$^+$
$^1$H-NMR (400 MHz, DMSO-d$_6$): δ=8.55 (s, 1H), 7.54 (d, 2H), 7.42-7.35 (m, 5H), 7.01 (d, 2H), 5.31-5.24 (m, 1H), 3.82 (s, 3H), 1.79 (t, 2H), 1.52-1.40 (m, 2H), 1.39-1.31 (m, 2H), 1.21 (s, 3H), 1.21-1.06 (m, 2H).
$[α]_D^{20}$=−32.0°, c=0.145, dimethylsulphoxide.

Example 71

(−)-6-{[5-(4-Methoxyphenyl)-6-phenylfuro[2,3-d]pyrimidin-4-yl]oxy}heptanoic acid bisethanol-amine salt

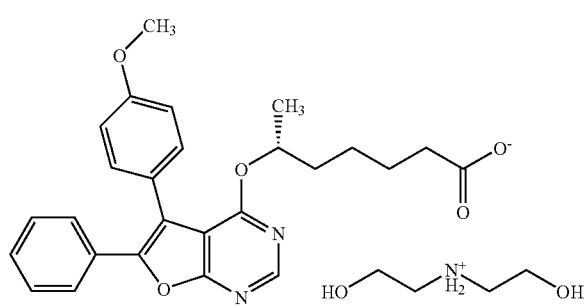

Add 250 μl demineralized water (Millipore ion exchanger) to 26.8 mg (0.060 mmol) (−)-6-{[5-(4-methoxyphenyl)-6- phenylfuro[2,3-d]pyrimidin-4-yl]oxy}heptanoic acid. Add 6.3 mg (0.060 mmol) 2,2'-iminodiethanol and stir for 30 min at RT. Next, treat for a few minutes in an ultrasonic bath. Add a few drops of dioxan, then lyophilize overnight. 33.0 mg (99.7% of theor.) of the target compound is obtained.

LC-MS (Method 8): $R_t$=2.93 min; m/z=447 (M+H)$^+$ $^1$H-NMR (400 MHz, DMSO-d$_6$): δ=8.55 (s, 1H), 7.53 (d, 2H), 7.42-7.35 (m, 5H), 7.01 (d, 2H), 5.31-5.24 (m, 1H), 3.82 (s, 3H), 3.44 (t, 4H), 2.61 (t, 3H), 2.10 (t, 2H), 1.52-1.45 (m, 2H), 1.45-1.35 (m, 2H), 1.22 (d, 3H), 1.22-1.06 (m, 2H).

$[α]_D^{20}$=−36.0°, c=0.325, dimethylsulphoxide.

Example 72

(+/−)-6-{[5-(4-Ethylphenyl)-6-phenylfuro[2,3-d]pyrimidin-4-yl]oxy}heptanoic acid methyl ester

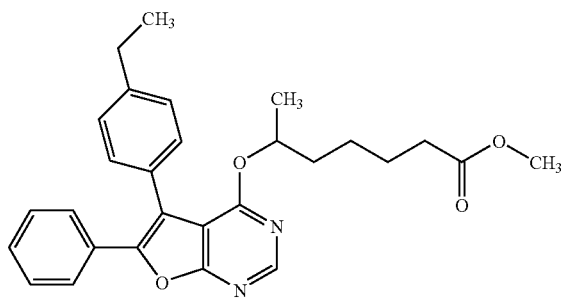

Put 717 mg (4.48 mmol) (+/−)-6-hydroxyheptanoic acid methyl ester under argon in 10 ml THF and cool to 0° C. Add 2.25 ml (4.48 mmol) of a 2 M solution of phosphazene base P2-tert.-butyl in THF and stir for a further 10 min at RT. Then cool to 0° C. again. Add 1.0 g (2.99 mmol) 4-chloro-5-(4-ethylphenyl)-6-phenylfuro[2,3-d]pyrimidine and continue stirring overnight at RT. Dilute with water, acidify with 10% aqueous citric acid solution and extract twice with ethyl acetate. Combine the ethyl acetate phases and wash once with satd. sodium chloride solution. Dry over magnesium sulphate, concentrate by evaporation and purify the residue by column chromatography on silica gel (solvent: cyclohexane/ethyl acetate 9:1). 640 mg (46.7% of theor.) of the target compound is obtained.

LC-MS (Method 8): $R_t$=3.44 min; m/z=459 (M+H)$^+$ $^1$H-NMR (400 MHz, CDCl$_3$): δ=8.50 (s, 1H), 7.64 (m, 2H), 7.38 (d, 2H), 7.31 (m, 3H), 7.24 (d, 2H), 5.35-5.26 (m, 1H), 3.63 (s, 3H), 2.76-2.67 (q, 2H), 2.21 (dd, 2H), 1.60-1.41 (m, 4H), 1.32-1.22 (m, 6H), 1.22-1.10 (m, 2H).

Example 73

(+/−)-6-{[5-(4-Ethylphenyl)-6-phenylfuro[2,3-d]pyrimidin-4-yl]oxy}heptanoic acid

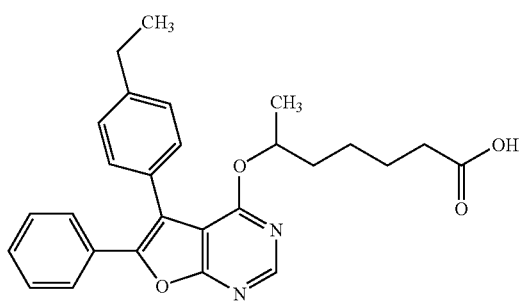

Put 1.38 g (3.0 mmol) (+/−)-6-{[5-(4-ethylphenyl)-6-phenylfuro[2,3-d]pyrimidin-4-yl]oxy}-heptanoic acid methyl ester in 25 ml THF. Add 13.8 ml 1 N sodium hydroxide solution and stir overnight at RT. Dilute with water and ethyl acetate and then add 1 M hydrochloric acid up to a pH value of approx. 2. Separate the phases and extract the aqueous phase twice more with ethyl acetate. Combine the ethyl acetate phases and wash once with satd. sodium chloride solution. Dry over magnesium sulphate and concentrate by evaporation. 600 mg (98.2% of theor.) of the target compound is obtained.

LC-MS (Method 8): $R_t$=3.32 min; m/z=445 (M+H)$^+$ $^1$H-NMR (400 MHz, CDCl$_3$): δ=8.51 (s, 1H), 7.62 (m, 2H), 7.37 (d, 2H), 7.30 (m, 3H), 7.23 (m, 2H), 5.34-5.25 (m, 1H), 2.76-2.58 (q, 2H), 2.24 (dd, 2H), 1.59-1.49 (m, 4H), 1.32-1.23 (m, 6H), 1.23-1.12 (m, 2H).

Separation of the Enantiomers:

Dissolve 600 mg (+/−)-6-{[5-(4-ethylphenyl)-6-phenylfuro[2,3-d]pyrimidin-4-yl]oxy}heptanoic acid in 20 ml 2-propanol/20 ml iso-hexane and separate the racemate by preparative chiral-phase HPLC into the enantiomers [column: Daicel Chiralpak AS-H, 5 μm, 250 mm×20 mm; flow: 15 ml/min; detection: 220 nm; injection volume: 400 μl; temperature: 40° C.; eluent: 80% iso-hexane/20% 2-propanol+0.2% TFA+1% water] (see Examples 74 and 75).

Example 74

(+)-6-{[5-(4-Ethylphenyl)-6-phenylfuro[2,3-d]pyrimidin-4-yl]oxy}heptanoic acid (Enantiomer 1)

$[α]_D^{20}$=+83.4°, c=0.580, methanol.
LC-MS (Method 8): $R_t$=3.28 min; m/z=445 (M+H)$^+$.

Example 75

(−)-6-{[5-(4-Ethylphenyl)-6-phenylfuro[2,3-d]pyrimidin-4-yl]oxy}heptanoic acid (Enantiomer 2)

$[α]_D^{20}$=−81.3°, c=0.520, methanol.
LC-MS (Method 8): $R_t$=3.17 min; m/z=445 (M+H)$^+$.

Example 76

{[(3R)-3-{[5-(4-Methoxyphenyl)-6-phenylfuro[2,3-d]pyrimidin-4-yl]oxy}butyl]oxy}acetic acid tert.-butyl ester

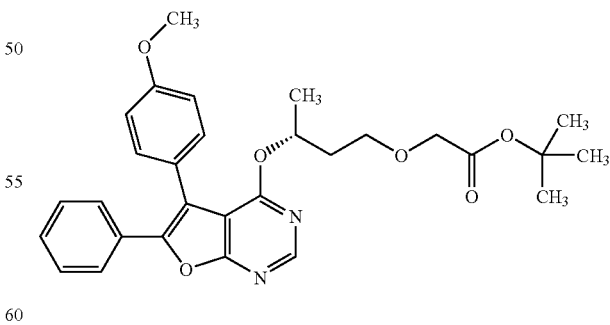

Put 455 mg (2.23 mmol) {[(3R)-3-hydroxybutyl]oxy}acetic acid tert.-butyl ester (which contains up to approx. 10% {[(1R)-3-hydroxy-1-methylpropyl]oxy}acetic acid tert.-butyl ester) under argon in 5 ml THF and cool to 0° C. Add 1.15 ml (2.23 mmol) of a 2 M solution of phosphazene base P2-tert.-butyl in THF and stir for a further 10 min at RT. Then cool to 0° C. again. Add 500 mg (1.49 mmol) 4-chloro- 5-(4-methoxyphenyl)-6-phenylfuro[2,3-d]pyrimidine and stir overnight at RT. Then dilute with water, acidify with 10% aqueous citric acid solution and extract twice with ethyl acetate. Combine the ethyl acetate phases and wash once with satd. sodium chloride solution. Dry over magnesium sulphate and concentrate by evaporation. Purify the residue by chromatography on silica gel (solvent: cyclohexane/ethyl acetate 9:1). 450 mg (60.1% of theor.) of the target compound is obtained. 75 mg (9.0% of theor.) of (−)-{[(1R)-3-{[5-(4-methoxyphenyl)-6-phenylfuro[2,3-d]pyrimidin-4-yl]oxy}-1-methylpropyl]oxy}acetic acid tert.-butyl ester is isolated as by-product (see Example 77).

LC-MS (Method 2): $R_t$=3.15 min; m/z=405 (M+H)$^+$
$^1$H-NMR (400 MHz, DMSO-$d_6$): δ=8.51 (s, 1H), 7.62 (m, 2H), 7.37 (d, 2H), 7.31 (m, 3H), 6.94 (d, 2H), 5.53-5.45 (m, 1H), 3.72 (s, 2H), 3.47-3.32 (m, 2H), 1.86 (m, 2H), 1.43 (s, 9H), 1.32 (d, 3H).

Example 77

(−)-{[(1R)-3-{[5-(4-Methoxyphenyl)-6-phenylfuro[2,3-d]pyrimidin-4-yl]oxy}-1-methylpropyl]-oxy}acetic acid tert.-butyl ester

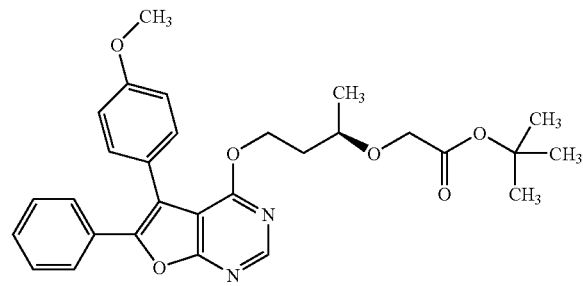

The title compound is obtained as a by-product in the preparation of Example 76.

LC-MS (Method 5): $R_t$=3.26 min; m/z=405 (M+H)$^+$
$^1$H-NMR (400 MHz, DMSO-$d_6$): δ=8.52 (s, 1H), 7.62 (m, 2H), 7.37 (d, 2H), 7.31 (m, 3H), 6.94 (d, 2H), 4.54 (m, 2H), 3.82 (m, 2H), 3.36-3.27 (m, 1H), 1.95-1.83 (m, 1H), 1.79-1.69 (m, 1H), 1.42 (s, 9H), 1.099 (d, 3H).
$[\alpha]_D^{20}$=−96.8°, c=0.380, methanol.

Example 78

(−)-{[3-{[5-(4-Methoxyphenyl)-6-phenylfuro[2,3-d]pyrimidin-4-yl]oxy}butyl]oxy}acetic acid

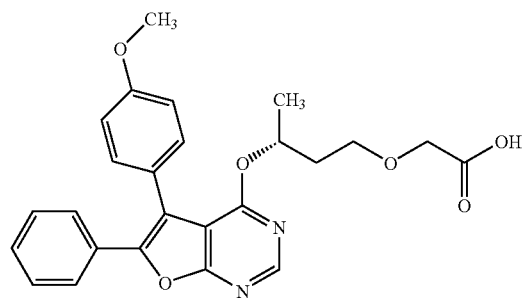

Put 350 mg (0.69 mmol) {[(3R)-3-{[5-(4-methoxyphenyl)-6-phenylfuro[2,3-d]pyrimidin-4-yl]oxy}-butyl]oxy}acetic acid tert.-butyl ester in 7 ml dichloromethane. Add 1.75 ml TFA and stir overnight at RT. Then concentrate by evaporation and purify the residue by chromatography on silica gel (solvent: cyclohexane/ethyl acetate 1:1). 110 mg (35.4% of theor.) of the target compound is obtained.

LC-MS (Method 10): $R_t$=2.67 min; m/z=449 (M+H)$^+$
$^1$H-NMR (400 MHz, CDCl$_3$): δ=8.50 (s, 1H), 7.61 (m, 2H), 7.36 (m, 2H), 7.31 (m, 3H), 6.93 (d, 2H), 5.52 (m, 1H), 3.96 (d, 2H), 3.47-3.36 (m, 2H), 1.92-1.80 (m, 2H), 1.34 (d, 3H).
$[\alpha]_D^{20}$=−79.6°, c=0.42, acetonitrile.

Example 79

(−)-{[3-{[5-(4-Methoxyphenyl)-6-phenylfuro[2,3-d]pyrimidin-4-yl]oxy}-1-methylpropyl]oxy}-acetic acid

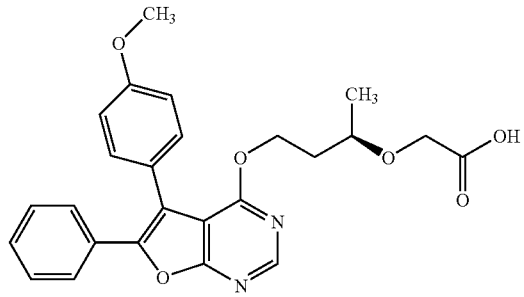

Put 45 mg (0.089 mmol) (−)-{[3-{[5-(4-methoxyphenyl)-6-phenylfuro[2,3-d]pyrimidin-4-yl]oxy}-1-methylpropyl]oxy}acetic acid tert.-butyl ester in 1 ml dichloromethane. Add 250 μl TFA and stir overnight at RT. Then concentrate by evaporation and purify the residue by chromatography on a silica-gel thick-layer plate (solvent: cyclohexane/ethyl acetate 1:1). Extract the product zone with dichloromethane/methanol 95:5. 8 mg (21.5% of theor.) of the target compound is obtained.

LC-MS (Method 8): $R_t$=2.65 min; m/z=449 (M+H)$^+$
$^1$H-NMR (400 MHz, CDCl$_3$): δ=8.49 (s, 1H), 7.58 (m, 2H), 7.34 (m, 2H), 7.27 (m, 3H), 6.94 (d, 2H), 5.58-4.45 (m, 2H), 3.75 (s, 2H), 3.36-3.24 (m, 1H), 1.92-1.81 (m, 1H), 1.81-1.71 (m, 1H), 1.11 (d, 3H).
$[\alpha]_D^{20}$=−77.1°, c=0.370, methanol.

The following two compounds are obtained similarly:

Example 80

(−)-{[3-{[5-(4-Ethylphenyl)-6-phenylfuro[2,3-d]pyrimidin-4-yl]oxy}butyl]oxy}acetic acid

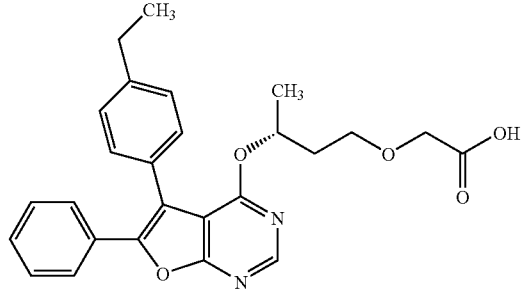

React 500 mg (0.99 mmol) {[(3R)-3-{[5-(4-ethylphenyl)-6-phenylfuro[2,3-d]pyrimidin-4-yl]oxy}-butyl]oxy}acetic acid tert.-butyl ester with TFA similarly to the synthesis procedure described above. 447 mg (92.3% of theor.) of the target compound is obtained.

LC-MS (Method 8): $R_t$=3.00 min; m/z=447 (M+H)$^+$ $^1$H-NMR (400 MHz, CDCl$_3$): δ=8.49 (s, 1H), 7.60 (m, 2H), 7.33 (d, 2H), 7.27 (m, 3H), 7.22 (d, 2H), 5.52-5.43 (m, 1H), 3.97-3.87 (dd, 2H), 3.45-3.32 (m, 2H), 2.75-2.68 (q, 2H), 1.90-1.75 (m, 2H), 1.32 (t, 3H), 1.28 (d, 3H).

$[α]_D^{20}$=−94°, c=0.530, methanol.

Example 81

(−)-{[3-{[5-(4-Ethylphenyl)-6-phenylfuro[2,3-d]pyrimidin-4-yl]oxy}butyl]oxy}acetic acid tert.-butyl ester

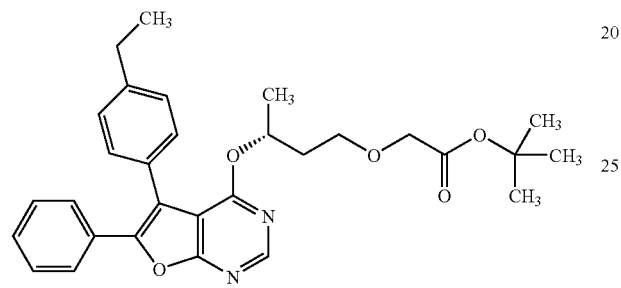

React 800 mg (2.39 mmol) {[(3R)-3-hydroxybutyl]oxy}acetic acid tert.-butyl ester (which contains up to approx. 10% {[(1R)-3-hydroxy-1-methylpropyl]oxy}acetic acid tert.-butyl ester) with 4-chloro-5-(4-ethylphenyl)-6-phenylfuro[2,3-d]pyrimidine similarly to the synthesis procedure described above. 690 mg (57.4% of theor.) of the target compound is obtained.

LC-MS (Method 2): $R_t$=3.35 min; m/z=503 (M+H)$^+$ $^1$H-NMR (400 MHz, DMSO-d$_6$): δ=8.50 (s, 1H), 7.62 (m, 2H), 7.37 (d, 2H), 7.31 (m, 3H), 7.22 (d, 2H), 5.50-5.41 (m, 1H), 3.71 (s, 2H), 3.42-3.28 (m, 2H), 2.75-2.68 (q, 2H), 1.82 (m, 2H), 1.43 (s, 9H), 1.33 (t, 3H), 1.30 (d, 3H).

$[α]_D^{20}$=−90.7°, c=0.370, acetonitrile.

Example 82

(+)-3-[2-{[5-(4-Methoxyphenyl)-6-phenylfuro[2,3-d]pyrimidin-4-yl]oxy}-1-methylethoxy]-propionic acid tert.-butyl ester

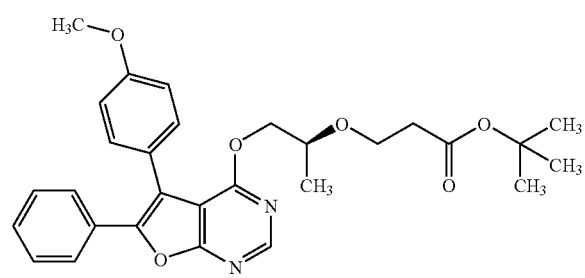

Cool a suspension of 2.548 g (7.57 mmol) 4-chloro-5-(4-methoxyphenyl)-6-phenylfuro[2,3-d]-pyrimidine and 1.70 g (8.32 mmol) (+)-3-[(1S)-2-hydroxy-1-methylethoxy]propionic acid tert.-butyl ester in 8 ml DMF to 0° C. and add in portions, over 30 min, 272 mg (6.81 mmol, 60%) sodium hydride. Then add 0.5 ml abs. THF, and stir the mixture for 10 min at 0° C., before adding a little acetic acid and then adding the mixture to water. Extract the aqueous phase three times with dichloromethane. Combine the organic phases, dry over magnesium sulphate and concentrate under vacuum. The raw product can be purified either by chromatography on silica gel (solvent: cyclohexane/ethyl acetate 10:1→8:1) or by preparative RP-HPLC (gradient: acetonitrile/water). 2.27 g (59.5% of theor.) of the target compound is obtained.

LC-MS (Method 8): $R_t$=3.27 min; m/z=505 (M+H)$^+$ $^1$H-NMR (400 MHz, DMSO-d$_6$): δ=8.60 (s, 1H), 7.54 (d, 2H), 7.45-7.39 (m, 5H), 7.03 (d, 2H), 4.38-4.32 (m, 2H), 3.81 (s, 3H), 3.65-3.59 (m, 1H), 3.50-3.40 (m, 2H), 2.28 (t, 2H), 1.35 (s, 9H), 1.00 (d, 3H).

$[α]_D^{20}$=+22.4°, c=0.515, chloroform.

Example 83

(+)-3-{[(2S)-2-{[5-(4-Methoxyphenyl)-6-phenylfuro[2,3-d]pyrimidin-4-yl]oxy}-1-methylethoxy]-oxy}propionic acid

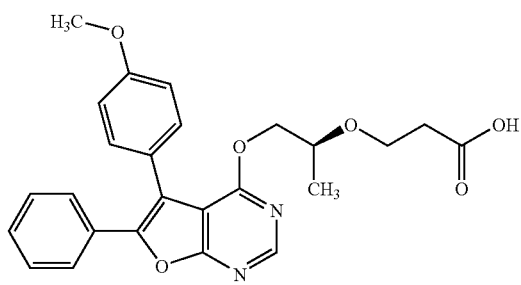

Dissolve 3.17 g (6.28 mmol) (+)-3-[2-{[5-(4-methoxyphenyl)-6-phenylfuro[2,3-d]pyrimidin-4-yl]oxy}-1-methylethoxy]propionic acid tert.-butyl ester in 21 ml dichloromethane and, at RT, add 12.1 ml TFA. Stir the reaction mixture for 2.5 h at RT and then carefully concentrate by vacuum evaporation. Take up the residue in dichloromethane, wash with water, dry over sodium sulphate and concentrate by vacuum evaporation. Purify the residue by chromatography on silica gel (solvent: dichloromethane/acetone 10:1→3:1). Combine the fractions containing the product and concentrate under vacuum. Mix the resultant residue with petroleum ether. After filtration and drying at high vacuum, 1.77 g (62.8% of theor.) of the target product is obtained.

LC-MS (Method 8): $R_t$=2.63 min; m/z=449 (M+H)$^+$ $^1$H-NMR (400 MHz, DMSO-d$_6$): δ=12.1 (s, 1H), 8.60 (s, 1H), 7.54 (d, 2H), 7.43-7.37 (m, 5H), 7.03 (d, 2H), 4.38-4.30 (m, 2H), 3.82 (s, 3H), 3.67-3.60 (m, 1H), 3.53-3.44 (m, 2H), 2.31 (t, 2H), 1.00 (d, 3H).

$[α]_D^{20}$=+30.6°, c=0.495, chloroform.

Example 84

(+)-3-[2-{[5-(4-Ethylphenyl)-6-phenylfuro[2,3-d]pyrimidin-4-yl]oxy}-1-methylethoxy]propionic acid

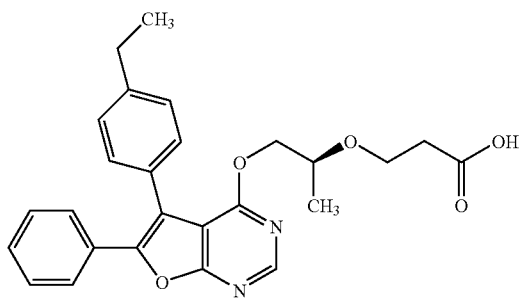

Put 1.14 g (3.05 mmol) of a mixture of (2S)-1-{[5-(4-ethylphenyl)-6-phenylfuro[2,3-d]pyrimidin-4-yl]oxy}propan-2-ol and (2S)-2-{[5-(4-ethylphenyl)-6-phenylfuro[2,3-d]pyrimidin-4-yl]oxy}propan-1-ol together with 1.951 g (15.22 mmol) acrylic acid tert.-butyl ester and 207 mg (0.609 mmol) tetra-n-butylammonium hydrogensulphate in 10 ml dichloromethane and cool to 0° C. Add 2.5 ml of 50% sodium hydroxide solution and stir vigorously for 1 h at 0° C. Then dilute with dichloromethane and lightly acidify with 10% citric acid solution. Separate the phases, extract the aqueous phase once with dichloromethane, combine the organic phases, dry over magnesium sulphate and concentrate by evaporation. Dissolve the residue obtained in 30 ml dichloromethane. Add 7.5 ml TFA and stir for 1 h at RT. Then concentrate the mixture by evaporation and dry the residue at high vacuum. Firstly, purify by chromatography on silica gel (solvent: cyclohexane/ethyl acetate 1:1), obtaining 1.15 g of a mixture of regioisomers.

Dissolve the mixture of regioisomers obtained (1.15 g) in a mixture of 5 ml isohexane and 5 ml ethyl acetate and separate into the isomers by chiral-phase chromatography [column: chiral silica-gel phase based on the selector poly(N-methacryloyl-L-leucine-tert.-butyl amide), 500 mm×30 mm; flow: 50 ml/min; detection: 260 nm; injection volume: 300 μl; temperature: 24° C.; eluent: isohexane/ethyl acetate 1:1]. 287 mg (25.6% of theor.) of the title compound and 255 mg (22.8% of theor.) of the regioisomer (+)-3-{[2-{[5-(4-ethylphenyl)-6-phenyfuro[2,3-d]pyrimidin-4-yl]oxy}propyl]oxy}propionic acid (see Example 85) are obtained in this way.

$[\alpha]_D^{20}=+50.1°$, c=0.500, methanol.

LC-MS (Method 8): $R_t$=2.82 min; m/z=447 (M+H)$^+$ $^1$H-NMR (400 MHz, DMSO-d$_6$): δ=12.12 (br. s, 1H), 8.49 (s, 1H), 7.52 (d, 2H), 7.39 (m, 5H), 7.30 (d, 2H), 4.31 (m, 2H), 3.63-3.55 (m, 1H), 3.53-3.38 (m, 2H), 2.72-2.65 (q, 2H), 2.30 (t, 2H), 1.22 (t, 3H), 0.93 (d, 3H).

Example 85

(+)-3-{[2-{[5-(4-Ethylphenyl)-6-phenylfuro[2,3-d]pyrimidin-4-yl]oxy}propyl]oxy}propionic acid

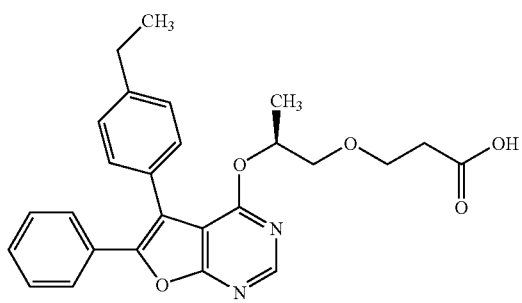

For preparation see above, Example 84.

LC-MS (Method 8): $R_t$=2.85 min; m/z=447 (M+H)$^+$ $^1$H-NMR (400 MHz, DMSO-d$_6$): δ=12.12 (br. s, 1H), 8.49 (s, 1H), 7.53 (d, 2H), 7.39 (m, 5H), 7.29 (d, 2H), 5.45-5.36 (m, 1H), 3.52-3.32 (m, 4H), 2.72-2.65 (q, 2H), 2.30 (t, 2H), 1.22 (t, 3H), 1.20 (d, 3H).

$[\alpha]_D^{20}=+46.0°$, c=0.590, methanol.

The compounds presented in the following table are prepared similarly to the synthesis described above. The details of separation of the regioisomers are as follows:

Example 86 and Example 87

Dissolve 1.00 g (1.99 mmol) of a mixture of (−)-3-[2-{[5-(4-ethylphenyl)-6-phenylfuro[2,3-d]pyrimidin-4-yl]oxy}-1-methylethoxy]propionic acid (Example 86) and (−)-3-{[2-{[5-(4-ethylphenyl)-6-phenylfuro[2,3-d]pyrimidin-4-yl]oxy}propyl]oxy}propionic acid (Example 87) in a mixture of 5 ml isohexane and 5 ml ethyl acetate and separate into the isomers by chiral-phase chromatography; column: chiral silica-gel phase based on the selector poly(N-methacryloyl-L-leucine-dicyclopropylmethylamide), 680 mm×40 mm; flow: 50 ml/min; detection: 260 nm; injection volume: 1700 μl; temperature: 24° C.; eluent: 50% isohexane/50% ethyl acetate.

Example 83 and Example 88

Dissolve 7.80 g (15.45 mmol) of a mixture of (+)-3-[2-{[5-(4-methoxyphenyl)-6-phenylfuro[2,3-d]pyrimidin-4-yl]oxy}-1-methylethoxy]propionic acid (Example 83) and (+)-3-{[2-{[5-(4-methoxyphenyl)-6-phenylfuro[2,3-d]pyrimidin-4-yl]oxy}propyl]oxy}propionic acid (Example 88) in a mixture of 50 ml isohexane and 50 ml ethyl acetate and separate into the isomers by chiral-phase chromatography; column: chiral silica-gel phase based on the selector poly(N-methacryloyl-L-leucine-1-methylamide), 250 mm×30 mm; flow: 50 ml/min; detection: 260 nm; injection volume: 400 μl; temperature: 24° C.; eluent: 50% isohexane/50% ethyl acetate.

Example 83 can also be prepared in an alternative manner (for description see above).

Example 89 and Example 90

Dissolve 250 mg (0.56 mmol) of a mixture of (−)-3-[2-{[5-(4-methoxyphenyl)-6-phenylfuro[2,3-d]-pyrimidin-4-yl]oxy}-1-methylethoxy]propionic acid (Example 89) and (−)-3-{[2-{[5-(4-methoxyphenyl)-6-phenylfuro[2,3-d]pyrimidin-4-yl]oxy}propyl]oxy}propionic acid (Example 90) in a mixture of 2 ml isohexane and 2 ml ethyl acetate and separate into the isomers by chiral-phase chromatography; column: chiral silica-gel phase based on the selector poly(N-methacryloyl-L-leucine-dicyclopropylmethyl amide), 680 mm×40 mm; flow: 50 ml/min; detection: 260 nm; injection volume: 4000 μl; temperature: 24° C.; eluent: t=0 min 60% isohexane/40% ethyl acetate→t=13 min 45% isohexane/55% ethyl acetate.

| Example | Structure | Analytical data |
|---------|-----------|-----------------|
| 86 | 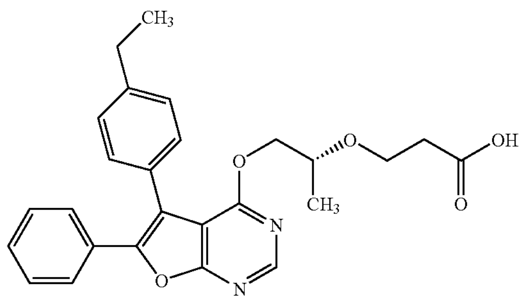 | $[\alpha]_D^{20}$ = −44.4°, c = 0.475, methanol; LC-MS (Method 7): $R_t$ = 4.12 min; m/z = 447 (M + H)⁺ ¹H-NMR (400 MHz, CDCl₃): δ = 8.51 (s, 1 H), 7.60 (m, 2 H), 7.38 (d, 2 H), 7.31-7.22 (m, 5 H), 4.40-4.30 (m, 2 H), 3.69-3.61 (m, 1 H), 3.56-3.43 (m, 2 H), 2.70 (q, 2 H), 2.42 (t, 2 H), 1.29 (t, 3 H), 1.06 (d, 3 H). |
| 87 | 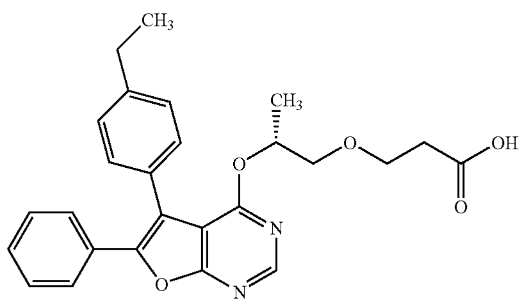 | $[\alpha]_D^{20}$ = −45.2°, c = 0.430, methanol; LC-MS (Method 7): $R_t$ = 4.16 min; m/z = 447 (M + H)⁺ ¹H-NMR (400 MHz, CDCl₃): δ = 8.51 (s, 1 H), 7.61 (m, 2 H), 7.38 (d, 2 H), 7.31-7.28 (m, 3 H), 7.22 (d, 2 H), 5.55-5.45 (m, 1 H), 3.55-3.45 (m, 4 H), 2.70 (q, 2 H), 2.43 (t, 2 H), 1.29 (t, 3 H), 1.25 (d, 3 H). |
| 83 | 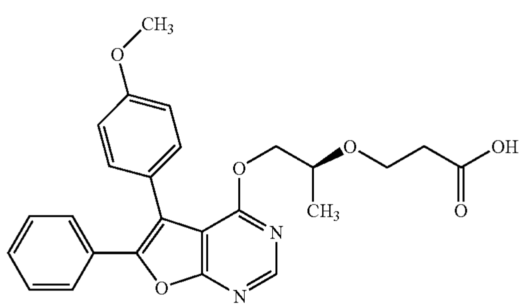 | $[\alpha]_D^{20}$ = +59.6°, c = 0.432, methanol; LC-MS (Method 2): $R_t$ = 2.41 min; m/z = 449 (M + H)⁺ ¹H-NMR (400 MHz, CDCl₃): δ = 8.51 (s, 1 H), 7.60 (m, 2 H), 7.38 (d, 2 H), 7.31-7.28 (m, 3 H), 6.95 (d, 2 H), 4.49 (d, 2 H), 3.86 (s, 3 H), 3.75-3.65 (m, 1 H), 3.61-3.45 (m, 2 H), 2.43 (t, 2 H), 1.12 (d, 3 H). |
| 88 | 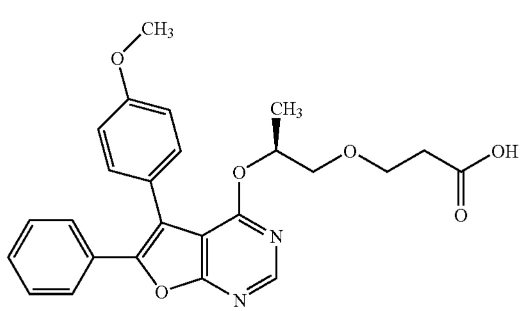 | $[\alpha]_D^{20}$ = +48.1°, c = 0.425, acetonitrile; LC-MS (Method 8): $R_t$ = 2.73 min; m/z = 449 (M + H)⁺ ¹H-NMR (400 MHz, CDCl₃): δ = 8.51 (s, 1 H), 7.60 (m, 2 H), 7.39 (d, 2 H), 7.31-7.27 (m, 3 H), 6.93 (d, 2 H), 5.55-5.48 (m, 1 H), 3.86 (s, 3 H), 3.60-3.48 (m, 4 H), 2.48 (t, 2 H), 1.26 (d, 3 H). |

| Example | Structure | Analytical data |
|---|---|---|
| 89 | 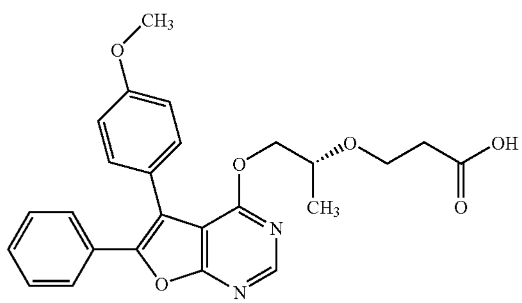 | $[\alpha]_D^{20}$ = −41.1°, c = 0.3655, acetonitrile; LC-MS (Method 2): $R_t$ = 2.41 min; m/z = 449 (M + H)⁺ ¹H-NMR (400 MHz, CDCl₃): δ = 8.51 (s,1 H), 7.60 (m, 2 H), 7.38 (d, 2 H), 7.31-7.28 (m, 3 H), 6.95 (d, 2 H), 4.49 (d, 2 H), 3.86 (s, 3 H), 3.75-3.65 (m, 1 H), 3.61-3.45 (m, 2 H), 2.43 (t, 2 H), 1.12 (d, 3 H). |
| 90 | 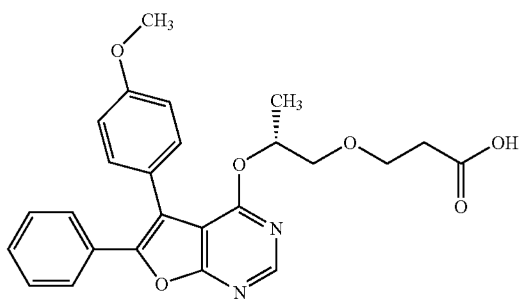 | $[\alpha]_D^{20}$ = −31.5°, c = 0.415, acetonitrile; LC-MS (Method 8): $R_t$ = 2.73 min; m/z = 449 (M + H)⁺ ¹H-NMR (400 MHz, CDCl₃): δ = 8.51 (s, 1 H), 7.60 (m, 2 H), 7.39 (d, 2 H), 7.31-7.27 (m, 3 H), 6.93 (d, 2 H), 5.55-5.48 (m, 1 H), 3.86 (s, 3 H), 3.60-3.48 (m, 4 H), 2.48 (t, 2 H), 1.26 (d, 3 H). |

Example 91

(+/−)-4-[(2-{[5-(4-Methoxyphenyl)-6-phenylfuro[2,3-d]pyrimidin-4-yl]oxy}propyl)(methyl)-amino]butanoic acid methyl ester Put 25 mg (0.064 mmol) (+/−)-2-{[5-(4-methoxyphenyl)-6-phenylfuro[2,3-d]pyrimidin-4-yl]oxy}-N-methylpropane-1-amine with 13 mg (0.128 mmol) triethylamine in 250 μl dichloromethane. Add 23.2 mg (0.128 mmol) 4-bromobutyric acid methyl ester and stir overnight at RT. Add the same amounts of triethylamine and 4-bromobutyric acid methyl ester again and stir for a further 24 h at RT. Then concentrate by evaporation and purify the residue by thick-layer chromatography on silica gel (solvent: dichloromethane/methanol 95:5). Extract the product-containing zone with dichloromethane/methanol 9:1. 22.4 mg of the target compound is obtained as raw product.

LC-MS (Method 8): $R_t$=1.84 min; m/z=490 (M+H)⁺.

Example 92

(+/−)-4-[(2-{[5-(4-Methoxyphenyl)-6-phenylfuro[2,3-d]pyrimidin-4-yl]oxy}propyl)(methyl)-amino]butanoic acid Put 20 mg (0.027 mmol) (+/−)-4-[(2-{[5-(4-methoxyphenyl)-6-phenylfuro[2,3-d]pyrimidin-4-yl]oxy}propyl)(methyl)amino]butanoic acid methyl ester in 0.8 ml THF. Add 0.27 ml (0.27 mmol) 1 N sodium hydroxide solution and stir overnight at RT. Then concentrate by evaporation and purify the residue by thick-layer chromatography on silica gel (solvent: dichloromethane/methanol 9:1). Extract the product zone with dichloromethane/methanol 7:3. 8.5 mg (66.3% of theor.) of the target compound is obtained.

LC-MS (Method 10): $R_t$=1.70 min; m/z=476 (M+H)⁺

¹H-NMR (400 MHz, DMSO-d₆): δ=8.57 (s, 1H), 7.52 (m, 2H), 7.43-7.35 (m, 5H), 7.02 (d, 2H), 5.57-5.48 (m, 1H), 3.81

(s, 3H), 3.6-3.4 (br. s, 2H), 2.36-2.25 (br. s, 2H), 2.14-2.06 (m, 5H), 1.57-1.45 (m, 2H), 1.22 (d, 3H).

Example 93

3-[2-{[5-(4-Methoxyphenyl)-6-phenylfuro[2,3-d]pyrimidin-4-yl]amino}-1-methylethoxy]propionic acid

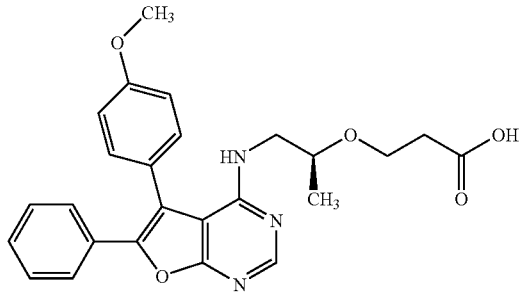

Put 100 mg (0.27 mmol) (+)-1-{[5-(4-methoxyphenyl)-6-phenylfuro[2,3-d]pyrimidin-4-yl]amino}-propan-2-ol with 170 mg (1.33 mmol) acrylic acid tert.-butyl ester and 18.1 mg (0.053 mmol) tetra-n-butylammonium hydrogensulphate in 2 ml dichloromethane and cool to 0° C. Then add 250 µl 50% sodium hydroxide solution and stir the mixture vigorously at 0° C. for 1 h. Leave to return to RT and continue stirring overnight at RT. Then dilute with dichloromethane and water. Acidify with 10% citric acid solution and separate the phases. Re-extract the aqueous phase once with dichloromethane. Combine the organic phases, wash once with satd. sodium chloride solution, dry over magnesium sulphate and concentrate by evaporation. Dissolve the residue thus obtained in 2.5 ml dichloromethane, add 600 µl trifluoroacetic acid and stir for a further 2 h at RT. Then concentrate by evaporation and purify the residue by chromatographing twice on a silica-gel thick-layer plate (solvent: dichloromethane/methanol 9:1). Extract the product zone with dichloromethane/methanol 9:1. After concentrating by evaporation and drying, 38 mg (42.8% of theor.) of the target compound is obtained.

LC-MS (Method 8): $R_t$=2.41 min; m/z=448 (M+H)$^+$ $^1$H-NMR (400 MHz, CDCl$_3$): δ=8.32 (s, 1H), 7.44 (m, 4H), 7.38-7.30 (m, 3H), 7.13 (d, 2H), 5.18 (t, 1H), 3.84 (s, 3H), 3.66-3.45 (m, 3H), 3.39-3.15 (m, 2H), 2.26 (m, 2H), 1.01 (d, 3H).

Example 94

(3-{[5-(4-Methoxyphenyl)-6-phenylfuro[2,3-d]pyrimidin-4-yl]oxy}-2,2-dimethylpropoxy)acetic acid tert.-butyl ester

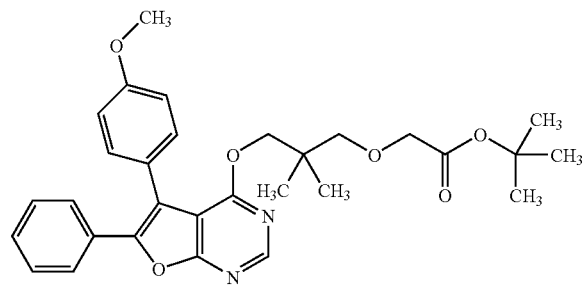

Put 300 mg (0.742 mmol) 3-{[5-(4-methoxyphenyl)-6-phenylfuro[2,3-d]pyrimidin-4-yl]oxy}-2,2-dimethylpropan-1-ol with 723 mg (3.71 mmol) bromoacetic acid tert.-butyl ester and 50 mg (0.148 mmol) tetra-n-butylammonium hydrogensulphate in 6 ml dichloromethane. Cool to 0° C. Then add 750 µl 50% sodium hydroxide solution and stir vigorously for a few minutes at 0° C. Stirring vigorously, allow to return to RT, and continue stirring vigorously overnight. Then dilute with dichloromethane and lightly acidify with 10% citric acid solution. Separate the phases and extract the aqueous phase once with dichloromethane. Combine the organic phases and wash once with satd. sodium chloride solution, dry over magnesium sulphate and concentrate by evaporation. Purify the residue by chromatography on silica gel (solvent: cyclohexane/ethyl acetate 9:1). 295 mg (76.7% of theor.) of the target compound is obtained.

LC-MS (Method 8): $R_t$=3.33 min; m/z=419 (M+H)$^+$ $^1$H-NMR (400 MHz, CDCl$_3$): δ=8.51 (s, 1H), 7.61 (m, 2H), 7.49 (d, 2H), 7.30 (m, 3H), 6.98 (d, 2H), 4.21 (s, 2H), 3.87 (s, 3H), 3.77 (s, 2H), 3.02 (s, 2H), 1.44 (s, 9H), 0.82 (s, 6H).

Example 95

(3-{[5-(4-Methoxyphenyl)-6-phenylfuro[2,3-d]pyrimidin-4-yl]oxy}-2,2-dimethylpropoxy)acetic acid

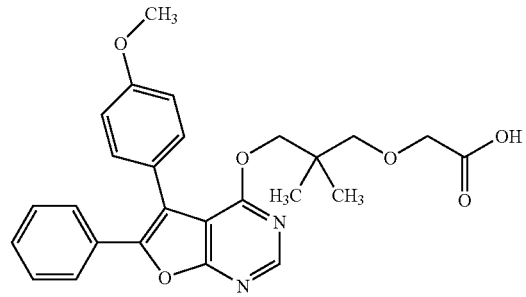

Put 280 mg (0.54 mmol) (3-{[5-(4-methoxyphenyl)-6-phenylfuro[2,3-d]pyrimidin-4-yl]oxy}-2,2-dimethylpropoxy)acetic acid tert.-butyl ester in 8 ml dichloromethane. Add 2 ml trifluoroacetic acid and stir for 1 h at RT. Then concentrate by evaporation and mix the residue with petroleum ether. Filter the solid on a frit with suction, and dry at high vacuum. 220 mg (88.1% of theor.) of the target compound is obtained.

LC-MS (Method 7): $R_t$=4.03 min; m/z=463 (M+H)$^+$ $^1$H-NMR (400 MHz, CDCl$_3$): δ=8.56 (s, 1H), 7.54 (d, 2H), 7.42-7.35 (m, 5H), 7.02 (d, 2H), 4.12 (s, 2H), 3.86 (s, 2H), 3.81 (s, 3H), 3.01 (s, 2H), 0.72 (s, 6H).

Example 96

(3-{[5-(4-Methoxyphenyl)-6-phenylfuro[2,3-d]pyrimidin-4-yl]oxy}propoxy)acetic acid

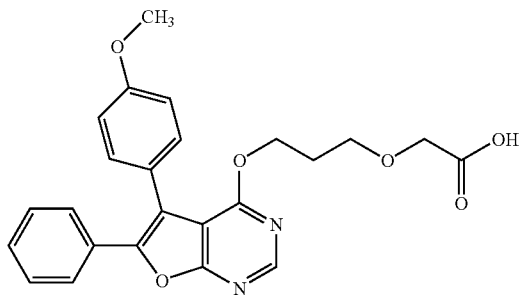

Put 200 mg (0.53 mmol) 3-{[5-(4-methoxyphenyl)-6-phenylfuro[2,3-d]pyrimidin-4-yl]oxy}propan-1-ol with 518 mg (2.66 mmol) bromoacetic acid tert.-butyl ester and 36 mg (0.106 mmol) tetra-n-butylammonium hydrogensulphate in 5 ml dichloromethane and cool to 0° C. Add 1.0 ml 50% sodium hydroxide solution and stir vigorously at 0° C. Then leave to return to RT and continue stirring vigorously overnight. Then dilute with dichloromethane and water, acidify with 10% citric acid solution and separate the phases. Re-extract the aqueous phase once with dichloromethane. Combine the organic phases, wash once with satd. sodium chloride solution, dry over magnesium sulphate and concentrate by evaporation. Dissolve the residue in 5 ml dichloromethane. Add 1.25 ml TFA and stir for 2 h at RT. Then concentrate by evaporation and dry at high vacuum. Purify the residue chromatographically on a silica-gel thick-layer plate (solvent: dichloromethane/methanol 95:5). Extract the product zone with dichloromethane/methanol 9:1. 50 mg (23.0% of theor.) of the target compound is obtained.

LC-MS (Method 7): $R_t$=3.68 min; m/z=435 (M+H)$^+$ $^1$H-NMR (400 MHz, CDCl$_3$): δ=12.58 (br. s, 1H), 8.59 (s, 1H), 7.54 (d, 2H), 7.42-7.35 (m, 5H), 7.02 (d, 2H), 4.43 (t, 2H), 3.82 (s, 3H), 3.39-3.31 (m, 4H), 1.84-1.78 (m, 2H).

Example 97

(−)-4-[2-{[5-(4-Methoxyphenyl)-6-phenylfuro[2,3-d]pyrimidin-4-yl]amino}-1-methylethoxy]-butyric acid

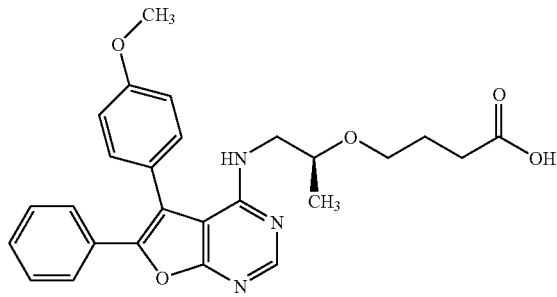

Put 110 mg (0.29 mmol) (+)-1-{[5-(4-methoxyphenyl)-6-phenylfuro[2,3-d]pyrimidin-4-yl]amino}-propan-2-ol with 327 mg (1.47 mmol) 4-bromobutyric acid tert.-butyl ester and 20 mg (0.059 mmol) tetra-n-butylammonium hydrogensulphate in 2 ml dichloromethane and cool to 0° C. Then add 500 µl 50% sodium hydroxide solution and stir for two days at RT. Once again, add the same amounts of 4-bromobutyric acid tert.-butyl ester, tetra-n-butylammonium hydrogensulphate and 50% sodium hydroxide solution and stir for a further 24 h at RT. Then heat under reflux for 24 h. Leave to cool, and dilute with dichloromethane and water. Acidify with 10% citric acid solution and separate the phases. Re-extract the aqueous phase once with dichloromethane. Combine the organic phases, wash once with satd. sodium chloride solution, dry over magnesium sulphate and concentrate by evaporation. Purify the residue by preparative HPLC. Dissolve the product thus obtained (30 mg) in 1 ml dichloromethane. Add 250 µl trifluoroacetic acid and stir overnight at RT. Then concentrate by evaporation and purify the residue chromatographically on a silica-gel thick-layer plate (solvent: dichloromethane/methanol 95:5). Extract the product zone with dichloromethane/methanol 9:1. 25 mg (21.2% of theor.) of the target compound is obtained.

LC-MS (Method 7): $R_t$=3.64 min; m/z=462 (M+H)$^+$ $^1$H-NMR (400 MHz, CDCl$_3$): δ=8.39 (s, 1H), 7.51 (m, 2H), 7.41 (d, 2H), 7.26 (m, 3H), 7.06 (d, 2H), 5.12 (t, 1H), 3.89 (s, 3H), 3.77-3.70 (m, 1H), 3.55-3.47 (m, 1H), 3.42-3.38 (m, 1H), 3.28-3.20 (m, 2H), 2.31 (t, 2H), 1.76-1.67 (m, 2H), 1.09 (d, 3H).

$[α]_D^{20}$=−20.0°, c=0.077, acetonitrile.

Example 98

3-{[(1R,2R)-2-{[5-(4-Methoxyphenyl)-6-phenylfuro[2,3-d]pyrimidin-4-yl]oxy}-1-methylpropyl]oxy}propionic acid tert.-butyl ester

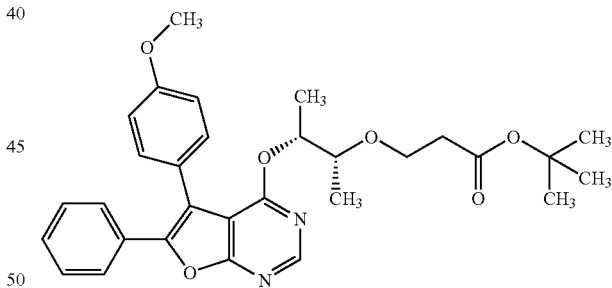

Add 157 mg (1.37 mmol) potassium tert.-butylate to a solution of 535 mg (1.37 mmol) (2R,3R)-3-{[5-(4-methoxyphenyl)-6-phenylfuro[2,3-d]pyrimidin-4-yl]oxy}butan-2-ol in 5 ml THF. After stirring for 15 min at RT, add 1.0 ml (878 mg, 6.65 mmol) tert.-butyl acrylate. After three hours, add 10 ml water, and concentrate the reaction mixture by vacuum evaporation. Purify the residue by preparative RP-HPLC (gradient: water/acetonitrile). 346 mg (47% of theor.) of the desired product is obtained.

LC-MS (Method 7): $R_t$=4.83 min; m/z=519 (M+H)$^+$ $^1$H-NMR (400 MHz, CDCl$_3$): δ=8.56 (s, 1H), 7.55 (d, 2H), 7.40-7.35 (m, 5H), 7.01 (d, 2H), 5.29 (dt, 1H), 3.81 (s, 3H), 3.63-3.40 (m, 3H), 2.26 (t, 2H), 1.33 (s, 9H), 1.15 (d, 3H), 0.88 (d, 3H).

Example 99

4-{[(2R)-2-{[5-(4-Ethylphenyl)-6-phenylfuro[2,3-d]pyrimidin-4-yl]oxy}propyl](methyl)amino}-butyric acid methyl ester

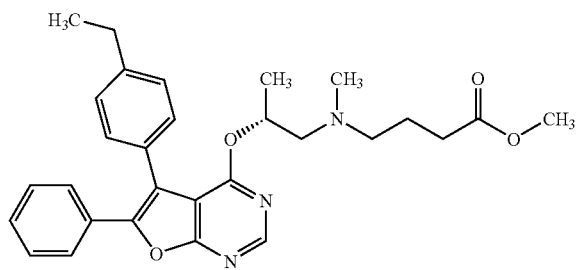

Add 797 mg (5.77 mmol) potassium carbonate to a solution of 1000 mg (2.31 mmol) (2R)-2-{[5-(4-ethylphenyl)-6-phenylfuro[2,3-d]pyrimidin-4-yl]oxy}-N-methylpropane-1-ammonium formate in 20 ml THF. After adding 0.35 ml (501 mg, 2.77 mmol) 4-bromobutyric acid methyl ester and 34 mg (0.09 mmol) tetra-n-butylammonium iodide, stir the reaction mixture 16 h at 80° C. After cooling to room temperature, filter off the inorganic salts and wash with THF. Concentrate the filtrate by vacuum evaporation. Take up the residue in acetonitrile and purify by preparative RP-HPLC (gradient: water/acetonitrile/ammonia). 308 mg (73% purity, 20% of theor.) of the desired product is obtained.

LC-MS (Method 8): $R_t$=1.91 min; m/z=488 (M+H)$^+$.

Example 100

(6R)-6-{[6-(2-Fluorophenyl)-5-(4-methoxyphenyl)furo[2,3-d]pyrimidin-4-yl]oxy}heptanoic acid tert.-butyl ester

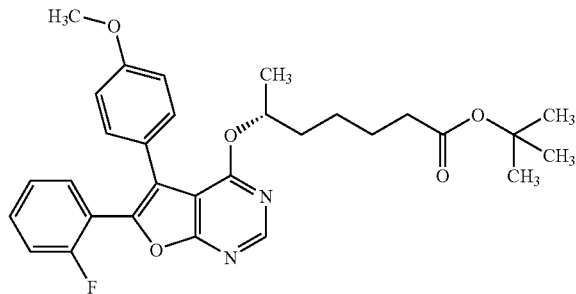

Add 87 mg (2.16 mmol) sodium hydride (60% dispersion in mineral oil) to a solution of 350 mg (1.73 mmol) (6R)-6-hydroxyheptanoic acid tert.-butyl ester in 5 ml THF, with ice cooling. After stirring for ten minutes with ice cooling, add a solution of 644 mg (1.82 mmol) 4-chloro-6-(2-fluorophenyl)-5-(4-methoxyphenyl)furo[2,3-d]pyrimidine in 5 ml THF and 32 mg (0.09 mmol) tetra-n-butylammonium iodide. Stir the reaction mixture for 48 h at RT. After adding water and ethyl acetate, wash the separated organic phase with 1 N hydrochloric acid and concentrate by vacuum evaporation. Take up the residue in acetonitrile/DMSO and purify by preparative RP-HPLC (gradient: water/acetonitrile). 425 mg (47% of theor.) of the desired product is obtained.

LC-MS (Method 8): $R_t$=3.37 min; m/z=521 (M+H)$^+$ $^1$H-NMR (400 MHz, DMSO-d$_6$): δ=8.60 (s, 1H), 7.55-7.50 (m, 2H), 7.34-7.28 (m, 4H), 6.93-6.91 (m, 2H), 5.41-5.34 (m, 1H), 3.77 (s, 3H), 2.10 (t, 2H), 1.60-1.55 (m, 2H), 1.46-1.39 (m, 2H), 1.34 (s, 9H), 1.28 (d, 3H), 1.25-1.15 (m, 2H).

Example 101

4-{[(2S)-2-{[6-(2-Fluorophenyl)-5-(4-methoxyphenyl)furo[2,3-d]pyrimidin-4-yl]oxy}propyl]-(methyl)amino}butyric acid tert.-butyl ester

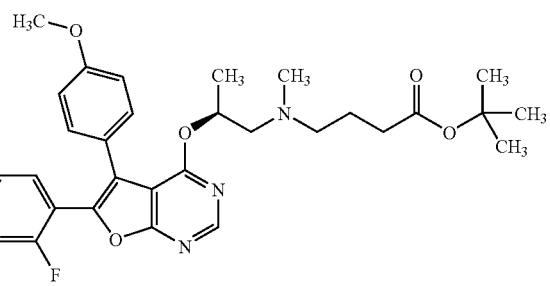

Add 22 mg (0.54 mmol) sodium hydride (60% dispersion in mineral oil) to a solution of 100 mg (0.43 mmol) 4-{[(2S)-2-hydroxypropyl](methyl)amino}butyric acid tert.-butyl ester in 1 ml THF, with ice cooling. After stirring for ten minutes with ice cooling, add a solution of 161 mg (0.45 mmol) 4-chloro-6-(2-fluorophenyl)-5-(4-methoxyphenyl)furo[2,3-d]pyrimidine in 2 ml THF and 8 mg (0.02 mmol) tetra-n-butylammonium iodide. Stir the reaction mixture for 16 hours at room temperature. After adding water and ethyl acetate, wash the separated organic phase with 1 N hydrochloric acid and concentrate by vacuum evaporation. Take up the residue in acetonitrile/DMSO and purify by preparative RP-HPLC (gradient: water/acetonitrile). 114 mg (93% purity, 45% of theor.) of the desired product is obtained.

LC-MS (Method 8): $R_t$=1.90 min; m/z=550 (M+H)$^+$ $^1$H-NMR (400 MHz, DMSO-d$_6$): δ=8.60 (s, 1H), 7.55-7.51 (m, 2H), 7.33-7.28 (m, 4H), 6.93-6.91 (m, 2H), 5.59-5.51 (m, 1H), 3.77 (s, 3H), 2.40-2.29 (m, 2H), 2.25-2.22 (m, 2H), 2.08 (s, 3H), 2.05-2.00 (m, 2H), 1.53-1.42 (m, 2H), 1.32 (s, 9H), 1.27 (d, 3H).

Example 102

6-{[5-(4-Ethylphenyl)-6-(2-fluorophenyl)furo[2,3-d]pyrimidin-4-yl]oxy}heptanoic acid tert.-butyl ester

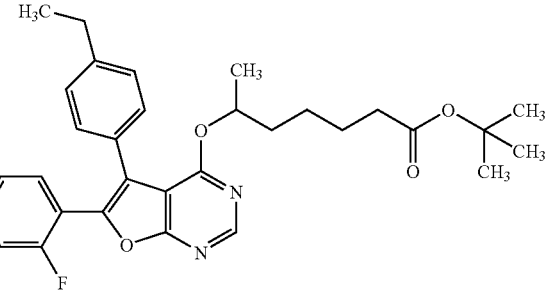

Add 49 mg (1.24 mmol) sodium hydride (60% dispersion in mineral oil) to a solution of 200 mg (0.99 mmol) 6-hydroxyheptanoic acid tert.-butyl ester in 5 ml THF. After stirring for ten minutes, add a solution of 407 mg (90% purity, 1.04 mmol) 4-chloro-5-(4-ethylphenyl)-6-(2-fluorophenyl)furo[2,3-d]pyrimidine in 5 ml THF and 18 mg (0.05 mmol) tetra-n-butylammonium iodide. Stir the reaction mixture for 40 hours at 75° C. After adding water and ethyl acetate, wash the separated organic phase with 1 N hydrochloric acid and concentrate by vacuum evaporation. Take up the residue in acetonitrile/DMSO and purify by preparative RP-HPLC (gradient: water/acetonitrile). 104 mg (19% of theor.) of the desired product (racemate) is obtained.

LC-MS (Method 8): R$_t$=3.59 min; m/z=519 (M+H)$^+$ $^1$H-NMR (400 MHz, DMSO-d$_6$): δ=8.61 (s, 1H), 7.55-7.51 (m, 2H), 7.33-7.27 (m, 4H), 7.20-7.18 (m, 2H), 5.39-5.31 (m, 1H), 2.63 (q, 2H), 2.08 (t, 2H), 1.60-1.50 (m, 2H), 1.45-1.37 (m, 2H), 1.34 (s, 9H), 1.28 (d, 3H), 1.24-1.16 (m, 5H).

Example 103

(6R)-6-{[5-(4-Ethylphenyl)-6-(2-fluorophenyl)furo[2,3-d]pyrimidin-4-yl]oxy}heptanoic acid tert.-butyl ester

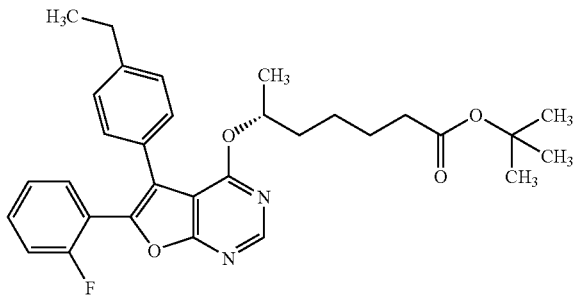

Add 87 mg (2.16 mmol) sodium hydride (60% dispersion in mineral oil) to a solution of 350 mg (1.73 mmol) (6R)-6-hydroxyheptanoic acid tert.-butyl ester in 5 ml THF, with ice cooling. After stirring for ten minutes with ice cooling, add a solution of 712 mg (90% purity, 1.82 mmol) 4-chloro-5-(4-ethylphenyl)-6-(2-fluorophenyl)furo[2,3-d]pyrimidine in 5 ml THF and 32 mg (0.09 mmol) tetra-n-butylammonium iodide. Stir the reaction mixture for 48 hours at room temperature. After adding water and ethyl acetate, wash the separated organic phase with 1 N hydrochloric acid and concentrate by vacuum evaporation. Take up the residue in acetonitrile/DMSO and purify by preparative RP-HPLC (gradient: water/acetonitrile). 459 mg (51% of theor.) of the desired product is obtained.

LC-MS (Method 8): R$_t$=3.51 min; m/z=519 (M+H)$^+$ $^1$H-NMR (400 MHz, DMSO-d$_6$): δ=8.61 (s, 1H), 7.55-7.51 (m, 2H), 7.33-7.27 (m, 4H), 7.20-7.18 (m, 2H), 5.39-5.31 (m, 1H), 2.63 (q, 2H), 2.08 (t, 2H), 1.60-1.50 (m, 2H), 1.45-1.37 (m, 2H), 1.34 (s, 9H), 1.28 (d, 3H), 1.24-1.16 (m, 5H).

Example 104

(3-{[5-(4-Methoxyphenyl)-6-phenylfuro[2,3-d]pyrimidin-4-yl]oxy}-1-methylbutoxy)acetic acid tert.-butyl ester

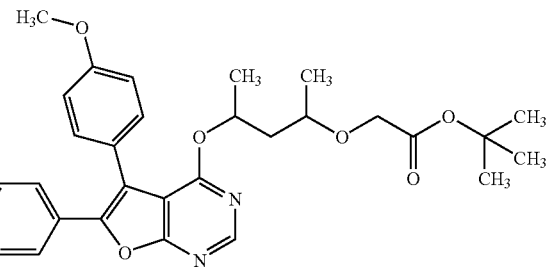

Add 4.8 ml of 11.25 N sodium hydroxide solution to a solution of 2.19 g (5.41 mmol) 4-{[5-(4-methoxyphenyl)-6-phenylfuro[2,3-d]pyrimidin-4-yl]oxy}pentan-2-ol in 20 ml toluene. After adding 184 mg (0.54 mmol) tetra-n-butylammonium hydrogensulphate and 2.11 g (10.83 mmol) tert.-butyl bromoacetate, stir the reaction mixture for 15 h at 70° C. After cooling to room temperature, adjust to pH 7 with concentrated hydrochloric acid. Extract three times with 50 ml dichloromethane each time. Wash the combined organic extracts with satd. aqueous sodium chloride solution, dry over sodium sulphate, and filter. Concentrate the filtrate by vacuum evaporation. Take up the residue in ethyl acetate and purify by flash chromatography on silica gel (solvent: ethyl acetate/methanol 1:0, 5:1). 0.08 g (92% purity, 3% of theor.) of the desired product is obtained as a racemic mixture of diastereomers.

LC-MS (Method 8): R$_t$=3.33 min; m/z=519 (M+H)$^+$ $^1$H-NMR (400 MHz, DMSO-d$_6$): [lesser stereoisomer in square brackets] δ=8.57 (s, 1H), [8.56, s, 1H], 7.55-7.51 (m, 2H), 7.43-7.37 (m, 5H), 7.04-7.01 (m, 2H), 5.54-5.46 (m, 1H), [5.39-5.30, m, 1H], 3.83-3.81 (m, 5H), 3.42-3.36 (m, 1H), 1.87-1.80 (m, 1H), 1.56-1.49 (m, 1H), 1.39 (s, 9H), [1.34, d, 3H], 1.27 (d, 3H), 1.00 (d, 3H), [0.89, d, 3H].

Example 105

[2-({[5-(4-Ethylphenyl)-6-phenylfuro[2,3-d]pyrimidin-4-yl]oxy}methyl)-3,3-dimethylbutoxy]-acetic acid tert.-butyl ester

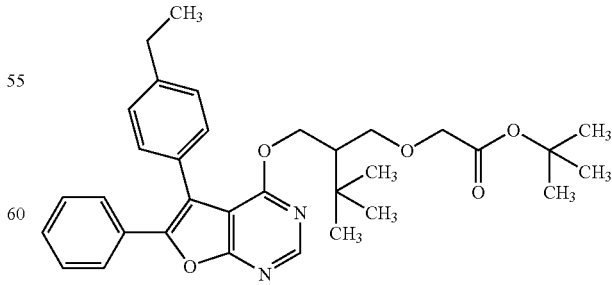

Add 0.5 ml of 11.25 N sodium hydroxide solution to a solution of 265 mg (0.62 mmol) 2-({[5-(4-ethylphenyl)-6-phenylfuro[2,3-d]pyrimidin-4-yl]oxy}methyl)-3,3-dimethylbutan-1-ol in 10 ml toluene. After adding 21 mg (0.06 mmol) tetra-n-butylammonium hydrogensulphate and 240 mg (1.23 mmol) 2-bromoacetic acid tert.-butyl ester, stir the reaction mixture for 16 h at 70° C. After cooling to room temperature, neutralize with 1 N hydrochloric acid and extract with ethyl acetate. Wash the organic phase with satd. aqueous sodium chloride solution, dry over sodium sulphate, and filter. Concentrate the filtrate by vacuum evaporation. Purify the residue by preparative RP-HPLC (gradient: water/acetonitrile). 170 mg (51% of theor.) of the desired product (racemate) is obtained.

LC-MS (Method 9): $R_t$=5.34 min; m/z=545 (M+H)$^+$ $^1$H-NMR (400 MHz, DMSO-d$_6$): δ=8.60 (s, 1H), 7.53-7.51 (m, 2H), 7.39-7.36 (m, 5H), 7.31-7.29 (m, 2H), 4.54-4.45 (m, 2H), 3.83 (dd, 2H), 3.30 (s, 2H), 2.69 (q, 2H), 1.55-1.49 (m, 1H), 1.39 (s, 9H), 1.24 (t, 3H), 0.73 (s, 9H).

Example 106

3-(2-{[5-(4-Methoxyphenyl)-6-phenylfuro[2,3-d]pyrimidin-4-yl]oxy}-1-methylpropoxy)propionic acid tert.-butyl ester

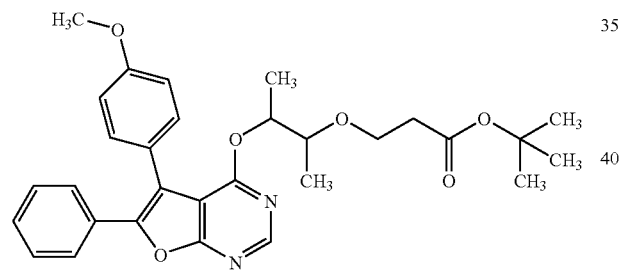

Add 2.2 ml of 45% sodium hydroxide solution to a mixture of 900 mg (2.31 mmol) 3-{[5-(4-methoxyphenyl)-6-phenylfuro[2,3-d]pyrimidin-4-yl]oxy}butan-2-ol, 1477 mg (11.53 mmol) tert.-butyl acrylate and 157 mg (0.46 mmol) tetra-n-butylammonium hydrogensulphate in 10 ml dichloromethane at 0° C., and stir at this temperature for one hour. After a further 16 hours at room temperature, filter the reaction mixture, and concentrate the filtrate by vacuum evaporation. Purify the raw product by preparative RP-HPLC (gradient: water/acetonitrile). 690 mg (57% of theor.) of the desired product is obtained as (R,S/S,R) racemate.

LC-MS (Method 7): $R_t$=4.82 min; m/z=519 (M+H)$^+$ $^1$H-NMR (400 MHz, DMSO-d$_6$): δ=8.57 (s, 1H), 7.53-7.50 (m, 2H), 7.42-7.36 (m, 5H), 7.03-6.99 (m, 2H), 5.43-5.37 (m, 1H), 3.81 (s, 3H), 3.49-3.45 (m, 1H), 3.41 (t, 2H), 2.24 (t, 2H), 1.31 (s, 9H), 1.19 (d, 3H), 0.88 (d, 3H).

Example 107

6-({5-(4-Methoxyphenyl)-6-[2-(trifluoromethyl)phenyl]furo[2,3-d]pyrimidin-4-yl}amino)hexanoic acid methyl ester

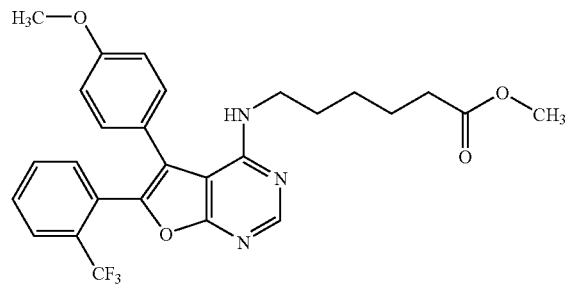

Add 0.5 ml of 2 M aqueous potassium carbonate solution to a mixture of 224 mg (0.50 mmol) 6-{[6-bromo-5-(4-methoxyphenyl)furo[2,3-d]pyrimidin-4-yl]amino}hexanoic acid methyl ester and 29 mg (0.03 mmol) tetrakis(triphenylphosphine)palladium(0) in 2.5 ml 1,2-dimethoxyethane. Next, add 119 mg (0.63 mmol) (2-trifluoromethyl)phenylboronic acid and stir the mixture for 15 h under reflux. Filter the reaction mixture and purify directly by preparative RP-HPLC (gradient: water/acetonitrile). 118 mg (46% of theor.) of the desired product is obtained.

LC-MS (Method 2): $R_t$=2.74 min; m/z=514 (M+H)$^+$ $^1$H-NMR (400 MHz, DMSO-d$_6$): δ=8.36 (s, 1H), 7.89 (dd, 1H), 7.69-7.63 (m, 2H), 7.44 (dd, 1H), 7.23 (d, 2H), 6.98 (d, 2H), 5.50 (t, NH), 3.76 (s, 3H), 3.57 (s, 3H), 3.41 (q, 2H), 2.29 (t, 2H), 1.55-1.44 (m, 4H), 1.28-1.19 (m, 2H).

Example 108

6-{[6-(2-Chlorophenyl)-5-(4-methoxyphenyl)furo[2,3-d]pyrimidin-4-yl]amino}hexanoic acid methyl ester

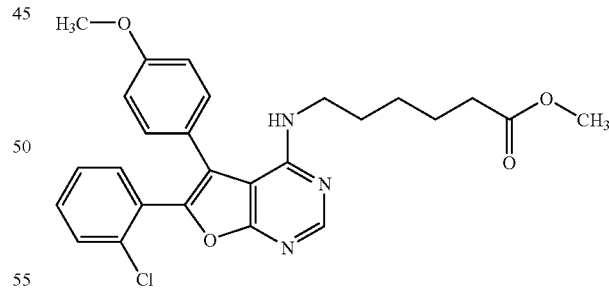

Add 229 mg (1.08 mmol) potassium phosphate to a mixture of 220 mg (0.49 mmol) 6-{[6-bromo-5-(4-methoxyphenyl)furo[2,3-d]pyrimidin-4-yl]amino}hexanoic acid methyl ester and 17 mg (0.03 mmol) bis(triphenylphosphine)palladium(II) chloride in 2.2 ml toluene. Next, add 176 mg (0.74 mmol) (2-chlorophenyl)boronic acid pinacol ester and stir the mixture for 15 h at 80° C. Purify the reaction mixture directly by preparative RP-HPLC (gradient: water/acetonitrile). 101 mg (42% of theor.) of the desired product is obtained.

LC-MS (Method 10): $R_t$=2.81 min; m/z=481 (M+H)$^+$

¹H-NMR (400 MHz, DMSO-d₆): δ=8.36 (s, 1H), 7.58 (dd, 1H), 7.50-7.44 (m, 2H), 7.36 (dd, 1H), 7.24 (d, 2H), 6.98 (d, 2H), 5.54 (t, NH), 3.77 (s, 3H), 3.58 (s, 3H), 3.42 (q, 2H), 2.29 (t, 2H), 1.55-1.45 (m, 4H), 1.27-1.19 (m, 2H).

Example 109

6-{[6-(2,6-Difluorophenyl)-5-(4-methoxyphenyl)furo[2,3-d]pyrimidin-4-yl]amino}hexanoic acid methyl ester

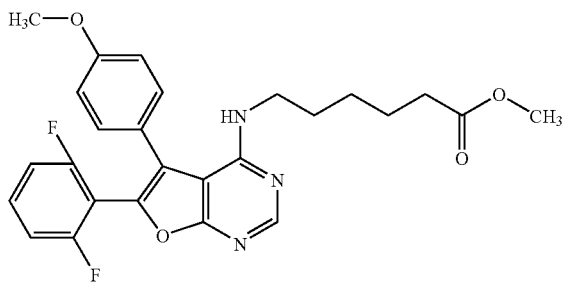

Dissolve 150 mg (0.34 mmol) 6-{[6-bromo-5-(4-methoxyphenyl)furo[2,3-d]pyrimidin-4-yl]amino}hexanoic acid methyl ester and 106 mg (0.70 mmol) (2,6-difluorophenyl)boronic acid in 3.5 ml toluene and 1.0 ml ethanol, and add 0.34 ml of 2 M aqueous sodium carbonate solution and 25 mg (0.03 mmol) 1,1'-bis(diphenylphosphano)ferrocene palladium(II) chloride. Next, stir for 15 h at 70° C. Purify the reaction mixture directly by preparative RP-HPLC (gradient: water/acetonitrile). 13 mg (8% of theor.) of the desired product is obtained.

LC-MS (Method 10): $R_t$=2.72 min; m/z=482 (M+H)⁺

¹H-NMR (300 MHz, DMSO-d₆): δ=8.37 (s, 1H), 7.63-7.57 (m, 1H), 7.26-7.10 (m, 4H), 6.98 (d, 2H), 5.65 (t, NH), 3.78 (s, 3H), 3.57 (s, 3H), 3.42 (q, 2H), 2.29 (t, 2H), 1.55-1.47 (m, 4H), 1.28-1.24 (m, 2H).

Example 110

6-{[6-(2-Methoxyphenyl)-5-(4-methoxyphenyl)furo[2,3-d]pyrimidin-4-yl]amino}hexanoic acid methyl ester

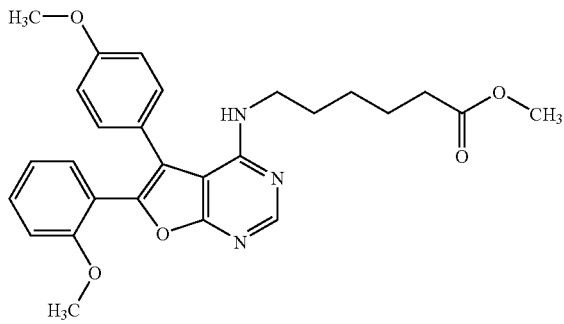

Add 0.45 ml of a 2 M aqueous sodium carbonate solution to a mixture of 200 mg (0.45 mmol) 6-{[6-bromo-5-(4-methoxyphenyl)furo[2,3-d]pyrimidin-4-yl]amino}hexanoic acid methyl ester and 16 mg (0.02 mmol) bis(triphenylphosphine)palladium(II) chloride in 10 ml dimethylsulphoxide. Next, add 85 mg (0.56 mmol) (2-methoxyphenyl)boronic acid and stir the mixture for 15 h at 80° C. Filter the reaction mixture and purify directly by preparative RP-HPLC (gradient: water/acetonitrile). 63 mg (42% of theor.) of the desired product is obtained.

LC-MS (Method 10): $R_t$=2.72 min; m/z=476 (M+H)⁺

¹H-NMR (400 MHz, DMSO-d₆): δ=8.32 (s, 1H), 7.42 (dd, 1H), 7.30 (dd, 1H), 7.23 (d, 2H), 7.05 (d, 1H), 7.00-6.94 (m, 3H), 5.37 (t, NH), 3.78 (s, 3H), 3.58 (s, 3H), 3.54 (s, 3H), 3.41 (q, 2H), 2.28 (t, 2H), 1.54-1.43 (m, 4H), 1.26-1.18 (m, 2H).

Example 111

6-{[5-(4-Methoxyphenyl)-6-(2-vinylphenyl)furo[2,3-d]pyrimidin-4-yl]amino}hexanoic acid methyl ester

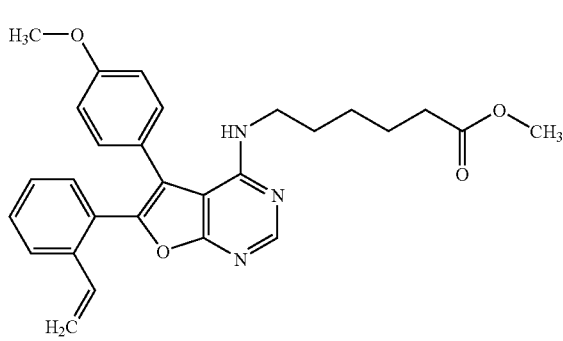

Add 0.5 ml of 2 M aqueous potassium carbonate solution to a mixture of 224 mg (0.50 mmol) 6-{[6-bromo-5-(4-methoxyphenyl)furo[2,3-d]pyrimidin-4-yl]amino}hexanoic acid methyl ester and 29 mg (0.03 mmol) tetrakis(triphenylphosphine)palladium(0) in 2.5 ml 1,2-dimethoxyethane. Next, add 92 mg (0.63 mmol) (2-vinylphenyl)boronic acid and stir the mixture for 15 h under reflux. Filter the reaction mixture and purify directly by preparative RP-HPLC (gradient: water/acetonitrile). 82 mg (35% of theor.) of the desired product is obtained.

LC-MS (Method 2): $R_t$=2.77 min; m/z=472 (M+H)⁺

¹H-NMR (400 MHz, DMSO-d₆): δ=8.35 (s, 1H), 7.70 (d, 1H), 7.46-7.42 (m, 1H), 7.30 (d, 2H), 7.23 (d, 2H), 6.97 (d, 2H), 6.61 (dd, 1H), 5.72 (d, 1H), 5.48 (t, NH), 5.17 (d, 1H), 3.76 (s, 3H), 3.58 (s, 3H), 3.42 (q, 2H), 2.29 (t, 2H), 1.55-1.46 (m, 4H), 1.27-1.22 (m, 2H).

Example 112

6-{[6-(2-Ethylphenyl)-5-(4-methoxyphenyl)furo[2,3-d]pyrimidin-4-yl]amino}hexanoic acid methyl ester

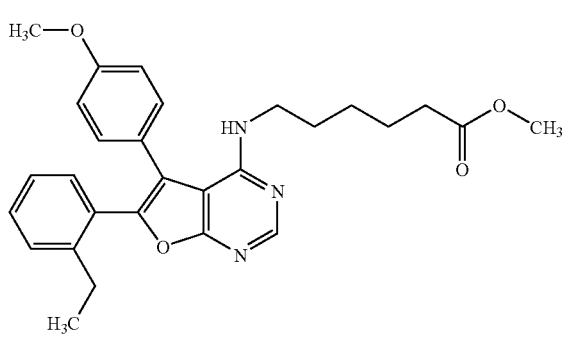

Add 0.50 ml of 2 M aqueous sodium carbonate solution to a mixture of 224 mg (0.50 mmol) 6-{[6-bromo-5-(4-methoxyphenyl)furo[2,3-d]pyrimidin-4-yl]amino}hexanoic acid methyl ester and 18 mg (0.03 mmol) bis(triphenylphosphine)palladium(II) chloride in 11.2 ml DMSO. Next, add 187 mg (1.25 mmol) (2-ethylphenyl)boronic acid and stir the mixture for 15 h at 80° C. Filter the reaction mixture and purify directly by preparative RP-HPLC (gradient: water/acetonitrile). 69 mg (29% of theor.) of the desired product is obtained.

LC-MS (Method 2): $R_t$=2.83 min; m/z=474 (M+H)$^+$ $^1$H-NMR (400 MHz, DMSO-d$_6$): δ=8.33 (s, 1H), 7.39-7.31 (m, 2H), 7.26-7.17 (m, 4H), 6.98 (d, 2H), 5.42 (t, NH), 3.76 (s, 3H), 3.58 (s, 3H), 3.41 (q, 2H), 2.49 (q, 2H), 2.29 (t, 2H), 1.55-1.44 (m, 4H), 1.27-1.19 (m, 2H), 1.00 (t, 3H).

Example 113
6-{[6-(2-Fluorophenyl)-5-(4-methoxyphenyl)furo[2,3-d]pyrimidin-4-yl]amino}hexanoic acid methyl ester

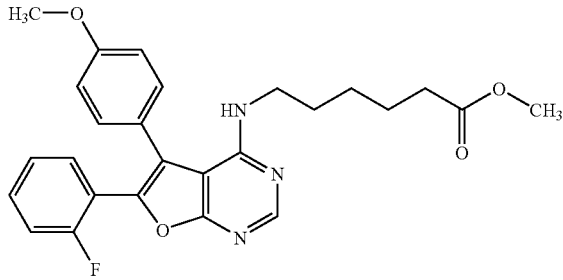

Add 0.22 ml of a 2 M aqueous sodium carbonate solution to a mixture of 100 mg (0.22 mmol) 6-{[6-bromo-5-(4-methoxyphenyl)furo[2,3-d]pyrimidin-4-yl]amino}hexanoic acid methyl ester and 8 mg (0.01 mmol) bis(triphenylphosphine)palladium(II) chloride in 5.0 ml DMSO. Next, add 39 mg (0.28 mmol) (2-fluorophenyl)boronic acid and stir the mixture for 15 h at 80° C. Filter the reaction mixture and purify directly by preparative RP-HPLC (gradient: water/acetonitrile). 69 mg (29% of theor.) of the desired product is obtained.

LC-MS (Method 5): $R_t$=2.82 min; m/z=464 (M+H)$^+$ $^1$H-NMR (400 MHz, DMSO-d$_6$): δ=8.35 (s, 1H), 7.48-7.41 (m, 2H), 7.31 (d, 2H), 7.26-7.21 (m, 2H), 7.03 (d, 2H), 5.43 (t, NH), 3.80 (s, 3H), 3.58 (s, 3H), 3.41 (q, 2H), 2.29 (t, 2H), 1.54-1.42 (m, 4H), 1.22-1.18 (m, 2H).

Example 114
6-{[5-(4-Methoxyphenyl)-6-(2-methylphenyl)furo[2,3-d]pyrimidin-4-yl]amino}hexanoic acid methyl ester

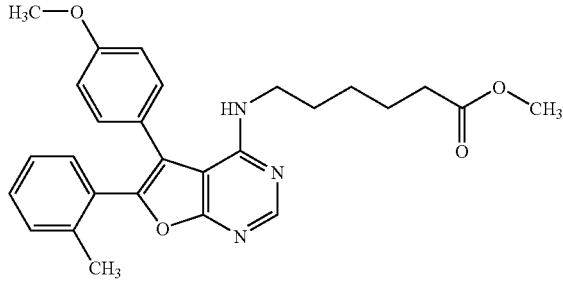

Add 0.5 ml of 2 M aqueous potassium carbonate solution to a mixture of 224 mg (0.50 mmol) 6-{[6-bromo-5-(4-methoxyphenyl)furo[2,3-d]pyrimidin-4-yl]amino}hexanoic acid methyl ester and 29 mg (0.03 mmol) tetrakis(triphenylphosphine)palladium(0) in 2.5 ml 1,2-dimethoxyethane. Next, add 85 mg (0.63 mmol) (2-methylphenyl)boronic acid and stir the mixture for 15 h under reflux. Filter the reaction mixture and purify directly by preparative RP-HPLC (gradient: water/acetonitrile). 68 mg (30% of theor.) of the desired product is obtained.

LC-MS (Method 8): $R_t$=2.97 min; m/z=460 (M+H)$^+$ $^1$H-NMR (400 MHz, DMSO-d$_6$): δ=8.32 (s, 1H), 7.34-7.14 (m, 6H), 6.98 (d, 2H), 5.44 (t, NH), 3.77 (s, 3H), 3.57 (s, 3H), 3.42 (q, 2H), 2.29 (t, 2H), 2.10 (s, 3H), 1.55-1.44 (m, 4H), 1.27-1.19 (m, 2H).

Example 115
6-{[6-(2-Fluoro-6-methoxyphenyl)-5-(4-methoxyphenyl)furo[2,3-d]pyrimidin-4-yl]amino}hexanoic acid methyl ester

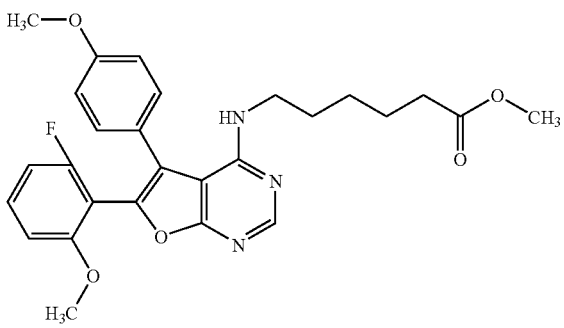

Dissolve 150 mg (0.34 mmol) 6-{[6-bromo-5-(4-methoxyphenyl)furo[2,3-d]pyrimidin-4-yl]amino}hexanoic acid methyl ester and 142 mg (0.84 mmol) (2-fluoro-6-methoxyphenyl)boronic acid in 2.0 ml 1,2-dimethoxyethane and add 0.34 ml of 2 M aqueous sodium carbonate solution and 24 mg (0.03 mmol) 1,1'-bis(diphenylphosphano)ferrocene palladium(II) chloride. Next, stir for 15 h at 80° C. Purify the reaction mixture directly by preparative RP-HPLC (gradient: water/acetonitrile). 56 mg (34% of theor.) of the desired product is obtained.

LC-MS (Method 2): $R_t$=2.57 min; m/z=494 (M+H)$^+$ $^1$H-NMR (400 MHz, DMSO-d$_6$): δ=8.33 (s, 1H), 7.48 (dd, 1H), 7.20 (d, 2H), 6.98-6.94 (m, 3H), 6.86 (dd, 1H), 5.55 (t, NH), 3.76 (s, 3H), 3.67 (s, 3H), 3.57 (s, 3H), 3.42 (q, 2H), 2.29 (t, 2H), 1.55-1.45 (m, 4H), 1.28-1.21 (m, 2H).

Example 116
6-({5-(4-Methoxyphenyl)-6-[2-(trifluoromethyl)phenyl]furo[2,3-d]pyrimidin-4-yl}amino)hexanoic acid

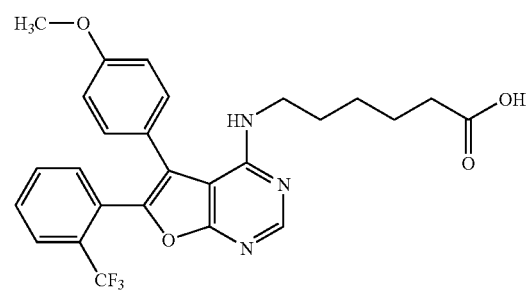

Dissolve 85 mg (0.17 mmol) 6-({5-(4-methoxyphenyl)-6-[2-(trifluoromethyl)phenyl]furo[2,3-d]pyrimidin-4-yl}amino)hexanoic acid methyl ester in 2.5 ml dioxan and add 0.5 ml 1 N sodium hydroxide solution. Stir for 16 h at RT, then add 0.5 ml 1 N hydrochloric acid and 6 ml ethyl acetate.

Separate the organic phase, dry over sodium sulphate, filter and concentrate by evaporation. 68 mg (82% of theor.) of the target compound is obtained.

LC-MS (Method 2): $R_t$=2.38 min; m/z=514 (M+H)$^+$ $^1$H-NMR (400 MHz, DMSO-d$_6$): δ=11.98 (s, 1H), 8.35 (s, 1H), 7.89 (dd, 1H), 7.69-7.63 (m, 2H), 7.44 (dd, 1H), 7.23 (d, 2H), 6.98 (d, 2H), 5.50 (t, NH), 3.76 (s, 3H), 3.42 (q, 2H), 2.19 (t, 2H), 1.52-1.44 (m, 4H), 1.27-1.20 (m, 2H).

Example 117

6-{[6-(2-Chlorophenyl)-5-(4-methoxyphenyl)furo[2,3-d]pyrimidin-4-yl]amino}hexanoic acid

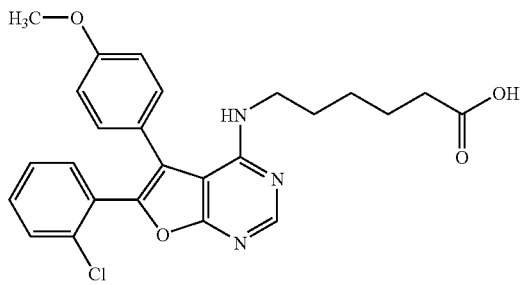

Dissolve 65 mg (0.14 mmol) 6-{[6-(2-chlorophenyl)-5-(4-methoxyphenyl)furo[2,3-d]pyrimidin-4-yl]amino}hexanoic acid methyl ester in 2.5 ml dioxan and add 0.5 ml 1 N sodium hydroxide solution. Stir for 16 h at RT, then add 0.5 ml 1 N hydrochloric acid and 6 ml ethyl acetate. Separate the organic phase, dry over sodium sulphate, filter and concentrate by evaporation. 44 mg (70% of theor.) of the target compound is obtained.

LC-MS (Method 2): $R_t$=2.34 min; m/z=467 (M+H)$^+$ $^1$H-NMR (400 MHz, DMSO-d$_6$): δ=12.00 (s, 1H), 8.36 (s, 1H), 7.56 (d, 1H), 7.49-7.44 (m, 2H), 7.39-7.35 (m, 1H), 7.24 (d, 2H), 6.99 (d, 2H), 5.55 (t, NH), 3.77 (s, 3H), 3.42 (q, 2H), 2.20 (t, 2H), 1.53-1.45 (m, 4H), 1.27-1.20 (m, 2H).

Example 118

6-{[6-(2-Methoxyphenyl)-5-(4-methoxyphenyl)furo[2,3-d]pyrimidin-4-yl]amino}hexanoic acid

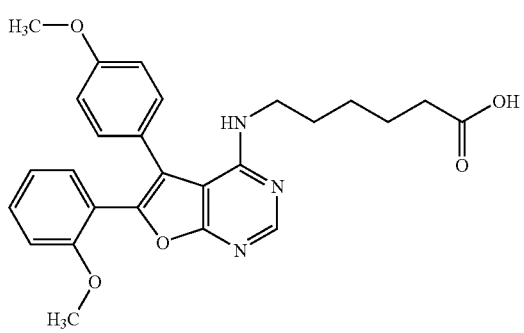

Dissolve 55 mg (0.12 mmol) 6-{[6-(2-methoxyphenyl)-5-(4-methoxyphenyl)furo[2,3-d]pyrimidin-4-yl]amino}hexanoic acid methyl ester in 2.5 ml dioxan and add 0.5 ml 1 N sodium hydroxide solution. Stir for 16 h at RT, then add 0.5 ml 1 N hydrochloric acid and 6 ml ethyl acetate. Separate the organic phase, dry over sodium sulphate, filter and concentrate by evaporation. 42 mg (77% of theor.) of the target compound is obtained.

LC-MS (Method 2): $R_t$=2.25 min; m/z=462 (M+H)$^+$ $^1$H-NMR (300 MHz, DMSO-d$_6$): δ=12.00 (s, 1H), 8.32 (s, 1H), 7.42-7.37 (m, 1H), 7.29 (dd, 1H), 7.23 (d, 2H), 7.05 (d, 1H), 6.99 (d, 2H), 6.97-6.93 (m, 1H), 5.37 (t, NH), 3.77 (s, 3H), 3.41 (q, 2H), 2.20 (t, 2H), 1.53-1.43 (m, 4H), 1.27-1.20 (m, 2H).

Example 119

6-{[5-(4-Methoxyphenyl)-6-(2-vinylphenyl)furo[2,3-d]pyrimidin-4-yl]amino}hexanoic acid

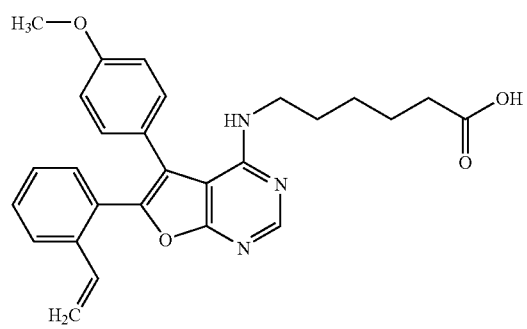

The title compound is formed as a by-product in the synthesis of 6-{[5-(4-methoxyphenyl)-6-(2-vinylphenyl)furo[2,3-d]pyrimidin-4-yl]amino}hexanoic acid methyl ester (Example 111) and is isolated by preparative RP-HPLC (gradient: water/acetonitrile). 36 mg (16% of theor.) of the title compound is obtained.

LC-MS (Method 10): $R_t$=2.58 min; m/z=458 (M+H)$^+$ $^1$H-NMR (400 MHz, DMSO-d$_6$): δ=8.33 (s, 1H), 7.69 (d, 1H), 7.45-7.40 (m, 1H), 7.31-7.26 (m, 2H), 7.22 (d, 2H), 6.98 (d, 2H), 6.61 (dd, 1H), 5.70 (d, 1H), 5.41 (t, NH), 5.15 (d, 1H), 3.76 (s, 3H), 3.41 (q, 2H), 1.90 (t, 2H), 1.48-1.36 (m, 4H), 1.22-1.15 (m, 2H).

Example 120

6-{[6-(2-Ethylphenyl)-5-(4-methoxyphenyl)furo[2,3-d]pyrimidin-4-yl]amino}hexanoic acid

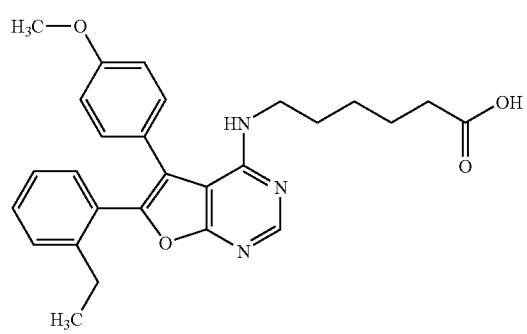

Dissolve 45 mg (0.10 mmol) 6-{[6-(2-ethylphenyl)-5-(4-methoxyphenyl)furo[2,3-d]pyrimidin-4-yl]amino}hexanoic acid methyl ester in 2.0 ml dioxan and add 0.5 ml 1 N sodium hydroxide solution. Stir for 16 h at RT, then add 0.5 ml 1 N hydrochloric acid and 5 ml ethyl acetate. Separate the organic phase, dry over sodium sulphate, filter and concentrate by evaporation. 38 mg (87% of theor.) of the target compound is obtained.

LC-MS (Method 10): $R_t$=2.58 min; m/z=460 (M+H)$^+$ $^1$H-NMR (400 MHz, DMSO-d$_6$): δ=12.00 (br. s, 1H), 8.33 (s, 1H), 7.39-7.31 (m, 2H), 7.26-7.16 (m, 4H), 6.98 (d, 2H), 5.43 (t, NH), 3.76 (s, 3H), 3.41 (q, 2H), 2.49 (q, 2H), 2.19 (t, 2H), 1.52-1.45 (m, 4H), 1.28-1.16 (m, 2H), 1.00 (t, 3H).

Example 121

6-{[6-(2-Fluorophenyl)-5-(4-methoxyphenyl)furo[2,3-d]pyrimidin-4-yl]amino}hexanoic acid

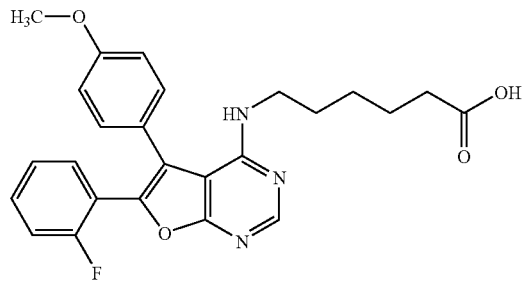

Dissolve 25 mg (0.05 mmol) 6-{[6-(2-fluorophenyl)-5-(4-methoxyphenyl)furo[2,3-d]pyrimidin-4-yl]amino}hexanoic acid methyl ester in 1.0 ml dioxan and add 0.16 ml 1 N sodium hydroxide solution. Stir for 16 h at RT, then add 0.17 ml 1 N hydrochloric acid and then 2 ml water and 5 ml dichloromethane. Separate the organic phase, dry over sodium sulphate, filter, and concentrate by evaporation. 23 mg (92% of theor.) of the target compound is obtained.

LC-MS (Method 8): R$_t$=2.52 min; m/z=450 (M+H)$^+$ $^1$H-NMR (400 MHz, DMSO-d$_6$): δ=12.01 (br. s, 1H), 8.35 (s, 1H), 7.49-7.42 (m, 2H), 7.31 (d, 2H), 7.26-7.21 (m, 2H), 7.03 (d, 2H), 5.41 (t, NH), 3.80 (s, 3H), 3.41 (q, 2H), 2.29 (t, 2H), 1.51-1.42 (m, 4H), 1.27-1.18 (m, 2H).

Example 122

6-{[5-(4-Methoxyphenyl)-6-(2-methylphenyl)furo[2,3-d]pyrimidin-4-yl]amino}hexanoic acid

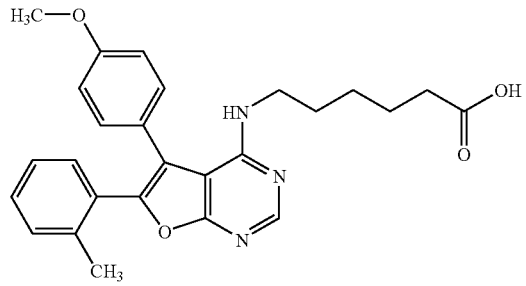

Dissolve 65 mg (0.14 mmol) 6-{[5-(4-methoxyphenyl)-6-(2-methylphenyl)furo[2,3-d]pyrimidin-4-yl] amino}hexanoic acid methyl ester in 2.5 ml dioxan and add 0.50 ml 1 N sodium hydroxide solution. Stir for 16 h at RT, then add 0.50 ml 1 N hydrochloric acid and then 6 ml methyl acetate. Separate the organic phase, dry over sodium sulphate, filter, and concentrate by evaporation. 53 mg (82% of theor.) of the target compound is obtained.

LC-MS (Method 2): R$_t$=2.35 min; m/z=446 (M+H)$^+$ $^1$H-NMR (400 MHz, DMSO-d$_6$): δ=12.00 (br. s, 1H), 8.34 (s, 1H), 7.34-7.16 (m, 6H), 6.98 (d, 2H), 5.45 (t, NH), 3.77 (s, 3H), 3.42 (q, 2H), 2.29 (t, 2H), 2.10 (s, 3H), 1.50-1.45 (m, 4H), 1.28-1.20 (m, 2H).

Example 123

6-{[6-(2-Fluoro-6-methoxyphenyl)-5-(4-methoxyphenyl)furo[2,3-d]pyrimidin-4-yl]amino}-hexanoic acid

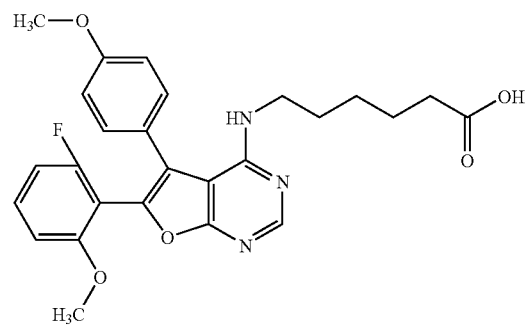

Dissolve 42 mg (0.09 mmol) 6-{[6-(2-fluoro-6-methoxyphenyl)-5-(4-methoxyphenyl)furo[2,3-d]pyrimidin-4-yl] amino}hexanoic acid methyl ester in 1.0 ml dioxan and add 0.26 ml 1 N sodium hydroxide solution. Stir for 16 h at RT, then add 0.26 ml 1 N hydrochloric acid and then 2 ml water and 5 ml dichloromethane. Separate the organic phase, dry over sodium sulphate, filter, and concentrate by evaporation. 39 mg (96% of theor.) of the target compound is obtained.

LC-MS (Method 2): R$_t$=2.22 min; m/z=480 (M+H)$^+$ $^1$H-NMR (400 MHz, DMSO-d$_6$): δ=11.99 (s, 1H), 8.33 (s, 1H), 7.48 (dd, 1H), 7.20 (d, 2H), 6.98-6.94 (m, 3H), 6.85 (dd, 1H), 5.55 (t, NH), 3.76 (s, 3H), 3.68 (s, 3H), 3.42 (q, 2H), 2.19 (t, 2H), 1.53-1.45 (m, 4H), 1.29-1.21 (m, 2H).

Example 124

(3-{[5-(4-Methoxyphenyl)-6-phenylfuro[2,3-d]pyrimidin-4-yl]oxy}-2-methylpropoxy)acetic acid tert.-butyl ester

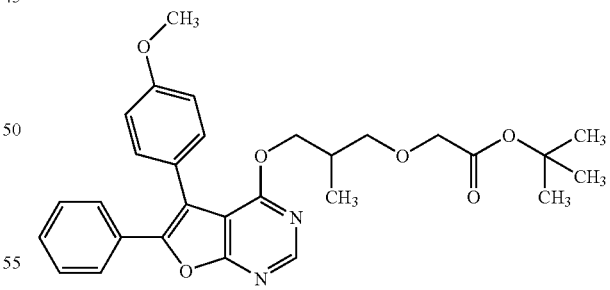

Add 1.14 ml of 12.5 N sodium hydroxide solution to a solution of 500 mg (1.28 mmol) 3-{[5-(4-methoxyphenyl)-6-phenylfuro[2,3-d]pyrimidin-4-yl]oxy}-2-methylpropan-1-ol in 10 ml toluene at 70° C. After adding 44 mg (0.13 mmol) tetra-n-butylammonium hydrogensulphate and 500 mg (2.56 mmol) tert.-butyl bromoacetate, stir the reaction mixture for 20 h at 70° C. After cooling to room temperature, adjust to pH 7 with concentrated hydrochloric acid and extract three times with 50 ml dichloromethane each time. Wash the combined organic extracts with satd. aqueous sodium chloride solution, dry over sodium sulphate, filter, and concentrate by vacuum evaporation. Purify the raw product by preparative RP-HPLC (gradient: water/acetonitrile). 298 mg (46% of theor.) of the desired product is obtained as racemate.

LC-MS (Method 8): $R_t$=3.41 min; m/z=505 (M+H)$^+$ $^1$H-NMR (400 MHz, DMSO-$d_6$): δ=8.58 (s, 1H), 7.54 (dd, 2H), 7.51-7.37 (m, 5H), 7.03 (d, 2H), 4.35-4.26 (m, 2H), 3.85 (s, 2H), 3.82 (s, 3H), 3.19 (d, 2H), 2.02-1.97 (m, 1H), 1.39 (s, 9H), 0.76 (d, 3H).

Example 125

(3-{[5-(4-Methoxyphenyl)-6-phenylfuro[2,3-d]pyrimidin-4-yl]oxy}-2-methylpropoxy)acetic acid tert.-butyl ester (Enantiomer 1)

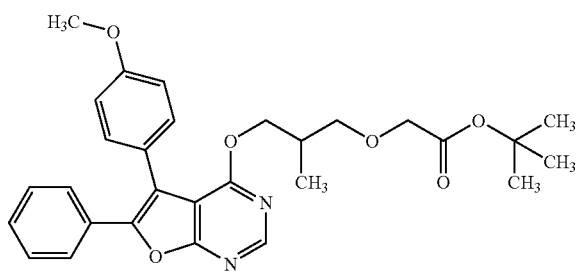

Separate 298 mg (0.59 mmol) rac.-(3-{[5-(4-methoxyphenyl)-6-phenylfuro[2,3-d]pyrimidin-4-yl]oxy}-2-methylpropoxy)acetic acid tert.-butyl ester by chiral-phase chromatography into the enantiomers [column: Daicel Chiralpak IA, 250 mm×20 mm; flow: 15 ml/min; detection: 220 nm; temperature: 30° C.; eluent: 50% iso-hexane/50% tert.-butylmethyl ether]. In this way, 51 mg (17% of theor.) of Enantiomer 1 is obtained.

HPLC: $R_t$=7.46 min [column material as above, 250 mm×4.6 mm; flow: 1 ml/min; eluent: 50% iso-hexane/50% tert.-butylmethyl ether; temperature: 25° C.]

LC-MS (Method 2): $R_t$=3.14 min; m/z=505 (M+H)$^+$ $^1$H-NMR (400 MHz, DMSO-$d_6$): δ=8.58 (s, 1H), 7.55-7.54 (m, 2H), 7.42-7.38 (m, 5H), 7.04-7.03 (m, 2H), 4.35-4.27 (m, 2H), 3.83 (s, 3H), 1.39 (s, 9H), 0.77 (d, 3H).

Example 126

(3-{[5-(4-Methoxyphenyl)-6-phenylfuro[2,3-d]pyrimidin-4-yl]oxy}-2-methylpropoxy)acetic acid tert.-butyl ester (Enantiomer 2)

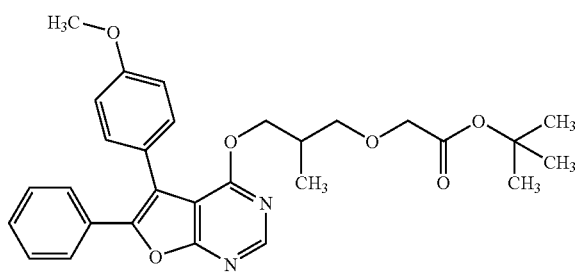

Separate 298 mg (0.59 mmol) rac.-(3-{[5-(4-methoxyphenyl)-6-phenylfuro[2,3-d]pyrimidin-4-yl]oxy}-2-methylpropoxy)acetic acid tert.-butyl ester by chiral-phase chromatography into the enantiomers [column: Daicel Chiralpak IA, 250 mm×20 mm; flow: 15 ml/min; detection: 220 nm; temperature: 30° C.; eluent: 50% iso-hexane/50% tert.-butylmethyl ether]. In this way, 56 mg (19% of theor.) of Enantiomer 2 is obtained.

HPLC: $R_t$=7.94 min [column material as above, 250 mm×4.6 mm; flow: 1 ml/min; eluent: 50% iso-hexane/50% tert.-butylmethyl ether; temperature: 25° C.]

LC-MS (Method 8): $R_t$=3.36 min; m/z=505 (M+H)$^+$ $^1$H-NMR (400 MHz, DMSO-$d_6$): δ=8.58 (s, 1H), 7.55-7.54 (m, 2H), 7.42-7.38 (m, 5H), 7.04-7.03 (m, 2H), 4.35-4.27 (m, 2H), 3.83 (s, 3H), 1.39 (s, 9H), 0.77 (d, 3H).

Example 127

(3-{[5-(4-Methoxyphenyl)-6-phenylfuro[2,3-d]pyrimidin-4-yl]oxy}-2-methylpropoxy)acetic acid

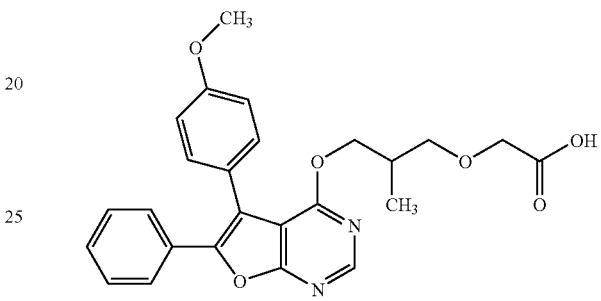

Dissolve 70 mg (0.14 mmol) rac.-(3-{[5-(4-methoxyphenyl)-6-phenylfuro[2,3-d]pyrimidin-4-yl]oxy}-2-methylpropoxy)acetic acid tert.-butyl ester in 2.0 ml 4 N hydrogen chloride in dioxan and stir for 16 h at RT. Purify directly by preparative RP-HPLC (gradient: water/acetonitrile). 48 mg (76% of theor.) of the desired product is obtained as racemate.

LC-MS (Method 7): $R_t$=3.86 min; m/z=449 (M+H)$^+$ $^1$H-NMR (400 MHz, DMSO-$d_6$): δ=12.64 (br. s, 1H), 8.58 (s, 1H), 7.55 (d, 2H), 7.41-7.36 (m, 5H), 7.03 (d, 2H), 4.35-4.27 (m, 2H), 3.88 (s, 2H), 3.81 (s, 3H), 3.19 (d, 2H), 2.01-1.97 (m, 1H), 0.76 (d, 3H).

Example 128

(+)-(3-{[5-(4-Methoxyphenyl)-6-phenylfuro[2,3-d]pyrimidin-4-yl]oxy}-2-methylpropoxy)acetic acid (Enantiomer 1)

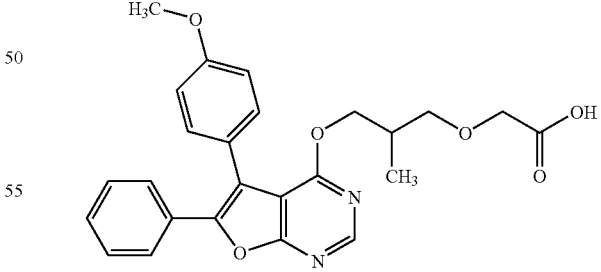

Dissolve 41 mg (0.08 mmol) (3-{[5-(4-methoxyphenyl)-6-phenylfuro[2,3-d]pyrimidin-4-yl]oxy}-2-methylpropoxy)acetic acid tert.-butyl ester (Enantiomer 1) in 0.5 ml dioxan, add 0.2 ml 4 N hydrogen chloride in dioxan and stir for 48 h at RT. Then add a further 0.4 ml 4 N hydrogen chloride in dioxan to the reaction mixture and stir again for 16 h at RT. Concentrate the reaction solution by evaporation under vacuum and then purify the residue by preparative RP-HPLC (gradient: water/acetonitrile). 27 mg (74% of theor.) of the desired product is obtained as Enantiomer 1.

LC-MS (Method 8): $R_t$=2.67 min; m/z=449 (M+H)$^+$ $^1$H-NMR (400 MHz, DMSO-d$_6$): δ=8.57 (s, 1H), 7.56-7.53 (m, 2H), 7.42-7.37 (m, 5H), 7.05-7.01 (m, 2H), 4.41-4.37 (m, 1H), 4.24-4.20 (m, 1H), 3.82 (s, 3H), 3.42 (s, 2H), 3.21-3.14 (m, 2H), 2.00-1.93 (m, 1H), 0.71 (d, 3H).

$[α]_D^{20}$=+21°, c=0.400, chloroform.

Example 129

(−)-(3-{[5-(4-Methoxyphenyl)-6-phenylfuro[2,3-d]pyrimidin-4-yl]oxy}-2-methylpropoxy)acetic acid (Enantiomer 2)

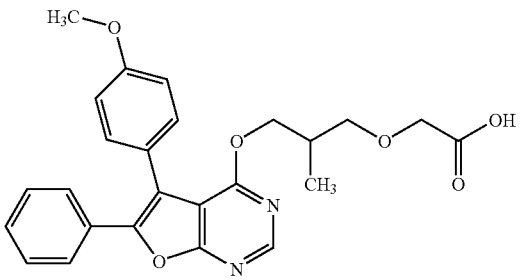

Dissolve 45 mg (0.09 mmol) (3-{[5-(4-methoxyphenyl)-6-phenylfuro[2,3-d]pyrimidin-4-yl]oxy}-2-methylpropoxy)acetic acid tert.-butyl ester (Enantiomer 2) in 0.5 ml dioxan, add 0.2 ml 4 N hydrogen chloride in dioxan and stir for 48 h at RT. Then add a further 0.4 ml 4 N hydrogen chloride in dioxan to the reaction mixture and stir again for 16 h at RT. After concentrating the reaction solution by evaporation under vacuum, purify the residue by preparative RP-HPLC (gradient: water/acetonitrile). 21 mg (53% of theor.) of the desired product is obtained as Enantiomer 2.

LC-MS (Method 2): $R_t$=2.45 min; m/z=449 (M+H)$^+$ $^1$H-NMR (400 MHz, DMSO-d$_6$): δ=8.57 (s, 1H), 7.56-7.53 (m, 2H), 7.42-7.37 (m, 5H), 7.05-7.01 (m, 2H), 4.41-4.37 (m, 1H), 4.24-4.20 (m, 1H), 3.82 (s, 3H), 3.42 (s, 2H), 3.21-3.14 (m, 2H), 2.00-1.93 (m, 1H), 0.71 (d, 3H).

Example 130

3-{[(1R,2R)-2-{[5-(4-Methoxyphenyl)-6-phenylfuro[2,3-d]pyrimidin-4-yl]oxy}-1-methylpropyl]oxy}propionic acid

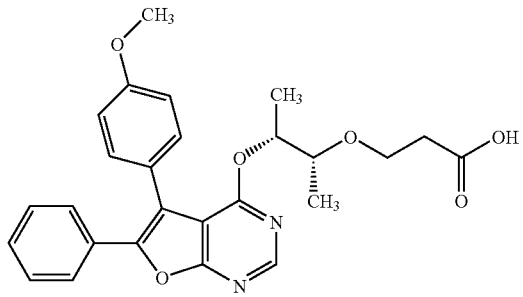

Add 1.2 ml 4 N hydrogen chloride in dioxan to 60 mg (0.12 mmol) 3-{[(1R,2R)-2-{[5-(4-methoxyphehyl)-6-phenylfuro[2,3-d]pyrimidin-4-yl]oxy}-1-methylpropyl]oxy}propionic acid tert.-butyl ester and stir for 16 h at RT. Then adjust to pH 7 with 1 N sodium hydroxide solution, extract the aqueous phase three times with 10 ml dichloromethane each time, and dry the combined organic extracts over sodium sulphate, filter, and concentrate by vacuum evaporation. 52 mg (93% of theor.) of the desired product is obtained.

LC-MS (Method 7): $R_t$=4.83 min; m/z=519 (M+H)$^+$ $^1$H-NMR (400 MHz, DMSO-d$_6$): δ=8.57 (s, 1H), 7.55 (d, 2H), 7.40-7.35 (m, 5H), 7.01 (d, 2H), 5.35 (dt, 1H), 3.81 (s, 3H), 3.52-3.40 (m, 3H), 2.26 (t, 2H), 1.16 (d, 3H), 0.88 (d, 3H).

Example 131

6-{[6-(3-Fluorophenyl)-5-(4-methoxyphenyl)furo[2,3-d]pyrimidin-4-yl]amino}hexanoic acid methyl ester

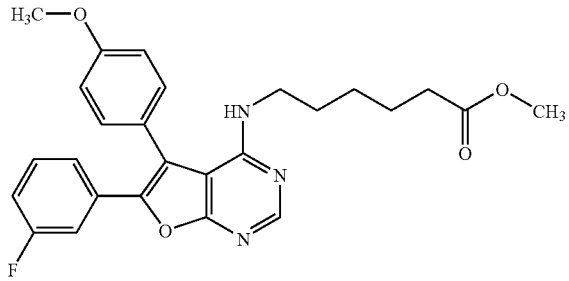

Add 3 mg (0.01 mmol) trans-bis(dicyclohexylamine)palladium(II) acetate [T. Bin, *J. Org. Chem.* 2004, 69, 4330-4335] to a mixture of 100 mg (0.22 mmol) 6-{[6-bromo-5-(4-methoxyphenyl)furo[2,3-d]pyrimidin-4-yl]amino}hexanoic acid methyl ester, 47 mg (0.34 mmol) 3-fluorophenylboronic acid and 145 mg (0.45 mmol) caesium carbonate in 5 ml dioxan, and stir for 16 h at 80° C. After adding 95 mg (0.45 mmol) potassium phosphate, a further 47 mg (0.34 mmol) 3-fluorophenylboronic acid and a spatula tip of trans-bis(dicyclohexylamin)palladium(II) acetate, stir the reaction mixture for a further 4 h at 80° C. Then filter the reaction mixture and purify directly by preparative RP-HPLC (gradient: water/acetonitrile). 57 mg (53% of theor.) of the desired product is obtained.

LC-MS (Method 2): $R_t$=2.81 min; m/z=464 (M+H)$^+$ $^1$H-NMR (400 MHz, DMSO-d$_6$): δ=8.34 (s, 1H), 7.47-7.45 (m, 2H), 7.42-7.39 (m, 1H), 7.28-7.26 (m, 1H), 7.19-7.15 (m, 4H), 5.14 (t, NH), 3.86 (s, 3H), 3.58 (s, 3H), 3.38-3.30 (m, 2H), 2.26 (t, 2H), 1.51-1.37 (m, 4H), 1.18-1.11 (m, 2H).

Example 132

6-{[6-(3-Fluorophenyl)-5-(4-methoxyphenyl)furo[2,3-d]pyrimidin-4-yl]amino}hexanoic acid

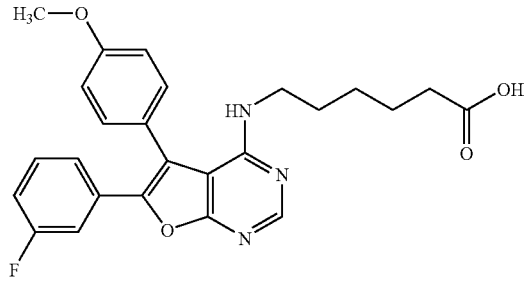

Add 0.5 ml 1 N sodium hydroxide solution to a solution of 45 mg (0.01 mmol) 6-{[6-(3-fluorophenyl)-5-(4-methoxyphenyl)furo[2,3-d]pyrimidin-4-yl]amino}hexanoic acid methyl ester in 2.5 ml dioxan, and stir for 16 h at RT. After adding 0.75 ml 1 N hydrochloric acid, concentrate the reaction solution by vacuum evaporation. Mix the residue with diethyl ether, filter, and dry under vacuum. 42 mg (93% of theor.) of the desired product is obtained.

LC-MS (Method 5): $R_t$=2.59 min; m/z=450 (M+H)$^+$ $^1$H-NMR (400 MHz, DMSO-d$_6$): δ=12.00 (br. s, 1H), 8.35 (s, 1H), 7.47-7.45 (m, 2H), 7.42-7.39 (m, 1H), 7.28-7.26 (m, 1H), 7.19-7.15 (m, 4H), 5.15 (t, NH), 3.86 (s, 3H), 3.39-3.34 (m, 2H), 2.17 (t, 2H), 1.48-1.37 (m, 4H), 1.19-1.11 (m, 2H).

Example 133

4-{[(2R)-2-{[5-(4-Ethylphenyl)-6-phenylfuro[2,3-d]pyrimidin-4-yl]oxy}propyl](methyl)amino}-butyric acid

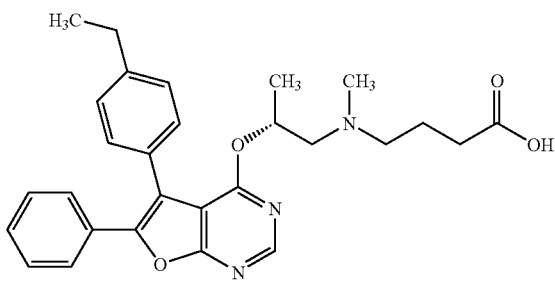

Add 0.6 ml 1 N sodium hydroxide solution to a solution of 100 mg (73% purity, 0.15 mmol) 4-{[(2R)-2-{[5-(4-ethylphenyl)-6-phenylfuro[2,3-d]pyrimidin-4-yl]oxy}propyl](methyl)amino}butyric acid methyl ester in 3 ml dioxan, and stir for 16 h at RT. After adding 0.7 ml 1 N hydrochloric acid, extract with ethyl acetate. Re-extract the aqueous phase twice more with ethyl acetate. Combine the organic phases, dry over sodium sulphate, and filter. Concentrate the filtrate by vacuum evaporation. Take up the oily residue in acetonitrile and purify by preparative RP-HPLC (gradient: water/acetonitrile). 57 mg (80% of theor.) of the desired product is obtained.

LC-MS (Method 8): $R_t$=1.88 min; m/z=474 (M+H)$^+$ $^1$H-NMR (400 MHz, DMSO-d$_6$): δ=12.17 (br. s, 1H), 8.57 (s, 1H), 7.55-7.53 (m, 2H), 7.42-7.37 (m, 5H), 7.30-7.28 (m, 2H), 5.50-5.42 (m, 1H), 2.69 (q, 2H), 2.44-2.30 (m, 2H), 2.20 (t, 2H), 2.06 (t, 2H), 2.01 (s, 3H), 1.52-1.41 (m, 2H), 1.26-1.19 (m, 6H).

Example 134

6-{[6-(4-Fluorophenyl)-5-(4-methoxyphenyl)furo[2,3-d]pyrimidin-4-yl]amino}hexanoic acid methyl ester

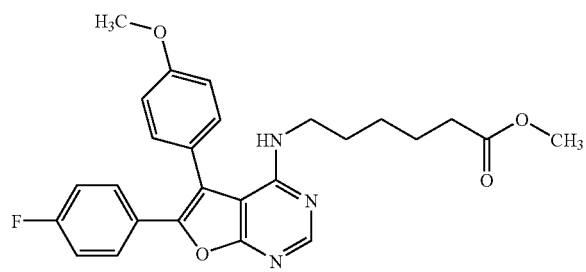

Add 3 mg (0.01 mmol) trans-bis(dicyclohexylamine)palladium(II) acetate [T. Bin, *J. Org. Chem.* 2004, 69, 4330-4335] to a mixture of 100 mg (0.22 mmol) 6-{[6-bromo-5-(4-methoxyphenyl)furo[2,3-d]pyrimidin-4-yl]amino}hexanoic acid methyl ester, 47 mg (0.34 mmol) 4-fluorophenylboronic acid and 95 mg (0.45 mmol) potassium phosphate in 5 ml dioxan, and stir for 21 h at 80° C. After filtering off the solid, concentrate the filtrate by vacuum evaporation. Purify the residue by preparative RP-HPLC (gradient: water/acetonitrile). 59 mg (57% of theor.) of the desired product is obtained.

LC-MS (Method 8): $R_t$=3.06 min; m/z=464 (M+H)$^+$ $^1$H-NMR (400 MHz, DMSO-d$_6$): δ=8.32 (s, 1H), 7.50-7.42 (m, 4H), 7.26-7.20 (m, 2H), 7.16-7.12 (m, 2H), 5.09 (t, NH), 3.85 (s, 3H), 3.58 (s, 3H), 3.38-3.30 (m, 2H), 2.26 (t, 2H), 1.51-1.37 (m, 4H), 1.18-1.11 (m, 2H).

Example 135

6-{[6-(4-Fluorophenyl)-5-(4-methoxyphenyl)furo[2,3-d]pyrimidin-4-yl]amino}hexanoic acid ethyl ester

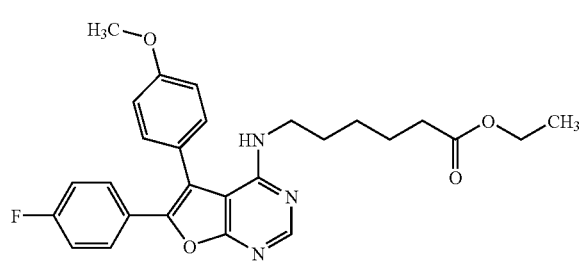

Add 3 mg (0.01 mmol) trans-bis(dicyclohexylamin)palladium(II) acetate [T. Bin, *J. Org. Chem.* 2004, 69, 4330-4335] to a mixture of 100 mg (0.22 mmol) 6-{[6-bromo-5-(4-methoxyphenyl)furo[2,3-d]pyrimidin-4-yl]amino}hexanoic acid methyl ester, 37 mg (0.27 mmol) 4-fluorophenylboronic acid and 95 mg (0.45 mmol) potassium phosphate in 5 ml ethanol, and stir, firstly for 16 h at RT and then for 3 h at 80° C. After filtering off the solid, concentrate the filtrate by vacuum evaporation. Purify the residue by preparative RP-HPLC (gradient: water/acetonitrile). 28 mg (26% of theor.) of the desired product is obtained.

LC-MS (Method 5): $R_t$=3.07 min; m/z=478 (M+H)$^+$ $^1$H-NMR (400 MHz, DMSO-d$_6$): δ=8.32 (s, 1H), 7.49-7.43 (m, 4H), 7.25-7.20 (m, 2H), 7.15-7.13 (m, 2H), 5.09 (t, NH), 4.04 (q, 2H), 3.85 (s, 3H), 3.38-3.30 (m, 2H), 2.24 (t, 2H), 1.51-1.37 (m, 4H), 1.18-1.11 (m, 5H).

Example 136

6-{[6-(4-Fluorophenyl)-5-(4-methoxyphenyl)furo[2,3-d]pyrimidin-4-yl]amino}hexanoic acid

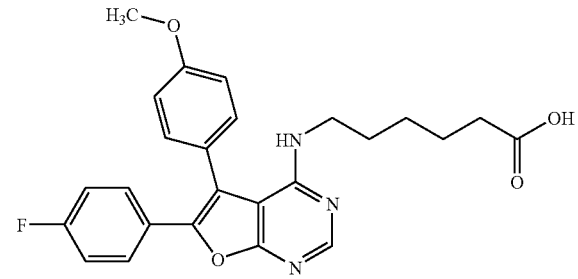

Add 1 ml 1 N sodium hydroxide solution to a solution of 169 mg (0.37 mmol) 6-{[6-(4-fluorophenyl)-5-(4-methoxyphenyl)furo[2,3-d]pyrimidin-4-yl]amino}hexanoic acid methyl ester in 5 ml dioxan and stir for 16 h at RT. After adding 3 ml 1 N hydrochloric acid, concentrate the reaction solution by vacuum evaporation. Mix the residue with diethyl ether, filter, and dry under vacuum. 165 mg (99% of theor.) of the desired product is obtained.

LC-MS (Method 2): $R_t$=2.39 min; m/z=450 (M+H)$^+$ $^1$H-NMR (400 MHz, DMSO-d$_6$): δ=14.25-10.15 (br. s, CO$_2$H), 8.33 (s, 1H), 7.49-7.43 (m, 4H), 7.25-7.21 (m, 2H), 7.15-7.13 (m, 2H), 5.13 (br. t, NH), 3.85 (s, 3H), 3.39-3.34 (m, 2H), 2.17 (t, 2H), 1.48-1.37 (m, 4H), 1.19-1.11 (m, 2H).

Example 137

(6R)-6-{[6-(2-Fluorophenyl)-5-(4-methoxyphenyl) furo[2,3-d]pyrimidin-4-yl]oxy}heptanoic acid

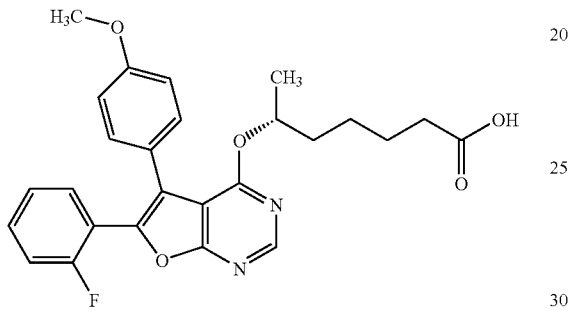

Dissolve 373 mg (0.72 mmol) (6R)-6-{[6-(2-fluorophenyl)-5-(4-methoxyphenyl)furo[2,3-d]pyrimidin-4-yl]oxy}heptanoic acid tert.-butyl ester in 4 ml 4 N hydrogen chloride in dioxan and stir for 16 h at RT. After concentrating the reaction solution by evaporation under vacuum, purify the residue by preparative RP-HPLC (gradient: water/acetonitrile). 171 mg (51% of theor.) of the desired product is obtained.

LC-MS (Method 8): $R_t$=2.78 min; m/z=465 (M+H)$^+$ $^1$H-NMR (400 MHz, DMSO-d$_6$): δ=11.98 (br. s, 1H), 8.60 (s, 1H), 7.55-7.50 (m, 2H), 7.33-7.28 (m, 4H), 6.94-6.91 (m, 2H), 5.40-5.33 (m, 1H), 3.77 (s, 3H), 2.14 (t, 2H), 1.60-1.55 (m, 2H), 1.48-1.40 (m, 2H), 1.31-1.17 (m, 3H), 1.28 (d, 3H).

Example 138

(+)-4-{[(2S)-2-{[6-(2-Fluorophenyl)-5-(4-methoxyphenyl)furo[2,3-d]pyrimidin-4-yl]oxy}propyl]-(methyl)amino}butyric acid

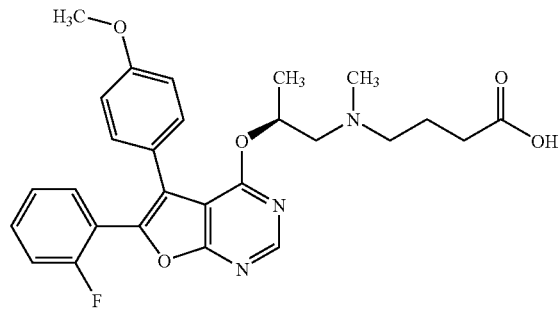

Dissolve 102 mg (93% purity, 0.19 mmol) 4-{[(2S)-2-{[6-(2-fluorophenyl)-5-(4-methoxyphenyl)furo[2,3-d]pyrimidin-4-yl]oxy}propyl](methyl)amino}butyric acid tert.-butyl ester in 2 ml 4 N hydrogen chloride in dioxan and stir for 16 h at RT. After concentrating the reaction solution by evaporation under vacuum, purify the residue by preparative RP-HPLC (gradient: water/acetonitrile). 48 mg (52% of theor.) of the desired product is obtained.

LC-MS (Method 8): $R_t$=1.68 min; m/z=494 (M+H)$^+$ $^1$H-NMR (400 MHz, DMSO-d$_6$): δ=12.11 (br. s, 1H), 8.60 (s, 1H), 7.55-7.50 (m, 2H), 7.33-7.28 (m, 4H), 6.93-6.91 (m, 2H), 5.60-5.53 (m, 1H), 3.77 (s, 3H), 2.47-2.37 (m, 2H), 2.31-2.33 (m, 2H), 2.13-2.05 (m, 5H), 1.54-1.46 (m, 2H), 1.28 (d, 3H).

$[α]_D^{20}$=+123°, c=0.260, chloroform.

Example 139

4-tert.-Butoxy-N-[(2S)-2-{[5-(4-ethylphenyl)-6-phenylfuro[2,3-d]pyrimidin-4-yl]oxy}propyl]-N-methyl-4-oxobutane-1-ammonium chloride

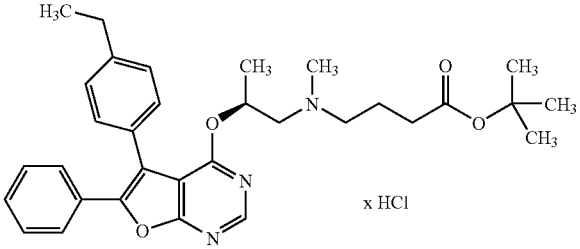

Add 43 mg (1.08 mmol) sodium hydride (60% dispersion in mineral oil) to a solution of 200 mg (0.87 mmol) 4-{[(2S)-2-hydroxypropyl](methyl)amino}butyric acid tert.-butyl ester in 2 ml THF, with ice cooling. After stirring for ten minutes with ice cooling, add a solution of 338 mg (0.91 mmol) 4-chloro-5-(4-ethylphenyl)-6-phenylfuro[2,3-d]pyrimidine in 3 ml THF and 16 mg (0.04 mmol) tetra-n-butylammonium iodide. Stir the reaction mixture for 16 h at RT. After adding water and ethyl acetate, wash the separated organic phase with 1 N hydrochloric acid, and concentrate by vacuum evaporation. Take up the residue in acetonitrile/DMSO and purify by preparative RP-HPLC (gradient: water/acetonitrile). 94 mg (19% of theor.) of the desired product is obtained.

LC-MS (Method 8): $R_t$=2.06 min; m/z=530 (M-HCl+H)$^+$ $^1$H-NMR (400 MHz, DMSO-d$_6$): δ=9.77-9.55 (m, NH), 8.65 (s, 1H), 7.56-7.51 (m, 2H), 7.44-7.40 (m, 4H), 7.35-7.32 (m, 2H), 5.80-5.64 (m, 1H), 3.16-2.76 (m, 4H), 2.71 (q, 2H), 2.66-2.59 (m, 2H), 2.33-2.29 (m, 2H), 2.24-2.16 (m, 2H), 1.77-1.53 (m, 2H), 1.38-1.33 (m, 12H), 1.09 (t, 3H).

Example 140

(+)-4-{[(2S)-2-{[5-(4-Ethylphenyl)-6-phenylfuro[2,3-d]pyrimidin-4-yl]oxy}propyl](methyl)amino}butyric acid

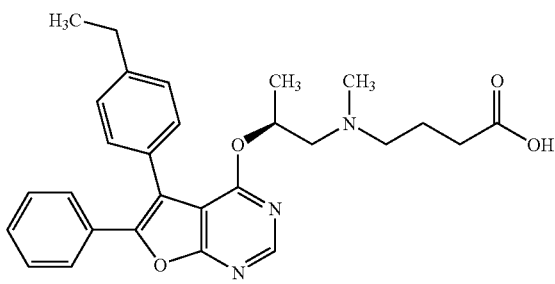

Dissolve 93 mg (0.16 mmol) 4-tert.-butoxy-N-[(2S)-2-{[5-(4-ethylphenyl)-6-phenylfuro[2,3-d]pyrimidin-4-yl]oxy}propyl]-N-methyl-4-oxobutane-1-ammonium chloride in 3 ml 4 N hydrogen chloride in dioxan, and stir for 16 h at RT. After concentrating the reaction solution by evaporation under vacuum, purify the residue by preparative RP-HPLC (gradient: water/acetonitrile). 50 mg (64% of theor.) of the desired product is obtained.

LC-MS (Method 8): $R_t$=1.87 min; m/z=474 (M+H)$^+$ $^1$H-NMR (400 MHz, DMSO-d$_6$): δ=12.13 (br. s, 1H), 8.57 (s, 1H), 7.55-7.52 (m, 2H), 7.42-7.37 (m, 5H), 7.31-7.29 (m, 2H), 5.53-5.46 (m, 1H), 2.68 (q, 2H), 2.50-2.42 (m, 2H), 2.32-2.21 (m, 2H), 2.10-2.02 (m, 5H), 1.51-1.42 (m, 2H), 1.26-1.21 (m, 6H).

$[α]_D^{20}$=+171°, c=0.200, chloroform.

Example 141

6-{[5-(4-Ethylphenyl)-6-(2-fluorophenyl)furo[2,3-d]pyrimidin-4-yl]oxy}heptanoic acid

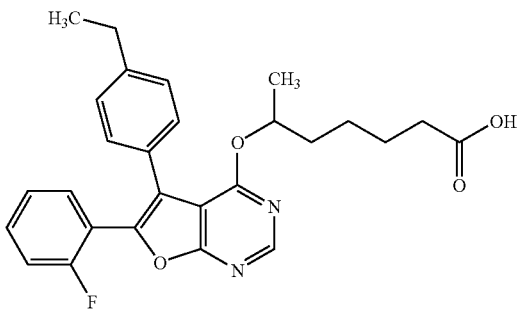

Dissolve 80 mg (0.15 mmol) 6-{[5-(4-ethylphenyl)-6-(2-fluorophenyl)furo[2,3-d]pyrimidin-4-yl]oxy}heptanoic acid tert.-butyl ester in 2 ml 4 N hydrogen chloride in dioxan and stir for 16 h at RT. After concentrating the reaction solution by evaporation under vacuum, purify the residue by preparative RP-HPLC (gradient: water/acetonitrile). 12 mg (16% of theor.) of the desired product is obtained as racemate.

LC-MS (Method 8): $R_t$=3.06 min; m/z=463 (M+H)$^+$ $^1$H-NMR (400 MHz, DMSO-d$_6$): δ=11.98 (br. s, 1H), 8.61 (s, 1H), 7.55-7.51 (m, 2H), 7.33-7.28 (m, 4H), 7.21-7.19 (m, 2H), 5.38-5.32 (m, 1H), 2.63 (q, 2H), 2.02 (t, 2H), 1.57-1.52 (m, 2H), 1.43-1.37 (m, 2H), 1.27-1.18 (m, 8H).

Example 142

(−)-(6R)-6-{[5-(4-Ethylphenyl)-6-(2-fluorophenyl)furo[2,3-d]pyrimidin-4-yl]oxy}heptanoic acid

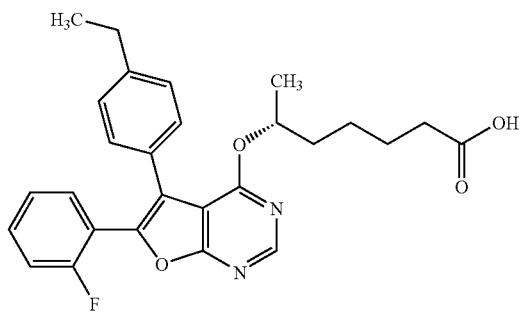

Dissolve 420 mg (0.81 mmol) (6R)-6-{[5-(4-ethylphenyl)-6-(2-fluorophenyl)furo[2,3-d]pyrimidin-4-yl]oxy}heptanoic acid tert.-butyl ester in 5.3 ml 4 N hydrogen chloride in dioxan and stir for 16 h at RT. After concentrating the reaction solution by evaporation under vacuum, purify the residue by preparative RP-HPLC (gradient: water/acetonitrile). 200 mg (53% of theor.) of the desired product is obtained.

LC-MS (Method 8): $R_t$=3.03 min; m/z=463 (M+H)$^+$ $^1$H-NMR (400 MHz, DMSO-d$_6$): δ=11.97 (br. s, 1H), 8.61 (s, 1H), 7.56-7.50 (m, 2H), 7.33-7.27 (m, 4H), 7.21-7.19 (m, 2H), 5.39-5.31 (m, 1H), 2.63 (q, 2H), 2.12 (t, 2H), 1.58-1.53 (m, 2H), 1.47-1.38 (m, 2H), 1.28-1.18 (m, 8H).

$[α]_D^{20}$=−62°, c=0.390, chloroform.

Example 143

(+)-(6S)-6-{[5-(4-Ethylphenyl)-6-(2-fluorophenyl)furo[2,3-d]pyrimidin-4-yl]oxy}heptanoic acid

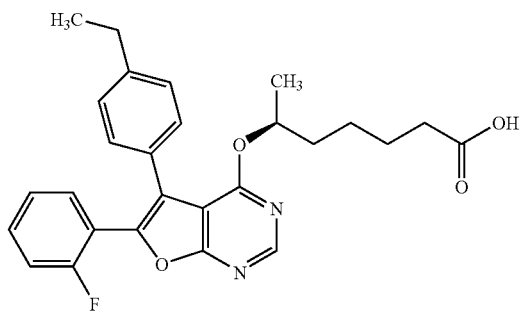

Separate 50 mg (0.11 mmol) rac.-6-{[5-(4-ethylphenyl)-6-(2-fluorophenyl)furo[2,3-d]pyrimidin-4-yl]oxy}heptanoic acid chromatographically into the enantiomers [column: Daicel Chiralpak AD-H, 5 µm, 250 mm×20 mm; flow: 20 ml/min; detection: 245 nm; temperature: 25° C.; eluent: 93% iso-hexane/7% ethanol]. 8 mg (16% of theor.) of the desired enantiomerically pure product is obtained.

HPLC: $R_t$=5.65 min [column: Daicel Chiralpak AD-H, 5 µm, 250 mm×4 mm; flow: 1 ml/min; detection: 245 nm; temperature: 25° C.; eluent: 85% iso-hexane/15% ethanol]

$^1$H-NMR (400 MHz, DMSO-d$_6$): δ=11.97 (br. s, 1H), 8.61 (s, 1H), 7.56-7.50 (m, 2H), 7.33-7.28 (m, 4H), 7.21-7.19 (m,

2H), 5.39-5.31 (m, 1H), 2.63 (q, 2H), 2.12 (t, 2H), 1.58-1.53 (m, 2H), 1.47-1.39 (m, 2H), 1.28-1.18 (m, 8H).

[α]$_D^{20}$=+50°, c=0.235, chloroform.

Example 144

(3-{[5-(4-Methoxyphenyl)-6-phenylfuro[2,3-d]pyrimidin-4-yl]oxy}-1-methylbutoxy)acetic acid

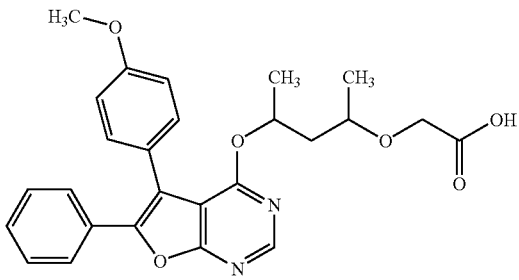

Add 4.8 ml of 11.25 N sodium hydroxide solution to a solution of 2.19 g (5.41 mmol) 4-{[5-(4-methoxyphenyl)-6-phenylfuro[2,3-d]pyrimidin-4-yl]oxy}pentan-2-ol in 20 ml toluene. After adding 184 mg (0.54 mmol) tetra-n-butylammonium hydrogensulphate and 2.11 g (10.83 mmol) tert.-butyl bromoacetate, stir the reaction mixture for 15 h at 70° C. After cooling to room temperature, adjust to pH 7 with concentrated hydrochloric acid and extract three times with 50 ml dichloromethane each time. Wash the combined organic extracts with satd. aqueous sodium chloride solution, dry over sodium sulphate, and filter. Concentrate the filtrate by vacuum evaporation. Take up the residue in ethyl acetate and purify by flash chromatography on silica gel (solvent: first ethyl acetate, then ethyl acetate/methanol 5:1). Purify the product obtained once more by preparative RP-HPLC (gradient: water/acetonitrile). 0.29 g (11% of theor.) of the desired product is obtained as a racemic mixture of diastereomers.

LC-MS (Method 8): R$_t$=2.76 min; m/z=463 (M+H)$^+$ $^1$H-NMR (400 MHz, DMSO-d$_6$): [lesser stereoisomer in square brackets] δ=12.49 (br. s, 1H), 8.57 (s, 1H), [8.55, s, 1H], 7.55-7.52 (m, 2H), 7.42-7.37 (m, 5H), 7.04-6.99 (m, 2H), 5.53-5.46 (m, 1H), [5.41-5.34, m, 1H], 3.88 (d, 2H), 3.82 (s, 3H), 3.47-3.39 (m, 1H), 1.89-1.82 (m, 1H), 1.55-1.48 (m, 1H), 1.28 (d, 3H), 1.00 (d, 3H).

Example 145

(3-{[5-(4-Methoxyphenyl)-6-phenylfuro[2,3-d]pyrimidin-4-yl]oxy}-1-methylbutoxy)acetic acid (Enantiomer 1)

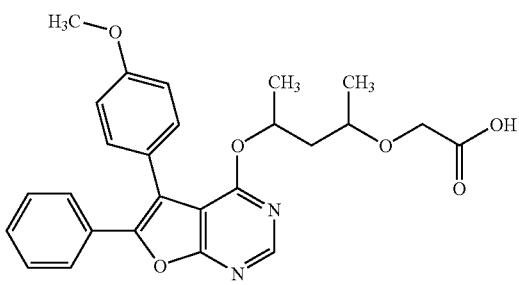

280 mg (0.61 mmol) (3-{[5-(4-methoxyphenyl)-6-phenylfuro[2,3-d]pyrimidin-4-yl]oxy}-1-methyl-butoxy)acetic acid is separated chromatographically into the stereoisomers [column: chiral silica-gel phase based on the selector poly(N-methacryloyl-L-leucine-dicyclopropylmethyl amide), 670 mm×40 mm; flow: 80 m/min; detection: 260 nm; temperature: 24° C.; eluent: 60% iso-hexane/40% ethyl acetate]. 108 mg (39% of theor.) of the diastereomerically pure Enantiomer 1 is obtained.

HPLC: R$_t$=3.40 min [column material as above, 250 mm×4.6 mm; flow: 2 ml/min; eluent: 50% iso-hexane/50% ethyl acetate; temperature: 25° C.]

LC-MS (Method 9): R$_t$=3.79 min; m/z=463 (M+H)$^+$ $^1$H-NMR (400 MHz, DMSO-d$_6$): δ=12.50 (br. s, 1H), 8.57 (s, 1H), 7.55-7.52 (m, 2H), 7.42-7.37 (m, 5H), 7.03-7.00 (m, 2H), 5.53-5.45 (m, 1H), 3.88 (d, 2H), 3.81 (s, 3H), 3.47-3.39 (m, 1H), 1.88-1.81 (m, 1H), 1.55-1.48 (m, 1H), 1.28 (d, 3H), 1.00 (d, 3H).

Example 146

(3-{[5-(4-Methoxyphenyl)-6-phenylfuro[2,3-d]pyrimidin-4-yl]oxy}-1-methylbutoxy)acetic acid (Enantiomer 2)

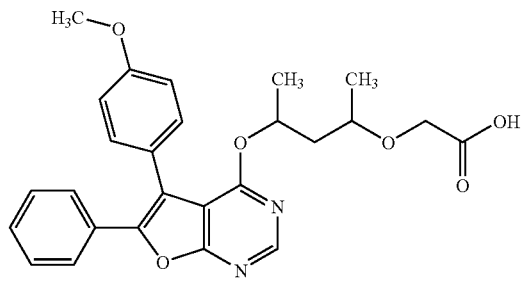

280 mg (0.61 mmol) (3-{[5-(4-methoxyphenyl)-6-phenylfuro[2,3-d]pyrimidin-4-yl]oxy}-1-methyl-butoxy)acetic acid is separated chromatographically into the stereoisomers [column: chiral silica-gel phase based on the selector poly(N-methacryloyl-L-leucine-dicyclopropylmethyl amide), 670 mm×40 mm; flow: 80 ml/min; detection: 260 nm; temperature: 24° C.; eluent: 60% iso-hexane/40% ethyl acetate]. 116 mg (41% of theor.) of the diastereomerically pure Enantiomer 2 is obtained.

HPLC: R$_t$=3.80 min [column material as above, 250 mm×4.6 mm; flow: 2 ml/min; eluent: 50% iso-hexane/50% ethyl acetate; temperature: 25° C.]

LC-MS (Method 9): R$_t$=3.78 min; m/z=463 (M+H)$^+$ $^1$H-NMR (400 MHz, DMSO-d$_6$): δ=12.50 (br. s, 1H), 8.57 (s, 1H), 7.55-7.52 (m, 2H), 7.42-7.37 (m, 5H), 7.03-7.00 (m, 2H), 5.53-5.45 (m, 1H), 3.88 (d, 2H), 3.81 (s, 3H), 3.47-3.39 (m, 1H), 1.88-1.81 (m, 1H), 1.55-1.48 (m, 1H), 1.28 (d, 3H), 1.00 (d, 3H).

Example 147

[2-({[5-(4-Ethylphenyl)-6-phenylfuro[2,3-d]pyrimidin-4-yl]oxy}methyl)-3,3-dimethylbutoxy]-acetic acid

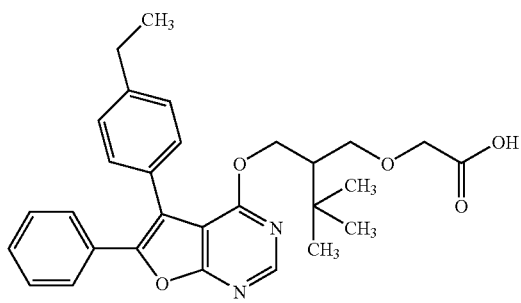

Add 1.0 ml 4 N hydrogen chloride in dioxan to 155 mg (0.29 mmol) [2-({[5-(4-ethylphenyl)-6-phenylfuro[2,3-d]pyrimidin-4-yl]oxy}methyl)-3,3-dimethylbutoxy]acetic acid tert.-butyl ester and stir for 48 h at RT. After concentrating the reaction solution by evaporation under vacuum, purify the residue by preparative RP-HPLC (gradient: water/acetonitrile). 122 mg (88% of theor.) of the desired product (racemate) is obtained.

LC-MS (Method 9): $R_t$=4.47 min; m/z=489 (M+H)$^+$ $^1$H-NMR (400 MHz, DMSO-d$_6$): δ=12.57 (br. s, 1H), 8.59 (s, 1H), 7.53-7.51 (m, 2H), 7.39-7.36 (m, 5H), 7.31-7.29 (m, 2H), 4.53 (dd, 1H), 4.47 (dd, 1H), 3.88 (dd, 2H), 3.38-3.29 (m, 2H), 2.68 (q, 2H), 1.54-1.49 (m, 1H), 1.24 (t, 3H), 0.71 (s, 9H).

Example 148

3-(2-{[5-(4-Methoxyphenyl)-6-phenylfuro[2,3-d]pyrimidin-4-yl]oxy}-1-methylpropoxy)propionic acid

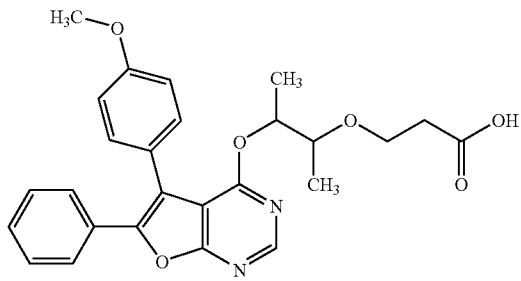

Add 4.0 ml 4 N hydrogen chloride in dioxan to 500 mg (0.96 mmol) 3-(2-{[5-(4-methoxyphenyl)-6-phenylfuro[2,3-d]pyrimidin-4-yl]oxy}-1-methylpropoxy)propionic acid tert.-butyl ester and stir for 16 h at RT. After concentrating the reaction solution by evaporation under vacuum, purify the residue by preparative RP-HPLC (gradient: water/acetonitrile). 249 mg (56% of theor.) of the desired product is obtained as (R,S/S,R) racemate.

LC-MS (Method 8): $R_t$=2.72 min; m/z=463 (M+H)$^+$ $^1$H-NMR (400 MHz, DMSO-d$_6$): δ=12.09 (br. s, 1H), 8.57 (s, 1H), 7.54-7.51 (m, 2H), 7.42-7.36 (m, 5H), 7.03-6.99 (m, 2H), 5.41-5.34 (m, 1H), 3.81 (s, 3H), 3.50-3.41 (m, 3H), 2.27 (t, 2H), 1.18 (d, 3H), 0.88 (d, 3H).

Example 149

3-(2-{[5-(4-Methoxyphenyl)-6-phenylfuro[2,3-d]pyrimidin-4-yl]oxy}-1-methylpropoxy)propionic acid (Enantiomer 1)

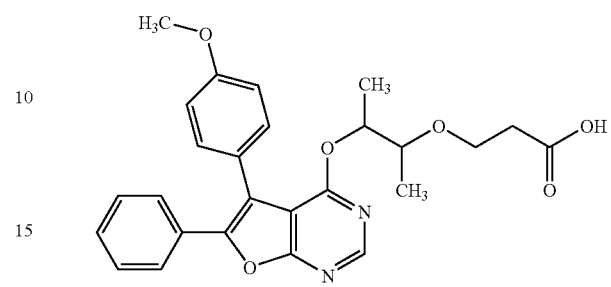

240 mg (0.46 mmol) 3-(2-{[5-(4-methoxyphenyl)-6-phenylfuro[2,3-d]pyrimidin-4-yl]oxy}-1-methylpropoxy)propionic acid ((R,S/S,R)-Racemate) is separated into the enantiomers by chiral-phase chromatography [column: chiral silica-gel phase based on the selector poly(N-methacryloyl-L-leucine-dicyclopropylmethyl amide), 670 mm×40 mm; flow: 80 ml/min; detection: 260 nm; temperature: 24° C.; eluent: 60% iso-hexane/40% ethyl acetate]. 119 mg (50% of theor.) of Enantiomer 1 is obtained.

HPLC: $R_t$=3.60 min [column material as above, 250 mm×4.6 mm; flow: 2 ml/min; eluent: 50% iso-hexane/50% ethyl acetate; temperature: 25° C.]

LC-MS (Method 8): $R_t$=2.81 min; m/z=463 (M+H)$^+$ $^1$H-NMR (400 MHz, DMSO-d$_6$): δ=12.06 (br. s, 1H), 8.57 (s, 1H), 7.54-7.51 (m, 2H), 7.41-7.36 (m, 5H), 7.03-6.99 (m, 2H), 5.41-5.36 (m, 1H), 3.81 (s, 3H), 3.50-3.41 (m, 3H), 2.27 (t, 2H), 1.18 (d, 3H), 0.88 (d, 3H).

Example 150

3-(2-{[5-(4-Methoxyphenyl)-6-phenylfuro[2,3-d]pyrimidin-4-yl]oxy}-1-methylpropoxy)propionic acid (Enantiomer 2)

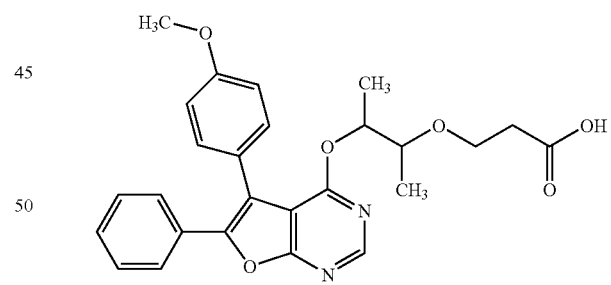

240 mg (0.46 mmol) 3-(2-{[5-(4-methoxyphenyl)-6-phenylfuro[2,3-d]pyrimidin-4-yl]oxy}-1-methylpropoxy)propionic acid ((R,S/S,R) racemate) is separated into the enantiomers by chiral-phase chromatography [column: chiral silica-gel phase based on the selector poly(N-methacryloyl-L-leucine-dicyclopropylmethyl amide), 670 mm×40 mm; flow: 80 ml/min; detection: 260 nm; temperature: 24° C.; eluent: 60% iso-hexane/40% ethyl acetate]. 110 mg (46% of theor.) of Enantiomer 2 is obtained HPLC: $R_t$=4.31 min [column material as above, 250 mm×4.6 mm; flow: 2 ml/min; eluent: 50% iso-hexane/50% ethyl acetate; temperature: 25° C.]

LC-MS (Method 8): $R_t$=2.80 min; m/z=463 (M+H)$^+$.

$^1$H-NMR (400 MHz, DMSO-d$_6$): δ=12.06 (br. s, 1H), 8.57 (s, 1H), 7.54-7.51 (m, 2H), 7.41-7.36 (m, 5H), 7.03-6.99 (m, 2H), 5.41-5.36 (m, 1H), 3.81 (s, 3H), 3.50-3.41 (m, 3H), 2.27 (t, 2H), 1.18 (d, 3H), 0.88 (d, 3H).

Example 151

(−)-{[(2R)-3-{[5-(4-Ethylphenyl)-6-(2-fluorophenyl)furo[2,3-d]pyrimidin-4-yl]oxy}-2-methyl-propyl]oxy}ethyl acetate

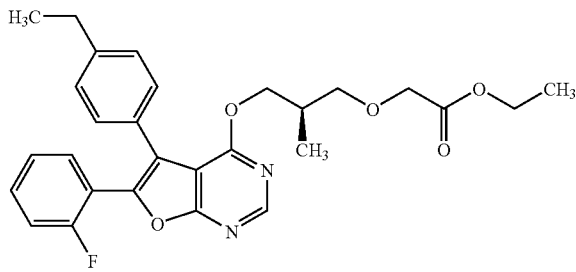

Cool a solution of 397 mg (90% purity, 1.01 mmol) 4-chloro-5-(4-ethylphenyl)-6-(2-fluorophenyl)-furo[2,3-d]pyrimidine and 250 mg (2.5 mmol) (−)-{[(2S)-3-hydroxy-2-methylpropyl]oxy}ethyl acetate in 2.8 ml abs. THF to 0° C. and add 1.27 ml (1.27 mmol) phosphazene base P4-t-Bu (1 M solution in hexane). At the end of addition, heat to RT and stir for 2.5 h at RT, then add water to the reaction mixture and neutralize with 1 N hydrochloric acid. Extract with dichloromethane, dry the organic phase over sodium sulphate and concentrate under vacuum. Purify the raw product by preparative RP-HPLC (gradient: water/acetonitrile). Combine the product fractions obtained, concentrate by vacuum evaporation and purify the residue further by repeated chromatography on silica gel (gradient: cyclohexane/ethyl acetate 30:1→5:1). 121.1 mg (24.3% of theor.) of the target product is obtained.

LC-MS (Method 8): R$_t$=3.32 min; m/z=493 (M+H)$^+$ $^1$H-NMR (400 MHz, DMSO-d$_6$): δ=8.63 (s, 1H), 7.58-7.51 (m, 2H), 7.35-7.28 (m, 4H), 7.20 (d, 2H), 4.40 (dd, 1H), 4.35 (dd, 1H), 4.09 (q, 2H), 3.99 (s, 2H), 3.28 (d, 2H), 2.63 (q, 2H), 2.08 (m, 1H), 1.20-1.14 (m, 6H), 0.71 (d, 3H).

[α]$_D^{20}$=−9.1°, c=0.455, chloroform.

Example 152

(−)-{[(2R)-3-{[5-(4-Methoxyphenyl)-6-(2-fluorophenyl)furo[2,3-d]pyrimidin-4-yl]oxy}-2-methyl-propyl]oxy}acetic acid ethyl ester

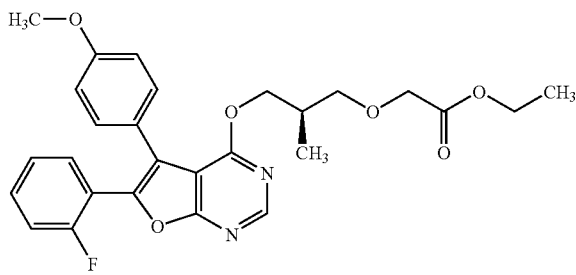

Cool a solution of 359.5 mg (1.01 mmol) 4-chloro-5-(4-methoxyphenyl)-6-(2-fluorophenyl)furo[2,3-d]pyrimidine and 250 mg (2.5 mmol) (−)-{[(2S)-3-hydroxy-2-methylpropyl]oxy}ethyl acetate in 2.8 ml abs. THF to 0° C. and add 1.27 ml (1.27 mmol) phosphazene base P4-t-Bu (1 M solution in hexane). At the end of addition, heat to RT and stir for 2.5 h at RT, then add water to the reaction mixture and neutralize with 1 N hydrochloric acid. Extract with dichloromethane, dry the organic phase over sodium sulphate and concentrate under vacuum. Purify the raw product by preparative RP-HPLC (gradient: water/acetonitrile). 77.6 mg (15.5% of theor.) of the target product is obtained.

LC-MS (Method 9): R$_t$=4.11 min; m/z=495 (M+H)$^+$ $^1$H-NMR (400 MHz, DMSO-d$_6$): δ=8.62 (s, 1H), 7.55-7.50 (m, 2H), 7.34-7.28 (m, 4H), 6.94 (d, 2H), 4.44 (dd, 1H), 4.37 (dd, 1H), 4.06 (q, 2H), 4.02 (s, 2H), 3.78 (s, 3H), 3.32-3.28 (m, 2H), 2.09 (m, 1H), 1.18 (t, 3H), 0.85 (d, 3H).

[α]$_D^{20}$=−4.4°, c=0.58, chloroform.

Example 153

(+)-3-[(1S)-2-{[5-(4-Ethylphenyl)-6-(2-fluorophenyl)furo[2,3-d]pyrimidin-4-yl]oxy}-1-methyl-ethoxy]propionic acid tert.-butyl ester

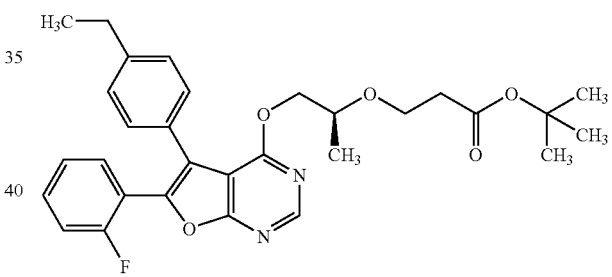

Cool a solution of 487.1 mg (90% purity, 1.24 mmol) 4-chloro-5-(4-ethylphenyl)-6-(2-fluorophenyl)furo[2,3-d]pyrimidine and 300 mg (approx. 1.47 mmol) (+)-3-[(1S)-2-hydroxy-1-methylethoxy]propionic acid tert.-butyl ester in 3.5 ml abs. THF to −20° C. and add 1.13 ml (1.13 mmol) phosphazene base P4-t-Bu (1M solution in hexane). At the end of addition, slowly heat to RT and stir for 2 h at RT, then add water to the reaction mixture and neutralize with 1 N hydrochloric acid. Extract with dichloromethane, dry the organic phase over sodium sulphate and concentrate under vacuum. Purify the raw product by preparative RP-HPLC (gradient: water/acetonitrile). 101.2 mg (15.6% of theor.) of the target product is obtained.

LC-MS (Method 9): R$_t$=4.67 min; m/z=521 (M+H)$^+$ $^1$H-NMR (400 MHz, DMSO-d$_6$): δ=8.64 (s, 1H), 7.56-7.51 (m, 2H), 7.35-7.29 (m, 4H), 7.20 (d, 2H), 4.43 (dd, 1H), 4.38 (dd, 1H), 3.75-3.67 (m, 1H), 3.33-3.45 (m, 2H), 2.62 (q, 2H), 2.29 (t, 2H), 1.32 (s, 9H), 1.20 (t, 3H), 1.03 (d, 2H).

[α]$_D^{20}$=+19.5°, c=0.47, chloroform.

Example 154

(−)-{[(2R)-3-{[5-(4-Ethylphenyl)-6-(2-fluorophenyl)furo[2,3-d]pyrimidin-4-yl]oxy}-2-methyl-propyl]oxy}acetic acid

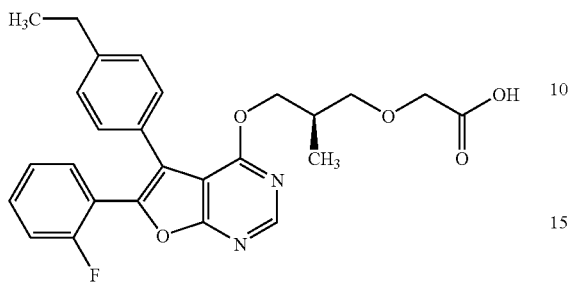

Dissolve 95.0 mg (0.19 mmol) (−)-{[(2R)-3-{[5-(4-ethylphenyl)-6-(2-fluorophenyl)furo[2,3-d]pyrimidin-4-yl]oxy}-2-methylpropyl]oxy}ethyl acetate in 1 ml THF and 0.3 ml methanol, and add 0.96 ml 1 N sodium hydroxide solution. Stir the mixture for 30 min at RT, then neutralize with 1 N hydrochloric acid and extract with dichloromethane. Concentrate the organic phase by vacuum evaporation. 57.1 mg of the target product (63.7% of theor.) is isolated from the residue after preparative RP-HPLC (gradient: acetonitrile/water).

LC-MS (Method 8): $R_t$=2.98 min; m/z=465 (M+H)$^+$ $^1$H-NMR (400 MHz, DMSO-d$_6$): δ=8.62 (s, 1H), 7.58-7.51 (m, 2H), 7.35-7.28 (m, 4H), 7.21 (d, 2H), 4.45 (dd, 1H), 4.28 (dd, 1H), 3.45 (s, 2H), 3.23 (d, 2H), 2.63 (q, 2H), 2.04 (m, 1H), 1.20 (t, 3H), 0.78 (d, 3H).

$[α]_D^2$=−32.5°, c=0.505, chloroform.

Example 155

(−)-{[(2R)-3-{[5-(4-Methoxyphenyl)-6-(2-fluorophenyl)furo[2,3-d]pyrimidin-4-yl]oxy}-2-methyl-propyl]oxy}acetic acid

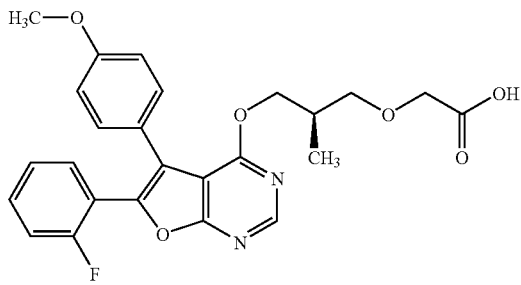

Dissolve 80.5 mg (0.16 mmol) (−)-{[(2R)-3-{[5-(4-methoxyphenyl)-6-(2-fluorophenyl)furo[2,3-d]pyrimidin-4-yl]oxy}-2-methylpropyl]oxy}acetic acid ethyl ester in 0.9 ml THF and 0.25 ml methanol, and add 0.81 ml 1 N sodium hydroxide solution. Stir the mixture for 30 min at RT, then neutralize with 1 N hydrochloric acid and extract with dichloromethane. Concentrate the organic phase by vacuum evaporation. 17.2 mg of the target product (22.7% of theor.) is isolated from the residue after preparative RP-HPLC (gradient: acetonitrile/water).

LC-MS (Method 8): $R_t$=2.73 min; m/z=467 (M+H)$^+$ $^1$H-NMR (400 MHz, DMSO-d$_6$): δ=8.62 (s, 1H), 7.57-7.50 (m, 2H), 7.35-7.28 (m, 4H), 6.95 (d, 2H), 4.47 (dd, 1H), 4.30 (dd, 1H), 3.79 (s, 3H), 3.47 (s, 2H), 3.28 (d, 2H), 2.05 (m, 1H), 0.79 (d, 3H).

$[α]_D^{20}$=−16.8°, c=0.45, chloroform.

Example 156

3-[(1S)-2-{[5-(4-Ethylphenyl)-6-(2-fluorophenyl)furo[2,3-d]pyrimidin-4-yl]oxy}-1-methylethoxy]-propionic acid

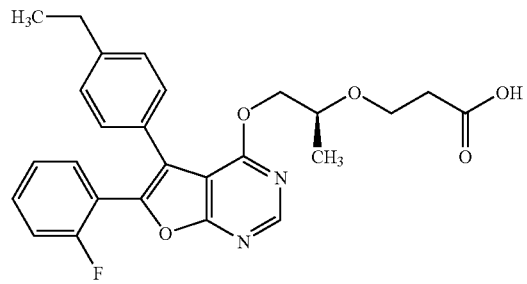

Dissolve 78.5 mg (0.151 mmol) (+)-3-[(1S)-2-{[5-(4-ethylphenyl)-6-(2-fluorophenyl)furo[2,3-d]pyrimidin-4-yl]oxy}-1-methylethoxy]propionic acid tert.-butyl ester in 0.5 ml dichloromethane and, at RT, add 0.17 ml TFA. After 1.5 h at RT, add a further 0.17 ml TFA, and stir the reaction mixture for a further 30 min at RT, then concentrate by vacuum evaporation. Take up the residue in dichloromethane, wash with water, dry over sodium sulphate and concentrate by vacuum evaporation. Purify the raw product by RP-HPLC (gradient: acetonitrile/water). 61.8 mg (88.2% of theor.) of the target product is obtained.

LC-MS (Method 8): $R_t$=2.87 min; m/z=465 (M+H)$^+$ $^1$H-NMR (400 MHz, DMSO-d$_6$): δ=12.12 (br. s, 1H), 8.63 (s, 1H), 7.57-7.50 (m, 2H), 7.35-7.28 (m, 4H), 7.21 (d, 2H), 4.45-4.35 (m, 2H), 3.73-3.68 (m, 1H), 3.60-3.47 (m, 2H), 2.64 (q, 2H), 2.34 (t, 2H), 1.19 (t, 3H), 1.04 (d, 3H).

$[α]_D^{20}$=+30.5°, c=0.48, chloroform.

Example 157

(+/−)-2-Methoxy-3-{[5-(4-methoxyphenyl)-6-phenylfuro[2,3-d]pyrimidin-4-yl]oxy}propoxy)acetic acid tert.-butyl ester

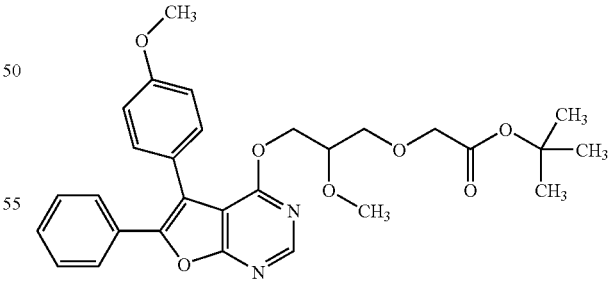

Put 550 mg (1.35 mmol) (+/−)-2-methoxy-3-{[5-(4-methoxyphenyl)-6-phenylfuro[2,3-d]pyrimidin-4-yl]oxy}propan-1-ol with 1.0 ml (6.77 mmol) tert.-butyl bromoacetate and 92 mg (0.27 mmol) tetrabutylammonium hydrogensulphate in 15 ml dichloromethane, and cool to 0° C. Add 2.75 ml of 50% sodium hydroxide solution and stir for a few minutes at 0° C. Then leave to return to RT and stir overnight at RT. Next, dilute with dichloromethane and water, acidify with 10% citric acid solution and separate the phases. Re-extract the aqueous phase once with dichloromethane. Combine the dichloromethane phases and wash once with satd. sodium chloride solution. Dry over magnesium sulphate, concentrate by evaporation and purify the residue by chromatography on silica gel (solvent: cyclohexane/ethyl acetate 85:15). 550 mg (78.1% of theor.) of the target compound is obtained.

LC-MS (Method 7): $R_t$=4.50 min; m/z=521 (M+H)$^+$
$^1$H-NMR (400 MHz, CDCl$_3$): δ=8.52 (s, 1H), 7.61 (m, 2H), 7.41 (d, 2H), 7.30 (m, 3H), 6.98 (d, 2H), 4.67-4.62 (m, 1H), 4.50-4.44 (m, 1H), 3.90 (s, 2H), 3.87 (s, 3H), 3.60 (m, 1H), 3.52-3.45 (m, 2H), 3.31 (s, 3H), 1.47 (s, 9H).

Example 158

(+/−)-(2-Methoxy-3-{[5-(4-methoxyphenyl)-6-phenylfuro[2,3-d]pyrimidin-4-yl]oxy}propoxy)acetic acid

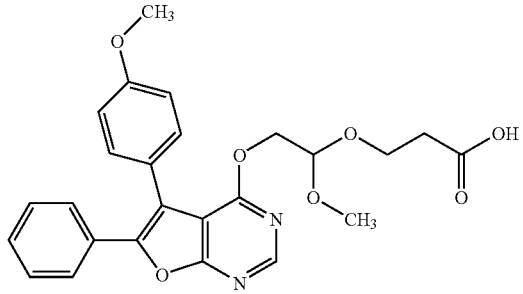

Dissolve 500 mg (0.96 mmol) (+/−)-2-methoxy-3-{[5-(4-methoxyphenyl)-6-phenylfuro[2,3-d]pyrimidin-4-yl]oxy}propoxy)acetic acid tert.-butyl ester in 10 ml dichloromethane. Add 2.5 ml (32.4 mmol) trifluoroacetic acid and stir for a further 1 h at RT. Then concentrate by evaporation and dry at high vacuum. 390 mg (87.4% of theor.) of the target compound is obtained.

LC-MS (Method 9): $R_t$=3.46 min; m/z=465 (M+H)$^+$
$^1$H-NMR (400 MHz, CDCl$_3$): δ=8.52 (s, 1H), 7.61 (m, 2H), 7.45 (d, 2H), 7.40 (m, 3H), 6.97 (d, 2H), 4.70-4.65 (m, 1H), 4.46-4.42 (m, 1H), 4.10-3.96 (dd, 2H), 3.88 (s, 3H), 3.64-3.53 (m, 2H), 3.36 (s, 3H), 3.36-3.30 (m, 1H).

Example 159

6-{[5-(4-Methoxyphenyl)-6-phenylfuro[2,3-d]pyrimidin-4-yl]amino}heptanoic acid methyl ester

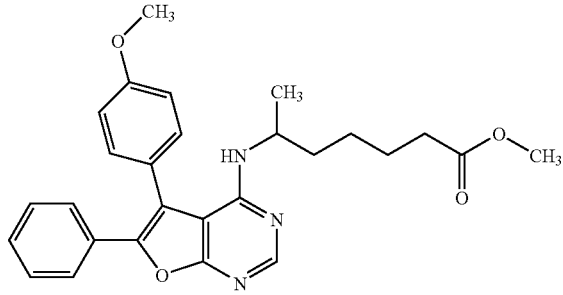

Hydrogenate 1.00 g (3.80 mmol) 6-{[(1R)-1-phenylethyl]amino}heptanoic acid methyl ester in the presence of 100 mg palladium on charcoal (10%) in 10 ml methanol and 1 ml acetic acid overnight at normal pressure. Then filter on diatomite with suction, wash with methanol and concentrate by evaporation. Because, according to HPLC, conversion is not yet complete, hydrogenate again in 10 ml methanol and 1 ml acetic acid in the presence of 100 mg palladium on charcoal (10%) at 4 bar for a period of 6 h. Once again filter on diatomite with suction, wash with methanol and concentrate by evaporation (HPLC: educt no longer present). The 6-aminoheptanoic acid methyl ester thus obtained is used directly as raw product in further reactions.

Add 260 mg (approx. 1.19 mmol) of the 6-aminoheptanoic acid methyl ester obtained above and 307 mg (2.38 mmol) N,N-diisopropylamine to 200 mg (0.59 mmol) of 4-chloro-5-(4-methoxyphenyl)-6-phenylfuro[2,3-d]pyrimidine in 1 ml DMSO and stir at 100° C. overnight. Then leave to cool, and concentrate by evaporation. Purify the residue by preparative HPLC. 80 mg (29.3% of theor.) of the target compound is obtained.

LC-MS (Method 7): $R_t$=4.32 min; m/z=460 (M+H)$^+$
$^1$H-NMR (400 MHz, CDCl$_3$): δ=8.39 (s, 1H), 7.55 (m, 2H), 7.39 (d, 2H), 7.27 (m, 3H), 7.08 (d, 2H), 4.52 (d, 1H), 4.28-4.17 (m, 1H), 3.91 (s, 3H), 3.65 (s, 3H), 2.27 (t, 2H), 1.62-1.52 (m, 2H), 1.44-1.13 (m, 4H), 1.06 (d, 3H).

HPLC [column: Daicel Chiralpak AD 250 mm×2 mm; eluent: 99% n-heptane, 1% ethanol with 0.2% trifluoroacetic acid; flow: 0.2 ml/min; detection: 322 nm; temperature 25° C.]:
Enantiomer 1: $R_t$=29.8 min, 18.6%
Enantiomer 2: $R_t$=32.7 min, 81.4%
ee=62.8%.

Example 160

6-{[5-(4-Methoxyphenyl)-6-phenylfuro[2,3-d]pyrimidin-4-yl]amino}heptanoic acid

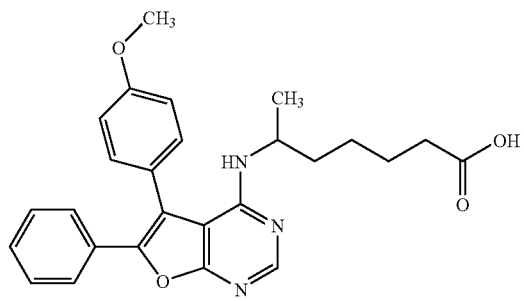

Put 65 mg (0.141 mmol) 6-{[5-(4-methoxyphenyl)-6-phenylfuro[2,3-d]pyrimidin-4-yl]amino}-heptanoic acid methyl ester in 2.5 ml THF. Add 1.42 ml (1.42 mmol) 1 N sodium hydroxide solution and stir overnight at RT. Then dilute with tert.-butylmethyl ether and adjust to approx. pH 5-6 with 10% citric acid solution. Extract the aqueous phase once with tert.-butylmethyl ether, dry the combined organic phases over magnesium sulphate and concentrate by evaporation. 59.5 mg (94.4% of theor.) of the target compound is obtained.

LC-MS (Method 8): $R_t$=2.75 min; m/z=446 (M+H)$^+$
$^1$H-NMR (400 MHz, CDCl$_3$): δ=8.39 (s, 1H), 7.53 (m, 2H), 7.39 (d, 2H), 7.26 (m, 3H), 7.05 (d, 2H), 4.51 (d, 1H), 4.26-4.17 (m, 1H), 3.91 (s, 3H), 2.30 (t, 2H), 1.64-1.54 (m, 2H), 1.40-1.15 (m, 4H), 1.06 (d, 3H).

B. ASSESSMENT OF PHARMACOLOGICAL EFFICACY

The pharmacological action of the compounds according to the invention can be demonstrated in the following assays:

B-1. Studies of Binding to Prostacyclin Receptors (IP Receptors) of Human Thrombocyte Membranes Thrombocyte membranes are obtained by centrifuging 50 ml human blood (Buffy coats with CDP Stabilizer, from Maco Pharma, Langen) for 20 min at 160×g. Remove the supernatant (platelet-rich plasma, PRP) and then centrifuge again at 2000×g for 10 min at room temperature. Resuspend the sediment in 50 mM tris-(hydroxymethyl)-aminomethane, which has been adjusted to a pH of 7.4 with 1 N hydrochloric acid, and store at −20° C. overnight. On the next day, centrifuge the suspension at 80000×g and 4° C. for 30 min. Discard the supernatant. Resuspend the sediment in 50 mM tris-(hydroxymethyl)-aminomethane/hydrochloric acid, 0.25 mM ethylene diamine tetraacetic acid (EDTA), pH 7.4, and then centrifuge once again at 80000×g and 4° C. for 30 min. Take up the membrane sediment in binding buffer (50 mM tris-(hydroxymethyl)-aminomethane/hydrochloric acid, 5 mM magnesium chloride, pH 7.4) and store at −70° C. until the binding test.

For the binding test, incubate 3 nM $^3$H-Iloprost (592 GBq/mmol, from AmershamBioscience) for 60 min with 300-1000 µg/ml human thrombocyte membranes per charge (max. 0.2 ml) in the presence of the test substances at room temperature. After stopping, add cold binding buffer to the membranes and wash with 0.1% bovine serum albumin. After adding Ultima Gold Scintillator, quantify the radioactivity bound to the membranes using a scintillation counter. The nonspecific binding is defined as radioactivity in the presence of 1 µM Iloprost (from Cayman Chemical, Ann Arbor) and is as a rule <25% of the bound total radioactivity. The binding data ($IC_{50}$ values) are determined using the program GraphPad Prism Version 3.02.

Representative results for the compounds according to the invention are shown in Table 1:

TABLE 1

| Example No. | $IC_{50}$ [nM] |
|---|---|
| 1 | 206 |
| 4 | 34 |
| 14 | 49 |
| 15 | 82 |
| 33 | 64 |
| 36 | 217 |
| 45 | 895 |
| 49 | 159 |
| 63 | 37 |
| 69 | 9 |
| 80 | 22 |
| 83 | 20 |
| 85 | 470 |
| 92 | 219 |
| 95 | 10 |
| 113 | 51 |
| 117 | 84 |
| 122 | 48 |
| 128 | 33 |
| 138 | 53 |
| 140 | 52 |
| 142 | 2.5 |
| 146 | 7 |
| 152 | 3.7 |
| 154 | 3.8 |
| 156 | 13 |

B-2. IP-Receptor Stimulation on Whole Cells

The IP-agonistic action of test substances is determined by means of the human erythroleukaemia line (HEL), which expresses the IP-receptor endogenously [Murray, R., *FEBS Letters* 1989, 1: 172-174]. For this, the suspension cells ($4 \times 10^7$ cells/ml) are incubated with the particular test substance for 5 minutes at 30° C. in buffer [10 mM HEPES (4-(2-hydroxyethyl)-1-piperazineethanesulphonic acid)/PBS (phosphate-buffered saline, from Oxoid, UK)], 1 mM calcium chloride, 1 mM magnesium chloride, 1 mM IBMX (3-isobutyl-1-methylxanthine), pH 7.4. Next, the reaction is stopped by addition of 4° C. cold ethanol and the charges are stored for a further 30 minutes at 4° C. Then the samples are centrifuged at 10000×g and 4° C. The resultant supernatant is discarded and the sediment is used for determination of the concentration of cyclic adenosine monophosphate (cAMP) in a commercially available cAMP-radioimmunoassay (from IBL, Hamburg). In this test, IP agonists lead to an increase in cAMP concentration, but IP antagonists have no effect. The effective concentration ($EC_{50}$ value) is determined using the program GraphPad Prism Version 3.02.

B-3. Inhibition of Thrombocyte Aggregation In vitro

Inhibition of thrombocyte aggregation is determined using blood from healthy test subjects. Mix 9 parts blood with one part 3.8% sodium citrate solution as coagulant. Centrifuge the blood at 900 rev/min for 20 min. Adjust the pH value of the platelet-rich plasma obtained to pH 6.5 with ACD solution (sodium citrate/citric acid/glucose). Then remove the thrombocytes by centrifugation, take up in buffer and centrifuge again. Take up the thrombocyte deposit in buffer and additionally resuspend with 2 mmol/l calcium chloride.

For the measurements of aggregation, incubate aliquots of the thrombocyte suspension with the test substance for 10 min at 37° C. Next, aggregation is induced by adding ADP and is determined by the turbidimetric method according to Born in the Aggregometer at 37° C. [Born G. V. R., *J. Physiol.* (*London*) 168, 178-179 (1963)].

B-4. Measurement of Blood Pressure of Anaesthetized Rats

Anaesthetize male Wistar rats with a body weight of 300-350 g with thiopental (100 mg/kg i.p.). After tracheotomy, catheterize the arteria femoralis for blood pressure measurement. Administer the test substances as solution, orally by oesophageal tube or intravenously via the femoral vein in a suitable vehicle.

C. EXAMPLES OF APPLICATION FOR PHARMACEUTICAL COMPOSITIONS

The compounds according to the invention can be converted to pharmaceutical preparations as follows:

Tablet:

Composition:

100 mg of the compound according to the invention, 50 mg lactose (monohydrate), 50 mg maize starch (native), 10 mg polyvinylpyrrolidone (PVP 25) (from BASF, Ludwigshafen, Germany) and 2 mg magnesium stearate.

Tablet weight 212 mg. Diameter 8 mm, radius of convex portion 12 mm.

Production:

The mixture of compound according to the invention, lactose and starch is granulated with a 5% solution (w/w) of PVP in water. After drying, the granules are mixed with the magnesium stearate for 5 minutes. This mixture is compressed using an ordinary tablet press (tablet format: see above). A guide value for the pressing force for compaction is 15 kN.

Suspension for Oral Application:
Composition:
1000 mg of the compound according to the invention, 1000 mg ethanol (96%), 400 mg Rhodigel® (xanthan gum from the company FMC, Pa., USA) and 99 g water.
10 ml of oral suspension corresponds to a single dose of 100 mg of the compound according to the invention.
Production:
The Rhodigel is suspended in ethanol, and the compound according to the invention is added to the suspension. The water is added while stirring. It is stirred for approx. 6 h until swelling of the Rhodigel ceases.
Solution for Oral Application:
Composition:
500 mg of the compound according to the invention, 2.5 g polysorbate and 97 g polyethylene glycol 400. 20 g of oral solution corresponds to a single dose of 100 mg of the compound according to the invention.
Production:
The compound according to the invention is suspended in the mixture of polyethylene glycol and polysorbate with stirring. Stirring continues until the compound according to the invention has dissolved completely.
i.v. Solution:
The compound according to the invention is dissolved in a physiologically acceptable solvent (e.g. isotonic sodium chloride solution, glucose solution 5% and/or PEG 400 solution 30%) at a concentration below the saturation solubility. The solution is sterile-filtered and is packed in sterile, pyrogen-free injection containers.

The invention claimed is:
1. A compound of formula (I)

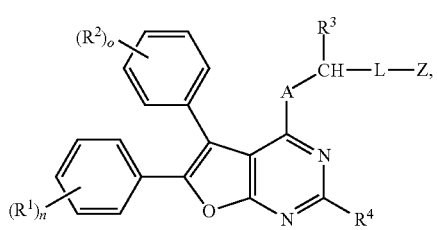

(I)

in which
A stands for O,
L stands for $(C_1-C_7)$ alkanediyl or $(C_2-C_7)$ alkenediyl, which can be substituted singly or doubly with fluorine, or for a group of formula *-$L^1$-Q-$L^2$, where
* denotes the point of linkage with the $CHR^3$ group,
$L^1$ denotes $(C_1-C_5)$ alkanediyl, which can be substituted with $(C_1-C_4)$ alkyl or $(C_1-C_4)$ alkoxy,
$L^2$ denotes a bond or $(C_1-C_3)$ alkanediyl, which can be substituted singly or doubly with fluorine,
and
Q denotes O or N—$R^6$, where
$R^6$ represents hydrogen, $(C_1-C_6)$ alkyl or $(C_3-C_7)$ cycloalkyl,
Z stands for a group of formula

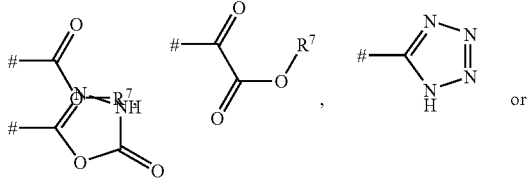

where
# denotes the point of linkage with group L
and
$R^7$ denotes hydrogen or $(C_1-C_4)$ alkyl,
$R^1$ and $R^2$, independently of one another, stand for a substituent selected from the group comprising halogen, cyano, nitro, $(C_1-C_6)$ alkyl, $(C_2-C_6)$ alkenyl, $(C_2-C_4)$ alkinyl, $(C_3-C_7)$ cycloalkyl, $(C_4-C_7)$ cycloalkenyl, $(C_1-C_6)$ alkoxy, trifluoromethyl, trifluoromethoxy, $(C_1-C_6)$ alkylthio, $(C_1-C_6)$ acyl, amino, mono-$(C_1-C_6)$ alkylamino, di-$(C_1-C_6)$ alkylamino and $(C_1-C_6)$ acylamino,
in which $(C_1-C_6)$ alkyl and $(C_1-C_6)$ alkoxy can in their turn each be substituted with cyano, hydroxy, $(C_1-C_4)$ alkoxy, $(C_1-C_4)$ alkylthio, amino, mono- or di-$(C_1-C_4)$ alkylamino,
or
two residues $R^1$ and/or $R^2$ bound to adjacent carbon atoms of the respective phenyl ring together form a group of formula —O—$CH_2$—O—, —O—CHF—O—, —O—$CF_2$—O—, —O—$CH_2$—$CH_2$—O— or —O—$CF_2$—$CF_2$—O—,
n and o, independently of one another, stand for the number 0, 1, 2 or 3,
and for the case when $R^1$ or $R^2$ occurs more than once, their meanings can in each case be identical or different,
$R^3$ stands for hydrogen or $(C_1-C_4)$ alkyl, which can be substituted with hydroxy or amino,
and
$R^4$ stands for hydrogen, $(C_1-C_4)$ alkyl or cyclopropyl,
or a salt thereof.
2. The compound of claim 1, in which
A stands for O,
L stands for $(C_1-C_7)$ alkanediyl or $(C_2-C_7)$ alkenediyl, which can be substituted singly or doubly with fluorine, or for a group of formula *-$L^1$-Q-$L^2$, where
* denotes the point of linkage with the $CHR^3$ group,
$L^1$ denotes $(C_1-C_5)$ alkanediyl,
$L^2$ denotes a bond or $(C_1-C_3)$ alkanediyl, which can be substituted singly or doubly with fluorine,
and
Q denotes O or N—$R^6$, where
$R^6$ represents hydrogen, $(C_1-C_6)$ alkyl or $(C_3-C_7)$ cycloalkyl,
Z stands for a group of formula

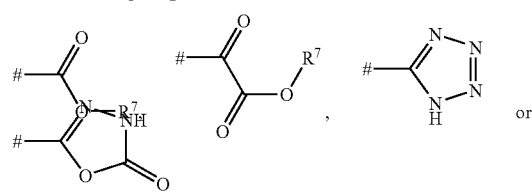

where
# denotes the point of linkage with group L
and
$R^7$ denotes hydrogen or $(C_1-C_4)$ alkyl,
$R^1$ and $R^2$, independently of one another, stand for a substituent selected from the group comprising halogen, cyano, nitro, $(C_1-C_6)$ alkyl, $(C_2-C_6)$ alkenyl, $(C_2-C_4)$ alkinyl, $(C_3-C_7)$ cycloalkyl, $(C_4-C_7)$ cycloalkenyl, $(C_1-C_6)$ alkoxy, trifluoromethyl, trifluoromethoxy, $(C_1-C_6)$ alkylthio, $(C_1-C_6)$ acyl, amino, mono-$(C_1-C_6)$ alkylamino, di-$(C_1-C_6)$ alkylamino and $(C_1-C_6)$ acylamino, and $(C_1-C_6)$ alkyl and $(C_1-C_6)$ alkoxy in their turn can each be substituted with hydroxy, $(C_1-C_4)$ alkoxy, amino, mono- or di-$(C_1-C_4)$ alkylamino, or two residues $R^1$ and/or $R^2$ bound to adjacent carbon atoms of the respective phenyl ring together form a group of formula —O—CH$_2$—O—, —O—CHF—O—, —O—CF$_2$—O—, —O—CH$_2$—CH$_2$—O— or —O—CF$_2$—CF$_2$—O—, n and o, independently of one another, stand for the number 0, 1, 2 or 3, and for the case when $R^1$ or $R^2$ occurs more than once, their meanings can in each case be identical or different, $R^3$ stands for hydrogen or $(C_1-C_4)$ alkyl, which can be substituted with hydroxy or amino, and $R^4$ stands for hydrogen, $(C_1-C_4)$ alkyl or cyclopropyl, or a salt thereof.

3. The compound of claim 1, in which

A stands for O

L stands for $(C_3-C_7)$ alkanediyl or $(C_3-C_7)$ alkenediyl, which can be substituted singly or doubly with fluorine, or for a group of formula *-L$^1$-Q-L$^2$-, where

* denotes the point of linkage with the CHR$^3$ group,

L$^1$ denotes $(C_1-C_3)$ alkanediyl,

L$^2$ denotes $(C_1-C_3)$ alkanediyl, which can be substituted singly or doubly with fluorine, and Q denotes O or N—R$^6$, where R$^6$ represents hydrogen, $(C_1-C_3)$ alkyl or cyclopropyl, Z stands for a group of formula

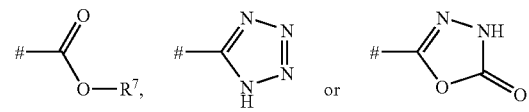

where # denotes the point of linkage with group L and

R$^7$ denotes hydrogen, methyl or ethyl, $R^1$ and $R^2$, independently of one another, stand for a substituent selected from the group comprising fluorine, chlorine, cyano, $(C_1-C_5)$ alkyl, $(C_2-C_5)$ alkenyl, $(C_3-C_6)$ cycloalkyl, $(C_4-C_6)$ cycloalkenyl, $(C_1-C_4)$ alkoxy, trifluoromethyl, trifluorometh-oxy, $(C_1-C_4)$ alkylthio, $(C_1-C_5)$ acyl, amino, mono-$(C_1-C_4)$ alkylamino, di-$(C_1-C_4)$ alkylamino and $(C_1-C_4)$ acylamino or two residues $R^1$ and/or $R^2$ bound to adjacent carbon atoms of the respective phenyl ring together form a group of formula —O—CH$_2$—O—, —O—CHF—O— or —O—CF$_2$—O—, n and o, independently of one another, stand for the number 0, 1, 2 or 3, and for the case when $R^1$ or $R^2$ occurs more than once, their meanings can in each case be identical or different, $R^3$ stands for hydrogen or $(C_1-C_3)$ alkyl, which can be substituted with hydroxy or amino, and $R^4$ stands for hydrogen or $(C_1-C_3)$ alkyl, or a salt thereof.

4. The compound of claim 1, in which

A stands for O,

L stands for $(C_3-C_7)$ alkanediyl, $(C_3-C_7)$ alkenediyl or for a group of formula *-L$^1$-O-L$^2$, where

* denotes the point of linkage with the CHR$^3$ group and

L$^1$ and L$^2$, independently of one another, denote $(C_1-C_3)$ alkanediyl,

Z stands for a group of formula

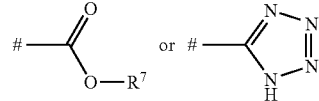

where # denotes the point of linkage with group L and

R$^7$ denotes hydrogen, methyl or ethyl, $R^1$ and $R^2$, independently of one another, stand for a substituent selected from the group comprising fluorine, chlorine, cyano, $(C_1-C_5)$ alkyl, $(C_2-C_5)$ alkenyl, $(C_3-C_6)$ cycloalkyl, $(C_4-C_6)$ cycloalkenyl, $(C_1-C_4)$ alkoxy, trifluoromethyl, trifluorometh-oxy, $(C_1-C_4)$ alkylthio, $(C_1-C_5)$ acyl, amino, mono-$(C_1-C_4)$ alkylamino, di-$(C_1-C_4)$ alkylamino and $(C_1-C_4)$ acylamino or two residues $R^1$ and/or $R^2$ bound to adjacent carbon atoms of the respective phenyl ring together form a group of formula —O—CH$_2$—O—, —O—CHF—O— or —O—CF$_2$—O—, n and o, independently of one another, stand for the number 0, 1 or 2, and for the case when $R^1$ or $R^2$ occurs twice, their meanings can in each case be identical or different, $R^3$ stands for hydrogen, methyl or ethyl and $R^4$ stands for hydrogen, or a salt thereof.

5. The compound of claim 1, in which

A stands for O,

L stands for a group of formula *-L$^1$-N(CH$_3$)-L$^2$, where

* denotes the point of linkage with the CHR$^3$ group and

L$^1$ and L$^2$, independently of one another, denote $(C_1-C_3)$ alkanediyl,

Z stands for a group of formula

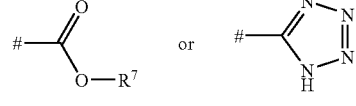

where # denotes the point of linkage with group L and

R$^7$ denotes hydrogen, methyl or ethyl, $R^1$ and $R^2$, independently of one another, stand for a substituent selected from the group comprising fluorine, chlorine, cyano, $(C_1-C_5)$ alkyl, $(C_2-C_5)$ alkenyl, $(C_3-C_6)$ cycloalkyl, $(C_4-C_6)$ cycloalkenyl, $(C_1-C_4)$ alkoxy, trifluoromethyl, trifluorometh-oxy, $(C_1-C_4)$ alkylthio, $(C_1-C_5)$ acyl, amino, mono-$(C_1-C_4)$ alkylamino, di-$(C_1-C_4)$ alkylamino and $(C_1-C_4)$ acylamino or two residues $R^1$ and/or $R^2$ bound to adjacent carbon atoms of the respective phenyl ring together form a group of formula —O—CH$_2$—O—, —O—CHF—O— or —O—CF$_2$—O—, n and o, independently of one another, stand for the number 0, 1 or 2, and for the case when $R^1$ or $R^2$ occurs twice, their meanings can in each case be identical or different, $R^3$ stands for hydrogen, methyl or ethyl and $R^4$ stands for hydrogen, or a salt thereof.

6. The compound of claim 1, in which

A stands for O,

L stands for (C$_3$-C$_7$) alkanediyl, (C$_3$-C$_7$) alkenediyl or for a group of formula *-L$^1$-Q-L$^2$, where
* denotes the point of linkage with the CHR$^3$ group,
L$^1$ and L$^2$, independently of one another, denote (C$_1$-C$_3$) alkanediyl and Q denotes O or N(CH$_3$), Z stands for a group of formula

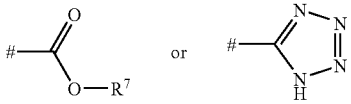

where # denotes the point of linkage with group L and $R^7$ denotes hydrogen, methyl or ethyl, $R^1$ stands for a substituent selected from the group comprising fluorine, chlorine, methyl, ethyl, vinyl, trifluoromethyl and methoxy, $R^2$ stands for a substituent selected from the group comprising fluorine, chlorine, cyano, methyl, ethyl, n-propyl, vinyl, trifluoromethyl, methoxy, ethoxy, trifluoromethoxy, methylthio, ethylthio, amino, methylamino and ethylamino, n and o, independently of one another, stand for the number 0, 1 or 2, and for the case when $R^1$ or $R^2$ occurs twice, their meanings can in each case be identical or different, $R^3$ stands for hydrogen, methyl or ethyl and $R^4$ stands for hydrogen, and their salts, solvates and solvates of the salts.

7. A method of making a compound of claim 1, comprising either

[A] reacting a compound of formula (II)

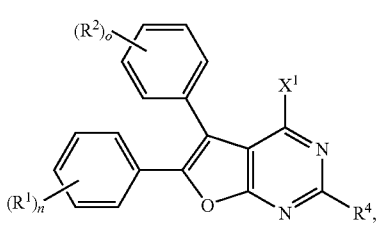

(II)

in which $R^1$, $R^2$, $R^4$, n and o have the respective meanings given in claim 1 and $X^1$ stands for a leaving group such as halogen, especially for chlorine, in the presence of a base if necessary in an inert solvent with a compound of formula (III)

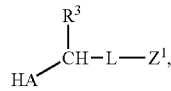

(III)

in which A, L and $R^3$ have the respective meanings given in claim 1 and $Z^1$ stands for cyano or a group of formula —[C(O)]$_y$—COOR$^{7A}$, where y denotes the number 0 or 1 and $R^{7A}$ denotes (C$_1$-C$_4$) alkyl, to produce a compounds of formula (IV)

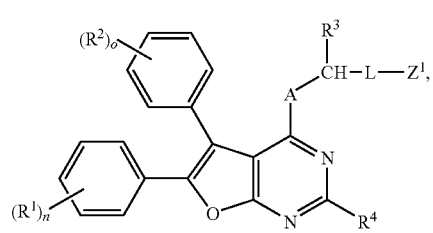

(IV)

in which A, L, $Z^1$, $R^1$, $R^2$, $R^3$, $R^4$, n and o have the respective meanings given above, or

[B] reacting a compound of formula (V-1)

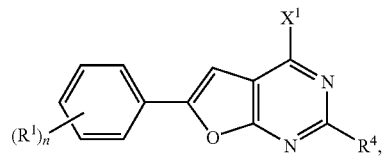

(V-1)

in which $R^1$, $R^4$, $X^1$ and n have the respective meanings given in claim 1, in the presence of a base if necessary in an inert solvent with a compound of formula (III) to produce a compound of formula (VI-1)

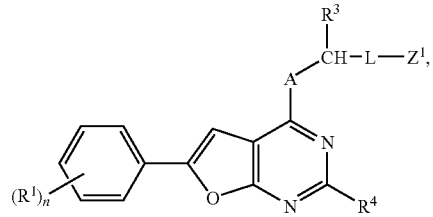

(VI-1)

in which A, L, $Z^1$, $R^1$, $R^3$, $R^4$ and n have the respective meanings given above, brominating the compound of formula (VI-1) in an inert solvent, to produce a compounds of formula (VII-1)

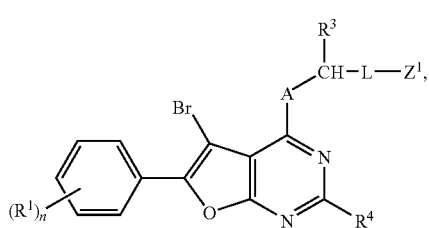
(VII-1)

in which A, L, $Z^1$, $R^1$, $R^3$, $R^4$ and n have the respective meanings given above, and coupling the compound of formula (VII-1) in an inert solvent in the presence of a base and a suitable palladium catalyst with a phenylboronic acid of formula (VIII-1)

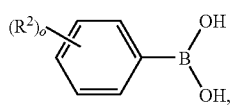
(VIII-1)

in which $R^2$ and o have the meanings given in claim 1, to produce the compound of formula (IV)

or

[α] reacting a compound of formula (V-2)

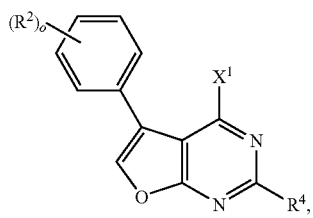
(V-2)

in which $R^2$, $R^4$, $X^1$ and o have the respective meanings given in claim 1, in the presence of a base if necessary in an inert solvent with a compound of formula (III), to produce a compounds of formula (VI-2)

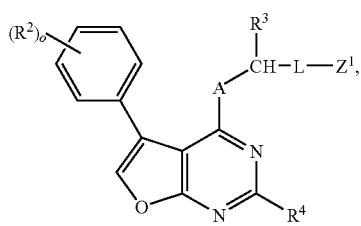
(VI-2)

in which A, L, $Z^1$, $R^2$, $R^3$, $R^4$ and o have the respective meanings given above, brominating the compound of formula (VI-2) in an inert solvent to produce a compounds of formula (VII-2)

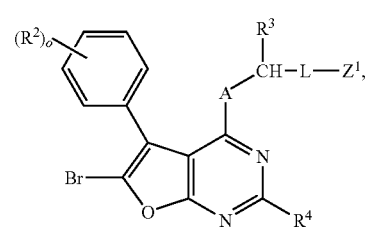
(VII-2)

in which A, L, $Z^1$, $R^2$, $R^3$, $R^4$ and o have the respective meanings given above, and coupling the compound of formula (VII-2) in an inert solvent in the presence of a base and a suitable palladium catalyst with a phenylboronic acid of formula (VIII-2)

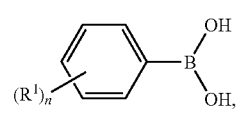
(VIII-2)

in which $R^1$ and n have the meanings given in claim 1, to produce the compound of formula (IV), and converting the compounds of formula (IV) produced in [A], [B], or [C] by hydrolysis of the ester or cyano group $Z^1$ to produce at carboxylic acid of formula (I-A)

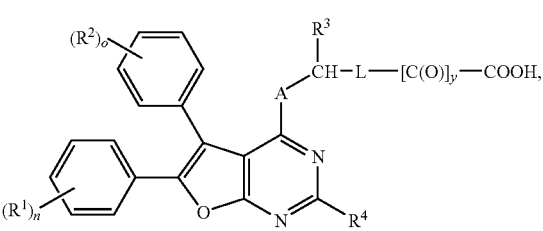
(I-A)

in which A, L, $R^1$, $R^2$, $R^3$, $R^4$, n, o and y have the respective meanings given above, and optionally converting the carboxylic acid of formula (I-A) with a corresponding (i) solvents and/or (ii) base or acid to a salt thereof.

8. A pharmaceutical composition comprising a compound of claim 1, and an inert, nontoxic, pharmaceutically acceptable excipient.

9. The pharmaceutical composition of claim 8, further comprising another active substance selected from the group consisting of an organic nitrate and NO-donor, a compound that inhibits the degradation of cyclic guanosine monophosphate and/or cyclic adenosine monophosphate, an NO-independent but haem-dependent stimulator of guanylate cyclase, an NO- and haem-independent activator of guanylate cyclise, a compound which inhibits human neutrophilic elase, a compound which inhibits the signal transduction cascade, a compound which influences the energy metabolism of the heart, an antithrombotic agent, an active substance for lowering blood pressure, and an active substance that modifies lipid metabolism.

\* \* \* \* \*